(12) United States Patent
Okumura et al.

(10) Patent No.: US 6,777,540 B1
(45) Date of Patent: Aug. 17, 2004

(54) HUMANIZED IMMUNOGLOBULIN REACTING SPECIFICALLY WITH FAS LIGAND OR ACTIVE FRAGMENTS THEREOF AND REGION INDUCING APOPTOSIS ORIGINATING IN FAS LIGAND

(75) Inventors: Ko Okumura, c/o Department of Immunology, Faculty of Medicine, Juntendo University, 2-2-1, Hongo, Bunkyo-ku, Tokyo-to (JP); Motomi Nakata, Yokohama (JP); Hirofumi Higuchi, Kikuchi-gun (JP); Yoshitaka Ushio, Kumamoto (JP); Hiroaki Maeda, Kumamoto (JP); Yasuyuki Eda, Kikuchi-gun (JP)

(73) Assignee: Ko Okumura, Tokyo-to (JP)

( * ) Notice: Subject to any disclaimer, the term of this patent is extended or adjusted under 35 U.S.C. 154(b) by 0 days.

(21) Appl. No.: 09/254,180

(22) PCT Filed: Aug. 27, 1997

(86) PCT No.: PCT/JP97/02983

§ 371 (c)(1),
(2), (4) Date: Apr. 15, 1999

(87) PCT Pub. No.: WO98/10070

PCT Pub. Date: Mar. 12, 1998

(30) Foreign Application Priority Data

Sep. 2, 1996 (JP) .............................................. 8/231742
Sep. 20, 1996 (JP) ............................................ 8/271546

(51) Int. Cl.$^7$ .............................................. C07K 16/00
(52) U.S. Cl. ............................... 530/387.9; 530/387.3; 530/388.1; 424/9.1; 424/130.1; 424/185.1
(58) Field of Search .......................... 530/387.3, 387.9, 530/388.1; 424/130.1, 9.1, 185.1

(56) References Cited

U.S. PATENT DOCUMENTS 5,530,101 A * 6/1996 Queen et al. ............. 530/387.3
6,114,507 A * 9/2000 Shirakawa et al. ....... 530/389.2

FOREIGN PATENT DOCUMENTS

| EP | 0 239 400 A2 | 9/1987 |
| EP | 06752000 A1 * | 4/1995 |
| EP | 0 675 200 A1 | 10/1995 |
| EP | 0 842 948 A1 | 5/1998 |
| WO | WO 95/18819 | 7/1995 |

OTHER PUBLICATIONS

Pillay et al. Review in Medical Virology, 10(4):231–53, 2000.*
Brawley, C, AIDs alert, 16 (9) : 109–10, 2001.*
Paul, W.E (ed) Fundamental Immunol. p. 242, 1993.*
Taub et al. J. B. C 264 : 259–265, 1990.*
Kayagaki, M. J. Exp. Med. 182 : 1777–1783, 1995.*
Burgess. J. Cell Biol II : 2129–2138, 1990.*
Kimmel et al. J. Neurosurg, 66:161–171, 1987.*
Freshney et al. Culture of Animal Cells, A Manual of Basic Technique, Alan R. Liss, Inc., 1983, New York, p4, Dermer. Bio/Technology, 1994, 12:320.*
"Metalloproteinase–mediated Release of Human Fas Ligand", N. Kayagaki et al., J. Exp. Med., vol. 182, Dec. 1995, pp. 1777–1783.
"Fas in Rheumatoid Arthritis Synovial Tissues/Examination on the Manifestation of Fas Ligand System (in Japanese)", Hiroshi Asahara et al., The Japanese Journal Clinical Medicine, vol. 54, (1996); p. 1960–1964 (particularly p. 1962, right column, 8$^{th}$ line to 6$^{th}$ line from the bottom).
"Human Fas ligand: gene structure, chromosomal location and species specificity", T. Takahashi et al., International Immunology, vol. 6, No. 20, Jun. 1994, pp. 1567–1574.
"Comparative Molecular Modelling of the Fas–Ligand and Other Members of the TNF Family", M.C. Peitsch et al., Molecular Immunology, vol. 32, No. 10, 1995, pp. 761–772.

* cited by examiner

Primary Examiner—Susan Ungar
Assistant Examiner—Minh Tam Davis
(74) Attorney, Agent, or Firm—McDermott, Will & Emery

(57) ABSTRACT

Novel humanized immunoglobulins and active fragments thereof which are specifically reactive to Fas ligand are provided, and a site on Fas ligand which is important to inhibit apoptosis induced by the Fas-Fas ligand interaction against Fas-expressing cells is demonstrated. The novel humanized immunoglobulins and active fragments thereof which are specifically reactive to Fas ligand are prepared from hybridomas which produce monoclonal antibodies specifically reactive to Fas ligand, via recombinant DNA techniques. The humanized immunoglobulins can inhibit the physiological reactions between Fas ligand and Fas such as apoptosis. Further, identification of the site which is on Fas ligand and responsible for apoptosis induction allows creation of recombinant proteins or peptides which are specifically reactive to the amino acids within the site so as to inhibit apoptosis, and to find new therapeutic or diagnostic agents.

9 Claims, 34 Drawing Sheets

Fig. 1

AAGCTTGCCGCCACC
HindIII      (MHL4.4 primer )

```
|  leader                                                        | FR1
        10        20        30        40        50        60
ATGGAATGGAGCTGGGTCTTTATCTTTCTCCTGTCAGTAACTGCAGGTGTCCACTCCCAG
 M  E  W  S  W  V  F  I  F  L  L  S  V  T  A  G  V  H  S  Q 70        80        90       100       110       120
GTCCACCTGCAGCAGTCTGGAGCTGAGCTGGTAAGGCCTGGGACTTCAGTGAAGATGTCC
 V  H  L  Q  Q  S  G  A  E  L  V  R  P  G  T  S  V  K  M  S

|    CDR1           |  FR2
       130       140       150       160       170       180
TGCAAGGCTGCTGGATACACCTTCACTAACTACTGGATAGGTTGGGTAAAGCAGAGGCCT
 C  K  A  A  G  Y  T  F  T  N  Y  W  I  G  W  V  K  Q  R  P

|   CDR2
       190       200       210       220       230       240
GGACATGGCCTTGAGTGGATTGGATATCTTTACCCTGGAGGTCTTTATACTAACTACAAT
 G  H  G  L  E  W  I  G  Y  L  Y  P  G  G  L  Y  T  N  Y  N

|  FR3
       250       260       270       280       290       300
GAGAAGTTCAAGGGCAAGGCCACACTGACTGCAGACACATCCTCCAGCACAGCCTACATG
 E  K  F  K  G  K  A  T  L  T  A  D  T  S  S  S  T  A  Y  M

|  CDR3
       310       320       330       340       350       360
CAGCTCAGCAGCCTGACATCTGAGGACTCTGCCATCTATTACTGTGCAAGATACAGGGAT
 Q  L  S  S  L  T  S  E  D  S  A  I  Y  Y  C  A  R  Y  R  D

|  FR4
       370       380       390       400       410       420
TACGACTATGCTATGGACTACTGGGGTCAAGGAACCTCAGTCACCGTCTCCTCAGGTGAGT
 Y  D  Y  A  M  D  Y  W  G  Q  G  T  S  V  T  V  S  S
```

GGATCC
BamHI (MHJ124 primer )

Fig. 2

AAGCTTCGCCACC
HindIII (MKL2.4 primer)

| leader
         10          20          30          40          50          60
ATGAAGTTGCCTGTTAGGCTGTTGGTGCTGCTATTGTTCATGAGTCCAGCTTCAAGCAGT
 M   K   L   P   V   R   L   L   V   L   L   F   M   S   P   A   S   S   S

|       FR1
         70          80          90         100         110         120
GATGTTGTTCTGACCCAAACTCCACTCTCTCTGCCTGTCAATATTGGAGATCAAGCCTCT
 D   V   V   L   T   Q   T   P   L   S   L   P   V   N   I   G   D   Q   A   S

|      CDR1                                              | FR2
            130         140         150         160         170         180
ATCTCTTGCAAGTCTACTAAGAGCCTTCTGAATAGTGATGGATTCACTTATTTGGGCTGG
 I   S   C   K   S   T   K   S   L   L   N   S   D   G   F   T   Y   L   G   W

|   CDR2
           190         200         210         220         230         240
TGCCTGCAGAAGCCAGGCCAGTCTCCACAGCTCCTAATATATTTGGTTTCTAATCGATTT
 C   L   Q   K   P   G   Q   S   P   Q   L   L   I   Y   L   V   S   N   R   F

|  FR3
           250         260         270         280         290         300
TCTGGAGTTCCAGACAGGTTCAGTGGTAGTGGGTCAGGGACAGATTTCACCCTCAAGATC
 S   G   V   P   D   R   F   S   G   S   G   S   G   T   D   F   T   L   K   I

|   CDR3
           310         320         330         340         350         360
AGCAGAGTGGAGGCTGAGGATTTGGGAGTTTATTATTGCTTCCAGAGTAACTATCTTCCT
 S   R   V   E   A   E   D   L   G   V   Y   Y   C   F   Q   S   N   Y   L   P

|   FR4
           370         380         390         400         410         420
CTTACGTTCGGATCGGGGACCAAGCTGGAAATAAAACGTAAGTGGATCC
 L   T   F   G   S   G   T   K   L   E   I   K        BamHI (MKJ124 primer)

Fig. 3
(a)
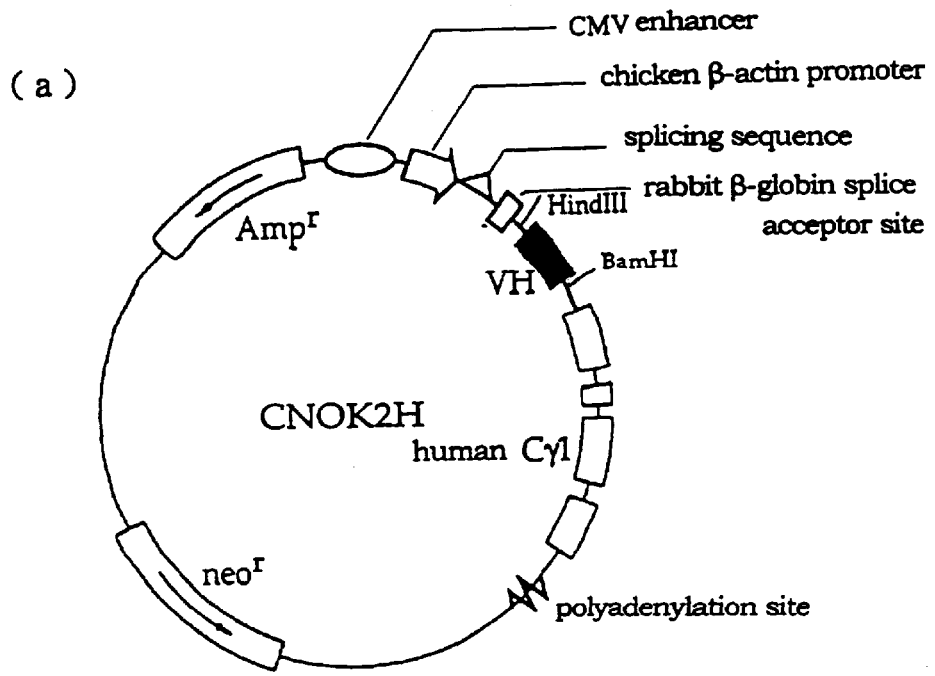
(b)
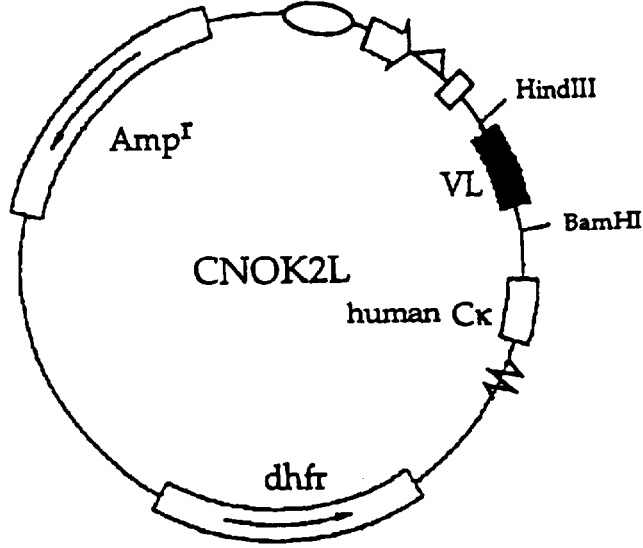

Fig. 5

```
                      FR1
                              10          20          30
NOK2VH          QVHLQQSGAE  LVRPGTSVKM  SCKAAGYTFT
SGI             QVqLvQSGAE  vkkPGaSVKv  SCKAsGYTFs
RNOK2VHver11    QVqLvQSGAE  vkkPGaSVKv  SCKAsGYTFT
RNOK2VHver12    QVqLvQSGAE  vkkPGaSVKv  SCKAsGYTFT CDR1    FR2                     CDR2
                                40               50          60
NOK2VH          NYWIG   WVKQR  PGHGLEWIG    Y  LYPGGLYTNY  NEKFKG
SGI                     WVrQa  PGqGLEWvG
RNOK2VHver11            WVKQa  PGqGLEWIG
RNOK2VHver12            WVKQa  PGqGLEWIG FR3
                             70          80          90
NOK2VH          KAIT  TADTSSSTAY   MQLSSLTSED  SAIYYCAR
SGI             rvTm  TlDTStnTAY   MeLSSLrSED  tAvYYCAsR
RNOK2VHver11    KAIm  TADTStnTAY   MeLSSLrSED  tAvYYCAR
RNOKVH2ver12    KAIT  TlDTStnTAY   MeLSSLrSED  tAvYYCAR CDR3          FR4
                100           110
NOK2VH          YR DYDYAMDY   WG  QGTSVTVSS
SGI                           WG  QGTlVTVSS
RNOK2VHver11                  WG  QGTlVTVSS
RNOKVH2ver12                  WG  QGTlVTVSS
```

Fig. 6

```
                          FR1                              CDR1
                               10          20                  30
NOK2VL              DVVLTQTPLS  LPVNIGDQAS  ISC        KSTKSLL
huVL-31             DiVmTQsPLS  LPVtpGepAS  ISC
huVL-19             DVVmTQsPLS  LPVtlGkpAS  ISC
RNOK2VLver21        DVVmTQTPLS  LPVtpGepAS  ISC
RNOK2VLver22        DVVmTQTPLS  LPVtlGkpAS  ISC
RNOK2VLver23        DVVmTQTPLS  LPVtpGkpAS  ISC
RNOK2VLver24        DVVmTQTPLS  LPVtlGepAS  ISC NOK2VL              DVVLTQTPLS  LPVNIGDQAS  ISC        KSTKSLL
REI                 DiqmTQSPsS  LsasvGDrvt  Itc
RNOK2VLver1         DVVmTQTPsS  LsasvGDrAS  ISC FR2              CDR2
                                40          50           60
NOK2VL              NSDGFTYLG  W CLQKPGQSPQ  LLIY   LVSNRF S
huVL-31                        W yLQKPGQSPQ  LLIY
huVL-19                        W fqQrPGQSPr  rLIY
RNOK2VLver21                   W CLQKPGQSPQ  LLIY
RNOK2VLver22                   W CLQKPGQSPQ  LLIY
RNOK2VLver23                   W CLQKPGQSPQ  LLIY
RNOK2VLver24                   W CLQKPGQSPQ  LLIY NOK2VL              NSDGFTYLG  W CLQKPGQSPQ  LLIY   LVSNRF S
REI                            W yqQKPGkaPk  LLIY
RNOK2VLver1                    W CqQKPGQSPQ  LLIY
```

Fig. 7

```
              FR3
              70          80          90
NOK2VL        GVPDRFSGS  GSGTDFTLKI  SRVEAEDLGV  YYC
huVL-31       GVPDRFSGS  GSGTDFTLKI  SRVEAEDvGV  YYC
huVL-19       GVPDRFSGS  GSGTDFTLKI  SRVEAEDvGV  YYC
RNOK2VLver21  GVPDRFSGS  GSGTDFTLKI  SRVEAEDvGV  YYC
RNOK2VLver22  GVPDRFSGS  GSGTDFTLKI  SRVEAEDvGV  YYC
RNOK2VLver23  GVPDRFSGS  GSGTDFTLKI  SRVEAEDvGV  YYC
RNOK2VLver24  GVPDRFSGS  GSGTDFTLKI  SRVEAEDvGV  YYC NOK2VL        GVPDRFSGS  GSGTDFTLKI  SRVEAEDLGV  YYC
REI           GVPsRFSGS  GSGTDFTftI  SslqpEDiat  YYC
RNOK2VLver1   GVPDRFSGS  GSGTDFTLKI  SslqpEDiat  YYC CDR3        FR4
              100         110
NOK2VL        FQSNYLP LT  FGSGTKLE  IKR
huVL-31                   FGqGTKLE  IKR
huVL-19                   FGqGTKLE  IKR
RNOK2VLver21              FGqGTKLE  IKR
RNOK2VLver22              FGqGTKLE  IKR
RNOK2VLver23              FGqGTKLE  IKR
RNOK2VLver24              FGqGTKLE  IKR NOK2VL        FQSNYLP LT  FGSGTKLE  IKR
REI                       FGqGTKvE  IKR
RNOK2VLver1               FGqGTKvE  IKR
```

Fig. 8

```
                                               HindIII          | Leader
                                               AAGCTTGCCGCCACC  ATG GAC TGG
                                                                Met Asp Trp

|FR1                    10                      20                      30                     40
              Thr Trp Arg Val Phe Cys Leu Leu Ala Val Ala Pro Gly Ala His Ser
              ACC TGG CGC GTG TTT TGC CTG CTC GCC GTG GCT CCT GGG GCC CAC AGC
RHC25         Gln Val Gln Leu Gln Val Gln Leu Val Gln Ser Gly Ala Glu Val Lys Lys Pro Gly Ala
              CAG GTG CAA CTA GTG CAG TCC GGG GCT GCC GAA GTG AAG AAA CCC GGT GCT 50                     60                    70                      80                     90  |CDR1
              Ser Val Lys Val Ser Cys Lys Ala Ser Gly Tyr Thr Phe Thr Asn Ser
              TCC GTG AAG GTG AGC TGT AAA GCT AGC GGT TAT ACC TTC ACT AAC TCC
RHC25                                                          TAT ACC TTC ACT AAC TAC
                                                  <<#01 3'-ATA TGA AAG TGA TTG ATG  Tyr

100                   |110 FR2              120                     130                    140
              Trp Ile Gly Trp Phe Arg Gln Ala Pro Gly Gln Gly Leu Glu Trp Ile
              TGG ATA GGT TGG TTT AGA CAG GCC CCA GGC CAA GGG CTC GAG TGG ATT
              TGG ATA GGT TGG GTA AAG TTC CAG GCC CCG GGC CAA GGG CTC GAG TGG ATT
    <<#01     ACC TAT CCA CAT TTC GTC        CCG GGT CCC GAG CTC ACC TAA
              Val Lys                                             XhoI

|CDR2            160                   170                    180                   190
              Gly Asp Ile Tyr Pro Gly Gly Gly Tyr Tyr Thr Asn Tyr Asn Glu Ile Phe
              GGC GAT ATT TAC CCT GGA GGT GGT TAT GGC ACA AAC TAT AAC GAG ATC TTT
              GGT TAC ATG GAA CCC CCA GGT CTT GAA TAT ACA AC
    <<#01     CCG ATA CTT CTT GGG CCC GGT CTT TAT ATA TG-5'
    #02>>     5'-TAT CTT CCC GGG CCT TAT ACA AAC TAT AAC GAG AAG TTT
    #03>>     5'-TAT CTT CCC GGG CCT TAT ACA AAC TAT AAC GAG AAG TTT
              Tyr Leu         XmaI                                         Lys
```

Fig. 9

```
                      |FR3                210             220             230           240
              Lys Gly Lys Ala Thr Met Thr Ala Asp Thr Ser Thr Asn Thr Ala Tyr
              AAG GGC AAG GCT ACA ATG ACA GCA GAC ACC TCT ACA AAC ACC GCC TAC
RHC25
    #02>> AAG GGC AAG GCT ACA ATG ACA GCA GAC ACC TCT ACA AAC ACC ACC-3'
    #03>> AAG GGC AAG GCT ACA ATG ACA GAC CTG ACC TCT ACA AAC ACC ACC-3'
                                        Leu Leu
                     250              260             270             280
          Met Glu Leu Ser Ser Leu Arg Ser Glu Asp Thr Ala Val Tyr Tyr Cys
RHC25     ATG GAA CTG TCC AGC CTG CGC TCC GAG GAC ACT GCA GTC TAC TAC TGC
                                                    ACT GCA GTC TAC TAC TGC
                                             <<#04 3'-TGA CGT CAG ATG ATG ACG 290             300         CDR3    310              320            330   FR4
          Ser Arg Gly Ile Pro Gly  ---  ---  Tyr Ala Met Asp Tyr     Trp Gly Gln Gly
RHC25     TCA AGG GGG ATA CCG GGA TAC ATG GAC TAC GCT ATG GAC TAT TGG GGA CAG GGT
          GCA AGG TAC ATG GAT CTA TCC ATG CTG GAC TAC GCT ATG GAC TAT TGG GGA CAG GGT
    <<#04 CGT TCC ATG TAC GAC CGA TAC CTG ATA ACC CCT GTC CCA
          Ala Tyr Arg Asp Tyr Asp 340             350
          Thr Leu Val Thr Val Ser Ser
RHC25     ACC CTT GTC ACC GTC AGT TCA G GTGAGTGGATCCGAATTC
          ACC CTT GT                         BamHI   EcoRI
    <<#04 TGG GAA CA-5'
          Kpnl
```

Fig. 10

```
                                                                                                <<SGI Leader
                                                                                              Ala His Ser
                                                                            #05>> 5'-GTCGG GCC CAC AGC
                                                                                             ApaI
          | FR1
                   10              20              30              40              50              60
          Asp Val Val Thr Gln Leu Thr Pro Leu Ser Leu Pro Val Asn Ile Gly Asp Gln Ala Ser
CNOK2VL   GAT GTT GTT ACC CAA ACT CTG ACC CCA CTC TCT CCT GTC AAT ATT GGA GAT CAA GCC TCT
#05>>     GAT GTT GTT ACC CAA ACT CCA ATG ACC CAA ACT CCA CTC TCT TCT GCC AGT GTT GGA GAT CGA GCC TCT
                                       Met                     Ser                         Arg

| CDR1                                                                        120
                  70              80              90              100             110
          Ile Ser Cys Lys Ser Thr Lys Ser Leu Leu Asn Ser Asp Gly Phe Thr Tyr Leu Gly Trp
CNOK2VL   ATC TCT TGC AAG TCT ACT AAG AGC CTT CTG AAT AGT GAT GGA TTC ACT TAT TTG GGC TGG
                                                                 ACT TAT TTG GGC TGG
                                                    <<#06 3'- TGA ATA AAC CCG ACC
                                                              #07>> 5'- GGC TGG
                                                                             BanI
#05>>     ATC TCT TGC AAG-3' #05>>

| FR2                                                       | CDR2
                  130             140             150             160             170             180
          Cys Leu Gln Lys Pro Gly Gln Ser Pro Gln Leu Leu Ile Tyr Leu Val Ser Asn Arg Phe
CNOK2VL   TGC CTG CAG AAG CCA GGC CAG TCT CCA CAG CTC CTA ATA TAT TTG GTT TCT AAT CGA TTT
          TGC CAG CAG AAG CC
<<#06     ACG GTC GTC TTC GG-5' <<#06
#07>>     TGC CAG CAG AAG CCA GGC CAG TCT-3' >>#07
              Gln
```

Fig. 11

```
            | FR3
              190           200           210           220           230           240
         Ser Gly Val Pro Asp Arg Phe Ser Gly Ser Gly Thr Asp Phe Thr Leu Lys Ile
CNOK2VL  TCT GGA GTT CCA GAC AGG TTC AGT GGT AGT GGG TCA GGG ACA GAT TTC ACC CTC AAG ATC
                                                                TTC ACC CTC AAG ATC
                                                      <<#08 3'- AAG TGG GAG TTC TAG

| CDR3
              250           260           270           280           290           300
         Ser Arg Val Glu Ala Glu Asp Leu Gly Val Tyr Tyr Cys Phe Gln Ser Asn Tyr Leu Pro
CNOK2VL  AGC AGA GTG GAG GCT GAG GAT TTG GGA GTT TAT TAT TGC TTC CAG AGT AAC TAT CTT CCT
         AGC AGT CTG CAG CCT GAG GAT                                                  CTT CCT
  <<#08  TCG TCA GAC GTC GGA CTC CTA TA-5'   <<#08
#09>>5'- AGC AGT CTG CAG CCT GAG GAT ATA GCT ACT TAT TAT TGC TTC CAG AGT AAC-3' #09>>
         Ser Leu Gln Pro                     Ile Ala Thr
                  PstI

| FR4
              310           320           330           340
         Leu Thr Phe Gly Ser Gly Thr Lys Leu Glu Ile Lys
CNOK2VL  CTT ACG TTC GGA TCG GGA ACC AAG CTG GAA ATC AAA CGTAAGTGGATCC
         CTT ACG TTC GGA TTC GGA ACC AAG GTG GAA ATA AAA CGTAAGTGGATCCGAG
  <<#10  GAA TGC AAG CCT GTC CCC TGG TTC CAC CTT TAT TTT GCATTCACCTAGGCTC-5'  <<#10
                                         Val                        BamHI
                 Gln
```

Fig. 12

```
                                                                    <<SGI Leader
                                                                     Ala His Ser
                                                        #11>> 5'-GTCGG GCC CAC AGC
                                                                      ApaI
       | FR1
                   10              20              30              40              50              60
         Asp Val Val Thr Gln Thr Pro Leu Ser Leu Pro Val Asn Ile Gly Asp Gln Ala Ser
CNOK2VL  GAT GTT GTT ACC CAA ACT CCA CTC TCT CTG CCT GTC AAT AT--T GGA G--AT CAA GCC TCT
 #11>>   GAT GTT GTT ATG ACC CAA ACT CCA CTC TCT CTG CCT GTC ACT CC/TT GGA G/CAG CCA GCC TCT
                 Met                                             Thr Pro/Leu Glu/Gln Pro

| CDR1                                                       | 120
                   70              80              90             100             110
         Ile Ser Cys Lys Ser Thr Lys Ser Leu Leu Asn Ser Asp Gly Phe Thr Tyr Leu Gly Trp
CNOK2VL  ATC TCT TGC AAG TCT ACT AAG AGC CTT CTG AAT AGT GAT GGA TTC ACT TAT TTG GGC TGG
 #11>>   ATC TCT TGC AAG-3'  #11>>

FR2                                                            | CDR2
                  130             140             150             160             170             180
         Cys Leu Gln Lys Pro Gly Gln Ser Pro Gln Leu Leu Ile Tyr Leu Val Ser Asn Arg Phe
CNOK2VL  TGC CTG CAG AAG CCA GGC CAG TCT CCA CAG CTC CTA ATA TAT TTG GTT TCT AAT CGA TTT
```

Fig. 13

```
         | FR3
         190              200              210              220              230              240
         Ser Gly Val Pro Asp Arg Phe Ser Gly Ser Gly Thr Asp Phe Thr Leu Lys Ile
CNOK2VL  TCT GGA GTT CCA GAC AGG TTC AGT GGT AGT GGG TCA GGG ACA GAT TTC ACC CTC AAG ATC

| CDR3
         250              260              270              280              290              300
         Ser Arg Val Glu Ala Glu Asp Leu Gly Val Tyr Tyr Tyr Cys Phe Gln Ser Asn Tyr Leu Pro
CNOK2VL  AGC AGA GTG GAG GCT GAG GAT TTG GGA GTT TAT TAT TAT TGC TTC CAG AGT AAC TAT CTT CCT
                             GCT GAG GAT CTA CAC ATA ATA ACG AAG GTC TCA TTG ATA GAA GGA
                                         Val
                     <<#12 3'- CGA CTC CTA CAC ATA ATA ACG AAG GTC TCA TTG ATA GAA GGA

| FR4
         310              320              330              340
         Leu Thr Phe Gly Ser Gly Thr Lys Leu Glu Ile Lys
CNOK2VL  CTT ACG TTC GGA TCG GGG ACC AAG CTG GAA ATC AAA  CGTAAGTGGATCC
         CTT ACG TTC GGA TCG CAG GGG ACC AAG CTG GAA ATA AAA  CGTAAGTGGATCCGAG
                         Gln
<<#12    GAA TGC AAG CCT GTC CCC TGG TTC GAC CTT TAT TTT  GCATTCACCTAGGCTC-5'  <<#12
                                                               BamHI
```

Fig. 16

```
         transmembrane                            EcoNI
              100          |                         110
GGA TTG GGC CTG GGG ATG TTT CAG CTC TTC CAC CTA CAG AAG GAG CTG
Gly Leu Gly Leu Gly Met Phe Gln Leu Phe His Leu Gln Lys Glu Leu>

120
GCA GAA CTC CGA GAG TCT ACC AGC CAG ATG CAC ACA GCA TCA TCT TTG
Ala Glu Leu Arg Glu Ser Thr Ser Gln Met His Thr Ala Ser Ser Leu>

130                         140
GAG AAG CAA ATA GGC CAC CCC AGT CCA CCC CCT GAA AAA AAG GAG CTG
Glu Lys Gln Ile Gly His Pro Ser Pro Pro Pro Glu Lys Lys Glu Leu>

150
AGG AAA GTG GCC CAT TTA ACA GGC AAG TCC AAC TCA AGG TCC ATG CCT
Arg Lys Val Ala His Leu Thr Gly Lys Ser Asn Ser Arg Ser Met Pro>

160                          170
CTG GAA TGG GAA GAC ACC TAT GGA ATT GTC CTG CTT TCT GGA GTG AAG
Leu Glu Trp Glu Asp Thr Tyr Gly Ile Val Leu Leu Ser Gly Val Lys>

180                                  190
TAT AAG AAG GGT GGC CTT GTG ATC AAT GAA ACT GGG CTG TAC TTT GTA
Tyr Lys Lys Gly Gly Leu Val Ile Asn Glu Thr Gly Leu Tyr Phe Val>

200
TAT TCC AAA GTA TAC TTC CGG GGT CAA TCT TGC AAC AAC CTG CCC CTG
Tyr Ser Lys Val Tyr Phe Arg Gly Gln Ser Cys Asn Asn Leu Pro Leu>

210                               220
AGC CAC AAG GTC TAC ATG AGG AAC TCT AAG TAT CCC CAG GAT CTG GTG
Ser His Lys Val Tyr Met Arg Asn Ser Lys Tyr Pro Gln Asp Leu Val>

230
ATG ATG GAG GGG AAG ATG ATG AGC TAC TGC ACT ACT GGG CAG ATG TGG
Met Met Glu Gly Lys Met Met Ser Tyr Cys Thr Thr Gly Gln Met Trp>

240                                  250
GCC CGC AGC AGC TAC CTG GGG GCA GTG TTC AAT CTT ACC AGT GCT GAT
Ala Arg Ser Ser Tyr Leu Gly Ala Val Phe Asn Leu Thr Ser Ala Asp>

260                                  270
CAT TTA TAT GTC AAC GTA TCT GAG CTC TCT CTG GTC AAT TTT GAG GAA
His Leu Tyr Val Asn Val Ser Glu Leu Ser Leu Val Asn Phe Glu Glu>

280
TCT CAG ACG TTT TTC GGC TTA TAT AAG CTC TAA GAGAAGCACTTTGGGAT
Ser Gln Thr Phe Phe Gly Leu Tyr Lys Leu ***>
```

Fig. 19

| mutated amino acids | NOK1 | NOK2 | NOK3 | RNOK201 | RNOK202 | RNOK203 |
|---|---|---|---|---|---|---|
| B1 | N.D | N.D | N.D | N.D | N.D | N.D |
| B2 | N.D | N.D | N.D | N.D | N.D | N.D |
| B3 | 0.876 | 0.000 | 0.590 | 0.254 | 0.208 | 0.204 |
| B4 | 0.147 | 0.035 | 0.000 | 0.116 | 0.194 | 0.097 |
| B5 | >1.000 | >1.000 | 0.000 | 0.999 | >1.000 | >1.000 |
| B6 | >1.000 | >1.000 | >1.000 | >1.000 | >1.000 | >1.000 |
| B7 | N.D | N.D | N.D | N.D | N.D | N.D |
| B8 | 0.000 | >1.000 | 0.000 | >1.000 | >1.000 | >1.000 |
| B9 | N.D | N.D | N.D | N.D | N.D | N.D |
| B10 | 0.107 | 0.174 | 0.000 | 0.157 | 0.069 | 0.100 |
| B11 | N.D | N.D | N.D | N.D | N.D | N.D |
| B12 | N.D | N.D | N.D | N.D | N.D | N.D |
| B13 | >1.000 | >1.000 | >1.000 | >1.000 | >1.000 | >1.000 |
| B14 | N.D | N.D | N.D | N.D | N.D | N.D |
| B15 | >1.000 | >1.000 | >1.000 | >1.000 | >1.000 | >1.000 |
| B16 | N.D | N.D | N.D | N.D | N.D | N.D |
| B17 | 0.652 | 0.781 | 0.350 | 0.704 | 0.772 | 0.697 |
| B18 | >1.000 | >1.000 | 0.802 | >1.000 | >1.000 | >1.000 |
| B19 | 0.793 | >1.000 | 0.604 | >1.000 | 0.816 | >1.000 |
| B20 | 0.758 | >1.000 | >1.000 | >1.000 | >1.000 | >1.000 |
| B21 | 0.638 | 0.809 | 0.585 | 0.838 | 0.748 | 0.885 |
| B22 | >1.000 | >1.000 | >1.000 | >1.000 | >1.000 | >1.000 |

Fig. 20

| mutated amino acids | NOK1 | NOK2 | NOK3 | RNOK201 | RNOK202 | RNOK203 |
|---|---|---|---|---|---|---|
| B23 | 0.379 | 0.613 | 0.602 | 0.673 | 0.721 | 0.558 |
| B24 | 0.713 | 0.968 | >1.000 | 0.903 | 0.923 | 0.768 |
| B25 | 0.028 | 0.085 | 0.000 | 0.082 | 0.121 | 0.068 |
| B26 | 0.145 | 0.218 | 0.266 | 0.213 | 0.312 | 0.175 |
| B27 | 0.439 | 0.508 | 0.311 | 0.524 | 0.455 | 0.411 |
| B28 | 0.817 | >1.000 | >1.000 | >1.000 | >1.000 | 0.842 |
| B29 | N.D | N.D | N.D | N.D | N.D | N.D |
| B30 | N.D | N.D | N.D | N.D | N.D | N.D |
| B31 | >1.000 | >1.000 | >1.000 | >1.000 | >1.000 | >1.000 |
| B32 | 0.406 | 0.686 | 0.885 | 0.924 | >1.000 | 0.589 |
| B33 | 0.250 | 0.861 | 0.083 | 0.402 | 0.335 | 0.290 |
| B34 | >1.000 | >1.000 | 0.576 | >1.000 | 0.882 | 0.721 |
| B35 | 0.964 | 0.370 | 0.000 | 0.138 | 0.132 | 0.128 |
| B36 | N.D | N.D | N.D | N.D | N.D | N.D |
| B37 | N.D | N.D | N.D | N.D | N.D | N.D |
| B38 | N.D | N.D | N.D | N.D | N.D | N.D |
| B39 | 0.851 | >1.000 | 0.606 | 0.928 | 0.865 | 0.708 |
| B40 | 0.800 | 0.862 | 0.723 | 0.888 | 0.812 | 0.823 |
| B41 | N.D | N.D | N.D | N.D | N.D | N.D |
| B42 | 0.247 | 0.445 | 0.091 | 0.539 | 0.388 | 0.379 |
| B43 | 0.840 | 0.000 | 0.080 | 0.000 | 0.000 | 0.000 |
| B44 | N.D | N.D | N.D | N.D | N.D | N.D |
| B45 | N.D | N.D | N.D | N.D | N.D | N.D |

Fig. 21

```
FAS-L(Nagata)  103:QLFHLQKELAELRESTSQMHTASSLEKQIGHPSPPPEKKELRKVAHLTGKSNSRSMPLEW 162
FAS-L(Model)     1:                                      RKVAHLTGKSNSRSMPLEW  19
1TNF             6:                              RTPSDKPVAHVVANPQAEG-QLQW  28
1TNR_a          28:                                   KPAAHLIGDPSKQN-SLLW  45

FAS-L(Nagata)  163:EDTYGIVLL--SGVKYKKGGLVINETGLYFVYSKVYFRGQS------CNN--LPLSHKVYMRNSKY 218
FAS-L(Model)    20:EDTYGIVLL--SGVKYKKGGLVINETGLYFVYSKVYFRGQS------CNN--LPLSHKVYMRNSKY  75
1TNF            29:LNRRANALLANGVELRDNQLVVPSEGLYLIYSQVLFKGQG------CPSTHVLLTHTISRIAVSY  87
1TNR_a          46:RANTDRAFLQDGFSLSNNSLLVPTSGIYFVYSQVVFSGKAYSPKATSSPLYLAHEVQLFSSQY  108

FAS-L(Nagata)  219:PQDLVMMEGKMMSYCTTGQ------------MWARSSYLGAVFNLTSADHLYVNVSELSLVNFEES-- 272
FAS-L(Model)    76:PQDLVMMEGKMMSYCTTGQ------------MWARSSYLGAVFNLTSADHLYVNVSELSLVNFEES-- 129
1TNF            88:QTKVNLLSAIK-SPCQRETPEGAEAKPWYEPIYLGGVFQLEKGDRLSAEINRPDYLDFAESG       148
1TNR_a         109:PFHVPLLSSQKMVYPGLQE----------PWLHSMYHGAAFQLTQGDQLSTHTDGIPHLVLSPS---  162

FAS-L(Nagata)  273:QTFFGLYKL 281
FAS-L(Model)   130:QTFFGLYKL 138
1TNF           149:QVYFGIIAL 157
1TNR_a         163:TVFFGAFAL 171
```

Fig. 25

```
                10         20         30         40         50         60
NOK2H   QVHLQQSGAE LVRPGTSVKM SCKAAGYTFT NYWIGWVKQR PGHGLEWIGY LYPGGLYTNY
1FOR_H  QGQLQQSGAE LVRPGSSVKI SCKASGYAFS SFWVNWVKQR PGQGLEWIGQ IYPGDGDNKY 70         80         90        100        110        120
NOK2H   NEKFKGKATL TADTSSSTAY MQLSSLTSED SAIYYCARYR DYDYAMDYWG QGTSVTVSSA
1FOR_H  NGKFKGKATL TADKSSTTAY MQLYSLTSED SAVYFCARSG NYPYAMDYWG QGTSVTVSSA 130        140        150        160        170        180
NOK2H   KTTAPSVYPL APVCGGTTGS SVTLGCLVKG YFPEPVTLTW NSGSLSSGVH TFPAVLQSGL
1FOR_H  KTTAPSVYPL APVCGGTTGS SVTLGCLVKG YFPEPVTLTW NSGSLSSGVH TFPAVLQSGL 190        200        210
NOK2H   YTLSSSVTVT SSTWPSQTIT CNVAHPASST KVDKKIEPR
1FOR_H  YTLSSSVTVT SSTWPSQTIT CNVAHPASST KVDKKIEPR
```

Fig. 26

```
                 10         20         30         40         50         60
NOK2L    DVVLTQTPLS LPVNIGDQAS ISCKSTKSLL NSDGFTYLGW CLQKPGQSPQ LLIYLVSNRF
1TET_L   DVLMTQTPLS LPVSLGDQAS ISCKSSQSIV HSSGNTYFEW YLQKPGQSPK LLIYKVSNRF 70         80         90        100        110        120
NOK2L    SGVPDRFSGS GSGTDFTLKI SRVEAEDLGV YYCFQSNYLP LTFGSGTKLE IKRADAAPTV
1TET_L   SGVPDRFSGS GSGTDFTLKI SRVEAEDLGV YYCFQGSHIP FTFGSGTKLE IKRADAAPTV 130        140        150        160        170        180
NOK2L    SIFPPSSEQL TSGGASVVCF LNNFYPKDIN VKWKIDGSER QNGVLNSWTD QDSKDSTYSM
1TET_L   SIFPPSSEQL TSGGASVVCF LNNFYPKDIN VKWKIDGSER QNGVLNSWTD QDSKDSTYSM 190        200        210
NOK2L    SSTLTLTKDE YEWHNSYTCE ATHKTSTSPI VKSFNR
1TET_L   SSTLTLTKDE YEWHNSYTCE ATHKTSTSPI VKSFNR
```

HUMANIZED IMMUNOGLOBULIN REACTING SPECIFICALLY WITH FAS LIGAND OR ACTIVE FRAGMENTS THEREOF AND REGION INDUCING APOPTOSIS ORIGINATING IN FAS LIGAND

CONTINUATION INFORMATION

This application claims the benefit of Japanese application No. 8/231742 filed on Sep. 2, 1996 and Japanese Application No. 8/271546 filed on Sep. 20, 1996 which are incorporated herein by reference.

FIELD OF THE INVENTION

This invention relates to novel humanized immunoglobulins, and is based on information about a site on Fas ligand which is important to suppress apoptosis which is induced in Fas-expressing cells through the Fas-Fas ligand interaction. Specifically, the invention relates to humanized immunoglobulins or active fragments thereof which are specifically reactive to Fas ligand. Said immunoglobulins and said site are useful in clinical applications to diseases which are provoked by apoptosis induced by the physiological reactions between Fas antigen and Fas ligand, and for example, are useful in elucidation of Fas system in cell death, in immunological therapy and diagnosis, in detection for Fas ligand, or in the related industrial fields.

PRIOR ART

The homeostasis of multicellular organisms is maintained by the growth and death of cells, which are delicately controlled. During the processes of ontogeny, a large number of cells are eliminated through cell death. Organs in adults also maintain their functions by continuously keeping the balance of the growth and death of the organ-constituted cells. Such cell death is referred to as "programmed cell death", which is a predetermined death, and is discriminated from accidental cell death [Raff, M. C., Nature, vol. 356, p.397–400, 1992].

These two cell deaths are different from each other in process. It has been understood that the programmed cell death is caused by apoptosis process whereas the accidental cell death is caused by necrosis process resulting in cell death [Kerr, J. F., Brit. J. Cancer, vol. 26, p.239–257, 1972].

Fas antigen is a cell surface protein which mediates the programmed cell death, apoptosis, and the cDNA of the antigen has been cloned [Nagata, et al., Cell, vol. 66, p.223–243, 1991]. The structure of the resulting cDNA has revealed that human Fas antigen is a transmembrane type protein which consists of 319 amino acid residues containing one transmembrane domain. The extracellular domain of Fas antigen consists of 157 amino acid residues and is rich in cysteine residues. Mouse Fas antigen consists of 306 amino acid residues, and shows 49.3% homology to human Fas antigen.

The structure of the extracellular domain in Fas antigen which is cysteine-rich has been demonstrated to be a well conservative structure also found in low-affinity receptors for nerve growth factor (NGF) and receptors of tumor necrosis factor (TNF), showing that Fas antigen is a cell surface protein which belongs to a family of NGF/TNF receptor. In 1993, a group of Dr. Nagata, Shigekazu and his coworkers identified the ligand molecule of rat Fas antigen [Nagata, et al., Cell, vol. 75, p.1169–1178, 1993], which had been expected to exist within the living body in the light of the fact that most proteins of this family co-exsit with their ligands in body. Subsequently, the same group identified the molecules of mouse and human Fas ligands [Nagata, et al., Int. Immunol., vol.6, No. 10, p.1567–1574, 19941.

Dr. Nagata et al. showed that Fas ligand is a protein consisting of 278 amino acids with a molecular weight of 31,138, and that it contains four N-glycosidic linkage sites and thus is a glycoprotein [Nagata, et al., Cellular Engineering, vol.13 No. 8, p.738–744, 19941]. Further, it has been shown that a soluble Fas ligand molecule induces apoptosis in target cells expressing Fas antigen on their cell surfaces (Nagata, et al., J. Exp. Med., vol. 179, p.873–879, 1994].

Hanabuchi et al. reported that the analysis on mechanism for the cytotoxicity of target cells by killer T cells via Fas antigen reveals that transmission of apoptosis signals via Fas antigen on the target cells may be responsible for the cytotoxicity of the target cells by CD4-positive T cells (CTLs) which does not express perforin, and thereby it was revealed that Fas ligand exists on the cell surface of CD4-positive CTLs [Hanabuchi, et al., Proc. Natl. Acad. Sci. USA, vol.91, No. 11, p.4930–4934, 1994].

As described above, Fas antigen appears to transmit a signal causing "death" to cells, and it has been shown that the inactivation of the proteins mediating apoptosis such as Fas antigen and Fas ligand causes the overgrowth of cells, while, on the contrary, the extraordinary activation of such proteins causes a certain inflammatory reaction.

For example, it has been reported that there is a mutation in the Fas gene of a mice which has lpr (lymphoproliferation) mutation causing an autoimmune disease-like symptom, whereas there is a mutation in Fas ligand itself of a mice which has gld (generalized lymphoproliferative disease) mutation also causing an autoimmune disease-like symptom [Nagata, et al., Cell, vol. 76, p.969–979, 1994].

Further, recent investigations have shown that the physiological reactions between Fas antigen and Fas ligand may cause various diseases.

For example, it has been reported that tat protein derived from HIV, the AIDS-causative virus, expedites the expression of Fas ligand to induce apoptosis of the T cells expressing Fas antigen, via the interaction of Fas-Fas ligand [Westerndrop, M., et al., Nature, vol. 375, p.497–500, 1995], and the expression of Fas on HIV-infected T cells has been actually found [Kobayashi, et al., Proc. Natl. Acad. Sci. USA, vol. 87, p.9620–9624, 1990]. These reports show that apoptosis induced by the interaction of Fas-Fas ligand may be one of the mechanisms of elimination of CD4-positive T cells in AIDS. Further, there are reports, each of which shows that the mice to which anti-Fas antibody (Jo-2) has been administered intra-abdominally develop fulminant hepatitis to lead death [Ogasawara, et al., Nature, vol. 364, p.806–809, 1993], that the Fas expression is observed in viral hepatitis [Hiramatsu, et al., Hepatology, vol. 19, p. 1354–1359, 1994], and that the Fas expression is also observed in diabetes mellitus and autoimmune diseases such as systemic lupus erythematosus (SLE) and rheumatoid arthritis (RA), and therefore, it is speculated that these diseases as mentioned above would be caused by Fas ligand, which is reactive to Fas antigen.

Under the circumstances, creation of agents exhibiting suppressive (inhibitory) activity against the binding between Fas and Fas ligand to lead to suppression of apoptosis will be extremely significant for advanced exploration of the above studies and in particular, treatment of diseases in a future clinical application.

The inventors of the present invention found the mouse monoclonal antibodies which are specifically reactive to Fas ligand to suppress (inhibit) the physiological reactions between Fas and Fas ligand, and filed a patent application therefor (the Japanese Patent Application No. 303492/1995). abandoned, and to which priority is claimed by PCT Application No. WO96/29350. It has been believed that since the monoclonal antibodies bind to Fas ligand more strongly than Fas, the antibodies may inhibit the physiological reactions of Fas-Fas ligand in vivo.

It is natural that such highly active monoclonal antibodies are desirable in clinical application, but, unfortunately, non-human immunoglobulins such as the aforementioned mouse monoclonal antibodies suffer disadvantages in application to human, which are provided below. The non-human immunoglobulins show the relatively shorter half life in vivo, and require more frequent administrations to maintain the predetermined level in blood compared to human antibody. It should be noted that the non-human immunoglobulins contain an amino acid sequence which may exert antigenicity on the administration to human. Thus, in the case of frequent administration of the non-human immunoglobulins to human, an immune response elicited by the administration eliminates the immunoglobulins administered at the later stages, and ultimately may cause anaphylaxis-like shocks.

In order to resolve the above problems, so called chimeric antibody, an immunoglobulin having a constant region from human immunoglobulin combined to a variable region from mouse immunoglobulin has been created [LoBuglio, et al., Proc. Natl. Acad. Sci. USA, vol. 86, p.4220–4224, 1989]. This described that the half life of the chimeric antibody in human was prolonged six times compared to the mouse antibody, but the period is still only about ⅓ of that of the common human immunoglobulin. Also, the article reported that the immune response to the chimeric antibody was observed in one of three patients receiving the chimeric antibody. This immune response was believed to be derived from the variable region from the mouse immunoglobulin since the response could be absorbed when anti-mouse immunoglobulins were reacted with the chimeric antibody.

To resolve the problem which could not be overcome by the chimera technique with human immunoglobulin, Winter, et al. reported the process for constructing humanized immunoglobulin which is more analogous to the human immunoglobulin than the chimeric antibody, which comprises transplanting the complementarity determining region (hereinafter may be referred to as CDR) directly binding to an antigen, which is within the variable region (V region), into the CDR in the variable region of human immunoglobulin according to genetic engineering techniques [Winter, et al., Nature, vol. 321, p.522–525, 1986].

As reviewed in Bendig, A Companion to Methods in Enzymology, vol. 8, p.83–93, 1995, diverse humanized immunoglobulins have been previously prepared by procedures as mentioned above. However, compared to the original mouse immunoglobulins, which are donors of the CDR, most of humanized immunoglobulins involve significant decrease in their activity, and several maintain the same activity, above all, very few show the higher activity. Needless to say, no reports describe any preparation of a humanized immunoglobulin directed to Fas ligand according to the present invention.

The recent investigation has reported a putative three-dimensional structure of mouse Fas ligand [Manuel C. P., et al., Molecular Immunology, vol. 32 (10), p.761–772, 1996]. In this report, the authors believed that mouse Fas ligand should form a trimer structure to exhibit its biological activity similarly to TNF-α and TNF-β (hereinafter referred together to as TNF, simply), and, making reference to the structure of TNF trimer and the interaction site between TNF and TNF receptor, they predicted a interaction site between mouse Fas ligand monomers, and a interaction site between mouse Fas ligand and Fas antigen, after preparation of a trimer model for mouse Fas ligand. However, this prediction has not been supported therein any more.

On the other hand, any putative three-dimensional structure model for human Fas ligand as shown in the above literature has not been reported, and there have been no reports that show the interaction site between the Fas ligand monomers and the interaction site of the Fas-Fas ligand. Under the circumstances, it has been still unknown which regions in Fas ligand or Fas should be targeted to suppress (or inhibit) apoptosis induced by the physiological reactions of Fas-Fas ligand.

The decrease in the activity of humanized immunoglobulin compared to the original mouse immunoglobulin is believed to be mainly due to less antigen-binding activity induced by structural change in the CDR to be transplanted, which change is on the basis of the difference in stereochemical structure of the framework region between mouse immunoglobulin as CDR donor and human immunoglobulin as CDR acceptor. In order to avoid such decrease in the activity, any modification is required in the process for humanization of an antibody by CDR transplantation.

The monoclonal antibodies specifically reactive to Fas ligand which are encompassed within the scope of the invention of the Japanese Patent Application No. 303492/1995, have the useful activity to suppress (or inhibit) the physiological reactions between Fas and Fas ligand. However, the antibodies are a mouse monoclonal antibody, and therefore, cannot be practically applied to the clinical field of human in the light of the safety (induction of antigenicity) and the efficacy (shortening of half life).

DISCLOSURE OF THE INVENTION

As a major embodiment, the present invention provides humanized immunoglobulins or active fragments thereof which are specifically reactive to Fas ligand, and in particular, provides humanized immunoglobulins which are specifically reactive to Fas ligand to be able to suppress (or inhibit) the physiological reactions between Fas and Fas ligand.

So far, the interaction site between human Fas and Fas ligand has not been shown, and a modelling or a crystal structure analysis for the Fas-Fas ligand complex has not been performed, and therefore, it has been impossible to identify a site to effectively suppress (or inhibit) apoptosis induced by the physiological reactions of Fas-Fas ligand.

As another embodiment, the present invention demonstrates for the first time a site on human Fas ligand associated with apoptosis-suppressing activity, by means of examining the reactivities of diverse Fas ligand molecules introduced with an amino acid substitution (Fas ligand variants) with diverse anti-Fas ligand monoclonal antibodies having the high apoptosis-suppressing activity, constructing a molecular model for the human Fas ligand trimer, and further confirming the distribution of the site identified in the above experiment within the human Fas ligand trimer.

BRIEF DESCRIPTION OF DRAWINGS

FIG. 1 depicts the nucleic acid and amino acid sequence of the variable region of the heavy chain of NOK2 antibody (SEQ ID NO: 142 and SEQ ID NO: 143), wherein the underlined portions represent primers used in the cloning (SEQ ID NO: 141 and 144).

FIG. 2 depicts the nucleic acid and amino acid sequences of the variable region of the light chain of NOK2 antibody (SEQ ID NO: 146 and SEQ ID NO: 147), wherein the underlined portions represent primers used in the cloning (SEQ ID NO: 145 and SEQ ID NO: 148).

FIG. 3 depicts (a) the expression plasmid for the heavy chain of chimeric NOK2 antibody, and (b) the expression plasmid for the light chain of chimeric NOK2 antibody.

FIG. 5 depicts the amino acid sequences of the variable regions of the heavy chains of NOK2 antibody (SEQ ID NO: 149), SGI antibody (SEQ ID NO: 150), and humanized NOK2 (RNOK2) immunoglobulins (RNOK2VHver11 (SEQ ID NO: 151) and RNOK2VHver12 (SEQ ID NO: 152)).

FIG. 6 depicts the amino acid sequences of the variable regions of the light chains of NOK2 antibody (SEQ ID NO: 153), REI antibody (SEQ ID NO: 160), huVL19 (SEQ ID NO: 155) and huVL31 (SEQ ID NO: 154) immunoglobulins from human, and RNOK2 immunoglobulins (RNOK2VLver1 (SEQ ID NO: 161), RNOK2VLver21 (SEQ ID NO: 156), RNOK2VLver22 (SEQ ID NO: 157), RNOK2VLver23 (SEQ ID NO: 158) and RNOK2VLver24 (SEQ ID NO: 159)).

FIG. 7 depicts the amino acid sequences of the variable regions of the light chains of NOK2 antibody (SEQ ID NO: 153), REI antibody (SEQ ID NO: 160), huVL19 (SEQ ID NO: 155) and huVL31 (SEQ ID NO: 154) immunoglobulins from human, and RNOK2 immunoglobulins (RNOK2VLver1 (SEQ ID NO: 161), RNOK2VLver21 (SEQ ID NO: 156), RNOK2VLver22 (SEQ ID NO: 157), RNOK2VLver23 (SEQ ID NO: 158) and RNOK2VLver24 (SEQ ID NO: 159)) continued from FIG. 6.

FIG. 8 illustrates the annealing of primers (#01 (SEQ ID NO: 162), #02 (SEQ ID NO: 163) and #03 (SEQ ID NO: 164)) with a template wherein the primers are used in preparation of the genes of the variable regions of the heavy chains of RNOK2 immunoglobulins (RNOK2VHver11 and RNOK2VHver12), and the template is the variable region of the heavy chain of RC25 immunoglobulin.

FIG. 9 illustrates the annealing of primers (#02 (SEQ ID NO: 163), #03 (SEQ ID NO: 164) and #04 (SEQ ID NO: 165)) with a template wherein the primers are used in preparation of the genes of the variable regions of the heavy chains of RNOK2 immunoglobulins (RNOK2VHver11 and RNOK2VHver12), and the template is the variable region of the heavy chain of RC25 immunoglobulin.

FIG. 10 illustrates the annealing of primers (#05 (SEQ ID NO: 166), #06 (SEQ ID NO: 167) and #07 (SEQ ID NO: 168)) with a template wherein the primers are used in the preparation of the gene of the variable region of the light chain of RNOK2 immunoglobulin (RNOK2VLver1), and the template is the light chain of NOK2 antibody.

FIG. 11 illustrates the annealing of primers (#08 (SEQ ID NO: 169), #09 (SEQ ID NO: 170) and #10 (SEQ ID NO: 171)) with a template wherein the primers are used in the preparation of the gene of the variable region of the light chain of RNOK2 immunoglobulin (RNOK2VLver1), and the template is the light chain of NOK2 antibody.

FIG. 12 illustrates the annealing of a primer (#11 (SEQ ID NO: 172)) with a template wherein the primer is used in preparation of the genes of the variable regions of the light chains of RNOK2 immunoglobulins (RNOK2VLver21, RNOK2VLver22, RNOK2VLver23 and RNOK2VLver24), and the template is the light chain of NOK2 antibody.

FIG. 13 illustrates the annealing of a primer (#12 (SEQ ID NO: 173)) with a template wherein the primer is used in preparation of the genes of the variable regions of the light chains of RNOK2 immunoglobulins (RNOK2VLver21, RNOK2VLver22, RNOK2VLver23 and RNOK2VLver24), and the template is the light chain of NOK2 antibody.

FIG. 16 depicts parts of the nucleic acid sequence (upper line) (SEQ ID NO: 174) and amino acid sequence (lower line) (SEQ ID NO: 175) of Fas ligand. Numerical order of the amino acid is in accordance with Nagata, et al. Int. Immunology, vol. 6, p.1567–1574, 1994.

FIG. 19 shows the relative ability of NOK and humanized NOK2 antibodies to recognize each of the Fas ligand variants. N.D. means "not done".

FIG. 20 shows the relative ability of NOK and humanized NOK2 antibodies to recognize each of the Fas ligand variants. N.D. means "not done".

FIG. 21 depicts the alignment of the amino acid sequence of Fas ligand with that of TNF-α and -β. The first line represents the amino acid sequence of the extracellular domain of human Fas ligand as shown in Nagata, et al., Int. Immunology, vol. 6, p.1567–1574, 1994 (SEQ ID NO: 176), the second line represents amino acid sequence of the region undergoing the modeling (SEQ ID NO: 177), and the third and fourth lines represent amino acid sequences of TNF-α (1TNF) (SEQ ID NO: 178) and TNF-β (1TNR) (SEQ ID NO: 179), respectively.

FIG. 25 depicts that alignment of the VH region of NOK2 antibody (SEQ ID NO: 180) with that of 1FOR antibody (SEQ ID NO: 181). The constant region which resides downstream of the VH region is from 1FOR antibody.

FIG. 26 depicts the alignment of the VL region of NOK2 antibody (SEQ ID NO: 182) with that of 1TET antibody (SEQ ID NO: 183). The constant region which resides downstream of the VL region is from 1TET antibody.

In FIG. 32, the upper represents the Fas ligand trimer, the lower represents the Fab portion of NOK2 antibody, and the intermediate represents the complementarity determining region (CDR) of NOK2 antibody. The size of the CDR of NOK2 antibody as shown in FIG. 33 is nearly equal to the circle of about 17 Å radius.

BEST MODE FOR CARRYING OUT THE INVENTION

Figure 4:
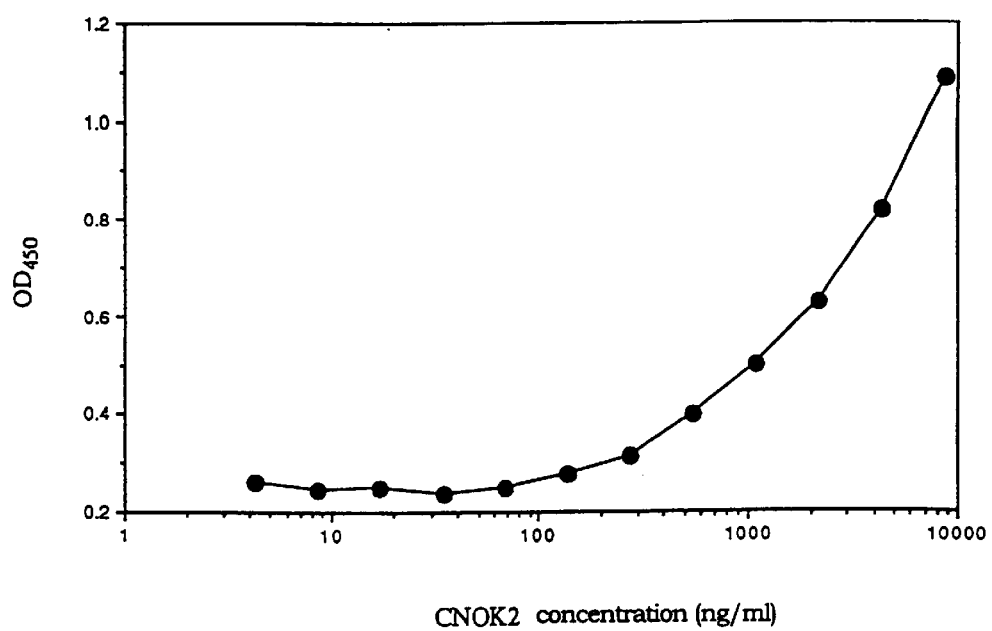
FIG. 4 shows the result of ELISA for assaying the ability of chimeric NOK2 antibody to recognize Fas ligand.

Practical usage of the mouse monoclonal antibodies which are specifically reactive to Fas ligand, within the invention of the Japanese Patent Application No. 303492/1995 requires to convert them into a human-like immunoglobulin which both retains the property to suppress (inhibit) the physiological reactions between Fas and Fas ligand by specifically reacting with Fas, and does not induce antigenicity in human body. The possible method therefor includes alteration of the mouse immunoglobulin to form the human immunoglobulin by genetic engineering techniques as detailed in, for example, Winter, et al., Nature, vol. 321, p.522–525, 1986. Many humanized antibodies prepared according to such method as this, however, decrease significantly in their activity compared to the original mouse antibody, a donor for CDR, as described above and therefore, there have been a demand for an improved method on the basis of CDR implantation to prepare the humanized antibody retaining the high activity.

Previously, it has been suggested that the amino acids within a framework region (FR) (hereinafter may be referred to as FR amino acids) would reside near the CDR in terms of either primary structure or stereochemistry, which are responsible for maintaining the stereochemical structure of CDR leading to retaining the activity of immunoglobulin, in the reports such as Winter, et al., Nature, vol.332, p.323–327, 1988 as to humanization of mouse immunoglobulin, and Chothia, et al., J. Mol. Biol, vol. 196, p.901–917, 1987 as to the stereochemical structure of immunoglobulin CDR.

In humanization of the monoclonal antibody specifically reactive to Fas ligand according to the present invention, the FR amino acids which are selected using the computer modelling together with the CDR were transplanted into a recipient human antibody on the basis of the above information, so that the humanized antibody having the activity equal to or above the original mouse antibody successfully have been prepared.

First, computer modelling of antibody was performed to predict significant amino acids in the FR which are responsible for maintaining the stereochemical structure of the CDR leading to retaining the activity of antibody. For example, QUANTA/CHARMm or Modeler which is a software for molecular design starting on Silicongraphics (both are produced by Molecular Simulations Inc.) can be used for the computer modelling. On the basis of the data for the three-dimensional structure of antibody constructed using such software, the FR amino acids which are responsible for maintaining the stereochemical structure of CDR are selected. Specifically, the amino acids which form hydrogen bond or undergo energy contact directly or indirectly to any CDR amino acid are selected using calculation program installed in the software. Amino acids to be transplanted together with the CDR are selected from these amino acids, provided that the amino acids should not lead to any amino acid sequences which are not found in human antibodies and may elicit antigenicity in human body in the course of transplantation.

The relationship in each amino acid in the variable regions between mouse and human antibodies is readily understood from the classification of Kabat, et al., Sequence of Proteins of Immunological Interest, 4th ed., Public Health Service, NIH, Washington D.C., 1987, which is a standard in the art.

In accordance with the above procedures, the present invention has been accomplished. Thus, the invention provides humanized immunoglobulins which can be specifically reactive to Fas ligand to suppress (inhibit) the physiological reactions between Fas and Fas ligand without inducing antigenicity in human, and which have the activity equal to or above the original mouse antibody.

Nowadays, the interaction site between human Fas and Fas ligand has not been shown, and a modelling or a crystal structure analysis for the Fas-Fas ligand complex has not been also performed, and therefore, it has been unknown which site in Fas ligand or Fas antibody should be blocked to effectively suppress (or inhibit) apoptosis induced by the physiological reactions of the Fas-Fas ligand.

Then, the recognition sites which are recognized by various anti-Fas ligand monoclonal antibodies having the high apoptosis-suppressing activity was examined in order to identify a site on human Fas ligand which is important to suppress (inhibit) apoptosis. Specifically, the inventors prepared diverse Fas ligand molecules incorporated with an amino acid substitution (i.e., Fas ligand variants), examined their reactivities to anti-Fas ligand monoclonal antibodies produced by the hybridomas, NOK1, NOK2, NOK3, and NOK4 as well as the humanized immunoglobulin of the present invention, and identified the site on the human Fas ligand molecules recognized by the above antibodies, so as to demonstrate the important site to suppress apoptosis; hereinafter the aforementioned anti-Fas ligand monoclonal antibodies may be referred to as NOK1, NOK2, NOK3, and NOK4 immunoglobulin (antibody), respectively; the aforementioned hybridomas have been deposited at the National Institute of Bioscience and Human Technology, Ministry of International Trade and Industry (1-1-3 Higashi, Tsukuba shi, Ibaraki) under Accession Nos. FERM BP-5044, FERM BP-5045, FERM BP-5046, and FERM BP-5047; and the antibodies generically may be referred to as NOK antibody.

FERM BP-5045 was deposited on Mar. 20, 1995, under the terms of the Budapest Treaty. Applicants have deposited NOK 2 with the National Institute of Bioscience and Human-Technology Agency of Industrial Science and Technology (NIBHTAIST), 1–3, Higashi 1 chome Tsukuba-shi Ibaraki-ken, 305 Japan. The NOK 2 samples deposited with the NIBHTAIST are taken from the same deposit maintained by Sumitomo Electric Industries, Ltd., 5–33, Kitahama 4-chome, Chuo-ku, Osaka-shi, Osaka 541 Japan since prior to the filing date of this application. The deposits of the NOK 2 samples will be maintained without restriction in the NIBHTAIST depository for a period of 30 years, or 5 years after the most recent request, or for the effective life of the patent, whichever is longer, and will be replaced if the deposit becomes non-viable during that period.

Further, the inventors constructed a human Fas ligand trimer model, and confirmed the distribution of the site identified as shown above within the human Fas ligand trimer, thereby demonstrating for the first time the site on the Fas ligand associated with apoptosis-inhibitory activity.

As described above, Fas ligand (hereinafter may be referred to as FasL) is a ligand for Fas antigen which is a cell surface protein which mediates programmed cell death (apoptosis), and Fas ligand has been identified from human, rat, and mouse, so far. The present invention may cover a general Fas ligand, and among them, Fas ligands from human and mouse are preferred. Thus, the invention preferably provides humanized immunoglobulins and active fragments thereof which are specifically reactive to a ligand for human Fas antigen or a ligand for mouse Fas antigen.

As used herein, "immunoglobulin" means a protein which consists of one or more polypeptides essentially encoded by a immunoglobulin gene. The immunoglobulin genes include the genes of a kappa, a lambda, an alpha, a gamma, a delta, an epsilon, and a mu constant regions and the gene of myriad immunoglobulin variable region. The immunoglobulin of the present invention also encompasses active fragments. The active fragments mean fragments of antibody having an antigen-antibody reaction activity, and include $F(ab')_2$, Fab', Fab, Fv, and recombinant Fv.

As used herein, "chimeric antibody" means an antibody derived from a gene which is combined by segments of the immunoglobulin genes wherein the light and heavy chain genes are derived from different species, typically according to genetic engineering techniques. For example, the segment of the variable region (hereinafter referred to as V region) gene from mouse monoclonal antibody may be combined with the segment of the human constant region (hereinafter referred to as C region) gene, e.g., γ1 or γ4. Accordingly, the typical chimeric antibody for therapeutic purpose includes a hybrid protein which composes of the V region or antigen-binding region from the mouse antibody and the C region or effector region from the human immunoglobulin, although any other mammalian species can be used.

As used herein, "framework region" means parts of the variable regions of the light and heavy chains of immunoglobulins, which is relatively conserved among various immunoglobulins within a single specie, or which is other than CDR. "Human framework region" is substantially the same (about 85% or above) as a frame work region of a naturally-occurring human immunoglobulin or the same as a common sequence among such immunoglobulins.

"Humanized immunoglobulin" means an immunoglobulin which contains the human framework and at least one CDR from non-human immunoglobulin, and of which the constant region is substantially identical, i.e., about 85–90% identical, preferably, at least 95% identical to that of the human immunoglobulin in terms of the amino acid sequence of the protein. Accordingly, all parts of the humanized immunoglobulin except the CDR may be substantially the same as the corresponding parts of one or more natural human immunoglobulins.

Humanized immunoglobulin possesses at least three possible advantages over mouse antibody from the standpoint of therapeutic application to human.

(1) Humanized immunoglobulin is compatible with other aspects of the immune system in human since the effector part thereof is from human, and for example it can cause more effective dissolution of the targeted cells by complement-dependent cytolysis (CDC) or antibody-dependent cell-mediated cytotoxicity (ADCC);

(2) Human immune system does not recognize the framework or the C region of humanized immunoglobulin, and therefore, the level of undesirable immune responses to humanized immunoglobulin is lower than mouse antibody in which the whole is xenogenic and the chimeric antibody in which the part is xenogenic; and (3) It has been reported that mouse antibody has the much shorter half life than common human antibodies when infused in human (Shaw, D R et al., J. Immnol., vol. 138, p.4534–4538, 1987). On the other hand, humanized immunoglobulin has the half life nearer to naturally-occurring human antibodies compared to mouse antibody, and therefore, can be expected to provide the lower dose and the lower frequency of the administration.

The humanized immunoglobulins of the present invention may be limitless as long as they are specifically reactive to Fas ligand, and those which can inhibit (suppress) the physiological reactions between Fas ligand and Fas are especially preferred. As used herein, an immunoglobulin which inhibits the physiological reactions means an immunoglobulin which can specifically bind to the binding site of Fas ligand to be bound to Fas so as to interfere with Fas ligand in binding to Fas under the circumstances that cells expressing Fas ligand or the solubilized Fas ligand (hereinafter may be referred to as sFas ligand or soluble Fas ligand) are bound to cells expressing Fas to afford signals causing death by apoptosis to the Fas-expressing cells. In other words, immunoglobulins which inhibit the physiological reactions between Fas ligand and Fas prevent the Fas ligand-expressing cells or sFas ligand from killing the Fas-expressing cells. Preferably, the immunoglobulins used in this situation are those having the higher ability to bind to Fas ligand than Fas. Specifically, the binding ability may be examined by using as an indicator a chimeric molecule comprising Fas combined by the Fc of IgG (hereinafter may be referred to as Fas-Ig). The Fas-Ig can bind to Fas ligand as strongly as Fas in body. Thus, when an immunoglobulin directed to Fas ligand can inhibit the binding between Fas ligand and Fas at the lower concentration than that by the Fas-Ig chimera molecule, then the immunoglobulin would be practically able to inhibit various actions in body caused by Fas ligand.

The humanized immunoglobulins of the present invention which are specifically reactive to human Fas ligand include, for example, RNOK201, RNOK202, and RNOK203 antibodies, which are obtained by humanizing NOK2 antibody, as a donor antibody, which is included in the invention of the Japanese Patent Application No. 303492/ 1995 and is produced by hybridoma NOK2, which has been deposited at the National Institute of Bioscience and Human Technology, Ministry of International Trade and Industry under Accession No. FERM BP-5045 (hereinafter, the antibodies humanized from NOK2 antibody may be referred to as humanized NOK2 antibody, humanized NOK2 immunoglobulin, RNOK2 antibody or RNOK2 immunoglobulin).

The following is presented by way of illustration of certain suitable embodiments of steps for humanization of NOK2 antibody, which should not be construed as limiting to this, but any antibodies leading to the humanized immunoglobulin which is specifically reactive to Fas ligand may be used.

First, the cloning of the gene of variable region (V region) from NOK2 antibody is necessary to convert NOK2 antibody into a molecule having the amino acid sequence of human immunoglobulin by genetic engineering techniques.

The V region gene may be cloned by conventional gene manipulation techniques. For example, the techniques include the cloning of the V region gene from chromosomal DNA of cells according to the conventional method such as T. Maniatis, Molecular Cloning Harbor Laboratories, 1982, and the cloning of the V region gene by preparing cDNA from mRNA in cells according to the conventional method such as D. M. Glover ed., DNA Cloning, vol. 1, IRL press, 1985.

In either method, DNA probes which are synthesized making reference to the nucleic acid sequence of the mouse immunoglobulin gene as previously reported such as Sakano et al., Nature, vol. 286, p.676, 1980 and E. E. Max et al., J. Biol. Chem. vol. 256, p.5116, 1981, may be utilized as probes for the cloning of the V region gene. Also, the cloning by polymerase chain reaction (PCR) can be utilized (R. Orlandi et al., Proc. Natl. Acad. Sci. USA, vol. 86, p.3883, 1989; W. D. Huse et al., Science, vol. 246, p.1275, 1989). According to these typical methods, the gene of the V region of NOK2 antibody may be cloned from the NOK2 antibody-producing hybridoma to determine the base sequence of the gene and the amino acid sequence corresponding thereto. See FIGS. 1 and 2.

The chimeric NOK2 antibody gene may be prepared by ligating the V region gene segment to the upstream of the constant region of human immunoglobulin. ELISA reveals that said chimeric NOK2 antibody binds to the Fas ligand molecule in a concentration-dependent manner, confirming that the gene of the variable region of immunoglobulin cloned by the present inventors should encode the anti-Fas ligand activity. See FIG. 4.

The gene of humanized NOK2 antibody, which is more closely related to human immunoglobulin than the chimeric antibody may be prepared according to the method of Winter et al., Nature, vol. 321, p.522–525, 1986 by transplanting the complementarity determining regions (CDR) which reside within the V region and directly bind to antigens into the CDR in the variable region of human immunoglobulin. Previously, it has been suggested that the amino acids within the framework (FR) (hereinafter may be referred to as FR amino acids) which are responsible for maintaining the stereochemical structure of the CDR and responsible for retaining the activity of immunoglobulin would reside near the CDR on either primary structure or stereochemistry, in the reports such as Winter, et al., Nature, vol. 332, p.323–327, 1988 as to re-shaping of mouse immunoglobulin, and Chothia, et al., J. Mol. Biol, vol. 196, p.901–917, 1987 as to the stereochemical structure of the immunoglobulin CDR. On the basis of these findings, the FR amino acids which have been suggested to be responsible for maintaining stereochemical structure of the CDR and responsible for retaining the activity of immunoglobulin are also transplanted together with the CDR. The FR amino acids to be transplanted are selected from those which are shown by the computer modelling of NOK2 antibody to interact directly or indirectly with the amino acids of the CDR (hereinafter may be referred to as CDR amino acids).

That is to say, first, the three-dimensional structure of NOK2 antibody may be estimated with the modelling using QUANTA/CHARMm or Modeler which is a software starting on Silicongraphics (both are produced by Molecular Simulations Inc.). For example, the QUANTA/CHARMm or Modeler, a software for molecular design, can be used according to the manufacture's instructions to estimate the structure of NOK2 antibody by utilizing as a template for the three-dimensional structure the variable region of the H chain (VH) of PDB ID:1FOR and the variable region of the L chain (VL) of PDB ID:1TET recorded on Brookhaven Protein Data Bank (PDB), which show the high homology to the VH and the VL of NOK2 antibody, although the used template is not limited to such variable regions of the antibody, and other data on the higher-order structure of an antibody which shows homology to the variable region of NOK2 antibody may be used if available. Further, not only QUANTA/CHARMm or Modeler, but also a software for the molecular design which is available for any other proteins as a whole may be used as a software.

Then, by using the installed program, the amino acids within the FR are selected which form the hydrogen bond to the CDR of the H and L chains in the above estimated three-dimensional structure of NOK2 antibody (the first group), and further, the amino acids within the FR which form the hydrogen bond to the resulting amino acids (the second group) are selected. Similarly, using the installed program, the amino acids within the FR are selected which form the energy contact to the CDR in the H and L chains of NOK2 antibody (the first group), and further, the amino acids within the FR which form the energy contact to the resulting amino acids (the second group) are selected. The energy contact herein includes so-called electrostatic interaction and van der Waals forces. The amino acids which are transplanted into the FR in the variable region of human immunoglobulin together with the CDR amino acids are selected from a group consisting of the first group and the second group as shown above. It should be noted that when the transplantation of any FR amino acids among the above FR amino acids into the relevant site in human immunoglobulin raises any sequences which can not be cited as the variable amino acid sequences of human immunoglobulin in the classification of Kabat, et al., Sequence of Proteins of Immunological Interest, 4th ed., Public Health Service, NIH, Washington D.C., 1987, and a software for information retrieval, Entrez (trademark), which has developed by and National Center for Biotechnology Information: NCBI, then such FR amino acids should not be transplanted. This reduces the possibility to elicit the antigenicity as much as possible when the humanized immunoglobulin is administered to human. With respect to the amino acid sequence of the CDR of NOK2 antibody, the sequences of the heavy chains CDR1, CDR2, and CDR3 are each described in SEQ ID Nos: 1, 2, and 3 in the sequence listing, and the sequences of the light chains CDR1, CDR2, and CDR3 are each described in SEQ ID Nos: 4, 5, and 6 in the sequence listing. The condition of the spans of FR and CDR herein is in accordance with the classification of Kabat, et al., as shown above.

It is preferred that the amino acid sequence of the variable region of human immunoglobulin which receives the transplantation has the high homology to those of the variable region of mouse immunoglobulin to be humanized. Empirically, it is desirable that the amino acid sequence of the framework region of the recipient human immunoglobulin has at least 60% homology to those of the framework region of the donor antibody (e.g. a mouse immunoglobulin). Usually, any human immunoglobulin having the high homology to the mouse immunoglobulin to be humanized is selected using the available database and utilized. The preferred embodiment of the invention involves transplantation of the CDR of NOK2 antibody into the variable region of human immunoglobulin. Specifically, the CDR in the VH region (the variable region of the heavy chain) of NOK2 antibody is transplanted into SGI (SEQ ID No. 7: distributed by Dr. Bendig of MRC Collaborative Center, United Kingdom), which is the VH region containing the FR (framework) region of human subgroup II. The CDR in the VL region (the variable region of the light chain) of NOK2 antibody is transplanted into REI as previously reported, which is the VL region containing the FR of the human κ chain (W. Palm et al., Physiol.Chem., vol. 356, p167, 1975), and into the VL region containing the FR of the κ chain cloned from the cDNA library derived from human peripheral blood lymphocytes (huVL-19: SEQ ID No. 8 and huVL-31: SEQ ID No. 9). Practical transplantation of the amino acids is performed at the genetic level by PCR mutagenesis whereby mutations are introduced by PCR using the VH gene of RC25 antibody, a humanized anti-HIV immunoglobulin (the International Publication No. WO94/20632) as a template for the VH, and using the VL gene of the chimeric NOK2 prepared as shown above as a template for the VL. For example, with respect to the genes of the H and L chains of humanized NOK2 antibody, two kinds of the H chain, and five kinds of the L chain, which combination affords 10 kinds of humanized NOK2 antibody, are prepared.

The immunoglobulins of the present invention which encompass the binding fragment and any other derivatives thereof may be readily prepared by various recombinant DNA techniques, and ultimately be expressed in the transfected cells, preferably the immortalized eucaryotic cells such as myeloma and the hybridoma. The polynucleotide which consists of a set of the first sequence encoding the framework of the humanized immunoglobulin and the second sequence encoding the complementarity determining region of the desired immunoglobulin is prepared synthetically or by the combination of the suitable cDNA and genomic DNA segments.

The genes which encodes the H and L chains for the construction of the humanized antibody and are prepared with the manner as described above are expressed in host cells after combining the sequence to an expression control sequence so as to work. The expression vectors are typically replicable in host cells as episome or a significant portion of the chromosomal DNA. The expression vectors usually contain selectable markers such as a gene for tetracycline resistance, G418 resistance or mycophenolic acid resistance, or HSV-tk, which permits to detect the cells into which the desired DNA sequence is transformed.

*Escherichia coli* is a prokaryotic host cell which is especially useful for the cloning of the DNA sequence of the present invention. Additionally, Bacilli such as *Bacillus subtilis*, and any other enterobacteria such as Salmonella, Serratia, and various Pseudomonas species may be used as host cells. The prokaryotic host cells may be used in the construction of expression vectors, which typically contain an expression control sequence which is suitable to the host cells. Also, the expression vectors may contain any number of diverse known promoters such as lactose-promoter system, tryptophan (trp)-promoter system, β-lactamase-promoter system or the promoter system from λ phage. Promoters regulate the expression, sometimes together with the operator sequence, and comprise the ribosome-binding site sequence, or the like, which permits to initiate and terminate the transcription and translation.

Other microorganisms such as yeast, for example, may be used as an eukaryotic host cell for the expression. Saccharomyces, which contain a suitable vector having an expression control sequence such as a promoter comprising a gene for 3-phosphoglycerate kinase or any other glycolytic enzymes, and a replication origin, a terminal sequence and a desired analogue, is a preferable host cell.

In the preparation of the humanized immunoglobulin of the present invention, insect cell cultures, typically the expression system on Baculoviridae also may be used. The humanized immunoglobulin also may be prepared by expressing the polynucleotide sequence encoding the humanized immunoglobulin according to the method reported in ZuPutlitz. J. et al., Bio/Technology, vol. 8, p.651–654, 1990.

In addition to the aforementioned host cells, mammalian cell cultures also may be used to express and prepare the humanized immunoglobulin of the present invention. For example, the preferable mammalian host includes CHO cell line, diverse COS cell lines, Hela cells, preferably myeloma cell line, or the transformed B cells or hybridoma, which are among many host cell lines which have been developed for secretion of whole immunoglobulin in the art. Expression vectors for these cells contain a expression control sequence such as a replication origin, a promoter, an enhancer and the necessary processing information site such as a ribosome-binding site, an RNA splicing site, a polyadenylation site, and a transcription terminator sequences. Preferable expression control sequences include an enhancer and a promoter which are derived from immunoglobulin gene, SV40, adenovirus, bovine papilloma virus, cytomegalovirus, chicken β-actin genes.

In the suitable embodiment of the invention, the genes prepared as described above encoding the H and L chains of humanized NOK2 antibody are each ligated into an expression vector which contains the gene of the constant region of human immunoglobulin (H chain: Cγ1, L chain: Cκ), the enhancer from cytomegalovirus, the promoter of chicken β-actin gene, splice acceptor site of rabbit β-globin gene, and a gene for a drug-resistant marker (H chain: neor, L chain: dhfr), and the resultant vector is introduced into a host cell by the well known methods involving any modifications depending on the type of host cell. For example, transfection with calcium chloride is usually applied to prokaryotic cells whereas the treatment by calcium phosphate, lipofection, biolysistics, transduction via virus, or electropolation are applied to any other cells.

Once the desired immunoglobulin is expressed, a whole immunoglobulin of the present invention, dimers thereof, individual light and heavy chains, or any other types of the immunoglobulin are purified according to a conventional method in the art. The method includes precipitation by ammonium sulfate, various ion-exchange chromatography, and affinity chromatography.

For the purpose of pharmaceuticals, the immunoglobulin is preferably substantially pure with at least about 90–95% homogeneity, and more preferably, 98–99% or above homogeneity.

The humanized immunoglobulin of the invention at a concentration of 0.06 µg/ml or above (i.e., effective concentration) can inhibit apoptosis of the Fas-expressing cells induced by the soluble Fas ligand, by 90% or above of apoptosis inhibition rate. The apoptosis inhibition rate herein means a viable rate of target cells to which the immunoglobulin was added in the cytotoxic reaction assay which comprises the steps of:

reacting both effector molecules which are the soluble Fas ligand prepared from the supernatant of culture of cells transfected with the Fas ligand gene, and target cells which are the cells transfected with the Fas gene, in a 100 µl reaction system on a 96-well plate; and 16 hours thereafter, determining the viable rate of the target cells by the usage of a reagent for counting vital cells.

In the case of the usage of either the aforementioned RNOK201, RNOK202 or RNOK203 as humanized immunoglobulins, the viable rate of the target cells, i.e., the apoptosis inhibition rate will be 90% or above, when the soluble Fas ligand contained in the supernatant of the cell culture transfected with the Fas ligand gene is used as an effector molecule whereas the cells transfected with the Fas gene (Fas/WR19L) are used as target cells, and 25 µl of the dilution of the effector molecule, 50 µl of $2 \times 10^5$ cells/ml liquid of the target cell, and 25 µl of the supernatant of the hybridoma culture containing any aforementioned immunoglobulin are all combined together, and the mixture is reacted at 37° C. for 17 hours.

Figure 15:
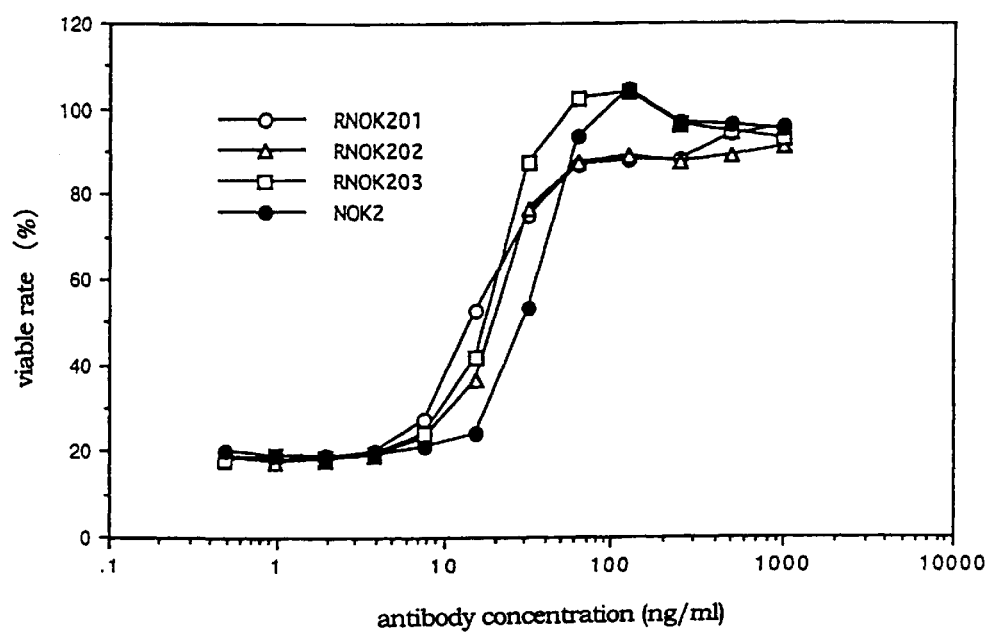
FIG. 15 shows the result of inhibitory activities of RNOK2 immunoglobulins and mouse NOK2 immunoglobulin against apoptosis mediated by Fas ligand and Fas.

The apoptosis inhibition rate of the humanized immunoglobulin of the invention is higher than the mouse immunoglobulin, which is the original donor antibody, at the same concentration as shown in FIG. 15. It is apparent that the humanized immunoglobulin of the present invention is a rare case of success, in the light of the fact that the humanized immunoglobulins previously reported have the greatly lowered activity compared to the original non-human immunoglobulins.

Further, the apoptosis-inhibitory activity of the present humanized immunoglobulin may be higher than the Fas-Ig chimeric molecule. This is because the mouse antibody, which is a donor antibody for the preparation of the humanized antibody of the present invention has been shown to exhibit the higher apoptosis-inhibitory activity at a concentration of 0.01–8 µg/ml (effective concentration) compared to the Fas-Ig chimeric molecule at the same concentration, as described in the PCT Application No. WO96/29350, therefore, it is apparent that the humanized antibody of the present invention, which has the higher apoptosis-inhibitory activity than the original mouse antibody exhibits the same or higher activity compared to the Fas-Ig chimeric molecule at a concentration of 0.01–8 µg/ml (i.e., effective concentration)

The humanized immunoglobulin of the present invention is not only useful for the immunological study but also for the immunological therapy and diagnosis. To accomplish these purposes, a whole immunoglobulin is not necessary, and a portion of the molecule can be used as long as the portion has the activity, which portion may be preferred in a certain case. This will be understood by those skilled in the art. Accordingly, the present invention encompasses the active fragments of the anti-Fas ligand immunoglobulins. Antibody is a homogeneous immunoglobulin which recognizes a specific antigenic substance. Active fragment means a fragment of the immunoglobulin showing the antigen-antibody reaction activity, and includes F(ab')2, Fab', Fab, Fv, and recombinant Fv. F(ab')2 fragment is a fragment which is obtained by the digestion of immunoglobulin, IgG, with pepsin. Digestion of IgG with pepsin at a pH of near 4.0 causes the cleavage of the H chains at the hinges thereof to provide the fragment with a molecular weight of about 100,000. The cleavage occurs down to the C-terminal from the disulfide bonds between the H chains. This fragment has two binding sites, and therefore can cause precipitation and aggregation reactions. Fab' fragment is a fragment with a molecular weight of about 50,000 which is obtained by the cleavage of the S—S bonds between the H chains by reducing F(ab')2 fragment with a reagent such as 2-mercaptoethanol and alkylating the reduced material with monoiodoacetic acid.

Fas fragment (antigen-binding fragment) is a fragment which is obtained by the digestion of IgG with papain. Digestion of IgG with papain in the presence of cysteine causes the cleavage of the H chains at the site toward the N-terminal from the disulfide bonds between the H chains at the hinge so as to provide two Fabs and one Fc (i.e., crystallizable fragment). Fab fragment is a fragment with a molecular weight of 45,000 wherein the Fd fragment corresponding to the half of the H chain at the N-terminal side (i.e. VH domain+CH1 domain) and the L chain are combined via disulfide bond. Fab fragment has one antigen-binding site. Fv fragment is an antigen-binding fragment which consists of the variable region of the H chain (VH) combined with the variable region of the L chain (LH) via non-covalent bond.

Recombinant Fv can be obtained by determining the base sequences encoding the VH and LH of the DNA from the immunoglobulin-producing hybridoma and then introducing the DNA fragments into a vector so as to prepare a monovalent active fragment of antibody having the structure: VL-linker-VH. The VH and the LH of IgG, Fab or F(ab')2 are combined together via S—S bond, whereas the recombinant Fv fragment has the linker inserted between the VH and LH to assume the stereochemistry similar to S—S bond. The latter fragment is also referred to as merely Fv, or scFv (single-chain Fv). The recombinant Fv also may be expressed in a microorganism such as *E. coli*, or bacteriophage.

The active fragments can be used alone, or if necessary, can be used as a new complex in which the fragments are conjugated with an agent such as albumin, and polyethylene glycol. In general, such complex often exert its effects to maximum capacity without decomposition for a prolonged period of time. The method for conjugating the active fragment with the agent such as albumin, and polyethylene glycol has been described in, for example, Antibodies, A. Laboratory Manual, Cold Spring Harbor Laboratories, 1988. Generally, divalent reactive reagents such as SPDP (Pharmasia) can be used to conjugate readily the active fragment with albumin or the like.

The immunoglobulin and the pharmaceutical composition thereof of the present invention are especially suitable for parenteral administration such as subcutaneous, intramuscular or intravenous administration, and are usually dissolved in an acceptable carrier, preferably in an aqueous carrier. For example, water, buffer, phosphate buffered saline (PBS), 0.4% physiological salt solution, 0.3% glycine, human albumin solution, or the like may be used as the aqueous carrier. The solutions are sterile, and generally contain no particulate. The composition is sterilized according to the conventional, well known methods for sterilization. If necessary, the composition may contain a pharmaceutically acceptable addictive, for example, a pH modulator and a buffering agent such as sodium acetate, sodium chloride, potassium chloride, calcium chloride, and sodium citrate for adapting to the physiological condition. The concentration of the immunoglobulin in the composition may be changed broadly, i.e., in the range from about 1 to 20% by weight, and is mainly determined on the basis of volume, viscosity and the like of the composition, depending on the choice of the type of administration.

The immunoglobulin of the present invention is frozen or lyophilized for storage, if necessary, and is reconstituted in a suitable dissoluble liquid prior to use.

Many Fas ligand variants in which an amino acid substitution is introduced into the amino acid sequence of Fas ligand can be used to identify the recognition site on Fas ligand which is bound to an anti-Fas ligand antibody. The inventors prepared 45 Fas ligand variants, each of which is introduced with one amino acid substitution into the region which is predicted to be recognized by NOK2 immunoglobulin, which may be referred to as NOK2 antibody, described in the PCT Application No. WO96/29350, said region encompassing 45 amino acids including 14 amino acids spanning Leu at position 207 to Gln at position 220 numbered from the N-terminus of Fas ligand, wherein the substitution is that the amino acids other than Ala are replaced by Ala, and Ala is replaced by Gly, and wherein the numerical order of amino acids is in accordance with Nagata, et al. Int. Immunology, vol. 6, p.1567–1574, 1994, unless otherwise indicated. Then, the Fas ligand variants were examined for the binding activity to the humanized NOK2 antibodies of the present invention as well as anti-Fas ligand antibodies (which represent NOK1 antibody, NOK2 antibody, NOK3 antibody, and NOK4 antibody, and generically may be referred to as NOK antibody) which have the high inhibitory activity to apoptosis occurred via the interaction of Fas-Fas ligand as described in the above application.

Consequently, it has been shown that the aforementioned NOK and humanized NOK2 antibodies can be bound to any position in the amino acid sequence included in the region spanning Arg at position 198 to Met at position 238 of Fas ligand. Further, with respect to NOK1, NOK2 and NOK4 antibodies, the mapping of the recognition site using the synthetic peptides revealed again that the aforementioned site of Fas ligand contains any amino acids which play an important role for NOK1, NOK2 and NOK4 antibodies to recognize and/or bind to the antigen.

The aforementioned NOK antibody is monoclonal antibodies which have been prepared by immunizing mouse with Fas ligand-expressing cell (see Example 1 at the detailed explanation of the invention in the specification of the PCT Application No. WO96/29350). Further, the aforementioned NOK antibody and humanized NOK2 antibody have the strong inhibitory activity to apoptosis induced in Fas-expressing cells by the interaction of Fas-Fas ligand (see Examples 1 and 2 at the detailed explanation of the invention in the specification of the Japanese Patent Application No. 303492/1995, and Example 4 at the detailed explanation of the invention in the specification of the present application). In other words, NOK antibody is the first anti-Fas ligand monoclonal antibodies which have been prepared by immunizing with Fas ligand having the native structure and which have the high inhibitory activity to apoptosis. These monoclonal antibodies are different from each other in terms of amino acid sequence of the CDR (i.e., complementarity determining region) and the class and subclass of antibody, and therefore, they are the independent antibodies from each other.

As described above, the site recognized by the different antibodies occupies a broad region which is composed of the amino acid sequence spanning Arg at position 198 to Met at position 328 of Fas ligand, and therefore, it can be concluded that the anti-Fas ligand antibodies having the high apoptosis-inhibitory activity should generally recognize the amino acids included in the aforementioned region as a recognition site. Thus, the aforementioned site, which resides on the Fas ligand molecule should arise the anti-Fas ligand antibody having the high apoptosis-inhibitory activity. This suggests that the aforementioned site is an important region for Fas ligand to exert the apoptosis-inducing activity, and an agent which can recognize and bind to this site would have apoptosis-inhibitory activity.

Features of the site to be bound to the aforementioned antibody having the high apoptosis-inhibitory activity can be demonstrated exhaustively when the model for the stereochemistry of Fas ligand molecule constructed using the commercially available software for molecular design is adapted to the data obtained in the analysis of the recognition site using the aforementioned Fas ligand variants and synthetic peptides.

Modeling of the monomer of Fas ligand molecule can be performed by using Modeler, which is a software for molecular design according to the manufacture's instructions utilizing as a template an X-ray crystal structure data of TNF-α (PDB ID:1TNF) and TNF-β (PDB ID:1TNR) having the high homology to Fas ligand, which have been recorded on Brookhaven Protein Data Bank (PDB). Model for the Fas ligand trimer can be constructed by superimposing the above Fas ligand monomer model on each segment of the TNF monomer on the atomic coordinates of PDB ID:1TNF, TNF-α trimer, using the software for molecular design, QUANTA/CHARMm (produced by Molecular Simulations).

Although Modeler and QUANTA/CHARMm (both are produced by Molecular Simulations) are used herein as a software for the molecular design, they are not exclusive, and any other software produced by any manufactures also can be used which is available as a software for general proteins. Further, TNF-α and -β are used herein as a template protein, but they are not exclusive, and any other protein which belongs to the TNF family also can be used.

Superimposition of the site to be bound to NOK and humanized NOK2 antibodies on the model obtained as shown above has revealed surprisingly that the antibodies bind to a broad region striding the two molecules of Fas ligand, which appears after the Fas ligand trimer is formed. Such finding with respect to the relationship between Fas ligand and anti-Fas ligand antibody is novel and has not been reported so far.

In general, it has been reported that the antigen-binding region in antibody is a region including six sites referred to as CDR (complementarity determining region), and the size of the region is in the range of from about 700 angstrom square (Sasatsuki, Tatehiko ed., Immunobiology, Nankodo, p. 128, 1995) to about 900 angstrom square (Tulip W. R., et al., J. Mol. Biol., vol. 227, p.122–148, 1992) for protein antigens with normal mass although the size varies depending on the particular antigen to be bound. The Fas ligand molecule usually occurs on the cell surface as a transmembrane type of protein with about 40 kD, and further, the molecule also may occurs as a free type of molecule with about 27 kD owing to the processing of the extracellular domain of the molecule. Additionally, it has been reported that the three molecules of Fas ligand monomer are associated with together to form a Fas ligand trimer. The protein is so large that the antibody comes into contact with the antigen surface-to-surface using the whole of CDR (Sasatsuki, Tatehiko ed., Immunobiology, Nankodo, p.128, 1995).

Consequently, the site associated with the apoptosis-inhibitory activity which resides on the Fas ligand trimer, which has been discovered by the present inventors can be illustrated as a plane. In general, the plane may be depicted as a flat plane defined by three points A (XA, YA, ZA), B (XB, YB, ZB), and C (XC, YC, ZC) which are not on a straight line.

The plane of the antigen defined on the Fas ligand trimer model may be estimated by assigning to the expression the data for the atomic coordinate of the amino acids recognized by antibodies, which is obtained from the Fas ligand trimer model. Any three amino acids which are optionally selected from the amino acids recognized by the antibodies are required to define such plane, and the preferred embodiment comprises Gln at position 200 which is on one of two adjacent Fas ligand molecules, and Asn at position 203 and Gln at position 220 which are on the other Fas ligand molecule. The plane defined by the combination of atomic coordinates of the α-carbons (Cα) of these amino acids can cover the region composed of the amino acids recognized by the antibodies. The effective plane which comes into contact with antibodies or the plane through which atoms of the antibodies approach to the Fas ligand trimer is believed to be a plane which resides opposite to the Fas ligand molecule being apart from the atomic coordinates of the Cα atoms by the length of the side chains of the amino acid residues plus about 4.1 Å of the cut off value of the common van der Waals contact.

Further, the size of the CDR of anti-Fas ligand antibody can lead to demonstration of amino acids which compose the region on the Fas ligand trimer, which is associated with apoptosis-inhibitory activity. It is believed that the CDR of anti-Fas ligand antibody is not different to some extent from the common antibodies in terms of size in the light of the length of amino acid sequence of the variable region. Stereochemistry model of NOK2 antibody is used as the representative of the anti-Fas ligand antibodies to demonstrate the size of the CDR of anti-Fas ligand antibodies, but any other NOK and humanized NOK2 antibodies can be used to demonstrate the size since the numbers of amino acid in the CDR of these antibodies are not different among them. Further, mere determination of the size of CDR will not be limited to usage of only these antibodies.

Investigation of the CDR of NOK2 antibody revealed that the CDR has substantially the same size as the circle with about 17 Å (angstrom) radius. Comparison between the circle with about 17 Å radius and the region composed of the amino acids on the Fas ligand trimer model, which are recognized by the antibodies has shown that the amino acids on the Fas ligand timer, which are recognized by NOK and humanized NOK2 antibodies are entirely covered within the circle with about 17 Å radius. This means that the anti-Fas ligand antibody having the high apoptosis-inhibitory activity in common recognizes the region composed of the amino acids encompassed in the circle, and in other words, the amino acids of the Fas ligand trimer within the circle could interact with the CDR amino acids of anti-Fas ligand antibody. A candidate for the amino acids which can interact with the CDR amino acids of the anti-Fas ligand antibody may be any one of amino acids which are within the circle, and are exposed on the Fas ligand trimer, and preferred amino acid is one selected from a group consisting of the amino acids, each of which is exposed on the surface of the Fas ligand trimer, and has an exposed area with 15 angstrom square or above. In particular, preferred amino acids include Ser at position 153, Tyr at position 166, Ile at position 168, Arg at position 198, Gly at position 199, Gln at position 200, Gln at position 237, Met at position 238, Arg at position 241, Ser at position 242, Phe at position 269, Glu at position 270, Glu at position 271, and Ser at position 272 of one of adjacent two Fas ligand molecules, as well as Ser at position 157, Met at position 158, Pro at position 159, Glu at position 161, Lys at position 178, Gly at position 179, Asn at position 203, Asn at position 204, Leu at position 205, Pro at position 206, Ser at position 208, Lys at position 210, Tyr at position 212, Arg at position 214, Tyr at position 218, Pro at position 219, Gln at position 220, Asp at position 221, Leu at position 222, Val at position 223, Lys at position 228, Met at position 230, Tyr at position 232, His at position 256, Tyr at position 258, Asn at position 260, Ser at position 262, Glu at position 263, Leu at position 264, and Ser at position 265 of the other Fas ligand molecule. Interaction with the amino acids encompassed in the region on the Fas ligand trimer is important for proteins, peptides, especially antibodies or analogues thereof to show the high apoptosis-inhibitory activity.

Agents which exert the apoptosis-inhibitory activity according to the present invention include, in addition to the humanized immunoglobulins which are specifically reactive to Fas ligand, substantially any agents which can specifically recognize and are able to be reactive to the aforementioned domain, region or the amino acids thereof which are on the Fas ligand and are important for the apoptosis-inhibitory activity. Particularly, agents which recognize and bind to the defined amino acid on the protein molecule such as immunoglobulin are preferable, and preferred agents include a fragment derived from immunoglobulin or an analogue thereof, and a receptor altered to be able to recognize the aforementioned region, and enzymes which recognize and react with the defined amino acids, and the like. These proteinaceous agents may be prepared by genetic engineering techniques, and therefore, they can be referred to as recombinant proteins. Additionally, there can be exemplified as a candidate for such agents, by a peptide synthesized based on the amino acid sequence derived from the above proteinaceous agents, a peptide having an absolutely novel sequence, which is obtained by the screening such as phage display system for its ability to recognize the domain, region or amino acids which are on Fas ligand and are important for the apoptosis-inhibitory activity from a peptide library consisting of random sequences, and a peptide-like substance which is composed of a non-naturally occurring synthetic peptide prepared based on these peptides.

As described above, recent investigations have shown that the physiological reaction between Fas and Fas ligand is associated with diverse diseases such as AIDS, graft-versus-host diseases in bone marrow transplantation (GVHD), fulminating hepatitis, autoimmune diseases (SLE, RA), and therefore, the humanized immunoglobulin of the present invention, which has ability to inhibit such physiological reactions can be used as a therapeutical agent for treating the above diseases.

Further, the site on Fas ligand required to induce apoptosis, which has been found for the first time by the present inventors is also significant to elicit anti-Fas ligand antibody having the high apoptosis-inhibitory activity. This finding afford the important information to design various other molecules for inhibiting apoptosis. Thus, the finding may be utilized to find a new therapeutic or diagnostic agent by creating a recombinant protein or peptide which is specifically reactive to the amino acids within the aforementioned site to inhibit apoptosis.

The following examples are presented for purpose of further illustration of the invention, and such examples are not intended to be limiting the invention in any respect.

EXAMPLES

NOK antibody described in Examples herein is included in the invention of the PCT Application No. WO96/29350 which is incorporated herein by this reference. The preparation is detailed in the application, and the outline is provided below.

First, the human Fas ligand gene was amplified by PCR with the primers prepared on the basis of the report of Nagata, et al., Cell, vol.75, p.1169–1178, 1993, using as a template the cDNA prepared conventionally from human killer T cells expressing Fas ligand. The restriction site which had been incorporated into the primers was utilized to ligate the amplified genes into the expression vector BCMG-SNeo (Karasuyama, Hajime, Experimental Medicine, Special number, Handbook for Genetic Engineering, Yodo Cor., p.297–299, 1992), providing the expression plasmid for Fas ligand. The expression plasmid was transformed into COS cell (ATCC CRL1650) by conventional DEAE-dextran method to provide the COS transformants for Fas ligand. The transformants were used to challenge MRL lpr/lpr mice intra-abdominally three times at intervals of a week, and the spleen was excised three days after the final challenge. The splenocytes from the excised spleen were fused with 8-azaguanine-resistant cells from mice, P3X63Ag8.653 (ATCC CRL1580), by the conventional method using polyethylene glycol. The immunoglobulins which were contained in the cultured supernatants of clones from the hybridomas cloned by limiting dilution was screened for the apoptosis-inhibitory activity by the determination as shown below, and the hybridoma producing monoclonal antibody NOK2 which were specifically reactive to Fas ligand was obtained, which had been deposited at the National Institute of Bioscience and Human Technology, Ministry of International Trade and Industry under Accession No. FERM BP-5045.

Similarly, NOK1, NOK3, and NOK4 antibodies were obtained.

Example 1

Preparation of Chimeric NOK2 Antibody (CNOK2)
1-1) Isolation of the Gene of the Variable Region of NOK2 Antibody Isolation of the gene of the variable region (V region) of the mouse immunoglobulin was performed as shown below. First, total RNA was extracted from the NOK2-producing hybridoma using ISOGEN (trade name), RNA extraction reagent produced by Nippon Gene. The procedures were performed according to the accompanied protocol. The hybridoma producing NOK2 antibody was the same as FERM BP-5045 deposited at the National Institute of Bioscience and Human Technology, Ministry of International Trade and Industry. Second, the mRNAs were prepared from the total RNA using POLY (A) QUIK mRNA ISOLATION kit (trade name) produced by STRATAGENE. The procedures were performed according to the accompanied protocol. Subsequently, single-stranded cDNAs were synthesized from the mRNAs as templates using First Strand cDNA Synthesis kit (trade name) of Pharmasia Biotech. The oligo (dT) primers accompanied therein were used as primers, and the procedures were performed according to the protocol accompanied therein. Polymerase chain reaction (PCR) was performed using the resultant single-stranded cDNAs as templates with DNA primers (the heavy chain/MHL4.4 primer: SEQ ID No: 10, MHJ124 primer: SEQ ID No: 11; the light chain/MKL2.4 primer: SEQ ID No: 12, MKJ124 primer: SEQ ID No: 13), which had been prepared on the basis of the base sequences of V regions and J regions classified by Kabat, et al., Sequence of Proteins of Immunological Interest, 4th ed., Public Health Service, NIH, Washington D.C., 1987. Both V region primers and J region primers contain the HindIII and BamHI sites.

PCR was performed using the kit of PERKIN ELMER according to the accompanied protocol. The condition of PCR comprises 35 cycles consisting of 94° C. for one minute, 60° C. for two minutes, and 72° C. for two minutes. After the PCR, the DNA segments were cloned into pCRII vector (trade name) of Invitrogen. The procedures were performed according to the accompanied protocol.
1-2) Base Sequence of the Gene of the V Region of Mouse NOK2 Antibody The reaction product was applied to an autosequencer to determine the sequence of the V region gene incorporated into pCRII by using Dye Primer Cycle Sequencing kit (trade name) of Perkin-Elmer. The base sequences of the variable regions of the heavy chain (VH) and of the light chain (VL) of NOK2 antibody are shown in FIGS. 1 and 2 (VH: SEQ ID No: 14, VL: SEQ ID No: 15). Further, the amino acid sequences derived from the base sequences (VH: SEQ ID No: 16, VL: SEQ ID No: 17) are also shown in FIGS. 1 and 2. Both base sequences were indicated to contain a reconstitution which is unique in the V region gene, and to form an open reading frame (ORF).
1-3) Construction of the Gene of Chimeric NOK2 Antibody (CNOK2H, CNOK2L)

Mouse-human chimeric antibody was prepared in order to determine if the isolated gene of the V region of NOK2 antibody encodes the V region which is responsible for the anti-Fas ligand activity. For the expression of the chimeric antibody, expression vectors PCAG-κ and pCAG-γ1 were used, which contain a promoter from the chicken β-actin gene, a splice acceptor sequence from the rabbit β-globin gene, and an enhancer from cytomegalovirus.

pCAG-κ had been prepared according to the usual genetic engineering procedures by ligating together the constant region gene of the human immunoglobulin κ chain and the polyadenylation site from RHC25 plasmid, an expression plasmid for the light chain of RC25, a humanized anti-HIV neutralizing monoclonal antibody described in the International Publication No. WO94/20632, the dhfr gene from pSV2-dhfr plasmid (Lee, F. et al., Nature, vol. 294, p.228–232, 1981) as a selectable marker suitable for eukaryotic cells, the SV40 promoter and polyadenylation site, the Ampr gene as a selectable marker suitable for prokaryotic cells described in the Japanese Patent Publication (kokai) No. 168087/1991, the enhancer from cytomegalovirus (CMV), the promoter from the chicken β-actin gene, and the splice acceptor site from the rabbit β-globin gene. The vector plasmid contains the HindIII site incorporated downstream from the splice acceptor site of the rabbit β-globin gene, and the BamHI site incorporated upstream from the constant region gene of the human immunoglobulin κ chain.

pCAG-γ1 had been prepared according to the usual genetic engineering procedure by ligating together the γ1 constant region gene of the human immunoglobulin and the polyadenylation site from HCMV-VH0.5β-γ1 plasmid described in Maeda, et al., Hum. Antibod. Hybridomas, vol.2, p124–134, 1991, the neor gene from pAd.RE.noe plasmid described in the Japanese Patent Publication (kokai) No. 5890/1990 as a selectable marker suitable for eukaryotic cells, the SV40 promoter and polyadenylation site, the Ampr gene as a selectable marker suitable for prokaryotic cells described in the Japanese Patent Publication (kokai) No. 168087/1991, the enhancer from cytomegalovirus (CMV), the promoter from the chicken β-actin gene, and the splice acceptor site from the rabbit β-globin gene. The vector plasmid contains the HindIII site incorporated downstream from the splice acceptor site of the rabbit β-globin gene, and the BamHI site incorporated upstream from the γ1 constant region gene of the human immunoglobulin.

The V region gene of NOK2 antibody prepared as described in 1-2) was digested with the restriction enzymes HindIII and BamHI (both are from Takara, and all of restriction enzymes used hereinafter are from Takara, unless otherwise stated), and the segments of the VH and the VL were incorporated into the HindIII-BamHI sites of pCAG-γ1 and pCAG-κ, respectively (CNOK2H and CNOK2L; FIG. 3).

1-4) Expression of Chimeric NOK2 Antibody (CNOK2)

The plasmid DNAs, CNOK2H and CNOK2L prepared as described above were transformed into CHO-DG44 cell (Chasin, L. A., et al., Somatic Cell. Mol. Genet., vol. 12, p.555–566, 1986) using Lipofect ACE (trade name) from Gibco BRL to provide the transformants producing chimeric NOK2 antibody (CNOK2). The procedures were performed substantially according to the protocol accompanied in Lipofect ACE. Briefly, CHO-DG44 cells were transformed with a mixture which comprised Lipofect ACE and the PvuI-linearized products of both plasmid DNA 1 μg prepared using a kit of QIAGEN, and the transformants were cultured on an α-MEM medium (Gibco BRL) without nucleotides containing 1 mM G418 (Gibco BRL) and 10% dialyzed fetal bovine serum (Gibco BRL) in a condition of 5%$CO_2$ at 37° C. for 2 weeks. The cells cotransformed with CNOK2H and CNOK2L plasmid DNAs were grown in the conditions. The resultant transformants were subculured and expanded on the above medium until reached confluent in a 75 $cm^2$ culture flask (CORNING), at this time, the medium was replaced by 20 ml of an ASF medium (trade name) (Ajinomoto Inc.), and the cells were cultured in a condition of 5%$CO_2$ at 37° C. for seven days, before recovering the supernatant.

1-5) Concentration of the Cultured Supernatant and Quantitative Analysis for CNOK2 Antibody Therein The ASF cultured supernatant was concentrated 10-fold using Centricon-10 Spine Column (trade name) produced by Amicon. The chimeric antibody included in the concentrated supernatant was quantified by ELISA assay. In detail, 2 μg/ml of a goat anti-human IgG (Fc) antibody (Cappel) was first added to a 96-well Maxisorp Plate (trade name) produced by InterMed at 50 μl/well. After incubation overnight at 40C, the plate was rinsed three times in 0.01M PBS with 0.05% Tween20. Then, PBS with 1% BSA was added at 100 μl/well, and the plate was incubated at 37° C. for three hours. The plate was again rinsed three times in 0.01M PBS with 0.05% Tween20, then the aforementioned concentration of the cultured supernatant was added thereto at 50 μl/well, and the plate was incubated at 37° C. for an hour. Then, the plate was rinsed three times in 0.01M PBS with 0.05% Tween20, and the 5,000-fold dilution of the HRP-labeled anti-human Ig-Cκ antibody (produced by Southern Biotechnology Associate) in PBS with 1% BSA as a secondary antibody was added at 50 μl/well. The plate was incubated at 37° C. for an hour, and was rinsed five times in 0.01M PBS with 0.05% Tween20. Finally, a solution of chromophoric substrate (0.5 mM TMBZ+hydrogen peroxide) was added at 50 μl/well to allow the reaction, and when a suitable development was obtained, the reaction was quenched with the addition of 0.3N sulfuric acid at 50 μl/well, followed by determining an absorbance at a wavelength of 450 nm using Microplate Reader (Molecular Devices). Concentration of RNOK2 was determined on the basis of the calibration curve created for the standard human IgG with known concentrations in accordance with a similar procedure. As the standard human IgG, a purified product (purity: 98% or above) of RC25 antibody, anti-HIV neutralizing monoclonal antibody having the same Fc and Cκ as chimeric NOK2 antibody (the International Publication No. WO94/20632) was used.

1-6) Preparation of Soluble Fas Ligand Molecule

The procedures of isolation of the Fas ligand gene, creation of the Fas ligand-expressing cells, and preparation of the soluble Fas ligand molecule are the same as those described in the PCT Application No. WO96/29350. Outline is provided below.

First, cDNAs were prepared from the mRNAs extracted from the human killer T cells which express human Fas ligand according to the conventional method. Second, PCR was performed using the cDNAs as templates with 5' and 3' primers each of which was incorporated with XhoI and NotI sites, respectively, described in Nagata, et al., Int. Immunol., vol. 6, No. 10, p.1567–1574, 1994, so as to provide the gene of human Fas ligand as an amplified product. The human Fas ligand gene was incorporated into the XhoI site and the NotI site of the expression vector BCMGSNeo (Karasuyama, hajime, Experimental Medicine, Special number, Handbook for Genetic Engineering, Yodo Cor., p.297–299, 1992), to provide human Fas ligand-BCMGSNeo, an expression plasmid for human Fas ligand. Subsequently, the plasmid was amplified in E. coli, and recovered, and the amplified plasmids were transformed into COS cells (ATCC CRL1650) by DEAE-dextran method (Experimental Medicine, Special number, Biomanual, series vol. 4, Yodo Cor., p.16–22, 1994) to provide the COS cells expressing Fas ligand. Then, the Fas ligand molecules released in the supernatant from the culture of the Fas ligand-expressing COS cells on a 10% FCS-DME medium were purified by an affinity chromatography on NOK1 antibody, the anti-Fas ligand antibody described in the PCT Application No. WO96/29350 which was produced by the hybridoma assigned with the accession No. FERM BP-5044, and sterilized by passage through 0.45 μm membrane filter so as to provide the soluble Fas ligand molecules. Observation of a single band on SDS-PAGE revealed that the Fas ligand was entirely purified. Concentration of the Fas ligand was determined by the absorbance at 280 nm.

1-7) Affirmation of Binding of CNOK2 Antibody Against the Soluble Fas Ligand

Activity of the chimeric antibody included in the concentrated supernatant was quantified by ELISA using the soluble Fas ligand and anti-human IgG. Specifically, a 50 ng/ml solution of the soluble Fas ligand prepared according to the procedure of 1-6) was first added to a 96-well Maxisorp Plate (trade name) produced by InterMed at 50 μl/well. After incubation overnight at 4° C., the plate was rinsed three times in 0.01M PBS with 0.05% Tween20. Then, PBS with 1% BSA was added at 100 μl/well, and the plate was incubated at 37° C. for two hours. The plate was again rinsed three times in 0.01M PBS with 0.05% Tween20, then the concentration of the cultured supernatant prepared as described in the aforementioned 1-4) was added thereto at 50 μl/well, and the plate was incubated at 37° C. for two hours. Then, the plate was rinsed three times in 0.01M PBS with 0.05% Tween20, and the 5,000-fold dilution of the HRP-labeled anti-human Ig-Cκ antibody (produced by Southern Biotechnology Associate) in PBS with 1% BSA as a secondary antibody was added at 50 μl/well. The plate was incubated at 37° C. for an hour, and was rinsed five times in 0.01M PBS with 0.05% Tween20.

Finally, a solution of chromophoric substrate (0.5 mM TMBZ+hydrogen peroxide) was added at 50 μl/well to allow the reaction, and when a suitable development was obtained, the reaction was quenched with the addition of 0.3N sulfuric acid at 50 μl/well, followed by determining an absorbance at a wavelength of 450 nm using Microplate Reader (produced by Molecular Devices). The expressed product by cotransformation with CNOK2H and CNOK2L plasmid DNAs was bound to Fas ligand depending on the concentration, suggesting that the isolated gene for the V region of NOK2 antibody certainly encodes the V region of an antibody having anti-Fas ligand activity (FIG. 4).

Example 2

Preparation of Humanized NOK2 Antibody (RNOK2)

2-1) Transplantation of the CDR of V Region of NOK2 Antibody Via PCR Mutagenesis The CDRs (complementarity determining regions, SEQ ID Nos: 1–6) in the VH and VL of the cloned NOK2 antibody were each transplanted into the VH and VL regions of human immunoglobulin. The procedures were performed according to the preparation of humanized immunoglobulins (the Japanese Patent Publication (kokai) No. 141095/1992). The CDR in the VH region of NOK antibody was transplanted into SGI, which is the VH region containing the FR (framework region) of human subgroup II (distributed by Dr. Bendig of MRC Collaborative Center, United Kingdom). The CDR in the VL region of NOK2 antibody was transplanted into REI as previously reported, a VL region containing the FR of the human κ chain (W. Palm et al., Physiol. Chem., vol. 356, p167, 1975), and into the VL region containing the FR of the κ chain cloned from the cDNA library derived from human peripheral blood lymphocytes (huVL-19 and huVL-31).

In the humanization of NOK2 antibody, the putative three-dimensional structure of NOK2 antibody was first constructed using a computer modelling. Specifically, screening for the homology to Brookhaven Protein Data Bank (PDB) was performed on the amino acid sequences of the variable regions of the heavy chain and the light chain of NOK2 antibody to select the variable regions of the heavy chain (PDB ID:1FOR) and of the light chain (PDB ID:1TET) of the antibody, which would be used as templates. Then, modelling was performed using QUANTA/ CHARMm which is a software running on Silicongraphics. The modelling steps were consisted of 1) copying the amino acid sequence of NOK2 antibody onto the atomic coordinate of the template of the aforementioned variable region amino acids, 2) energy-minimizing calculating (maximum gradient method), 3) chilling from 300K to 0K by taking 400 steps, 4) energy-minimizing calculating (maximum gradient method), 5) heating from 0K to 300K by taking 7,500 steps, 6) equilibrating by taking 30,000 steps (corresponding to 30 picoseconds), and 7) simulating by 20,000 steps (corresponding to 20 picoseconds). Next, one structure was extracted per 100 calculations to provide totally 200 structures, and they were divided into five groups using Cluster Analysis Program installed in the aforementioned software. Consequently, one structure obtained from the energy-minimizing calculation of the above 2), and five structures, each of which shows the minimum energy in the individual five groups as shown above were extracted to provide totally six structures and these six structures were assigned as an estimated three-dimensional structure of NOK2 antibody. Then, using the program installed in the same software, any amino acids within the FR which form the hydrogen bond to the CDR of the H chain and the L chain were selected in each of the aforementioned structures of NOK2 antibody (the second group), and further, any amino acids within the FR which form the hydrogen bond to them (the second group) were selected. Similarly, using the installed program, any amino acids within the FR which form the energy contact to the CDR were selected in the H chain and the L chain of NOK2 antibody (the first group), and further, any amino acids within the FR which form the energy contact to the resulting amino acids (the second group) were selected. The energy contact herein includes so-called electrostatic interaction and van der Waals forces. Initializations of the above program were used as parameters necessary for selection of any amino acids forming the hydrogen bond, and for the calculation of energy contact. Subsequently, from the FR amino acids of the first and second groups for the hydrogen bond, and the FR amino acids of the first and second groups for the energy contact, any FR amino acids which are included in FR amino acid clusters associated with four or more of the six estimated structures were selected as stereochemistry-responsible FR amino acids, and these were transplanted into the FR in the variable region of human immunoglobulin together with the CDR amino acids, provided that, when the transplantation of an FR amino acid among the selected FR amino acids into the relevant site in human immunoglobulin raises any sequences which can not be cited as the variable amino acid sequences of human immunoglobulin in the classification of Kabat, et al., Sequence of Proteins of Immunological Interest, 4th ed., Public Health Service, NIH, Washington D.C., 1987 and in a software for information retrieval, Entrez (trademark), which has been developed by National Center for Biotechnology Information: NCBI, then such FR amino acids were not be transplanted, so as to reduce the possibility to elicit the antigenicity as much as possible when the resulting humanized immunoglobulin is administered to human.

For humanized VH, two types of variants comprising two differences in FR3 amino acids were created (RNOK2VHver11: SEQ ID No: 18 and RNOK2VHver12: SEQ ID No: 19). For humanized VL, RNOK2VLver1 (SEQ ID No: 20) was created as a transplanted entity into the REI of the VL region of human immunoglobulin, whereas four types of variants (i.e., RNOK2VLver21: SEQ ID No: 21, RNOK2VLver22: SEQ ID No: 22, RNOK2VLver23: SEQ ID No: 23 and RNOK2VLver24: SEQ ID No: 24) comprising one or two differences in amino acids of the FR1 were created as a transplanted entity into huVL-19 and huVL-30 obtained from the cDNA library. So, totally five types of the variants were created for the VL.

The VH and VL amino acid sequences of NOK2 antibody, human immunoglobulin receiving transplantation, and humanized NOK2 antibody constructed are depicted in FIGS. 5 and 6. Large characters in the amino acid sequences represent the conservative sequence between NOK2 antibody and the human antibody receiving transplantation, whereas small characters represent the different amino acids from each other. The amino acids surrounded by box represent the FR amino acids to be transplanted together with the CDR amino acids, which were selected by the aforementioned procedure.

Actually, transplantation of the amino acids was performed at the genetic level by the PCR mutagenesis whereby mutations were introduced by PCR using the VH gene of RC25 antibody, a humanized anti-HIV immunoglobulin (the International Publication No. WO94/20632) as a template for the VH, and using the VL gene of chimeric NOK2 prepared as described previously as a template for the VL, so that the genes encoding the amino acid sequences of humanized NOK2 antibody as shown in FIGS. 5, 6 and 7 were constructed. FIGS. 8–13 show the annealing of the synthetic primers used in the PCR mutagenesis with the template VH and VL regions.

PCR was performed using a kit produced by Perkin-Elmer according to the accompanied protocol. The conditions of PCR comprise 30 cycles consisting of 95° C. for one minute, 60° C. for one minute, and 72° C. for two minutes.

In the case of the VH, the 5' of the VH gene was amplified using primer pAGF (SEQ ID No: 25) and primer #01 (SEQ ID No: 26), and the 3' of the VH gene was amplified using #02 (SEQ ID No: 27) or #03 (SEQ ID No: 28) and #04 (SEQ ID No: 29), provided that #02 was used for the preparation of RNOK2VHver11, and #03 was used for ver12, using plasmid RHC25 (the International publication No. WO94/20632) cloned with the variable gene of humanized C25 immunoglobulin as a template. Then, equal volumes of both amplified gene fragments obtained were combined together, and the combination was used as a template together with pAGF primer and #04 to perform PCR. The amplified gene fragments thus obtained were ligated into the KpnI site in the VH gene of humanized C25 antibody (the International Publication No. WO94/20632) to create RNOK2VHver11 and ver12, the VH genes of humanized NOK2 antibody.

In the case of VL, on the other hand, the 5' of the VL gene was amplified using primer #05 (SEQ ID No: 30) and primer #06 (SEQ ID No: 31), the intermediate of the VL gene was amplified using #07 (SEQ ID No: 32) and #08 (SEQ ID No: 33), and the 3' was amplified using #09 (SEQ ID No: 34) and #10 (SEQ ID No: 35), using the VL of chimeric NOK2 as a template. Then, equal volumes of three amplified gene fragments thus obtained were combined together, and the mixture was used as a template together with #05 and #10 to perform PCR. The amplified gene fragments thus obtained were ligated into the ApaI site in the leader region upstream from the VH gene of human immunoglobulin SGI to create RNOK2VLver1, the VL gene of humanized NOK2 antibody.

The remaining four variants of the VL were prepared in the following manner. First, PCR was performed with primer #11 (SEQ ID No: 36) and #12 (SEQ ID No: 37), using the VL of chimeric NOK2 as a template. Primer #11 comprises variations in the nucleic acid sequence to create the variants RNOK2VLver21, 22, 23, and 24. The amplified gene fragments thus obtained were ligated into the ApaI site in the leader region upstream from the VH gene of human immunoglobulin SGI to create RNOK2VLver21, 22, 23, and 24, the VL genes of humanized NOK2 antibody.

The base sequences of humanized VH and VL region genes constructed as described above were analyzed using a kit produced by Perkin-Elmer and an autosequencer in order to select a clone having the defined sequence.

The fragments of the humanized VH and VL region were digested with the restriction enzymes HindIII and BamHI, and the digested products were each introduced into the HindIII-BamHI site of pCAG-γ1 and pCAG-κ as described in the aforementioned preparation for the chimeric antibody (See Example 1) to provide the plasmids for expression of humanized NOK2 antibody genes, RHNOK2 and RLNOK2, which are generically referred to the variants of the humanized VH and VL, respectively.

2-2) Expression of Humanized NOK2 (RNOK2) Immunoglobulin

For the preparation of transformants producing RNOK2 immunoglobulin, plasmid DNAs for expression of human-ized NOK2 antibody genes, RHNOK2 and RLNOK2 were each introduced into CHO DG44 cells according to a procedure similar to the preparation of the chimeric antibody (See Example 1). This procedure was performed using Lipofect ACE as described in the case of chimeric antibody.

Since two types of the expression plasmids for the humanized variable region gene for the VH whereas five types for the VL were prepared as described in above, totally 10 types of humanized NOK2 immunoglobulin were expressed by the combination thereof. RNOK201, RNOK202, and RNOK203 described hereinafter are humanized NOK2 antibody which was each expressed in combinations of RNOK2VHver11 and RNOK2VLver1, RNOK2VHver11 and RNOK2VLver21, and RNOK2VHver11 and RNOK2VLver22, respectively. Hereinafter, these antibodies may be referred to as RNOK2 antibody(ies) or RNOK2 immunoglobulin(s).

After transformed with the expression plasmids, the transformants were cultured. ELISA of the cultured supernatants using the anti-human IgGγ1 and the anti-human IgGκ revealed that human immunoglobulin was produced in the cultured supernatants.

Example 3

Fas Ligand-binding Activity of RNOK2 Immunoglobulins 3-1) Preparation of Purified RNOK2 Immunoglobulins The cultured supernatants obtained by culturing RNOK2-expressing CHO-DG 44 cells prepared as described in Example 2 were recovered, and RNOK2 immunoglobulins included herein were purified. Specifically, the transformants expressing RNOK2 immunoglobulins obtained in Example 2 were first cultured on an α-MEM medium (Gibco BRL) without nucleotides containing 1 mM G418 (Gibco BRL) and 10% dialyzed fetal bovine serum (Gibco BRL) in a condition of 5%$CO_2$ at 37° C. in a 75 $cm^2$ culture flask (CORNING) until reached confluent. Then, the culture was expanded to two 225 $cm^2$ culture flasks (CORNING), and again cultured in the same conditions until reached confluent. The two cultures were expanded to eight 225 $cm^2$ culture flasks, and the medium was replaced by 65 ml of an ASF medium (trade name) (Ajinomoto Inc.) at the point when they reached confluent, followed by culturing in a condition of 5%$CO_2$ at 37° C. for seven days, before recovering totally about 500 ml of the supernatant.

From the cultured supernatant, only the protein G-adsorbed IgG was isolated using a protein G column (produced by Pharmasia Biotech) and a TPLC system (produced by Pharmasia Biotech). The concentration of the purified immunoglobulin was determined according to ELISA method described in Example 1. Further, SDS-PAGE electrophoresis was performed on the purified immunoglobulin in the reductive conditions, followed by CBB stain, observing no band of contaminant proteins but bands assuming to be the heavy chain and the light chain.

3-2) Binding Activity of RNOK2 to Fas Ligand

Figure 14:
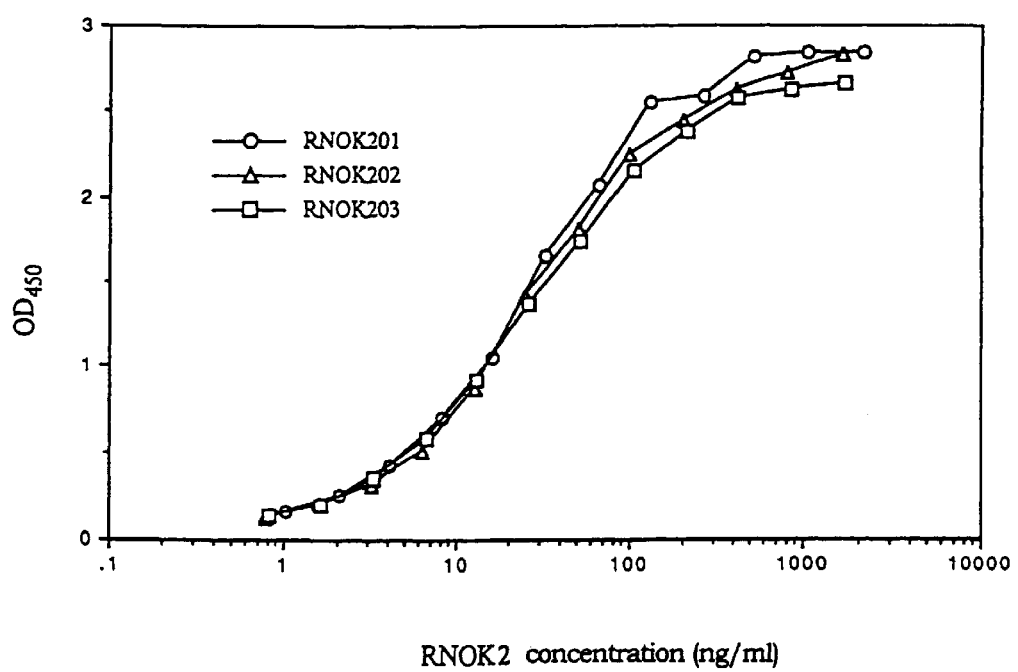
FIG. 14 shows the result of ELISA for assaying the ability of RNOK2 immunoglobulins to recognize Fas ligand.

The binding activities of RNOK201, RNOK202, and RNOK203 immunoglobulins among the purified RNOK immunoglobulins prepared as described in the above to Fas ligand were examined by ELISA method using the soluble Fas ligand and the anti-human IgG (Example 1), to confirm that RNOK2 immunoglobulins bind to Fas ligand in a concentration-dependent manner (FIG. 14).

Example 4
Determination of the Apoptosis-inhibitory Activity of RNOK2 Immunoglobulins 4-1) Preparation of Soluble Fas Ligand Molecule Soluble Fas ligand molecule was prepared according to the same procedure as in Example 1–6).

4-2) Preparation of RNOK2 Immunoglobulin Solution

The RNOK2 immunoglobulins purified with the manner as described in Example 3 were diluted in a 10%FCS RPMI1640 medium to prepare 12 solutions having the different immunoglobulin concentrations which are provided below. One hundred µl aliquots of the solutions each having immunoglobulin concentrations of 4 µg/ml, 2 µg/ml, 1 µg/ml, 0.5 µg/ml, 0.25 µg/ml, 0.125 µg/ml, 0.0625 µg/ml, 0.03125 µg/ml, 0.01563 µg/ml, 0.007813 µg/ml, 0.003906 µg/ml, or 0.001953 µg/ml were prepared.

The ¼ portions (i.e. 25 µl) of the solutions were finally added to 100 µl reaction systems, and therefore, the effective concentrations would be ¼ values of the above concentrations.

4-3) Preparation of Purified Mouse NOK2 Immunoglobulin

Each of Hybridoma NOK2, which had been deposited at the National Institute of Bioscience and Human Technology, Ministry of International Trade and Industry under Accession No. FERM BP-5045 was grown in a RPMI1640 medium with 10%FCS to $3 \times 10^7$ cells. Such preparation of the $3 \times 10^7$ cells was performed on a scale for cell culture by adding a 30 ml culture to a 75 cm$^2$ flask (CORNING). Specifically, starting from culturing at concentration of $2 \times 10^5$ cells/ml, the cells were recovered when they reached $1 \times 10^6$ cells/ml.

The recovered hybridomas were suspended in 1.5 ml of PBS, and the 0.5 ml portions corresponding to $1 \times 10^7$ cells of the suspensions were administered to nude mice intra-abdominally. After feeding for 10 days, the ascites deposited in the visceral cavity were recovered giving 6.7 ml/animal. The 10 ml portions of the ascites were purified.

Ten ml of a saturated solution of ammonium sulfate was added dropwise to the equal volume of the ascites such that the mixture was first purified on the salting-out with ammonium sulfate. After stirring at 4° C. for two hours, the mixture was centrifuged at 10,000 g for 15 minutes. The supernatant was removed, and the pellet was dissolved in 5 ml of PBS. Then, the solution was dialyzed overnight against 3 liters of PBS. Subsequently, the dialyzed sample was recovered, and then only the protein G-adsorbed IgG was isolated by FPLC system using protein G column (Pharmasia). The sample was further dialyzed overnight against PBS. On the following day, concentration and purity of the protein were determined.

The quantification of the protein was performed using a protein quantification reagent of BIO RAD. The procedure was in accordance with the protocol accompanied therein. SDS-PAGE electrophoresis was performed on the purified immunoglobulin in the reductive conditions, followed by CBB stain, observing no band of contaminant proteins but bands assuming to be the heavy chain and the light chain.

In accordance with a similar procedure to the aforementioned case of RNOK2 immunoglobulin, 12 solutions were prepared having the different concentrations of the purified NOK2 immunoglobulin thus obtained.

4-4) Preparation of Target Cells

As a target cell, WR19L cells which had been transformed with human Fas gene were used. The transformation of WR19L cells (ATCC TIB52) with human Fas gene was performed according to the conventional method. Specifically, the procedure was in accordance with Okumura, et al., Proc. Natl. Acad. Sci. USA, vol. 91, No. 11, p4930–4934, 1994. The resultant Fas-WR19L cells were cultured, and adjusted to $2 \times 10^5$ cells/ml in a 10%FCS-RPMI medium.

4-5) Determination of Apoptosis-inhibitory Activity of RNOK2 Immunoglobulin

First, the soluble Fas ligand molecules prepared in the above 4-1) were diluted at 18.5 ng/ml with a 10%FCS-DME medium. The 25 µl portion of the dilution was added to each well on a 96-well flat-bottomed plate. Then, each of the solutions with the various concentrations of RNOK2 immunoglobulins (RNOK201, RNOK202 and RNOK203) prepared in 4-2), and of mouse NOK2 immunoglobulin prepared in 4-3) was added to the every three wells of the plate at 25 µl/well. Then, the plate was incubated in 5%CO$_2$ atmosphere at 37° C. for an hour. Subsequently, the Fas-WR19L cell suspension prepared in the above 4-(4) as a target cell was added thereto at 50 µl/well, and the plate was incubated in 5%CO$_2$ atmosphere at 37° C. for 17 hours. Then, Alamer Blue purchased from COSMO BIO was added thereto at 10 µl/well, and the plate was further incubated in 5%CO$_2$ atmosphere at 37° C. for four hours. Subsequently, fluorescent strength was assayed at a determination wavelength of 590 nm using a Fluorescent Microplate Reader, Fluoroscan II (trade name) (produced by Titertek) with an excitation wavelength of 544 nm. The fluorescent strength represents viable cell numbers.

For a control of 100% viable, only a 10% FCS-RPMI1640 medium (neither soluble Fas ligand, RNOK2 immunoglobulin, nor mouse NOK2 immunoglobulin) was added to 50 µl of Fas-WR19L cells (target cell) in the well at 50 µl/well, whereas for a control of apoptosis, 25 µl of a 10% FCS-RPMI1640 medium and 50 µl of Fas-WR19L cells as a target were added to 25 µl of the soluble Fas ligand. The results are shown in FIG. 15.

FIG. 15 shows that all of humanized NOK2 immunoglobulins (RNOK201, RNOK202 and RNOK203) inhibit apoptosis by 90% or more in the range of concentrations of 0.06 µg/ml (effective concentration) or above. This demonstrates that all of the humanized immunoglobulins of the present invention are able to inhibit the apoptosis-inducing activity of the soluble Fas ligand against the Fas-expressing cells. Further, it should be especially noted that the activity of the humanized immunoglobulins of the present invention is equal to or more than the original mouse NOK2 immunoglobulin.

Further, mouse NOK2 immunoglobulin has been shown to have the much higher apoptosis-inhibitory activity at the antibody concentration of 0.01–8 µg/ml (effective concentration) compared to the Fas-Ig chimeric molecule at the same concentration as described in the PCT Application No. WO96/29350. Accordingly, it is apparent that the humanized immunoglobulins of the present invention have the higher affinity to Fas ligand and are more effective than the mouse Fas-Ig.

Additionally, this shows that either of the humanized immunoglobulins of the present invention bind to Fas ligand in body preceding the bind between Fas ligand and Fas, and therefore, it can be readily predicted that the humanized immunoglobulins of the present invention could inhibit satisfactorily the physiological reactions between Fas and Fas ligand in body.

Example 5

Preparation of Fas Ligand Introduced with Amino Acid Substitution (Fas Ligand Variant)

5-1) Construction of Expression Vector for Fas Ligand

In order to construct an expression vector for Fas ligand, the gene of the variable region of the light chain containing the leader sequence of C25 antibody described in the International Publication No. WO94/20632 was first excised with HindIII and BamHI, and ligated into the HindIII-BamHI site of the pCAG expression vector which was defective in the gene of the constant region of the κ chain in pCAG-κ expression vector described in Example 1–3). The plasmid was transformed into *E. coli* according to the conventional procedure, and the plasmid was recovered from the cultured transformants by the small scale plasmid preparation (Cold Spring Harbor Lab., Molecular Cloning, p.1.25, 1989). Subsequently, the leader sequence in part and the whole gene of the variable region gene which resided between the KpnI site in the leader sequence and the BamHI site downstream from the variable region of the C25 light chain were excised from the plasmid to provide the pCAG expression vector which was supplemented with the leader sequence from the light chain of C25 antibody.

5-2) Creation of Fas Ligand Gene Variants by PCR Mutagenesis and Construction of Expression Plasmids Thereof In order to identify a recognition site in the amino acid sequence of Fas ligand, which is a region to be bound by immunoglobulins having the high apoptosis-inhibitory activity, many variants having substitution of each one of the amino acid sequence in the extracellular domain of Fas ligand as shown in FIG. 16 with underline by Ala or Gly were prepared wherein the substitution in the amino acid of Fas ligand is that the amino acids other than Ala were replaced by Ala, and Ala is replaced by Glu. Hereinafter, the Fas ligands introduced with amino acid substitution are generically referred to as Fas ligand variants. Totally, 45 Fas ligand variants were prepared wherein the variant which has one amino acid substitution that the first Tyr of the underlined in FIG. 16 replaced by Ala is referred to as B1, afterwards, the variants prepared by the sequent replacement by Ala were referred to as B2, B3, . . . and the final variant prepared by the replacement of the last Ala by Gly was referred to as B45.

At first, PCR was performed with a sense primer, EP-02 primer (SEQ ID No: 38) and an anti-sense primer, EP-03 primer (SEQ ID No: 39), using as a template the Fas ligand gene of the expression vector (i.e., human Fas ligand-BCMGSNeo) described in Example 1–6), to provide the gene fragment of Fas ligand without amino acid substitution (hereinafter, referred to as native Fas ligand to avoid confusion).

PCR was performed using TAKARA Ex Taq (trade name) (Takara Co.), whereby preparing reaction solutions according to manufacture's instructions and carrying out the 30 cycles consisting of 95° C. for one minute, 60° C. for one minute, and 72° C. for two minutes. The amplified fragments were ligated into the pCAG expression vector described in 5-1) to provide the expression vector for native Fas ligand. Ep-02 primer contains the KpnI site for ligating the above PCAG expression vector, the remaining portion of the leader sequence gene of C25 antibody, the gene sequence encoding FLAG sequence described below, and the gene sequence encoding the sequence spanning the N-terminus to Ser at position 117.

FLAG sequence comprises eight amino acids, Asp-Tyr-Lys-Asp-Asp-Asp-Asp-Lys. Tagging the sequence to a protein which is to be expressed facilitates to identify and quantify the intended protein using an antibody directed to the sequence. In the experiment, FLAG sequence was tagged at Phe of the third position from the N-terminus in the extracellular region of Fas ligand. EP-03 primer contains the gene sequence encoding the amino acid sequence downstream from Phe of the sixth position from the C-terminus of Fas ligand, the termination codon, and the BamHI site for ligating into the expression vector.

The genes encoding the Fas ligand variants were prepared by PCR mutagenesis. Specifically, the N-terminuses of the extracellular domain of Fas ligand variants were each amplified with a sense primer, MF primer (SEQ ID No: 40) corresponding to the sequence spanning from His at the fourth position to Gln at the 18th position from the N-terminus in the extracellular domain of Fas ligand, and with anti-sense primers, primers for variants introduced with the codon for Ala or Gly at the position to be substituted (the primers of variant Fas ligands B1–B45 are each described in SEQ ID Nos: 41–85). The MF primer sequence contains EcoNI site. Then, the C-terminuses of variant Fas ligands were each amplified using primers complementary to the aforementioned variant primers (the primers complementary to primers of SEQ ID Nos: 41–85 are each described in SEQ ID Nos: 86–130) as sense primers, and using an anti-sense primer, EP-03 primer. In order to prepare the 45 Fas ligand variants, 45 kinds of the aforementioned variant primers and the complement primers thereof per Fas ligand variant were synthesized. Next, PCR was again performed with EP-02 and EP-03 primers, using as templates mixtures containing equal volumes of both amplified gene fragments of the N- and C-terminuses of the Fas ligand variants. Such PCR was performed on each Fas ligand variant to provide the gene encoding the extracellular domain of each of the 45 Fas ligand variants, B1 to B45, which were introduced with the amino acid substitution in the underlined of FIG. 16.

The gene fragments of the Fas ligand variants thus obtained were inserted into the expression vector for the native Fas ligand at the EcoNI-BamHI portion in place of the native Fas ligand gene, to provide each of expression vectors for Fas ligand variants. When the vectors were transformed into host cells, and the transformants were cultured, then proteins tagged with FLAG sequence at Phe of the third position from the N-terminus of the extracellular domain of Fas ligand would be secreted into the cultured supernatants.

5-3) Expressions of Fas Ligand Variants

The plasmids prepared as shown above were each transformed into *E. coli*, and the transformants were cultured. From the cultured transformants, the plasmids were recovered and purified using Plasmid Mini Kit (trade name) (produced by QIAGEN). Subsequently, the purified expression plasmids were each transformed into COS cells (ATCC CRL1650) and the transformants were cultured to provide the supernatants including the Fas ligand variants. Thus, a mixture of 1 μg of the above expression plasmid and Lipofect ACE was added to COS cells, and the cells were cultured overnight in a condition of 5%$CO_2$ at 37° C. Then, 4 ml of an ASF medium (trade name) (produced by Ajinomoto Inc.) was added thereto, and the cells were cultured in a condition of 5%$CO_2$ at 37° C. for four days, before recovering the supernatant. Additionally, the expression plasmid for the native Fas ligand was transformed into COS cells according to a similar procedure to provide the cultured supernatant. As a negative control, pCAG vector without the Fas ligand gene was transformed into COS cells according to a procedure similar to the above, and the transformants were cultured on the same medium for the same period of time before recovering the cultured supernatant.

5-4) Relative Assay for the Fas Ligands in the Cultured Supernatant Relative concentrations of the Fas ligand variant molecules in the cultured supernatants were determined by ELISA using as standard solution the cultured supernatant including the native Fas ligand prepared as described above. Specific procedures are as follows. First, serial twofold dilutions were performed up to seven times with an ASF medium on the cultured supernatants of the native Fas ligand, each of Fas ligand variant molecules, and the negative control, to prepare totally eight kinds of solutions per supernatant. Then, the solutions with various dilutions were each added to the eight wells in a lane of a 96-well Maxisorp plate (trade name) at 50 µl/well. The eight cultured supernatants including the Fas ligand variants were each added to the wells at the eight lanes of the 3th to 10th lanes from the left hand. Since lots of plates were used in this assay, the solutions including the native Fas ligand at various concentrations were each added to the eight wells at the second lane from the left-hand of the plates, and they were used as standard for determination of the relative concentration of the Fas ligand variant added to each plate. Further, in order to examine the non-specific chromophoric strength, the solutions of the supernatant of the negative control were each added to the eight wells at the 11th lane from the-left hand. Any end lane of the plate was not used.

Figure 17:
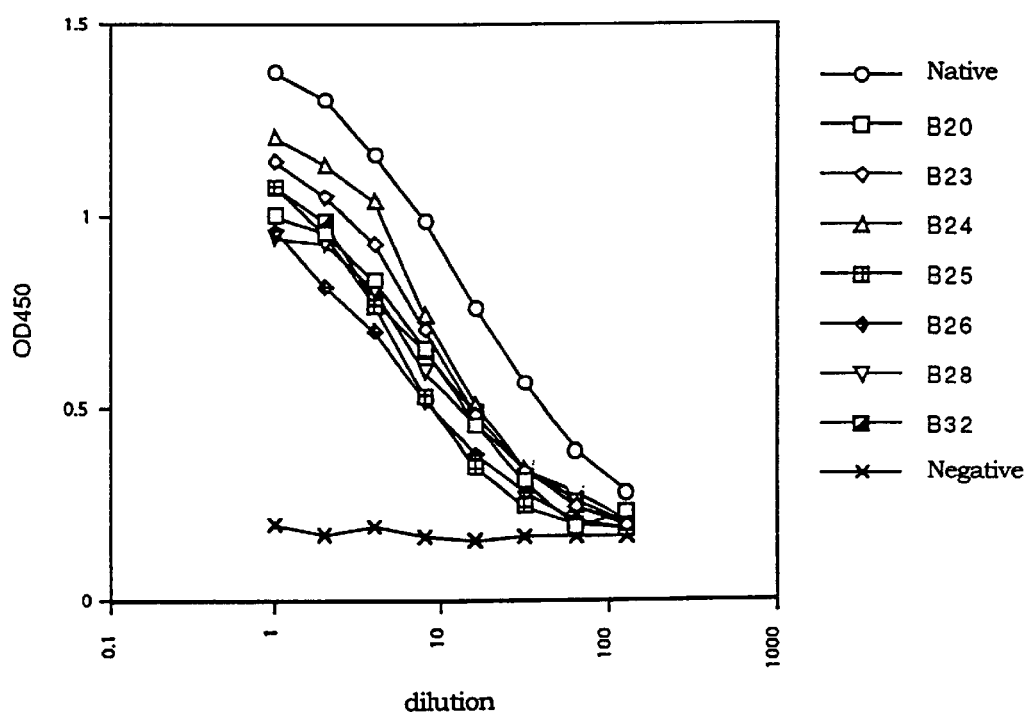
FIG. 17 shows, in part, the result of ELISA for assaying the ability of anti-FLAG antibody to recognize the expressed native Fas ligand and the Fas ligand variants.

Next, the plates were incubated overnight at 4° C., and then, the wells were rinsed three times in 0.01M PBS with 0.05% Tween20, followed by addition of PBS with 1% BSA at 100 µl/well. After incubation at 37° C. for an hour, the wells were rinsed three times in 0.01M PBS with 0.05% Tween20, and then 25 µg/ml anti-FLAGM2 mouse monoclonal antibody (trade name) (produced by Kodak) was added to each eight wells at 50 µl/well. After incubation at 37° C. for two hours, the wells were rinsed three times in 0.01M PBS with 0.05% Tween20, and then a 5,000-fold dilution of HRP-labeled anti-mouse Ig-Cκ antibody (produced by Southern Biotechonlogy Associate) in PBS with 1% BSA was added to each eight wells at 50 µl/well. Subsequently, the plates were incubated at 37° C. for an hour, and the wells were rinsed five times in 0.01M PBS with 0.05% Tween20, after which a solution of chromophoric substrate (0.5 mM TMBZ and hydrogen peroxide) was added at 50 µl/well, and when a suitable development was obtained, the reaction was quenched with the addition of 0.3N sulfuric acid at 50 µl/well, followed by determining an absorbance in each well at a wavelength of 450 nm using Microplate Reader (produced by Molecular Devices). In the wells including the cultured supernatants of the native Fas ligand and Fas ligand variant molecules, the developments were shown depending on the concentration of the anti-FLAGM2 antibody. No development was shown in the wells including the cultured supernatants of the negative control. The results in part are shown in FIG. 17. Consequently, it can be believed that the chromophoric strengths thus obtained (OD450 values) should be reflected to the concentrations of the native Fas ligand and Fas ligand variants tagged with FLAG sequence in the above cultured supernatants.

Next, relative volumes of the Fas ligand variants were determined using the chromophoric strength of the native Fas ligand as a standard. First, specific chromophoric strength in the well was determined by subtracting the $OD_{450}$ values of the wells which include negative control from the $OD_{450}$ values of the wells which include the native Fas ligand or the Fas ligand variant at the same dilution. Then, the $OD_{450}$, values were plotted against the dilutions of the cultured supernatant so as to select certain $OD_{450}$ value from the range within which the $OD_{450}$ values showed a linear decrease and every linear lines showed the same inclination, and the dilutions of the native Fas ligand and Fas ligand variant were determined from the plot against the selected $OD_{450}$ value. Finally, relative dilution for the Fas ligand variant was evaluated on the basis of the dilution for the native Fas ligand to get relative concentration for the Fas ligand variant to the native Fas ligand. Such evaluation was performed on each plate to provide the relative concentrations for all Fas ligand variants to the native Fas ligand.

5-5)

Among the relative concentrations obtained in 5-4), the lowest relative concentration was selected and used as a new standard, and the cultured supernatants having the higher concentrations of the Fas ligand variants were diluted to the same concentration as the standard with the aforementioned ASF medium. This adjusted the concentrations of the Fas ligand variants or the native Fas ligand in all solutions to the same ones.

Example 6

Analysis of Site Recognized by the Anti-Fas Ligand Antibody 6-1) Preparation of Solutions of Anti-Fas Ligand Monoclonal Antibodies Anti-Fas ligand monoclonal antibodies produced by the hybridomas, NOK1, NOK2, and NOK3 described in the international publication WO96/29350 (hereinafter may be referred to as NOK1, NOK2, and NOK3 immunoglobulin (antibody), respectively; they generically may be referred to as NOK antibody) were prepared and purified as described below.

First, hybridomas NOK1, NOK2, and NOK3 were each grew on an RPMI1640 medium supplemented with 10% FCS to $3 \times 10^7$ cells. Such $3 \times 10^7$ cells were prepared in a scale which comprises culturing 30 ml of the cultured cells in a 75 cm² culture flask (Pharcom). Specifically, starting from the culture at $2 \times 10^5$ cells/ml, the cells were recovered when reached $1 \times 10^6$ cells/ml.

The recovered hybridomas were suspended in 1.5 ml of PBS, and the 0.5 ml portions of the suspensions ($1 \times 10^7$ cells) were administered per nude mouse intra-abdominally. After feeding for 10–18 days, the ascites deposited in the visceral cavity were recovered. The 10 ml portions of the ascites were purified. The purification was performed firstly by salting-out with ammonium sulfate thereby adding 10 ml of a saturated solution of ammonium sulfate dropwise to the equal volume of the ascites to combine together. After stirring at 4° C. for two hours, the mixtures were centrifuged at 10,000 g for 15 minutes. The supernatants were removed, and the sediments were dissolved in 5 ml of PBS. Then, the solutions were dialyzed overnight against 3 liters of PBS.

For NOK1 and NOK2 antibodies, only the protein G-adsorbed IgGs were purified by FPLC system using protein G column (trade name) (produced by Pharmasia) after recovering the dialyzed samples. The resultant samples were further dialyzed overnight against PBS. On the following day, concentration and purity of the protein were determined. For NOK3 antibody, gel-filtration was performed on the recovered dialyzed samples by FPLC system using Superdex200 column (trade name) (produced by Pharmasia) for gel-filtration to provide IgM, which had been eluted at void volume. Concentration and purity of the IgM were also determined.

The quantification of the protein was performed using a protein quantification reagent produced by BIO RAD. The procedure was in accordance with the protocol accompanied therein. SDS-PAGE electrophoresis was performed on the purified immunoglobulin in the reductive conditions, followed by CBB stain, observing no band of contaminant proteins but bands assuming to be the heavy chain and the light chain.

Serial twofold dilutions were performed with PBS containing 1% BSA on the purified NOK antibodies and the three purified humanized NOK2 antibodies (RNOK201, RNOK202, and RNOK203), specifically, using, as a starting liquid, 10 µg/ml for NOK1 antibody, 50 µg/ml for NOK2 antibody, 0.1 µg/ml for NOK3 antibody, 3.57 µg/ml for RNOK201, 1.86 µg/ml for RNOK202, and 3.35 µg/ml for RNOK203, so as to prepare totally eight kinds of antibody solutions per antibody.

6-2) Identification of the Site Recognized by Each NOK Antibody with the Fas Ligand Variants Solutions of 29 of the Fas ligand variants prepared according to the procedure of Example 5-5), as well as the native Fas ligand were used to examine the site on Fas ligand to be bound to NOK antibody and humanized NOK2 antibody by ELISA as described below. In this experiment, the relative chromophoric strength for each Fas ligand variant on the basis of that ($OD_{450}$ value) for the native Fas ligand was determined by treatment with the same concentration of NOK antibody or humanized NOK2 antibody.

Figure 18:
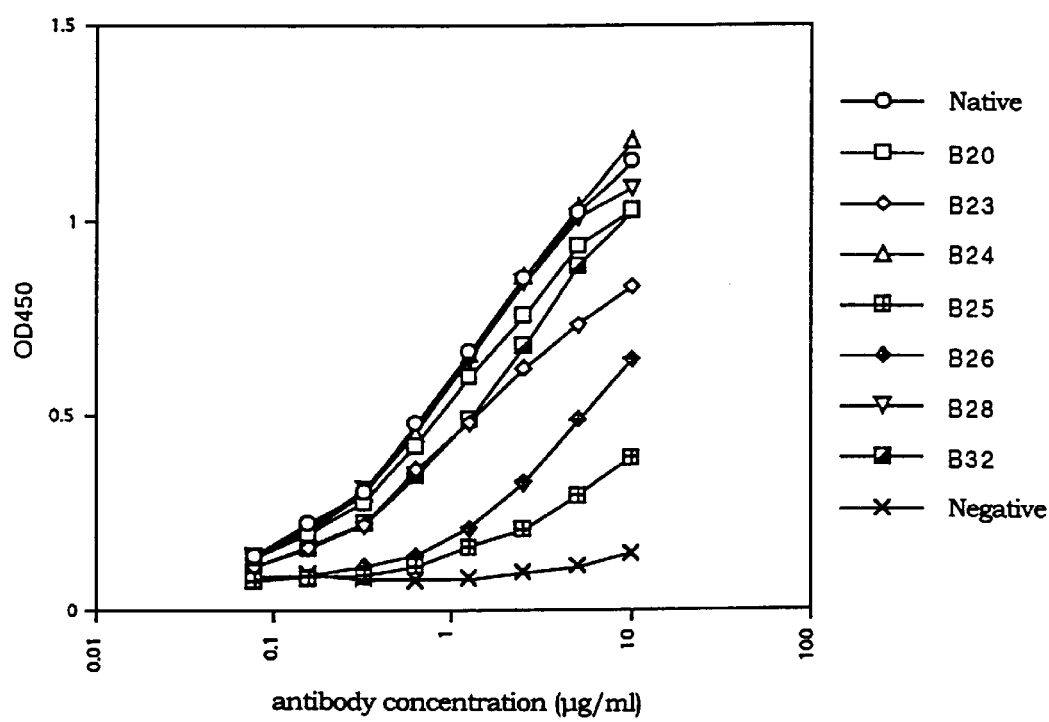
FIG. 18 shows, in part, the result of ELISA for assaying the ability of anti-Fas ligand antibody (NOK1 antibody) to recognize the expressed native Fas ligand and the Fas ligand variants.

First, the solutions with the native Fas ligand and the Fas ligand variants as well as the solution of negative control, as prepared in 5-5) were each added to the eight wells in a lane of a 96-well Maxisorp plate (trade name) at 50 µl/well. The relationship in the location of lanes is the same as in 5-4). After incubation overnight at 4° C., the wells were rinsed three times in 0.01M PBS with 0.05% Tween20, and PBS with 1% BSA was added thereto at 100 µl/well. After incubation at 37° C. for an hour, the wells were rinsed three times in 0.01M PBS with 0.05% Tween20. Then, the solutions with various concentrations of NOK and humanized NOK2 antibodies prepared previously were each added to the eight wells at 50 µl/well. Subsequently, after incubation at 37° C. for two hours, the wells were rinsed three times in 0.01M PBS with 0.05% Tween20, and then a 5,000-fold dilution of HRP-labeled anti-mouse Ig-Cκ antibody or HRP-labeled anti-human Ig-Cκ antibody (both are produced by Southern Biotechonlogy Associate) in PBS with 1% BSA was added thereto at 50 µl/well. After incubation at 37° C. for an hour, the wells were rinsed three times in 0.01M PBS with 0.05% Tween20, and then a solution of chromophoric substrate (0.5 mM TMBZ and hydrogen peroxide) was added at 50 µl/well, after which, when a suitable development was obtained, the reaction was quenched with the addition of 0.3N sulfuric acid at 50 µl/well, followed by determining an absorbance in each well at a wavelength of 450 nm using Microplate Reader (produced by Molecular Devices). In the wells including the cultured supernatant of the native Fas ligand, the developments were shown depending on the concentration of NOK and humanized NOK2 antibodies. No development was shown in the wells including the solution of the negative control. The results in part are shown in FIG. 18. Consequently, it can be believed that the chromophoric strengths thus obtained (OD450 values) should be reflected to the specific binding of NOK and humanized NOK2 antibodies to the native Fas ligand in the aforementioned solutions.

Next, relative binding activities of NOK and humanized NOK2 antibodies to each Fas ligand variant were examined on the basis of the chromophoric strength for the native Fas ligand. First, specific chromophoric strength in the well was determined by subtracting the $OD_{450}$ values of the wells in which the native Fas ligand or the Fas ligand variant was added to the wells including negative control from the $OD_{450}$ values of the wells including the native Fas ligand or the Fas ligand variant at the same dilution. Then, the $OD_{450}$ values were plotted against the dilutions of the cultured supernatant so as to select certain $OD_{450}$ value from the range within which the $OD_{450}$ values showed a linear decrease and every linear lines showed the same inclination, and the concentrations of NOK and humanized NOK2 antibodies were determined from the plots against the selected $OD_{450}$ value. Finally, relative concentrations of NOK and humanized NOK2 antibodies for each Fas ligand variant were evaluated on the basis of the antibody concentration for the native Fas ligand to provide relative binding activities of NOK and humanized NOK2 antibodies to each Fas ligand variant.

The relative binding activities of NOK and humanized NOK2 antibodies to each Fas ligand variant thus obtained are summarized in FIGS. 19 and 20.

As shown in these figures, the decrease in the binding activity of NOK2 antibody was observed to the range from Arg at position 198 to Met at position 238 from the N-terminus of Fas ligand, and especially significant decreases were observed in Arg at position 198, Gly at position 199, Leu at position 205, Gln at position 220, Asp at position 221, Leu at position 222, Met at position 230, Gln at position 237 and Met at position 238, which numerical order is in accordance with Nagata, et al. Int. Immunology, vol. 6, p.1567–1574, 1994.

The three types of humanized NOK2 antibodies, RNOK201, RNOK202, and RNOK203 have nearly the same binding pattern, and the decrease in the binding activity was observed to the range from Arg at position 198 to Met at position 238, and especially significant decreases were observed in Arg at position 198, Gly at position 199, Leu at position 205, Gln at position 220, Asp at position 221, Leu at position 222, Lys at position 228, Met at position 230, Gln at position 237, and Met at position 238. On the other hand, this pattern was different from that for NOK2 in Arg at position 198, Lys at position 228, and Met at position 230, and these differences may be due to humanization of the former. From this findings, it is believed that the higher apoptosis-inhibitory activity of RNOK2 antibody than that of NOK2 antibody (as described in Example 4) should be due to alteration of quality and strength of the binding to the aforementioned recognized amino acids by the humanization, to cause increase in the binding activity to Fas ligand.

In the case of NOK1 antibody, the decrease in binding activity was observed from Gly at position 199 to Gln at position 237, and especially in Gly at position 199, Asn at position 203, Leu at position 205, Tyr at position 218, Gln at position 220, Asp at position 221, Leu at position 222, Gly at position 227, Lys at position 228, and Gln at position 237. In the case of NOK3 antibody, the decrease in binding activity was observed from Gly at position 199 to Met at position 238, and especially, in Gly at position 199, Gln at position 200, Asn at position 203, Leu at position 205, Tyr at position 212, Gln at position 220, Asp at position 221, Leu at position 222, Lys at position 228, Met at position 230, Gin at position 237, and Met at position 238.

The above NOK antibody is a monoclonal antibody obtained by immunization of mouse with Fas ligand-expressing cells as described in Example 1 of the Japanese Patent Application No. 303492/1995. NOK and humanized NOK2 antibodies are ones having the high inhibitory activity against apoptosis induced in the Fas-expressing cells via the interaction of Fas-Fas ligand, as shown in Examples 1 and 2 of the international publication WO96/29350 and in Example 4 herein. In other words, NOK antibody is the first anti-Fas ligand monoclonal antibody which has been obtained by immunization with Fas ligand having the native structure, and which has been shown a high apoptosis-inhibitory activity. These monoclonal antibodies are different from each other in terms of the amino acid sequences of the CDRs (complementary-determining regions), and the class and subclass, and therefore, they are entirely independent. Since the different antibodies recognize the broad region of the amino acid sequence of Fas ligand between Arg at position 198 to Met at position 238, as described above, it can be concluded that the anti-Fas ligand antibodies having the high apoptosis-inhibitory activity should generally recognizes the amino acid residues within the aforementioned region as a recognition site. Thus, the site must be a predominant region in the Fas ligand molecule, which can elicit an anti-Fas ligand antibody having the high apoptosis-inhibitory activity. Further, the above site is important for Fas ligand to exert apoptosis-inducing activity, and therefore, agents which can recognize and bind to the site may show apoptosis-inhibitory activity.

Example 7

Mapping of the Site Recognized by NOK1, NOK2, and NOK4 Antibodies Using Synthetic Peptides 1. Peptide library was prepared, which composes of 34 kinds of 15-mer peptides which comprises the 15-mer peptide starting from the N-terminus of the extracellular domain of Fas ligand (Gln at position 103 from the N-terminus of Fas ligand), the 15-mer peptide from 6 to 20 positions, the 15-mer from 11 to 25, 15-mer from 16 to 30, and the likes which were synthesized in turn by starting from downstream by five mers from the foregoing one, using PepSet (trade mark, produced by Chiron).

2. Positions in Fas ligand to which Fas ligand-antibodies were reactive, were identified using the cultured supernatants of NOK1, NOK2, and NOK4 hybridomas according to the following manner.

(1) Each well on a 96-well plate (Maxisorp, trade name, produced by Nunc) was filled up with 4-fold dilution of Blocking solution (BlockAce, produced by Dainippon Pharmaceutical Con.), and the pin of PepSet in which the synthetic peptides were immobilized on its tip was immersed into each well on the plate to block the tip of the pin for two hours at room temperature.

(2) After completion of the blocking, the pin of PepSet was removed and washed with PBS.

(3) The cultured supernatants of the NOK1, NOK2, and NOK4 hybridomas were dispensed into a fresh 96-well plate at 100 μl/well. Antibody solution attached to PepSet was used as control. PepSet contains a pin as for both positive and negative control, and the antibody solutions against the same.

(4) Then, the pins were immersed into each well on the plate described in the aforementioned item (3), and the plate was reacted for two hours at room temperature.

(5) After removal of the pins from the plate of the aforementioned item (4), the pins were transferred to pads containing PBS to wash three times by shaking for 10 minutes.

(6) 1000-Fold dilution of HRP (horseradish peroxidase)-labeled anti-mouse IgG (produced by Cappel) with PBS was dispensed into a fresh 96-well plate at 100 μl/well, and the pins of PepSet were immersed into the wells to allow the reaction for two hours at room temperature.

(7) After the reaction, the pins of PepSet were removed, and washed three times in PBS by shaking for 10 minutes.

(8) Substrate solution having the following composition was portioned into a fresh 96-well plate at 100 μl/well, and the pins of PepSet were immersed into the wells to allow the reaction for 20 minutes at room temperature.

Composition of the substrate solution:

0.4 mg/ml OPD, 0.4 μl/ml 30% $H_2O_2$, 0.1M citrate phosphate buffer (pH5.1).

(9) After removal of the pins of PepSet from the plate, 50 μl of 2N $H_2SO_4$ was added to the wells to quench the reaction.

(10) Absorbance in the well liquids on the plate was determined by a plate reader (produced by BIO RAD).

(11) As a result, color changes by the enzymatic reaction of HRP conjugated to the peptide immobilized on the pins were observed in the wells immersed with the pins immobilized with the peptides, LYFVYSKVYFRGQSC (SEQ ID NO:133), SKVYFRGQSCNNLPL (SEQ ID NO:134), and RGQSCNNLPLSHKVY (SEQ ID NO:137), (i.e., 188–202 positions, 193–207 positions, 198–212 positions from the N-terminus of Fas ligand) for the cultured supernatants of NOK1 and NOK4 hybridomas, and in the wells with YPQDLVMMEGK-MMSY (SEQ ID NO:136) VMMEGKMMSYCTTGQ (SEQ ID NO:137), and KMMSYCTTGQMWARS (SEQ ID NO:138), for the NOK2 hybridoma (218–232 positions, 223–237 positions, 228–242 positions from the N-terminus of Fas ligand). Thus, it has been shown that the anti-Fas ligand antibody produced by NOK1 and NOK4 hybridomas recognize the region, LYFVYSKVY-FRGQSCNNLPLSHKVY (SEQ ID NO:139), of Fas ligand, whereas the anti-Fas ligand antibody of NOK2 hybridoma recognizes the region, YPQDLVMMEGK-MMSYCTTGQMWARS (SEQ ID NO:140), of Fas ligand.

Analysis of the site recognized by anti-Fas ligand antibodies using the Fas ligand variants as described in Example 6 shows that most of the sequences of the synthetic peptides which were observed to be reactive in this Example encompasses the aforementioned recognition site against anti-Fas ligand antibody as identified in the analysis. This shows again that the above site contains amino acids which play an important role for antigen-recognition/binding.

Example 8

Modelling for Fas Ligand

In order to examine the position at which the site recognized by the anti-Fas ligand antibodies resides on Fas ligand as identified in Example 6, modelling for Fas ligand was performed. Fas ligand is understood to belong to a TNF family, which includes TNF-α and TNF-β, and to form a trimer similar to TNF (Manuel C. P., et al., Molecular Immunology, vol. 32 (10), p.761–772, 1996). Thus, the model for the Fas ligand trimer was constructed by a molecular modelling using a computer with TNF as a template, and the examination was performed to seek for the position at which the site recognized by the anti-Fas ligand antibodies resides on Fas ligand which plays an important role to the apoptosis-inhibitory activity which had been confirmed in the binding experiment between the anti-Fas ligand antibody and the Fas ligand variants First, in the modelling for the Fas ligand trimer, the modelling was performed on its monomer. Specifically, Modeler (Molecular Simulations Inc.), a software for modelling which runs on Silicongraphics was utilized using as templates the three-dimensional structures of TNF-α and TNF-β, which are known to show the high homology to Fas ligand. The amino acid sequence of the extracellular domain of Fas ligand was aligned with those of TNF-α and TNF-β as shown in FIG. 21, and the results were inputted into Modeler. As templates, the data for the coordinates of TNF-α (PDB ID:1TNF) and TNF-β (PDB ID:1TNR) from Brookhaven Protein Data Bank (PDB) was inputted. Since PDB ID:1TNF represents a data for the crystal structure of the TNF-α trimer whereas PDB ID:1TNR represents a data for the crystal structure of the complex comprising TNF-β and TNF receptor 55, only data for the TNF-α monomer and TNF-β monomer was extracted from them. According to the Modeler's instructions, the modelling was performed modifying the conditions to obtain 10 models, such that Model No. 3 was selected as a Fas ligand model, which is lower in the energy following energy-minimizing calculation, the probability density function (i.e., PDF), and the value of Root Mean Square of all atoms (i.e., RMS).

Then, on the basis of the model for Fas ligand thus obtained, Fas ligand trimer was constructed. Specifically, the model for the above Fas ligand monomer was superimposed on the atomic coordinate of each segment of TNF monomer of the above TNF-α trimer, PDB ID:1TNF using QUANTA/CHARMm (produced by Molecular Simulations Inc.), a software running on Silicongraphics, and after correcting the bad contact, the energy-minimizing calculation was performed, so as to construct the model for the Fas ligand trimer. The monomers which form the trimer are each referred to as Fas ligand A molecule, B molecule, and C molecule, or A segment, B segment, and C segment. Data for the atomic coordinates (PDB format) is shown in Table 1.

TABLE 1

Atomic coordinates of the higher-order structure of Fas ligand

| Atom species | | Amino acid residues | | # | X | Y | Z | OCC | B |
|---|---|---|---|---|---|---|---|---|---|
| ATOM 1 | N | ARG | A | 1 | −1.389 | 71.752 | −6.218 | 1.00 | 5.73 |
| ATOM 2 | CA | ARG | A | 1 | −1.823 | 72.707 | −5.191 | 1.00 | 5.73 |
| ATOM 3 | C | ARG | A | 1 | −0.735 | 72.796 | −4.140 | 1.00 | 5.73 |
| ATOM 4 | O | ARG | A | 1 | 0.417 | 72.930 | −4.523 | 1.00 | 5.73 |
| ATOM 5 | CB | ARG | A | 1 | −3.207 | 72.348 | −4.642 | 1.00 | 5.73 |
| ATOM 6 | CG | ARG | A | 1 | −4.345 | 72.778 | −5.564 | 1.00 | 5.73 |
| ATOM 7 | CD | ARG | A | 1 | −5.708 | 72.545 | −4.915 | 1.00 | 5.73 |
| ATOM 8 | NE | ARG | A | 1 | −6.787 | 72.989 | −5.795 | 1.00 | 5.73 |
| ATOM 9 | CZ | ARG | A | 1 | −7.819 | 72.166 | −6.086 | 1.00 | 5.73 |
| ATOM 10 | NH1 | ARG | A | 1 | −8.790 | 72.608 | −6.883 | 1.00 | 5.73 |
| ATOM 11 | NH2 | ARG | A | 1 | −7.865 | 70.928 | −5.587 | 1.00 | 5.73 |
| ATOM 12 | 1H | ARG | A | 1 | −2.006 | 71.784 | −7.053 | 1.00 | 20.00 |
| ATOM 13 | 2H | ARG | A | 1 | −0.414 | 72.022 | −6.470 | 1.00 | 20.00 |
| ATOM 14 | 3H | ARG | A | 1 | −1.374 | 70.790 | −5.820 | 1.00 | 20.00 |
| ATOM 15 | HE | ARG | A | 1 | −6.744 | 73.925 | −6.147 | 1.00 | 20.00 |
| ATOM 16 | 1HH1 | ARG | A | 1 | −9.573 | 72.032 | −7.119 | 1.00 | 20.00 |
| ATOM 17 | 2HH1 | ARG | A | 1 | −8.753 | 73.531 | −7.268 | 1.00 | 20.00 |
| ATOM 18 | 1HH2 | ARG | A | 1 | −8.635 | 70.316 | −5.767 | 1.00 | 20.00 |
| ATOM 19 | 2HH2 | ARG | A | 1 | −7.118 | 70.572 | −5.022 | 1.00 | 20.00 |
| ATOM 20 | N | LYS | A | 2 | −1.115 | 72.708 | −2.849 | 1.00 | 19.49 |
| ATOM 21 | CA | LYS | A | 2 | −0.107 | 72.844 | −1.798 | 1.00 | 19.49 |
| ATOM 22 | C | LYS | A | 2 | 0.758 | 71.626 | −1.728 | 1.00 | 19.49 |
| ATOM 23 | O | LYS | A | 2 | 0.263 | 70.508 | −1.652 | 1.00 | 19.49 |
| ATOM 24 | CB | LYS | A | 2 | −0.703 | 73.923 | −0.403 | 1.00 | 19.49 |
| ATOM 25 | CG | LYS | A | 2 | −1.476 | 74.314 | −0.180 | 1.00 | 19.49 |
| ATOM 26 | CD | LYS | A | 2 | −2.836 | 74.287 | −0.849 | 1.00 | 19.49 |
| ATOM 27 | CE | LYS | A | 2 | −3.607 | 75.534 | −0.513 | 1.00 | 19.49 |
| ATOM 28 | NZ | LYS | A | 2 | −3.410 | 76.656 | −1.439 | 1.00 | 19.49 |
| ATOM 29 | H | LYS | A | 2 | −2.031 | 72.441 | −2.559 | 1.00 | 20.00 |
| ATOM 30 | 1HZ | LYS | A | 2 | −4.257 | 77.263 | −1.299 | 1.00 | 20.00 |
| ATOM 31 | 2HZ | LYS | A | 2 | −2.532 | 77.166 | −1.216 | 1.00 | 20.00 |
| ATOM 32 | 3HZ | LYS | A | 2 | −3.404 | 76.329 | −2.424 | 1.00 | 20.00 |
| ATOM 33 | N | VAL | A | 3 | 2.059 | 71.908 | −1.797 | 1.00 | 4.59 |
| ATOM 34 | CA | VAL | A | 3 | 3.037 | 70.833 | −1.778 | 1.00 | 4.59 |
| ATOM 35 | C | VAL | A | 3 | 4.182 | 71.303 | −0.907 | 1.00 | 4.59 |
| ATOM 36 | O | VAL | A | 3 | 4.460 | 72.496 | −0.816 | 1.00 | 4.59 |
| ATOM 37 | CB | VAL | A | 3 | 3.496 | 70.493 | −3.215 | 1.00 | 4.59 |
| ATOM 38 | CG1 | VAL | A | 3 | 4.575 | 69.408 | −3.278 | 1.00 | 4.59 |
| ATOM 39 | CG2 | VAL | A | 3 | 2.311 | 70.071 | −4.087 | 1.00 | 4.59 |
| ATOM 40 | H | VAL | A | 3 | 2.389 | 72.853 | −1.800 | 1.00 | 20.00 |
| ATOM 41 | N | ALA | A | 4 | 4.801 | 70.306 | −0.271 | 1.00 | 5.22 |
| ATOM 42 | CA | ALA | A | 4 | 6.025 | 70.518 | 0.478 | 1.00 | 5.22 |
| ATOM 43 | C | ALA | A | 4 | 6.854 | 69.270 | 0.324 | 1.00 | 5.22 |
| ATOM 44 | O | ALA | A | 4 | 6.323 | 68.166 | 0.274 | 1.00 | 5.22 |
| ATOM 45 | CB | ALA | A | 4 | 5.723 | 70.722 | 1.963 | 1.00 | 5.22 |
| ATOM 46 | H | ALA | A | 4 | 4.466 | 69.365 | −0.377 | 1.00 | 20.00 |
| ATOM 47 | N | HIS | A | 5 | 8.165 | 69.492 | 0.259 | 1.00 | 4.76 |
| ATOM 48 | CA | HIS | A | 5 | 9.087 | 68.363 | 0.340 | 1.00 | 4.76 |
| ATOM 49 | C | HIS | A | 5 | 10.319 | 68.911 | 0.995 | 1.00 | 4.76 |
| ATOM 50 | O | HIS | A | 5 | 10.920 | 69.784 | 0.402 | 1.00 | 4.76 |
| ATOM 51 | CB | HIS | A | 5 | 9.444 | 67.835 | −1.057 | 1.00 | 4.76 |
| ATOM 52 | CG | HIS | A | 5 | 10.391 | 66.663 | −0.935 | 1.00 | 4.76 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 53 | ND1 | HIS A | 5 | 9.969 | 65.394 | −0.856 | 1.00 | 4.76 |
| ATOM 54 | CD2 | HIS A | 5 | 11.788 | 66.678 | −0.853 | 1.00 | 4.76 |
| ATOM 55 | CE1 | HIS A | 5 | 11.082 | 64.614 | −0.722 | 1.00 | 4.76 |
| ATOM 56 | NE2 | HIS A | 5 | 12.201 | 65.396 | −0.719 | 1.00 | 4.76 |
| ATOM 57 | H | HIS A | 5 | 8.515 | 70.432 | 0.202 | 1.00 | 20.00 |
| ATOM 58 | HD1 | HIS A | 5 | 9.032 | 65.102 | −0.893 | 1.00 | 20.00 |
| ATOM 59 | N | LEU A | 6 | 10.630 | 68.419 | 2.199 | 1.00 | 6.04 |
| ATOM 60 | CA | LEU A | 6 | 11.725 | 68.990 | 2.981 | 1.00 | 6.04 |
| ATOM 61 | C | LEU A | 6 | 12.794 | 67.980 | 3.272 | 1.00 | 6.04 |
| ATOM 62 | O | LEU A | 6 | 12.501 | 66.802 | 3.412 | 1.00 | 6.04 |
| ATOM 63 | CB | LEU A | 6 | 11.244 | 69.442 | 4.348 | 1.00 | 6.04 |
| ATOM 64 | CG | LEU A | 6 | 10.107 | 70.438 | 4.321 | 1.00 | 6.04 |
| ATOM 65 | CD1 | LEU A | 6 | 9.730 | 70.798 | 5.745 | 1.00 | 6.04 |
| ATOM 66 | CD2 | LEU A | 6 | 10.447 | 71.671 | 3.495 | 1.00 | 6.04 |
| ATOM 67 | H | LEU A | 6 | 10.081 | 67.684 | 2.590 | 1.00 | 20.00 |
| ATOM 68 | N | THR A | 7 | 14.024 | 68.489 | 3.408 | 1.00 | 3.03 |
| ATOM 69 | CA | THR A | 7 | 15.080 | 67.561 | 3.795 | 1.00 | 3.03 |
| ATOM 70 | C | THR A | 7 | 15.620 | 67.841 | 5.183 | 1.00 | 3.03 |
| ATOM 71 | O | THR A | 7 | 15.443 | 68.922 | 5.735 | 1.00 | 3.03 |
| ATOM 72 | CB | THR A | 7 | 16.190 | 67.576 | 2.745 | 1.00 | 3.03 |
| ATOM 73 | OG1 | THR A | 7 | 16.533 | 68.925 | 2.406 | 1.00 | 3.03 |
| ATOM 74 | CG2 | THR A | 7 | 15.777 | 66.803 | 1.489 | 1.00 | 3.03 |
| ATOM 75 | H | THR A | 7 | 14.229 | 69.466 | 3.302 | 1.00 | 20.00 |
| ATOM 76 | HG1 | THR A | 7 | 17.405 | 68.899 | 2.033 | 1.00 | 20.00 |
| ATOM 77 | N | GLY A | 8 | 16.265 | 66.799 | 5.735 | 1.00 | 3.29 |
| ATOM 78 | CA | GLY A | 8 | 16.871 | 66.977 | 7.054 | 1.00 | 3.29 |
| ATOM 79 | C | GLY A | 8 | 18.225 | 67.663 | 7.023 | 1.00 | 3.29 |
| ATOM 80 | O | GLY A | 8 | 19.042 | 67.442 | 6.137 | 1.00 | 3.29 |
| ATOM 81 | H | GLY A | 8 | 16.315 | 65.930 | 5.237 | 1.00 | 20.00 |
| ATOM 82 | N | LYS A | 9 | 18.437 | 68.502 | 8.052 | 1.00 | 6.71 |
| ATOM 83 | CA | LYS A | 9 | 19.711 | 69.220 | 8.111 | 1.00 | 6.71 |
| ATOM 84 | C | LYS A | 9 | 20.941 | 68.381 | 8.395 | 1.00 | 6.71 |
| ATOM 85 | O | LYS A | 9 | 21.247 | 68.035 | 9.530 | 1.00 | 6.71 |
| ATOM 86 | CB | LYS A | 9 | 19.686 | 70.355 | 9.130 | 1.00 | 6.71 |
| ATOM 87 | CG | LYS A | 9 | 18.723 | 71.483 | 8.796 | 1.00 | 6.71 |
| ATOM 88 | CD | LYS A | 9 | 18.966 | 72.700 | 9.685 | 1.00 | 6.71 |
| ATOM 89 | CE | LYS A | 9 | 18.067 | 73.876 | 9.307 | 1.00 | 6.71 |
| ATOM 90 | NZ | LYS A | 9 | 18.085 | 74.872 | 10.386 | 1.00 | 6.71 |
| ATOM 91 | H | LYS A | 9 | 17.702 | 68.659 | 8.715 | 1.00 | 20.00 |
| ATOM 92 | 1HZ | LYS A | 9 | 17.311 | 75.551 | 10.252 | 1.00 | 20.00 |
| ATOM 93 | 2HZ | LYS A | 9 | 17.856 | 74.397 | 11.295 | 1.00 | 20.00 |
| ATOM 94 | 3HZ | LYS A | 9 | 19.002 | 75.344 | 10.467 | 1.00 | 20.00 |
| ATOM 95 | N | SER A | 10 | 21.685 | 68.152 | 7.300 | 1.00 | 13.61 |
| ATOM 96 | CA | SER A | 10 | 23.041 | 67.594 | 7.392 | 1.00 | 13.61 |
| ATOM 97 | C | SER A | 10 | 23.911 | 68.121 | 8.519 | 1.00 | 13.61 |
| ATOM 98 | O | SER A | 10 | 24.481 | 67.396 | 9.326 | 1.00 | 13.61 |
| ATOM 99 | CB | SER A | 10 | 23.781 | 67.790 | 6.072 | 1.00 | 13.61 |
| ATOM 100 | OG | SER A | 10 | 22.916 | 67.441 | 4.994 | 1.00 | 13.61 |
| ATOM 101 | H | SER A | 10 | 21.215 | 68.222 | 6.416 | 1.00 | 20.00 |
| ATOM 102 | HG | SER A | 10 | 23.463 | 67.394 | 4.221 | 1.00 | 20.00 |
| ATOM 103 | N | ASN A | 11 | 23.994 | 69.458 | 8.546 | 1.00 | 8.64 |
| ATOM 104 | CA | ASN A | 11 | 24.685 | 70.004 | 9.707 | 1.00 | 8.64 |
| ATOM 105 | C | ASN A | 11 | 23.743 | 70.544 | 10.757 | 1.00 | 8.64 |
| ATOM 106 | O | ASN A | 11 | 23.681 | 71.729 | 11.057 | 1.00 | 8.64 |
| ATOM 107 | CB | ASN A | 11 | 25.790 | 70.991 | 9.310 | 1.00 | 8.64 |
| ATOM 108 | CG | ASN A | 11 | 27.028 | 70.293 | 8.740 | 1.00 | 8.64 |
| ATOM 109 | OD1 | ASN A | 11 | 27.932 | 70.940 | 8.230 | 1.00 | 8.64 |
| ATOM 110 | ND2 | ASN A | 11 | 27.071 | 68.952 | 8.839 | 1.00 | 8.64 |
| ATOM 111 | H | ASN A | 11 | 23.538 | 70.027 | 7.862 | 1.00 | 20.00 |
| ATOM 112 | 1HD2 | ASN A | 11 | 26.361 | 68.361 | 9.233 | 1.00 | 20.00 |
| ATOM 113 | 2HD2 | ASN A | 11 | 27.896 | 68.522 | 8.476 | 1.00 | 20.00 |
| ATOM 114 | N | SER A | 12 | 23.018 | 69.574 | 11.324 | 1.00 | 14.76 |
| ATOM 115 | CA | SER A | 12 | 22.324 | 69.884 | 12.564 | 1.00 | 14.76 |
| ATOM 116 | C | SER A | 12 | 23.000 | 69.149 | 13.696 | 1.00 | 14.76 |
| ATOM 117 | O | SER A | 12 | 23.766 | 68.217 | 13.483 | 1.00 | 14.76 |
| ATOM 118 | CB | SER A | 12 | 20.841 | 69.520 | 12.478 | 1.00 | 14.76 |
| ATOM 119 | OG | SER A | 12 | 20.117 | 70.231 | 13.487 | 1.00 | 14.76 |
| ATOM 120 | H | SER A | 12 | 23.078 | 68.625 | 11.004 | 1.00 | 20.00 |
| ATOM 121 | HG | SER A | 12 | 19.207 | 70.232 | 13.210 | 1.00 | 20.00 |
| ATOM 122 | N | ARG A | 13 | 22.710 | 69.622 | 14.916 | 1.00 | 14.62 |
| ATOM 123 | CA | ARG A | 13 | 23.259 | 68.873 | 16.045 | 1.00 | 14.62 |
| ATOM 124 | C | ARG A | 13 | 22.596 | 67.516 | 16.200 | 1.00 | 14.62 |
| ATOM 125 | O | ARG A | 13 | 21.487 | 67.300 | 15.738 | 1.00 | 14.62 |
| ATOM 126 | CB | ARG A | 13 | 23.140 | 69.684 | 17.336 | 1.00 | 14.62 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 127 | CG | ARG A | 13 | 23.873 | 71.022 | 17.256 | 1.00 | 14.62 |
| ATOM 128 | CD | ARG A | 13 | 23.890 | 71.764 | 18.596 | 1.00 | 14.62 |
| ATOM 129 | NE | ARG A | 13 | 24.741 | 72.954 | 18.530 | 1.00 | 14.62 |
| ATOM 130 | CZ | ARG A | 13 | 26.079 | 72.866 | 18.718 | 1.00 | 14.62 |
| ATOM 131 | NH1 | ARG A | 13 | 26.832 | 73.955 | 18.580 | 1.00 | 14.62 |
| ATOM 132 | NH2 | ARG A | 13 | 26.647 | 71.703 | 19.037 | 1.00 | 14.62 |
| ATOM 133 | H | ARG A | 13 | 21.993 | 70.317 | 14.993 | 1.00 | 20.00 |
| ATOM 134 | HE | ARG A | 13 | 24.299 | 73.819 | 18.289 | 1.00 | 20.00 |
| ATOM 135 | 1HH1 | ARG A | 13 | 27.824 | 73.921 | 18.702 | 1.00 | 20.00 |
| ATOM 136 | 2HH1 | ARG A | 13 | 26.415 | 74.834 | 18.348 | 1.00 | 20.00 |
| ATOM 137 | 1HH2 | ARG A | 13 | 27.634 | 71.610 | 19.161 | 1.00 | 20.00 |
| ATOM 138 | 2HH2 | ARG A | 13 | 26.077 | 70.890 | 19.157 | 1.00 | 20.00 |
| ATOM 139 | N | SER A | 14 | 23.304 | 66.613 | 16.896 | 1.00 | 5.58 |
| ATOM 140 | CA | SER A | 14 | 22.754 | 65.263 | 17.042 | 1.00 | 5.58 |
| ATOM 141 | C | SER A | 14 | 21.436 | 65.109 | 17.792 | 1.00 | 5.58 |
| ATOM 142 | O | SER A | 14 | 20.787 | 64.074 | 17.725 | 1.00 | 5.58 |
| ATOM 143 | CB | SER A | 14 | 23.817 | 64.357 | 17.654 | 1.00 | 5.58 |
| ATOM 144 | OG | SER A | 14 | 25.103 | 64.770 | 17.172 | 1.00 | 5.58 |
| ATOM 145 | H | SER A | 14 | 24.270 | 66.737 | 17.123 | 1.00 | 20.00 |
| ATOM 146 | HG | SER A | 14 | 25.612 | 63.974 | 17.078 | 1.00 | 20.00 |
| ATOM 147 | N | MET A | 15 | 21.074 | 66.181 | 18.524 | 1.00 | 11.01 |
| ATOM 148 | CA | MET A | 15 | 19.750 | 66.148 | 19.147 | 1.00 | 11.01 |
| ATOM 149 | C | MET A | 15 | 18.545 | 66.382 | 18.225 | 1.00 | 11.01 |
| ATOM 150 | O | MET A | 15 | 17.669 | 65.533 | 18.172 | 1.00 | 11.01 |
| ATOM 151 | CB | MET A | 15 | 19.685 | 67.011 | 20.420 | 1.00 | 11.01 |
| ATOM 152 | CG | MET A | 15 | 20.747 | 66.686 | 21.473 | 1.00 | 11.01 |
| ATOM 153 | SD | MET A | 15 | 20.601 | 67.740 | 22.927 | 1.00 | 11.01 |
| ATOM 154 | CE | MET A | 15 | 18.959 | 67.225 | 23.457 | 1.00 | 11.01 |
| ATOM 155 | H | MET A | 15 | 21.654 | 66.991 | 18.538 | 1.00 | 20.00 |
| ATOM 156 | N | PRO A | 16 | 18.467 | 67.542 | 17.508 | 1.00 | 6.76 |
| ATOM 157 | CA | PRO A | 16 | 17.278 | 67.737 | 16.668 | 1.00 | 6.76 |
| ATOM 158 | C | PRO A | 16 | 17.336 | 67.088 | 15.288 | 1.00 | 6.76 |
| ATOM 159 | O | PRO A | 16 | 18.366 | 66.988 | 14.636 | 1.00 | 6.76 |
| ATOM 160 | CB | PRO A | 16 | 17.205 | 69.262 | 16.583 | 1.00 | 6.76 |
| ATOM 161 | CG | PRO A | 16 | 18.666 | 69.706 | 16.546 | 1.00 | 6.76 |
| ATOM 162 | CD | PRO A | 16 | 19.336 | 68.721 | 17.496 | 1.00 | 6.76 |
| ATOM 163 | N | LEU A | 17 | 16.124 | 66.718 | 14.845 | 1.00 | 6.37 |
| ATOM 164 | CA | LEU A | 17 | 15.919 | 66.590 | 13.404 | 1.00 | 6.37 |
| ATOM 165 | C | LEU A | 17 | 15.330 | 67.895 | 12.927 | 1.00 | 6.37 |
| ATOM 166 | O | LEU A | 17 | 14.283 | 68.315 | 13.399 | 1.00 | 6.37 |
| ATOM 167 | CB | LEU A | 17 | 14.948 | 65.447 | 13.094 | 1.00 | 6.37 |
| ATOM 168 | CG | LEU A | 17 | 14.792 | 65.085 | 11.612 | 1.00 | 6.37 |
| ATOM 169 | CD1 | LEU A | 17 | 16.115 | 64.679 | 10.956 | 1.00 | 6.37 |
| ATOM 170 | CD2 | LEU A | 17 | 13.719 | 64.012 | 11.424 | 1.00 | 6.37 |
| ATOM 171 | H | LEU A | 17 | 15.332 | 66.774 | 15.449 | 1.00 | 20.00 |
| ATOM 172 | N | GLU A | 18 | 16.051 | 68.537 | 12.005 | 1.00 | 14.08 |
| ATOM 173 | CA | GLU A | 18 | 15.485 | 69.803 | 11.562 | 1.00 | 14.08 |
| ATOM 174 | C | GLU A | 18 | 15.250 | 69.762 | 10.073 | 1.00 | 14.08 |
| ATOM 175 | O | GLU A | 18 | 15.974 | 69.085 | 9.353 | 1.00 | 14.08 |
| ATOM 176 | CB | GLU A | 18 | 16.398 | 70.960 | 11.964 | 1.00 | 14.08 |
| ATOM 177 | CG | GLU A | 18 | 15.640 | 72.251 | 12.305 | 1.00 | 14.08 |
| ATOM 178 | CD | GLU A | 18 | 16.589 | 73.436 | 12.387 | 1.00 | 14.08 |
| ATOM 179 | OE1 | GLU A | 18 | 17.778 | 73.270 | 12.652 | 1.00 | 14.08 |
| ATOM 180 | CE2 | GLU A | 18 | 16.177 | 74.559 | 12.109 | 1.00 | 14.08 |
| ATOM 181 | H | GLU A | 18 | 16.873 | 68.153 | 11.585 | 1.00 | 20.00 |
| ATOM 182 | N | TRP A | 19 | 14.198 | 70.475 | 9.654 | 1.00 | 6.20 |
| ATOM 183 | CA | TRP A | 19 | 13.914 | 70.460 | 8.224 | 1.00 | 6.20 |
| ATOM 184 | C | TRP A | 19 | 14.463 | 71.678 | 7.511 | 1.00 | 6.20 |
| ATOM 185 | O | TRP A | 19 | 14.779 | 72.689 | 8.129 | 1.00 | 6.20 |
| ATOM 186 | CB | TRP A | 19 | 12.411 | 70.326 | 7.984 | 1.00 | 6.20 |
| ATOM 187 | CG | TRP A | 19 | 11.882 | 69.013 | 8.517 | 1.00 | 6.20 |
| ATOM 188 | CD1 | TRP A | 19 | 10.955 | 68.849 | 9.558 | 1.00 | 6.20 |
| ATOM 189 | CD2 | TRP A | 19 | 12.215 | 67.672 | 8.093 | 1.00 | 6.20 |
| ATOM 190 | NE1 | TRP A | 19 | 10.707 | 67.532 | 9.795 | 1.00 | 6.20 |
| ATOM 191 | CE2 | TRP A | 19 | 11.460 | 66.767 | 8.913 | 1.00 | 6.20 |
| ATOM 192 | CE3 | TRP A | 19 | 13.072 | 67.161 | 7.097 | 1.00 | 6.20 |
| ATOM 193 | CZ2 | TRP A | 19 | 11.597 | 65.374 | 8.732 | 1.00 | 6.20 |
| ATOM 194 | CZ3 | TRP A | 19 | 13.198 | 65.767 | 6.923 | 1.00 | 6.20 |
| ATOM 195 | CH2 | TRP A | 19 | 12.464 | 64.877 | 7.736 | 1.00 | 6.20 |
| ATOM 196 | H | TRP A | 19 | 13.691 | 71.069 | 10.277 | 1.00 | 20.00 |
| ATOM 197 | HE1 | TRP A | 19 | 10.109 | 67.179 | 10.486 | 1.00 | 20.00 |
| ATOM 198 | N | GLU A | 20 | 14.553 | 71.530 | 6.181 | 1.00 | 5.13 |
| ATOM 199 | CA | GLU A | 20 | 15.101 | 72.623 | 5.385 | 1.00 | 5.13 |
| ATOM 200 | C | GLU A | 20 | 14.370 | 72.847 | 4.082 | 1.00 | 5.13 |

TABLE 1-continued

Atomic coordinates of the higher-order structure of Fas ligand

| Atom species | Amino acid residues | | | # | X | Y | Z | OCC | B |
|---|---|---|---|---|---|---|---|---|---|
| ATOM 201 | O | GLU | A | 20 | 13.839 | 71.906 | 3.505 | 1.00 | 5.13 |
| ATOM 202 | CB | GLU | A | 20 | 16.573 | 72.359 | 5.094 | 1.00 | 5.13 |
| ATOM 203 | CG | GLU | A | 20 | 17.460 | 73.452 | 5.688 | 1.00 | 5.13 |
| ATOM 204 | CD | GLU | A | 20 | 18.919 | 73.191 | 5.367 | 1.00 | 5.13 |
| ATOM 205 | OE1 | GLU | A | 20 | 19.233 | 72.953 | 4.202 | 1.00 | 5.13 |
| ATOM 206 | OE2 | GLU | A | 20 | 19.741 | 73.238 | 6.281 | 1.00 | 5.13 |
| ATOM 207 | H | GLU | A | 20 | 14.410 | 70.630 | 5.764 | 1.00 | 20.00 |
| ATOM 208 | N | ASP | A | 21 | 14.415 | 74.133 | 3.664 | 1.00 | 13.73 |
| ATOM 209 | CA | ASP | A | 21 | 13.739 | 74.576 | 2.440 | 1.00 | 13.73 |
| ATOM 210 | C | ASP | A | 21 | 14.628 | 74.779 | 1.224 | 1.00 | 13.73 |
| ATOM 211 | O | ASP | A | 21 | 14.264 | 74.520 | 0.083 | 1.00 | 13.73 |
| ATOM 212 | CB | ASP | A | 21 | 12.921 | 75.854 | 2.658 | 1.00 | 13.73 |
| ATOM 213 | CG | ASP | A | 21 | 12.016 | 75.767 | 3.873 | 1.00 | 13.73 |
| ATOM 214 | OD1 | ASP | A | 21 | 11.748 | 76.809 | 4.465 | 1.00 | 13.73 |
| ATOM 215 | OD2 | ASP | A | 21 | 11.587 | 74.672 | 4.233 | 1.00 | 13.73 |
| ATOM 216 | H | ASP | A | 21 | 14.787 | 74.814 | 4.289 | 1.00 | 20.00 |
| ATOM 217 | N | THR | A | 22 | 15.840 | 75.265 | 1.494 | 1.00 | 11.65 |
| ATOM 218 | CA | THR | A | 22 | 16.637 | 75.591 | 0.315 | 1.00 | 11.65 |
| ATOM 219 | C | THR | A | 22 | 17.551 | 74.473 | −0.160 | 1.00 | 11.65 |
| ATOM 220 | O | THR | A | 22 | 18.772 | 74.519 | −0.079 | 1.00 | 11.65 |
| ATOM 221 | CB | THR | A | 22 | 17.345 | 76.931 | 0.534 | 1.00 | 11.65 |
| ATOM 222 | OG1 | THR | A | 22 | 16.385 | 77.868 | 1.043 | 1.00 | 11.65 |
| ATOM 223 | CG2 | THR | A | 22 | 17.992 | 77.488 | −0.740 | 1.00 | 11.65 |
| ATOM 224 | H | THR | A | 22 | 16.146 | 75.452 | 2.424 | 1.00 | 20.00 |
| ATOM 225 | HG1 | THR | A | 22 | 16.826 | 78.699 | 1.148 | 1.00 | 20.00 |
| ATOM 226 | N | TYR | A | 23 | 16.867 | 73.447 | −0.685 | 1.00 | 6.57 |
| ATOM 227 | CA | TYR | A | 23 | 17.600 | 72.318 | −1.247 | 1.00 | 6.57 |
| ATOM 228 | C | TYR | A | 23 | 17.037 | 71.987 | −2.616 | 1.00 | 6.57 |
| ATOM 229 | O | TYR | A | 23 | 15.911 | 72.348 | −2.931 | 1.00 | 6.57 |
| ATOM 230 | CB | TYR | A | 23 | 17.557 | 71.133 | −0.264 | 1.00 | 6.57 |
| ATOM 231 | CG | TYR | A | 23 | 18.370 | 69.948 | −0.741 | 1.00 | 6.57 |
| ATOM 232 | CD1 | TYR | A | 23 | 17.700 | 68.824 | −1.269 | 1.00 | 6.57 |
| ATOM 233 | CD2 | TYR | A | 23 | 19.776 | 70.002 | −0.652 | 1.00 | 6.57 |
| ATOM 234 | CE1 | TYR | A | 23 | 18.456 | 67.738 | −1.741 | 1.00 | 6.57 |
| ATOM 235 | CE2 | TYR | A | 23 | 20.532 | 68.913 | −1.117 | 1.00 | 6.57 |
| ATOM 236 | CZ | TYR | A | 23 | 19.862 | 67.799 | −1.664 | 1.00 | 6.57 |
| ATOM 237 | OH | TYR | A | 23 | 20.596 | 66.735 | −2.145 | 1.00 | 6.57 |
| ATOM 238 | H | TYR | A | 23 | 15.866 | 73.514 | −0.747 | 1.00 | 20.00 |
| ATOM 239 | HH | TYR | A | 23 | 21.504 | 66.817 | −1.884 | 1.00 | 20.00 |
| ATOM 240 | N | GLY | A | 24 | 17.882 | 71.296 | −3.413 | 1.00 | 5.63 |
| ATOM 241 | CA | GLY | A | 24 | 17.582 | 70.981 | −4.814 | 1.00 | 5.63 |
| ATOM 242 | C | GLY | A | 24 | 16.127 | 70.704 | −5.132 | 1.00 | 5.63 |
| ATOM 243 | O | GLY | A | 24 | 15.478 | 71.429 | −5.877 | 1.00 | 5.63 |
| ATOM 244 | H | GLY | A | 24 | 18.771 | 71.050 | −3.033 | 1.00 | 20.00 |
| ATOM 245 | N | ILE | A | 25 | 15.625 | 69.623 | −4.516 | 1.00 | 5.38 |
| ATOM 246 | CA | ILE | A | 25 | 14.180 | 69.558 | −4.660 | 1.00 | 5.38 |
| ATOM 247 | C | ILE | A | 25 | 13.430 | 69.623 | −3.353 | 1.00 | 5.38 |
| ATOM 248 | O | ILE | A | 25 | 12.788 | 68.690 | −2.892 | 1.00 | 5.38 |
| ATOM 249 | CB | ILE | A | 25 | 13.710 | 68.418 | −5.561 | 1.00 | 5.38 |
| ATOM 250 | CG1 | ILE | A | 25 | 14.683 | 68.204 | −6.729 | 1.00 | 5.38 |
| ATOM 251 | CG2 | ILE | A | 25 | 12.320 | 68.814 | −6.063 | 1.00 | 5.38 |
| ATOM 252 | CD1 | ILE | A | 25 | 14.563 | 66.862 | −7.442 | 1.00 | 5.38 |
| ATOM 253 | H | ILE | A | 25 | 16.152 | 68.987 | −3.950 | 1.00 | 20.00 |
| ATOM 254 | N | VAL | A | 26 | 13.545 | 70.828 | −2.791 | 1.00 | 4.68 |
| ATOM 255 | CA | VAL | A | 26 | 12.714 | 71.139 | −1.645 | 1.00 | 4.68 |
| ATOM 256 | C | VAL | A | 26 | 11.801 | 72.307 | −1.948 | 1.00 | 4.68 |
| ATOM 257 | O | VAL | A | 26 | 12.200 | 73.343 | −2.466 | 1.00 | 4.68 |
| ATOM 258 | CB | VAL | A | 26 | 13.583 | 71.364 | −0.411 | 1.00 | 4.68 |
| ATOM 259 | CG1 | VAL | A | 26 | 12.770 | 71.947 | 0.726 | 1.00 | 4.68 |
| ATOM 260 | CG2 | VAL | A | 26 | 14.214 | 70.049 | 0.040 | 1.00 | 4.68 |
| ATOM 261 | H | VAL | A | 26 | 14.148 | 71.536 | −3.170 | 1.00 | 20.00 |
| ATOM 262 | N | LEU | A | 27 | 10.517 | 72.036 | −1.668 | 1.00 | 5.09 |
| ATOM 263 | CA | LEU | A | 27 | 9.501 | 72.981 | −2.119 | 1.00 | 5.09 |
| ATOM 264 | C | LEU | A | 27 | 8.486 | 73.335 | −1.082 | 1.00 | 5.09 |
| ATOM 265 | O | LEU | A | 27 | 8.301 | 72.647 | −0.082 | 1.00 | 5.09 |
| ATOM 266 | CB | LEU | A | 27 | 8.710 | 72.440 | −3.294 | 1.00 | 5.09 |
| ATOM 267 | CG | LEU | A | 27 | 9.651 | 71.772 | −4.264 | 1.00 | 5.09 |
| ATOM 268 | CD1 | LEU | A | 27 | 9.013 | 70.489 | −4.783 | 1.00 | 5.09 |
| ATOM 269 | CD2 | LEU | A | 27 | 10.301 | 72.777 | −5.224 | 1.00 | 5.09 |
| ATOM 270 | H | LEU | A | 27 | 10.302 | 71.172 | −1.210 | 1.00 | 20.00 |
| ATOM 271 | N | LEU | A | 28 | 7.815 | 74.434 | −1.464 | 1.00 | 7.30 |
| ATOM 272 | CA | LEU | A | 28 | 6.781 | 75.058 | −0.666 | 1.00 | 7.30 |
| ATOM 273 | C | LEU | A | 28 | 5.743 | 75.691 | −1.577 | 1.00 | 7.30 |
| ATOM 274 | O | LEU | A | 28 | 6.092 | 76.467 | −2.457 | 1.00 | 7.30 |

TABLE 1-continued

Atomic coordinates of the higher-order structure of Fas ligand

| Atom species | Amino acid residues | | | # | X | Y | Z | OCC | B |
|---|---|---|---|---|---|---|---|---|---|
| ATOM 275 | CB | LEU | A | 28 | 7.456 | 76.136 | 0.181 | 1.00 | 7.30 |
| ATOM 276 | CG | LEU | A | 28 | 6.478 | 76.882 | 1.074 | 1.00 | 7.30 |
| ATOM 277 | CD1 | LEU | A | 28 | 5.697 | 75.875 | 1.898 | 1.00 | 7.30 |
| ATOM 278 | CD2 | LEU | A | 28 | 7.142 | 77.965 | 1.922 | 1.00 | 7.30 |
| ATOM 279 | H | LEU | A | 28 | 8.075 | 74.917 | −2.301 | 1.00 | 20.00 |
| ATOM 280 | N | SER | A | 29 | 4.472 | 75.373 | −1.280 | 1.00 | 16.57 |
| ATOM 281 | CA | SER | A | 29 | 3.392 | 76.107 | −1.940 | 1.00 | 16.57 |
| ATOM 282 | C | SER | A | 29 | 2.221 | 76.367 | −1.012 | 1.00 | 16.57 |
| ATOM 283 | O | SER | A | 29 | 1.327 | 75.543 | −0.888 | 1.00 | 16.57 |
| ATOM 284 | CB | SER | A | 29 | 2.894 | 75.353 | −3.178 | 1.00 | 16.57 |
| ATOM 285 | OG | SER | A | 29 | 3.993 | 75.008 | −4.023 | 1.00 | 16.57 |
| ATOM 286 | H | SER | A | 29 | 4.316 | 74.571 | −0.697 | 1.00 | 20.00 |
| ATOM 287 | HG | SER | A | 29 | 3.640 | 74.527 | −4.758 | 1.00 | 20.00 |
| ATOM 288 | N | GLY | A | 30 | 2.248 | 77.534 | −0.342 | 1.00 | 4.20 |
| ATOM 289 | CA | GLY | A | 30 | 1.116 | 77.838 | 0.544 | 1.00 | 4.20 |
| ATOM 290 | C | GLY | A | 30 | 1.203 | 77.273 | 1.958 | 1.00 | 4.20 |
| ATOM 291 | O | GLY | A | 30 | 0.622 | 77.781 | 2.906 | 1.00 | 4.20 |
| ATOM 292 | H | GLY | A | 30 | 3.028 | 78.156 | −0.418 | 1.00 | 20.00 |
| ATOM 293 | N | VAL | A | 31 | 1.980 | 76.187 | 2.068 | 1.00 | 3.10 |
| ATOM 294 | CA | VAL | A | 31 | 2.296 | 75.687 | 3.406 | 1.00 | 3.10 |
| ATOM 295 | C | VAL | A | 31 | 3.237 | 76.702 | 4.061 | 1.00 | 3.10 |
| ATOM 296 | O | VAL | A | 31 | 3.778 | 77.570 | 3.384 | 1.00 | 3.10 |
| ATOM 297 | CB | VAL | A | 31 | 2.908 | 74.273 | 3.233 | 1.00 | 3.10 |
| ATOM 298 | CG1 | VAL | A | 31 | 3.349 | 73.565 | 4.517 | 1.00 | 3.10 |
| ATOM 299 | CG2 | VAL | A | 31 | 1.948 | 73.386 | 2.437 | 1.00 | 3.10 |
| ATOM 300 | H | VAL | A | 31 | 2.496 | 75.876 | 1.275 | 1.00 | 20.00 |
| ATOM 301 | N | LYS | A | 32 | 3.419 | 76.589 | 5.377 | 1.00 | 18.46 |
| ATOM 302 | CA | LYS | A | 32 | 4.512 | 77.387 | 5.919 | 1.00 | 18.46 |
| ATOM 303 | C | LYS | A | 32 | 5.317 | 76.556 | 6.881 | 1.00 | 18.46 |
| ATOM 304 | O | LYS | A | 32 | 4.778 | 75.698 | 7.565 | 1.00 | 18.46 |
| ATOM 305 | CB | LYS | A | 32 | 3.975 | 78.664 | 6.573 | 1.00 | 18.46 |
| ATOM 306 | CG | LYS | A | 32 | 5.064 | 79.664 | 6.979 | 1.00 | 18.46 |
| ATOM 307 | CD | LYS | A | 32 | 4.486 | 80.949 | 7.559 | 1.00 | 18.46 |
| ATOM 308 | CE | LYS | A | 32 | 3.612 | 80.698 | 8.786 | 1.00 | 18.46 |
| ATOM 309 | NZ | LYS | A | 32 | 3.014 | 81.976 | 9.189 | 1.00 | 18.46 |
| ATOM 310 | H | LYS | A | 32 | 2.890 | 75.938 | 5.925 | 1.00 | 20.00 |
| ATOM 311 | 1HZ | LYS | A | 32 | 2.376 | 81.823 | 9.995 | 1.00 | 20.00 |
| ATOM 312 | 2HZ | LYS | A | 32 | 3.769 | 82.643 | 9.447 | 1.00 | 20.00 |
| ATOM 313 | 3HZ | LYS | A | 32 | 2.473 | 82.359 | 8.387 | 1.00 | 20.00 |
| ATOM 314 | N | TYR | A | 33 | 6.623 | 76.837 | 6.903 | 1.00 | 6.60 |
| ATOM 315 | CA | TYR | A | 33 | 7.411 | 76.135 | 7.906 | 1.00 | 6.60 |
| ATOM 316 | C | TYR | A | 33 | 7.557 | 76.987 | 9.133 | 1.00 | 6.60 |
| ATOM 317 | O | TYR | A | 33 | 7.743 | 78.196 | 9.059 | 1.00 | 6.60 |
| ATOM 318 | CB | TYR | A | 33 | 8.765 | 75.728 | 7.327 | 1.00 | 6.60 |
| ATOM 319 | CG | TYR | A | 33 | 8.503 | 75.070 | 5.997 | 1.00 | 6.60 |
| ATOM 320 | CD1 | TYR | A | 33 | 8.852 | 75.754 | 4.819 | 1.00 | 6.60 |
| ATOM 321 | CD2 | TYR | A | 33 | 7.878 | 73.810 | 5.974 | 1.00 | 6.60 |
| ATOM 322 | CE1 | TYR | A | 33 | 8.566 | 75.159 | 3.581 | 1.00 | 6.60 |
| ATOM 323 | CE2 | TYR | A | 33 | 7.555 | 73.235 | 4.739 | 1.00 | 6.60 |
| ATOM 324 | CZ | TYR | A | 33 | 7.901 | 73.918 | 3.562 | 1.00 | 6.60 |
| ATOM 325 | OH | TYR | A | 33 | 7.546 | 73.347 | 2.360 | 1.00 | 6.60 |
| ATOM 326 | H | TYR | A | 33 | 7.036 | 77.555 | 6.344 | 1.00 | 20.00 |
| ATOM 327 | HH | TYR | A | 33 | 8.135 | 72.630 | 2.144 | 1.00 | 20.00 |
| ATOM 328 | N | LYS | A | 34 | 7.421 | 76.307 | 10.272 | 1.00 | 11.73 |
| ATOM 329 | CA | LYS | A | 34 | 7.606 | 77.087 | 11.484 | 1.00 | 11.73 |
| ATOM 330 | C | LYS | A | 34 | 8.708 | 76.511 | 12.360 | 1.00 | 11.73 |
| ATOM 331 | O | LYS | A | 34 | 9.847 | 76.398 | 11.928 | 1.00 | 11.73 |
| ATOM 332 | CB | LYS | A | 34 | 6.245 | 77.314 | 12.154 | 1.00 | 11.73 |
| ATOM 333 | CG | LYS | A | 34 | 6.241 | 78.556 | 13.045 | 1.00 | 11.73 |
| ATOM 334 | CD | LYS | A | 34 | 4.886 | 78.804 | 13.698 | 1.00 | 11.73 |
| ATOM 335 | CE | LYS | A | 34 | 4.936 | 80.002 | 14.643 | 1.00 | 11.73 |
| ATOM 336 | NZ | LYS | A | 34 | 3.589 | 80.254 | 15.171 | 1.00 | 11.73 |
| ATOM 337 | H | LYS | A | 34 | 7.171 | 75.336 | 10.244 | 1.00 | 20.00 |
| ATOM 338 | 1HZ | LYS | A | 34 | 3.625 | 81.026 | 15.866 | 1.00 | 20.00 |
| ATOM 339 | 2HZ | LYS | A | 34 | 2.962 | 80.522 | 14.387 | 1.00 | 20.00 |
| ATOM 340 | 3HZ | LYS | A | 34 | 3.221 | 79.390 | 15.620 | 1.00 | 20.00 |
| ATOM 341 | N | LYS | A | 35 | 8.357 | 76.118 | 13.597 | 1.00 | 6.70 |
| ATOM 342 | CA | LYS | A | 35 | 9.396 | 75.517 | 14.429 | 1.00 | 6.70 |
| ATOM 343 | C | LYS | A | 35 | 9.571 | 74.038 | 14.124 | 1.00 | 6.70 |
| ATOM 344 | O | LYS | A | 35 | 9.171 | 73.168 | 14.883 | 1.00 | 6.70 |
| ATOM 345 | CB | LYS | A | 35 | 9.069 | 75.758 | 15.904 | 1.00 | 6.70 |
| ATOM 346 | CG | LYS | A | 35 | 8.944 | 77.244 | 16.255 | 1.00 | 6.70 |
| ATOM 347 | CD | LYS | A | 35 | 8.458 | 77.457 | 17.690 | 1.00 | 6.70 |
| ATOM 348 | CE | LYS | A | 35 | 8.340 | 78.933 | 18.071 | 1.00 | 6.70 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 349 | NZ | LYS A | 35 | 7.794 | 79.038 | 19.432 | 1.00 | 6.70 |
| ATOM 350 | H | LYS A | 35 | 7.414 | 76.121 | 13.921 | 1.00 | 20.00 |
| ATOM 351 | 1HZ | LYS A | 35 | 7.760 | 80.036 | 19.723 | 1.00 | 20.00 |
| ATOM 352 | 2HZ | LYS A | 35 | 6.837 | 78.632 | 19.456 | 1.00 | 20.00 |
| ATOM 353 | 3HZ | LYS A | 35 | 8.404 | 78.508 | 20.088 | 1.00 | 20.00 |
| ATOM 354 | N | GLY A | 36 | 10.159 | 73.807 | 12.936 | 1.00 | 3.55 |
| ATOM 355 | CA | GLY A | 36 | 10.359 | 72.429 | 12.478 | 1.00 | 3.55 |
| ATOM 356 | C | GLY A | 36 | 9.086 | 71.673 | 12.118 | 1.00 | 3.55 |
| ATOM 357 | O | GLY A | 36 | 9.016 | 70.453 | 12.190 | 1.00 | 3.55 |
| ATOM 358 | H | GLY A | 36 | 10.443 | 74.595 | 12.382 | 1.00 | 20.00 |
| ATOM 359 | N | GLY A | 37 | 8.072 | 72.461 | 11.724 | 1.00 | 4.03 |
| ATOM 360 | CA | GLY A | 37 | 6.797 | 71.810 | 11.446 | 1.00 | 4.03 |
| ATOM 361 | C | GLY A | 37 | 6.030 | 72.498 | 10.347 | 1.00 | 4.03 |
| ATOM 362 | O | GLY A | 37 | 6.312 | 73.643 | 10.005 | 1.00 | 4.03 |
| ATOM 363 | H | GLY A | 37 | 8.173 | 73.450 | 11.645 | 1.00 | 20.00 |
| ATOM 364 | N | LEU A | 38 | 5.072 | 71.731 | 9.802 | 1.00 | 5.45 |
| ATOM 365 | CA | LEU A | 38 | 4.345 | 72.259 | 8.648 | 1.00 | 5.45 |
| ATOM 366 | C | LEU A | 38 | 3.006 | 72.827 | 9.040 | 1.00 | 5.45 |
| ATOM 367 | O | LEU A | 38 | 2.233 | 72.175 | 9.723 | 1.00 | 5.45 |
| ATOM 368 | CB | LEU A | 38 | 4.081 | 71.208 | 7.560 | 1.00 | 5.45 |
| ATOM 369 | CG | LEU A | 38 | 5.222 | 70.280 | 7.134 | 1.00 | 5.45 |
| ATOM 370 | CD1 | LEU A | 38 | 4.986 | 69.731 | 5.731 | 1.00 | 5.45 |
| ATOM 371 | CD2 | LEU A | 38 | 6.603 | 70.906 | 7.206 | 1.00 | S.45 |
| ATOM 372 | H | LEU A | 38 | 4.872 | 70.831 | 10.201 | 1.00 | 20.00 |
| ATOM 373 | N | VAL A | 39 | 2.762 | 74.052 | 8.560 | 1.00 | 2.74 |
| ATOM 374 | CA | VAL A | 39 | 1.428 | 74.630 | 8.718 | 1.00 | 2.74 |
| ATOM 375 | C | VAL A | 39 | 0.601 | 74.393 | 7.469 | 1.00 | 2.74 |
| ATOM 376 | O | VAL A | 39 | 1.009 | 74.750 | 6.369 | 1.00 | 2.74 |
| ATOM 377 | CB | VAL A | 39 | 1.511 | 76.139 | 8.992 | 1.00 | 2.74 |
| ATOM 378 | CG1 | VAL A | 39 | 0.146 | 76.704 | 9.401 | 1.00 | 2.74 |
| ATOM 379 | CG2 | VAL A | 39 | 2.595 | 76.487 | 10.013 | 1.00 | 2.74 |
| ATOM 380 | H | VAL A | 39 | 3.474 | 74.512 | 8.029 | 1.00 | 20.00 |
| ATOM 381 | N | ILE A | 40 | −0.574 | 73.782 | 7.679 | 1.00 | 15.04 |
| ATOM 382 | CA | ILE A | 40 | −1.419 | 73.524 | 6.512 | 1.00 | 15.04 |
| ATOM 383 | C | ILE A | 40 | −2.281 | 74.721 | 6.119 | 1.00 | 15.04 |
| ATOM 384 | O | ILE A | 40 | −2.953 | 75.347 | 6.928 | 1.00 | 15.04 |
| ATOM 385 | CB | ILE A | 40 | −2.234 | 72.225 | 6.707 | 1.00 | 15.04 |
| ATOM 386 | CG1 | ILE A | 40 | −1.310 | 71.002 | 6.665 | 1.00 | 15.04 |
| ATOM 387 | CG2 | ILE A | 40 | −3.290 | 72.032 | 5.615 | 1.00 | 15.04 |
| ATOM 388 | CD1 | ILE A | 40 | −0.602 | 70.638 | 7.970 | 1.00 | 15.04 |
| ATOM 389 | H | ILE A | 40 | −0.836 | 73.498 | 8.609 | 1.00 | 20.00 |
| ATOM 390 | N | ASN A | 41 | −2.205 | 75.014 | 4.808 | 1.00 | 16.19 |
| ATOM 391 | CA | ASN A | 41 | −2.949 | 76.147 | 4.249 | 1.00 | 16.19 |
| ATOM 392 | C | ASN A | 41 | −4.450 | 75.933 | 4.126 | 1.00 | 16.19 |
| ATOM 393 | O | ASN A | 41 | −5.246 | 76.807 | 4.443 | 1.00 | 16.19 |
| ATOM 394 | CB | ASN A | 41 | −2.364 | 76.513 | 2.878 | 1.00 | 16.19 |
| ATOM 395 | CG | ASN A | 41 | −2.784 | 77.887 | 2.355 | 1.00 | 16.19 |
| ATOM 396 | OD1 | ASN A | 41 | −1.976 | 78.785 | 2.188 | 1.00 | 16.19 |
| ATOM 397 | ND2 | ASN A | 41 | −4.069 | 78.015 | 2.001 | 1.00 | 16.19 |
| ATOM 398 | H | ASN A | 41 | −1.593 | 74.459 | 4.247 | 1.00 | 20.00 |
| ATOM 399 | 1HD2 | ASN A | 41 | −4.779 | 77.322 | 2.122 | 1.00 | 20.00 |
| ATOM 400 | 2HD2 | ASN A | 41 | −4.339 | 78.895 | 1.613 | 1.00 | 20.00 |
| ATOM 401 | N | GLU A | 42 | −4.813 | 74.765 | 3.577 | 1.00 | 4.33 |
| ATOM 402 | CA | GLU A | 42 | −6.216 | 74.615 | 3.193 | 1.00 | 4.33 |
| ATOM 403 | C | GLU A | 42 | −6.790 | 73.304 | 3.666 | 1.00 | 4.33 |
| ATOM 404 | O | GLU A | 42 | −6.080 | 72.368 | 4.002 | 1.00 | 4.33 |
| ATOM 405 | CB | GLU A | 42 | −6.372 | 74.715 | 1.672 | 1.00 | 4.33 |
| ATOM 406 | CG | GLU A | 42 | −6.946 | 76.041 | 1.145 | 1.00 | 4.33 |
| ATOM 407 | CD | GLU A | 42 | −6.707 | 76.142 | −0.358 | 1.00 | 4.33 |
| ATOM 408 | OE1 | GLU A | 42 | −7.088 | 75.222 | −1.087 | 1.00 | 4.33 |
| ATOM 409 | OE2 | GLU A | 42 | −6.089 | 77.124 | −0.796 | 1.00 | 4.33 |
| ATOM 410 | H | GLU A | 42 | −4.191 | 73.991 | 3.448 | 1.00 | 20.00 |
| ATOM 411 | N | THR A | 43 | −8.124 | 73.268 | 3.644 | 1.00 | 2.66 |
| ATOM 412 | CA | THR A | 43 | −8.755 | 71.982 | 3.908 | 1.00 | 2.66 |
| ATOM 413 | C | THR A | 43 | −8.660 | 71.049 | 2.711 | 1.00 | 2.66 |
| ATOM 414 | O | THR A | 43 | −8.742 | 71.458 | 1.551 | 1.00 | 2.66 |
| ATOM 415 | CB | THR A | 43 | −10.204 | 72.229 | 4.338 | 1.00 | 2.66 |
| ATOM 416 | OG1 | THR A | 43 | −10.229 | 73.269 | 5.322 | 1.00 | 2.66 |
| ATOM 417 | CG2 | THR A | 43 | −10.915 | 70.980 | 4.869 | 1.00 | 2.66 |
| ATOM 418 | H | THR A | 43 | −8.675 | 74.077 | 3.444 | 1.00 | 20.00 |
| ATOM 419 | HG1 | THR A | 43 | −11.124 | 73.328 | 5.631 | 1.00 | 20.00 |
| ATOM 420 | N | GLY A | 44 | −8.480 | 69.768 | 3.040 | 1.00 | 2.64 |
| ATOM 421 | CA | GLY A | 44 | −8.593 | 68.775 | 1.983 | 1.00 | 2.64 |
| ATOM 422 | C | GLY A | 44 | −7.723 | 67.583 | 2.265 | 1.00 | 2.64 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 423 | O | GLY A | 44 | −7.139 | 67.451 | 3.333 | 1.00 | 2.64 |
| ATOM 424 | H | GLY A | 44 | −8.285 | 69.503 | 3.991 | 1.00 | 20.00 |
| ATOM 425 | N | LEU A | 45 | −7.661 | 66.722 | 1.246 | 1.00 | 5.33 |
| ATOM 426 | CA | LEU A | 45 | −6.795 | 65.568 | 1.417 | 1.00 | 5.33 |
| ATOM 427 | C | LEU A | 45 | −5.362 | 65.899 | 1.116 | 1.00 | S.33 |
| ATOM 428 | O | LEU A | 45 | −5.039 | 66.562 | 0.140 | 1.00 | 5.33 |
| ATOM 429 | CB | LEU A | 45 | −7.292 | 64.429 | 0.543 | 1.00 | 5.33 |
| ATOM 430 | CG | LEU A | 45 | −8.661 | 63.988 | 1.046 | 1.00 | 5.33 |
| ATOM 431 | CD1 | LEU A | 45 | −9.547 | 63.464 | −0.073 | 1.00 | 5.33 |
| ATOM 432 | CD2 | LEU A | 45 | −8.540 | 63.031 | 2.227 | 1.00 | 5.33 |
| ATOM 433 | H | LEU A | 45 | −8.096 | 66.902 | 0.366 | 1.00 | 20.00 |
| ATOM 434 | N | TYR A | 46 | −4.524 | 65.406 | 2.019 | 1.00 | 3.53 |
| ATOM 435 | CA | TYR A | 46 | −3.103 | 65.518 | 1.767 | 1.00 | 3.53 |
| ATOM 436 | C | TYR A | 46 | −2.514 | 64.135 | 1.830 | 1.00 | 3.53 |
| ATOM 437 | O | TYR A | 46 | −2.907 | 63.306 | 2.645 | 1.00 | 3.53 |
| ATOM 438 | CB | TYR A | 46 | −2.433 | 66.444 | 2.791 | 1.00 | 3.53 |
| ATOM 439 | CG | TYR A | 46 | −2.815 | 67.896 | 2.581 | 1.00 | 3.53 |
| ATOM 440 | CD1 | TYR A | 46 | −4.070 | 68.372 | 3.021 | 1.00 | 3.53 |
| ATOM 441 | CD2 | TYR A | 46 | −1.885 | 68.747 | 1.952 | 1.00 | 3.53 |
| ATOM 442 | CE1 | TYR A | 46 | −4.405 | 69.722 | 2.821 | 1.00 | 3.53 |
| ATOM 443 | CE2 | TYR A | 46 | −2.215 | 70.099 | 1.758 | 1.00 | 3.53 |
| ATOM 444 | CZ | TYR A | 46 | −3.471 | 70.571 | 2.191 | 1.00 | 3.53 |
| ATOM 445 | OH | TYR A | 46 | −3.784 | 71.902 | 1.985 | 1.00 | 3.53 |
| ATOM 446 | H | TYR A | 46 | −4.861 | 64.899 | 2.815 | 1.00 | 20.00 |
| ATOM 447 | HH | TYR A | 46 | −3.042 | 72.329 | 1.581 | 1.00 | 20.00 |
| ATOM 448 | N | PHE A | 47 | −1.551 | 63.930 | 0.930 | 1.00 | 3.38 |
| ATOM 449 | CA | PHE A | 47 | −0.687 | 62.782 | 1.134 | 1.00 | 3.38 |
| ATOM 450 | C | PHE A | 47 | 0.524 | 63.235 | 1.911 | 1.00 | 3.38 |
| ATOM 451 | O | PHE A | 47 | 1.216 | 64.183 | 1.553 | 1.00 | 3.38 |
| ATOM 452 | CB | PHE A | 47 | −0.319 | 62.144 | −0.205 | 1.00 | 3.38 |
| ATOM 453 | CG | PHE A | 47 | 0.421 | 60.836 | −0.024 | 1.00 | 3.38 |
| ATOM 454 | CD1 | PHE A | 47 | −0.317 | 59.645 | 0.143 | 1.00 | 3.38 |
| ATOM 455 | CD2 | PHE A | 47 | 1.832 | 60.816 | −0.043 | 1.00 | 3.38 |
| ATOM 456 | CE1 | PHE A | 47 | 0.358 | 58.415 | 0.265 | 1.00 | 3.38 |
| ATOM 457 | CE2 | PHE A | 47 | 2.511 | 59.588 | 0.078 | 1.00 | 3.38 |
| ATOM 458 | CZ | PHE A | 47 | 1.767 | 58.399 | 0.221 | 1.00 | 3.38 |
| ATOM 459 | H | PHE A | 47 | −1.320 | 64.645 | 0.270 | 1.00 | 20.00 |
| ATOM 460 | N | VAL A | 48 | 0.684 | 62.519 | 3.024 | 1.00 | 2.79 |
| ATOM 461 | CA | VAL A | 48 | 1.767 | 62.784 | 3.956 | 1.00 | 2.79 |
| ATOM 462 | C | VAL A | 48 | 2.778 | 61.666 | 3.834 | 1.00 | 2.79 |
| ATOM 463 | O | VAL A | 48 | 2.439 | 60.507 | 4.037 | 1.00 | 2.79 |
| ATOM 464 | CB | VAL A | 48 | 1.176 | 62.831 | 5.373 | 1.00 | 2.79 |
| ATOM 465 | CG1 | VAL A | 48 | 2.228 | 63.144 | 6.436 | 1.00 | 2.79 |
| ATOM 466 | CG2 | VAL A | 48 | −0.015 | 63.792 | 5.439 | 1.00 | 2.79 |
| ATOM 467 | H | VAL A | 48 | 0.048 | 61.766 | 3.206 | 1.00 | 20.00 |
| ATOM 468 | N | TYR A | 49 | 4.015 | 62.046 | 3.491 | 1.00 | 3.73 |
| ATOM 469 | CA | TYR A | 49 | 5.042 | 61.011 | 3.405 | 1.00 | 3.73 |
| ATOM 470 | C | TYR A | 49 | 6.315 | 61.442 | 4.090 | 1.00 | 3.73 |
| ATOM 471 | O | TYR A | 49 | 6.596 | 62.627 | 4.212 | 1.00 | 3.73 |
| ATOM 472 | CB | TYR A | 49 | 5.328 | 60.612 | 1.948 | 1.00 | 3.73 |
| ATOM 473 | CG | TYR A | 49 | 5.835 | 61.784 | 1.135 | 1.00 | 3.73 |
| ATOM 474 | CD1 | TYR A | 49 | 7.218 | 62.059 | 1.114 | 1.00 | 3.73 |
| ATOM 475 | CD2 | TYR A | 49 | 4.907 | 62.574 | 0.429 | 1.00 | 3.73 |
| ATOM 476 | CE1 | TYR A | 49 | 7.681 | 63.168 | 0.391 | 1.00 | 3.73 |
| ATOM 477 | CE2 | TYR A | 49 | 5.372 | 63.683 | −0.293 | 1.00 | 3.73 |
| ATOM 478 | CZ | TYR A | 49 | 6.751 | 63.966 | −0.301 | 1.00 | 3.73 |
| ATOM 479 | OH | TYR A | 49 | 7.215 | 65.056 | −1.010 | 1.00 | 3.73 |
| ATOM 480 | H | TYR A | 49 | 4.241 | 63.009 | 3.317 | 1.00 | 20.00 |
| ATOM 481 | HH | TYR A | 49 | 6.524 | 65.714 | −1.072 | 1.00 | 20.00 |
| ATOM 482 | N | SER A | 50 | 7.083 | 60.431 | 4.508 | 1.00 | 5.02 |
| ATOM 483 | CA | SER A | 50 | 8.379 | 60.756 | 5.091 | 1.00 | 5.02 |
| ATOM 484 | C | SER A | 50 | 9.300 | 59.563 | 5.031 | 1.00 | 5.02 |
| ATOM 485 | O | SER A | 50 | 8.854 | 58.421 | 5.057 | 1.00 | 5.02 |
| ATOM 486 | CB | SER A | 50 | 8.204 | 61.253 | 6.529 | 1.00 | 5.02 |
| ATOM 487 | OG | SER A | 50 | 9.478 | 61.518 | 7.119 | 1.00 | 5.02 |
| ATOM 488 | H | SER A | 50 | 6.782 | 59.477 | 4.413 | 1.00 | 20.00 |
| ATOM 489 | HG | SER A | 50 | 9.364 | 62.204 | 7.763 | 1.00 | 20.00 |
| ATOM 490 | N | LYS A | 51 | 10.598 | 59.871 | 4.945 | 1.00 | 6.04 |
| ATOM 491 | CA | LYS A | 51 | 11.558 | 58.783 | 5.032 | 1.00 | 6.04 |
| ATOM 492 | C | LYS A | 51 | 12.786 | 59.177 | 5.813 | 1.00 | 6.04 |
| ATOM 493 | O | LYS A | 51 | 13.278 | 60.293 | 5.706 | 1.00 | 6.04 |
| ATOM 494 | CB | LYS A | 51 | 11.932 | 58.249 | 3.649 | 1.00 | 6.04 |
| ATOM 495 | CG | LYS A | 51 | 12.407 | 56.810 | 3.790 | 1.00 | 6.04 |
| ATOM 496 | CD | LYS A | 51 | 12.622 | 56.035 | 2.507 | 1.00 | 6.04 |

TABLE 1-continued

Atomic coordinates of the higher-order structure of Fas ligand

| Atom species | Amino acid residues | | | # | X | Y | Z | OCC | B |
|---|---|---|---|---|---|---|---|---|---|
| ATOM 497 | CE | LYS | A | 51 | 12.870 | 54.579 | 2.891 | 1.00 | 6.04 |
| ATOM 498 | NZ | LYS | A | 51 | 13.340 | 53.861 | 1.710 | 1.00 | 6.04 |
| ATOM 499 | H | LYS | A | 51 | 10.889 | 60.831 | 4.975 | 1.00 | 20.00 |
| ATOM 500 | 1HZ | LYS | A | 51 | 13.415 | 52.845 | 1.891 | 1.00 | 20.00 |
| ATOM 501 | 2HZ | LYS | A | 51 | 12.652 | 54.028 | 0.949 | 1.00 | 20.00 |
| ATOM 502 | 3HZ | LYS | A | 51 | 14.259 | 54.234 | 1.406 | 1.00 | 20.00 |
| ATOM 503 | N | VAL | A | 52 | 13.246 | 58.200 | 6.611 | 1.00 | 4.38 |
| ATOM 504 | CA | VAL | A | 52 | 14.492 | 58.383 | 7.348 | 1.00 | 4.38 |
| ATOM 505 | C | VAL | A | 52 | 15.390 | 57.179 | 7.244 | 1.00 | 4.38 |
| ATOM 506 | O | VAL | A | 52 | 14.962 | 56.050 | 7.000 | 1.00 | 4.38 |
| ATOM 507 | CB | VAL | A | 52 | 14.251 | 58.667 | 8.826 | 1.00 | 4.38 |
| ATOM 508 | CG1 | VAL | A | 52 | 13.746 | 60.087 | 9.048 | 1.00 | 4.38 |
| ATOM 509 | CG2 | VAL | A | 52 | 13.363 | 57.583 | 9.435 | 1.00 | 4.38 |
| ATOM 510 | H | VAL | A | 52 | 12.756 | 57.326 | 6.656 | 1.00 | 20.00 |
| ATOM 511 | N | TYR | A | 53 | 16.675 | 57.497 | 7.446 | 1.00 | 6.58 |
| ATOM 512 | CA | TYR | A | 53 | 17.683 | 56.448 | 7.424 | 1.00 | 6.58 |
| ATOM 513 | C | TYR | A | 53 | 18.569 | 56.505 | 8.625 | 1.00 | 6.58 |
| ATOM 514 | O | TYR | A | 53 | 18.938 | 57.561 | 9.130 | 1.00 | 6.58 |
| ATOM 515 | CB | TYR | A | 53 | 18.568 | 56.526 | 6.186 | 1.00 | 6.58 |
| ATOM 516 | CG | TYR | A | 53 | 17.789 | 56.086 | 4.979 | 1.00 | 6.58 |
| ATOM 517 | CD1 | TYR | A | 53 | 18.185 | 54.910 | 4.322 | 1.00 | 6.58 |
| ATOM 518 | CD2 | TYR | A | 53 | 16.689 | 56.855 | 4.553 | 1.00 | 6.58 |
| ATOM 519 | CE1 | TYR | A | 53 | 17.441 | 54.493 | 3.215 | 1.00 | 6.58 |
| ATOM 520 | CE2 | TYR | A | 53 | 15.948 | 56.439 | 3.450 | 1.00 | 6.58 |
| ATOM 521 | CZ | TYR | A | 53 | 16.343 | 55.265 | 2.798 | 1.00 | 6.58 |
| ATOM 522 | OH | TYR | A | 53 | 15.634 | 54.879 | 1.685 | 1.00 | 6.58 |
| ATOM 523 | H | TYR | A | 53 | 16.942 | 58.454 | 7.570 | 1.00 | 20.00 |
| ATOM 524 | HH | TYR | A | 53 | 15.854 | 55.548 | 1.030 | 1.00 | 20.00 |
| ATOM 525 | N | PHE | A | 54 | 18.891 | 55.284 | 9.038 | 1.00 | 6.05 |
| ATOM 526 | CA | PHE | A | 54 | 19.699 | 55.137 | 10.229 | 1.00 | 6.05 |
| ATOM 527 | C | PHE | A | 54 | 20.934 | 54.352 | 9.872 | 1.00 | 6.05 |
| ATOM 528 | O | PHE | A | 54 | 20.853 | 53.403 | 9.102 | 1.00 | 6.05 |
| ATOM 529 | CB | PHE | A | 54 | 18.892 | 54.390 | 11.294 | 1.00 | 6.05 |
| ATOM 530 | CG | PHE | A | 54 | 17.501 | 54.968 | 11.470 | 1.00 | 6.05 |
| ATOM 531 | CD1 | PHE | A | 54 | 16.381 | 54.136 | 11.251 | 1.00 | 6.05 |
| ATOM 532 | CD2 | PHE | A | 54 | 17.336 | 56.313 | 11.867 | 1.00 | 6.05 |
| ATOM 533 | CE1 | PHE | A | 54 | 15.086 | 54.630 | 11.499 | 1.00 | 6.05 |
| ATOM 534 | CE2 | PHE | A | 54 | 16.044 | 56.810 | 12.111 | 1.00 | 6.05 |
| ATOM 535 | CZ | PHE | A | 54 | 14.935 | 55.953 | 11.962 | 1.00 | 6.05 |
| ATOM 536 | H | PHE | A | 54 | 18.560 | 54.470 | 8.556 | 1.00 | 20.00 |
| ATOM 537 | N | ARG | A | 55 | 22.059 | 54.764 | 10.456 | 1.00 | 19.70 |
| ATOM 538 | CA | ARG | A | 55 | 23.214 | 53.875 | 10.457 | 1.00 | 19.70 |
| ATOM 539 | C | ARG | A | 55 | 23.770 | 53.786 | 11.852 | 1.00 | 19.70 |
| ATOM 540 | O | ARG | A | 55 | 23.368 | 54.498 | 12.762 | 1.00 | 19.70 |
| ATOM 541 | CB | ARG | A | 55 | 24.326 | 54.350 | 9.515 | 1.00 | 19.70 |
| ATOM 542 | CG | ARG | A | 55 | 25.023 | 53.313 | 8.631 | 1.00 | 19.70 |
| ATOM 543 | CD | ARG | A | 55 | 26.080 | 53.934 | 7.716 | 1.00 | 19.70 |
| ATOM 544 | NE | ARG | A | 55 | 27.229 | 54.454 | 8.465 | 1.00 | 19.70 |
| ATOM 545 | CZ | ARG | A | 55 | 28.227 | 55.085 | 7.803 | 1.00 | 19.70 |
| ATOM 546 | NH1 | ARG | A | 55 | 29.356 | 55.401 | 8.441 | 1.00 | 19.70 |
| ATOM 547 | NH2 | ARG | A | 55 | 28.077 | 55.393 | 6.514 | 1.00 | 19.7G |
| ATOM 548 | H | ARG | A | 55 | 22.082 | 55.627 | 10.971 | 1.00 | 20.00 |
| ATOM 549 | HE | ARG | A | 55 | 27.292 | 54.250 | 9.444 | 1.00 | 20.00 |
| ATOM 550 | 1HH1 | ARG | A | 55 | 30.074 | 55.929 | 7.985 | 1.00 | 20.00 |
| ATOM 551 | 2HH1 | ARG | A | 55 | 29.508 | 55.134 | 9.394 | 1.00 | 20.00 |
| ATOM 552 | 1HH2 | ARG | A | 55 | 28.856 | 55.594 | 5.913 | 1.00 | 20.00 |
| ATOM 553 | 2HH2 | ARG | A | 55 | 27.148 | 55.426 | 6.145 | 1.00 | 20.00 |
| ATOM 554 | N | GLY | A | 56 | 24.762 | 52.907 | 11.954 | 1.00 | 3.53 |
| ATOM 555 | CA | GLY | A | 56 | 25.605 | 52.945 | 13.132 | 1.00 | 3.53 |
| ATOM 556 | C | GLY | A | 56 | 26.750 | 52.008 | 12.892 | 1.00 | 3.53 |
| ATOM 557 | O | GLY | A | 56 | 26.704 | 51.160 | 12.006 | 1.00 | 3.53 |
| ATOM 558 | H | GLY | A | 56 | 24.906 | 52.215 | 11.243 | 1.00 | 20.00 |
| ATOM 559 | N | GLN | A | 57 | 27.776 | 52.217 | 13.712 | 1.00 | 16.13 |
| ATOM 560 | CA | GLN | A | 57 | 28.824 | 51.219 | 13.717 | 1.00 | 16.13 |
| ATOM 561 | C | GLN | A | 57 | 28.743 | 50.499 | 15.042 | 1.00 | 16.13 |
| ATOM 562 | O | GLN | A | 57 | 28.468 | 51.129 | 16.057 | 1.00 | 16.13 |
| ATOM 563 | CB | GLN | A | 57 | 30.150 | 51.927 | 13.473 | 1.00 | 16.13 |
| ATOM 564 | CG | GLN | A | 57 | 31.262 | 50.961 | 13.088 | 1.00 | 16.13 |
| ATOM 565 | CD | GLN | A | 57 | 32.402 | 51.756 | 12.499 | 1.00 | 16.13 |
| ATOM 566 | OE1 | GLN | A | 57 | 32.914 | 52.710 | 13.066 | 1.00 | 16.13 |
| ATOM 567 | NE2 | GLN | A | 57 | 32.767 | 51.325 | 11.291 | 1.00 | 16.13 |
| ATOM 568 | H | GLN | A | 57 | 27.763 | 52.914 | 14.428 | 1.00 | 20.00 |
| ATOM 569 | 1HE2 | GLN | A | 57 | 32.292 | 50.580 | 10.828 | 1.00 | 20.00 |
| ATOM 570 | 2HE2 | GLN | A | 57 | 33.548 | 51.796 | 10.886 | 1.00 | 20.00 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 571 | N | SER A | 58 | 28.933 | 49.166 | 14.969 | 1.00 | 30.56 |
| ATOM 572 | CA | SER A | 58 | 28.718 | 48.335 | 16.155 | 1.00 | 30.56 |
| ATOM 573 | C | SER A | 58 | 27.278 | 48.393 | 16.634 | 1.00 | 30.56 |
| ATOM 574 | O | SER A | 58 | 26.435 | 49.079 | 16.059 | 1.00 | 30.56 |
| ATOM 575 | CB | SER A | 58 | 29.718 | 48.673 | 17.271 | 1.00 | 30.56 |
| ATOM 576 | OG | SER A | 58 | 31.030 | 48.790 | 16.710 | 1.00 | 30.56 |
| ATOM 577 | H | SER A | 58 | 29.082 | 48.711 | 14.093 | 1.00 | 20.00 |
| ATOM 578 | HG | SER A | 58 | 31.560 | 49.229 | 17.360 | 1.00 | 20.00 |
| ATOM 579 | N | CYS A | 59 | 27.008 | 47.612 | 17.690 | 1.00 | 24.24 |
| ATOM 580 | CA | CYS A | 59 | 25.589 | 47.502 | 17.977 | 1.00 | 24.24 |
| ATOM 581 | C | CYS A | 59 | 25.271 | 47.326 | 19.436 | 1.00 | 24.24 |
| ATOM 582 | O | CYS A | 59 | 25.875 | 46.536 | 20.152 | 1.00 | 24.24 |
| ATOM 583 | CB | CYS A | 59 | 24.977 | 46.371 | 17.168 | 1.00 | 24.24 |
| ATOM 584 | SG | CYS A | 59 | 25.700 | 46.151 | 15.517 | 1.00 | 24.24 |
| ATOM 585 | H | CYS A | 59 | 27.672 | 47.049 | 18.180 | 1.00 | 20.00 |
| ATOM 586 | N | ASN A | 60 | 24.275 | 48.129 | 19.823 | 1.00 | 8.07 |
| ATOM 587 | CA | ASN A | 60 | 23.832 | 48.174 | 21.211 | 1.00 | 8.07 |
| ATOM 588 | C | ASN A | 60 | 22.321 | 48.085 | 21.167 | 1.00 | 8.07 |
| ATOM 589 | O | ASN A | 60 | 21.737 | 48.056 | 20.090 | 1.00 | 8.07 |
| ATOM 590 | CB | ASN A | 60 | 24.264 | 49.489 | 21.882 | 1.00 | 8.07 |
| ATOM 591 | CG | ASN A | 60 | 25.773 | 49.601 | 22.051 | 1.00 | 8.07 |
| ATOM 592 | OD1 | ASN A | 60 | 26.572 | 49.312 | 21.172 | 1.00 | 8.07 |
| ATOM 593 | ND2 | ASN A | 60 | 26.140 | 50.076 | 23.246 | 1.00 | 8.07 |
| ATOM 594 | H | ASN A | 60 | 23.781 | 48.668 | 19.143 | 1.00 | 20.00 |
| ATOM 595 | 1HD2 | ASN A | 60 | 25.478 | 50.333 | 23.947 | 1.00 | 20.00 |
| ATOM 596 | 2HD2 | ASN A | 60 | 27.119 | 50.181 | 23.412 | 1.00 | 20.00 |
| ATOM 597 | N | ASN A | 61 | 21.697 | 48.056 | 22.352 | 1.00 | 15.42 |
| ATOM 598 | CA | ASN A | 61 | 20.236 | 47.965 | 22.297 | 1.00 | 15.42 |
| ATOM 599 | C | ASN A | 61 | 19.573 | 49.326 | 22.249 | 1.00 | 15.42 |
| ATOM 600 | O | ASN A | 61 | 19.520 | 50.027 | 23.250 | 1.00 | 15.42 |
| ATOM 601 | CB | ASN A | 61 | 19.672 | 47.170 | 23.479 | 1.00 | 15.42 |
| ATOM 602 | CG | ASN A | 61 | 20.196 | 45.748 | 23.484 | 1.00 | 15.42 |
| ATOM 603 | OD1 | ASN A | 61 | 20.062 | 44.988 | 22.534 | 1.00 | 15.42 |
| ATOM 604 | ND2 | ASN A | 61 | 20.810 | 45.411 | 24.622 | 1.00 | 15.42 |
| ATOM 605 | H | ASN A | 61 | 22.191 | 48.206 | 23.207 | 1.00 | 20.00 |
| ATOM 606 | 1HD2 | ASN A | 61 | 20.893 | 46.060 | 25.377 | 1.00 | 20.00 |
| ATOM 607 | 2HD2 | ASN A | 61 | 21.180 | 44.488 | 24.701 | 1.00 | 20.00 |
| ATOM 608 | N | LEU A | 62 | 19.073 | 49.663 | 21.044 | 1.00 | 19.58 |
| ATOM 609 | CA | LEU A | 62 | 18.378 | 50.943 | 20.858 | 1.00 | 19.58 |
| ATOM 610 | C | LEU A | 62 | 17.243 | 50.828 | 19.852 | 1.00 | 19.58 |
| ATOM 611 | O | LEU A | 62 | 17.453 | 50.470 | 18.701 | 1.00 | 19.58 |
| ATOM 612 | CB | LEU A | 62 | 19.339 | 52.042 | 20.383 | 1.00 | 19.58 |
| ATOM 613 | CG | LEU A | 62 | 20.243 | 52.637 | 21.468 | 1.00 | 19.58 |
| ATOM 614 | CD1 | LEU A | 62 | 21.301 | 53.565 | 20.870 | 1.00 | 19.58 |
| ATOM 615 | CD2 | LEU A | 62 | 19.439 | 53.332 | 22.570 | 1.00 | 19.58 |
| ATOM 616 | H | LEU A | 62 | 19.213 | 49.055 | 20.262 | 1.00 | 20.00 |
| ATOM 617 | N | PRO A | 63 | 16.009 | 51.127 | 20.323 | 1.00 | 9.44 |
| ATOM 618 | CA | PRO A | 63 | 14.865 | 51.136 | 19.403 | 1.00 | 9.44 |
| ATOM 619 | C | PRO A | 63 | 14.814 | 52.410 | 18.571 | 1.00 | 9.44 |
| ATOM 620 | O | PRO A | 63 | 15.061 | 53.503 | 19.054 | 1.00 | 9.44 |
| ATOM 621 | CB | PRO A | 63 | 13.691 | 51.016 | 20.377 | 1.00 | 9.44 |
| ATOM 622 | CG | PRO A | 63 | 14.150 | 51.758 | 21.634 | 1.00 | 9.44 |
| ATOM 623 | CD | PRO A | 63 | 15.641 | 51.439 | 21.702 | 1.00 | 9.44 |
| ATOM 624 | N | LEU A | 64 | 14.475 | 52.225 | 17.289 | 1.00 | 5.10 |
| ATOM 625 | CA | LEU A | 64 | 14.438 | 53.428 | 16.462 | 1.00 | 5.10 |
| ATOM 626 | C | LEU A | 64 | 13.001 | 53.773 | 16.136 | 1.00 | 5.10 |
| ATOM 627 | O | LEU A | 64 | 12.226 | 52.890 | 15.781 | 1.00 | 5.10 |
| ATOM 628 | CB | LEU A | 64 | 15.228 | 53.219 | 15.162 | 1.00 | 5.10 |
| ATOM 629 | CG | LEU A | 64 | 16.355 | 52.172 | 15.218 | 1.00 | 5.10 |
| ATOM 630 | CD1 | LEU A | 64 | 16.845 | 51.816 | 13.819 | 1.00 | 5.10 |
| ATOM 631 | CD2 | LEU A | 64 | 17.513 | 52.528 | 16.152 | 1.00 | 5.10 |
| ATOM 632 | H | LEU A | 64 | 14.263 | 51.328 | 16.897 | 1.00 | 20.00 |
| ATOM 633 | N | SER A | 65 | 12.655 | 55.059 | 16.259 | 1.00 | 3.51 |
| ATOM 634 | CA | SER A | 65 | 11.281 | 55.367 | 15.885 | 1.00 | 3.51 |
| ATOM 635 | C | SER A | 65 | 11.171 | 56.506 | 14.900 | 1.00 | 3.51 |
| ATOM 636 | O | SER A | 65 | 12.012 | 57.393 | 14.846 | 1.00 | 3.51 |
| ATOM 637 | CB | SER A | 65 | 10.410 | 55.598 | 17.124 | 1.00 | 3.51 |
| ATOM 638 | OG | SER A | 65 | 10.714 | 56.856 | 17.733 | 1.00 | 3.51 |
| ATOM 639 | H | SER A | 65 | 13.262 | 55.762 | 16.640 | 1.00 | 20.00 |
| ATOM 640 | HG | SER A | 65 | 10.513 | 56.776 | 18.656 | 1.00 | 20.00 |
| ATOM 641 | N | HIS A | 66 | 10.086 | 56.430 | 14.119 | 1.00 | 11.85 |
| ATOM 642 | CA | HIS A | 66 | 9.823 | 57.498 | 13.168 | 1.00 | 11.85 |
| ATOM 643 | C | HIS A | 66 | 8.350 | 57.820 | 13.094 | 1.00 | 11.85 |
| ATOM 644 | O | HIS A | 66 | 7.555 | 57.029 | 12.600 | 1.00 | 11.85 |

TABLE 1-continued

Atomic coordinates of the higher-order structure of Fas ligand

| Atom species | Amino acid residues | | | # | X | Y | Z | OCC | B |
|---|---|---|---|---|---|---|---|---|---|
| ATOM 645 | CB | HIS | A | 66 | 10.332 | 57.106 | 11.790 | 1.00 | 11.85 |
| ATOM 646 | CG | HIS | A | 66 | 10.130 | 58.286 | 10.882 | 1.00 | 11.85 |
| ATOM 647 | ND1 | HIS | A | 66 | 9.149 | 58.363 | 9.972 | 1.00 | 11.85 |
| ATOM 648 | CD2 | HIS | A | 66 | 10.886 | 59.453 | 10.842 | 1.00 | 11.85 |
| ATOM 649 | CE1 | HIS | A | 66 | 9.287 | 59.565 | 9.347 | 1.00 | 11.85 |
| ATOM 650 | NE2 | HIS | A | 66 | 10.354 | 60.234 | 9.880 | 1.00 | 11.85 |
| ATOM 651 | H | HIS | A | 66 | 9.501 | 55.619 | 14.167 | 1.00 | 20.00 |
| ATOM 652 | HD1 | HIS | A | 66 | 8.428 | 57.723 | 9.829 | 1.00 | 20.00 |
| ATOM 653 | N | LYS | A | 67 | 8.015 | 58.998 | 13.627 | 1.00 | 4.98 |
| ATOM 654 | CA | LYS | A | 67 | 6.585 | 59.239 | 13.777 | 1.00 | 4.98 |
| ATOM 655 | C | LYS | A | 67 | 6.167 | 60.608 | 13.274 | 1.00 | 4.98 |
| ATOM 656 | O | LYS | A | 67 | 6.827 | 61.614 | 13.518 | 1.00 | 4.98 |
| ATOM 657 | CB | LYS | A | 67 | 6.188 | 59.042 | 15.243 | 1.00 | 4.98 |
| ATOM 658 | CG | LYS | A | 67 | 6.638 | 57.722 | 15.891 | 1.00 | 4.98 |
| ATOM 659 | CD | LYS | A | 67 | 6.505 | 57.778 | 17.413 | 1.00 | 4.98 |
| ATOM 660 | CE | LYS | A | 67 | 6.776 | 56.478 | 18.170 | 1.00 | 4.98 |
| ATOM 661 | NZ | LYS | A | 67 | 5.640 | 56.223 | 19.074 | 1.00 | 4.98 |
| ATOM 662 | H | LYS | A | 67 | 8.700 | 59.656 | 13.955 | 1.00 | 20.00 |
| ATOM 663 | 1HZ | LYS | A | 67 | 5.658 | 55.261 | 19.454 | 1.00 | 20.00 |
| ATOM 664 | 2HZ | LYS | A | 67 | 5.565 | 56.935 | 19.825 | 1.00 | 20.00 |
| ATOM 665 | 3HZ | LYS | A | 67 | 4.766 | 56.262 | 18.502 | 1.00 | 20.00 |
| ATOM 666 | N | VAL | A | 68 | 5.036 | 60.585 | 12.550 | 1.00 | 3.61 |
| ATOM 667 | CA | VAL | A | 68 | 4.409 | 61.824 | 12.099 | 1.00 | 3.61 |
| ATOM 668 | C | VAL | A | 68 | 3.206 | 62.128 | 12.970 | 1.00 | 3.61 |
| ATOM 669 | O | VAL | A | 68 | 2.331 | 61.288 | 13.159 | 1.00 | 3.61 |
| ATOM 670 | CB | VAL | A | 68 | 3.984 | 61.713 | 10.627 | 1.00 | 3.61 |
| ATOM 671 | CG1 | VAL | A | 68 | 3.409 | 63.031 | 10.092 | 1.00 | 3.61 |
| ATOM 672 | CG2 | VAL | A | 68 | 5.133 | 61.192 | 9.759 | 1.00 | 3.61 |
| ATOM 673 | H | VAL | A | 68 | 4.549 | 59.718 | 12.441 | 1.00 | 20.00 |
| ATOM 674 | N | TYR | A | 69 | 3.223 | 63.358 | 13.494 | 1.00 | 4.98 |
| ATOM 675 | CA | TYR | A | 69 | 2.180 | 63.799 | 14.410 | 1.00 | 4.98 |
| ATOM 676 | C | TYR | A | 69 | 1.417 | 64.972 | 13.843 | 1.00 | 4.98 |
| ATOM 677 | O | TYR | A | 69 | 1.943 | 65.742 | 13.046 | 1.00 | 4.98 |
| ATOM 678 | CB | TYR | A | 69 | 2.771 | 64.251 | 15.747 | 1.00 | 4.98 |
| ATOM 679 | CG | TYR | A | 69 | 3.695 | 63.223 | 16.352 | 1.00 | 4.98 |
| ATOM 680 | CD1 | TYR | A | 69 | 3.156 | 62.165 | 17.111 | 1.00 | 4.98 |
| ATOM 681 | CD2 | TYR | A | 69 | 5.082 | 63.379 | 16.162 | 1.00 | 4.98 |
| ATOM 682 | CE1 | TYR | A | 69 | 4.034 | 61.276 | 17.753 | 1.00 | 4.98 |
| ATOM 683 | CE2 | TYR | A | 69 | 5.958 | 62.490 | 16.801 | 1.00 | 4.98 |
| ATOM 684 | CZ | TYR | A | 69 | 5.422 | 61.470 | 17.610 | 1.00 | 4.98 |
| ATOM 685 | OH | TYR | A | 69 | 6.292 | 60.642 | 18.289 | 1.00 | 4.98 |
| ATOM 686 | H | TYR | A | 69 | 3.943 | 63.996 | 13.220 | 1.00 | 20.00 |
| ATOM 687 | HH | TYR | A | 69 | 7.151 | 60.697 | 17.892 | 1.00 | 20.00 |
| ATOM 688 | N | MET | A | 70 | 0.169 | 65.091 | 14.318 | 1.00 | 14.09 |
| ATOM 689 | CA | MET | A | 70 | −0.581 | 66.295 | 13.972 | 1.00 | 14.09 |
| ATOM 690 | C | MET | A | 70 | −1.068 | 67.055 | 15.185 | 1.00 | 14.09 |
| ATOM 691 | O | MET | A | 70 | −1.797 | 66.542 | 16.024 | 1.00 | 14.09 |
| ATOM 692 | CB | MET | A | 70 | −1.749 | 65.983 | 13.028 | 1.00 | 14.09 |
| ATOM 693 | CG | MET | A | 70 | −2.761 | 64.979 | 13.569 | 1.00 | 14.09 |
| ATOM 694 | SD | MET | A | 70 | −4.088 | 64.559 | 12.436 | 1.00 | 14.09 |
| ATOM 695 | CE | MET | A | 70 | −4.770 | 66.200 | 12.181 | 1.00 | 14.09 |
| ATOM 696 | H | MET | A | 70 | −0.182 | 64.407 | 14.961 | 1.00 | 20.00 |
| ATOM 697 | N | ARG | A | 71 | −0.653 | 68.321 | 15.228 | 1.00 | 7.41 |
| ATOM 698 | CA | ARG | A | 71 | −1.316 | 69.196 | 16.183 | 1.00 | 7.41 |
| ATOM 699 | C | ARG | A | 71 | −2.413 | 69.970 | 15.491 | 1.00 | 7.41 |
| ATOM 700 | O | ARG | A | 71 | −2.175 | 70.982 | 14.837 | 1.00 | 7.41 |
| ATOM 701 | CB | ARG | A | 71 | −0.326 | 70.141 | 16.857 | 1.00 | 7.41 |
| ATOM 702 | CG | ARG | A | 71 | −1.001 | 70.877 | 18.014 | 1.00 | 7.41 |
| ATOM 703 | CD | ARG | A | 71 | −0.053 | 71.792 | 18.777 | 1.00 | 7.41 |
| ATOM 704 | NE | ARG | A | 71 | −0.758 | 72.406 | 19.900 | 1.00 | 7.41 |
| ATOM 705 | CZ | ARG | A | 71 | −0.095 | 73.136 | 20.816 | 1.00 | 7.41 |
| ATOM 706 | NH1 | ARG | A | 71 | 1.225 | 73.293 | 20.725 | 1.00 | 7.41 |
| ATOM 707 | NH2 | ARG | A | 71 | −0.774 | 73.698 | 21.813 | 1.00 | 7.41 |
| ATOM 708 | H | ARG | A | 71 | −0.064 | 68.667 | 14.498 | 1.00 | 20.00 |
| ATOM 709 | HE | ARG | A | 71 | −1.742 | 72.229 | 19.966 | 1.00 | 20.00 |
| ATOM 710 | 1HH1 | ARG | A | 71 | 1.741 | 73.845 | 21.379 | 1.00 | 20.00 |
| ATOM 711 | 2HH1 | ARG | A | 71 | 1.721 | 72.836 | 19.986 | 1.00 | 20.00 |
| ATOM 712 | 1HH2 | ARG | A | 71 | −0.324 | 74.260 | 22.506 | 1.00 | 20.00 |
| ATOM 713 | 2HH2 | ARG | A | 71 | −1.762 | 73.555 | 21.881 | 1.00 | 20.00 |
| ATOM 714 | N | ASN | A | 72 | −3.623 | 69.413 | 15.643 | 1.00 | 8.42 |
| ATOM 715 | CA | ASN | A | 72 | −4.737 | 70.024 | 14.923 | 1.00 | 8.42 |
| ATOM 716 | C | ASN | A | 72 | −5.318 | 71.237 | 15.632 | 1.00 | 8.42 |
| ATOM 717 | O | ASN | A | 72 | −5.145 | 71.419 | 16.828 | 1.00 | 8.42 |
| ATOM 718 | CB | ASN | A | 72 | −5.787 | 68.956 | 14.582 | 1.00 | 8.42 |

TABLE 1-continued

Atomic coordinates of the higher-order structure of Fas ligand

| Atom species | Amino acid residues | | | # | X | Y | Z | OCC | B |
|---|---|---|---|---|---|---|---|---|---|
| ATOM 719 | CG | ASN | A | 72 | −6.738 | 69.453 | 13.505 | 1.00 | 8.42 |
| ATOM 720 | OD1 | ASN | A | 72 | −7.828 | 69.927 | 13.790 | 1.00 | 8.42 |
| ATOM 721 | ND2 | ASN | A | 72 | −6.282 | 69.348 | 12.253 | 1.00 | 8.42 |
| ATOM 722 | H | ASN | A | 72 | −3.733 | 68.663 | 16.298 | 1.00 | 20.00 |
| ATOM 723 | 1HD2 | ASN | A | 72 | −5.356 | 69.028 | 12.011 | 1.00 | 20.00 |
| ATOM 724 | 2HD2 | ASN | A | 72 | −6.841 | 69.633 | 11.478 | 1.00 | 20.00 |
| ATOM 725 | N | SER | A | 73 | −6.025 | 72.070 | 14.852 | 1.00 | 5.16 |
| ATOM 726 | CA | SER | A | 73 | −6.710 | 73.193 | 15.491 | 1.00 | 5.16 |
| ATOM 727 | C | SER | A | 73 | −7.837 | 72.760 | 16.419 | 1.00 | 5.16 |
| ATOM 728 | O | SER | A | 73 | −8.065 | 73.315 | 17.487 | 1.00 | 5.16 |
| ATOM 729 | CB | SER | A | 73 | −7.231 | 74.124 | 14.400 | 1.00 | 5.16 |
| ATOM 730 | OG | SER | A | 73 | −7.903 | 73.339 | 13.407 | 1.00 | 5.16 |
| ATOM 731 | H | SER | A | 73 | −6.188 | 71.908 | 13.877 | 1.00 | 20.00 |
| ATOM 732 | HG | SER | A | 73 | −8.242 | 73.954 | 12.766 | 1.00 | 20.00 |
| ATOM 733 | N | LYS | A | 74 | −8.530 | 71.707 | 15.947 | 1.00 | 5.76 |
| ATOM 734 | CA | LYS | A | 74 | −9.645 | 71.165 | 16.724 | 1.00 | 5.76 |
| ATOM 735 | C | LYS | A | 74 | −9.245 | 70.571 | 18.069 | 1.00 | 5.76 |
| ATOM 736 | O | LYS | A | 74 | −9.920 | 70.737 | 19.076 | 1.00 | 5.76 |
| ATOM 737 | CB | LYS | A | 74 | −10.404 | 70.129 | 15.890 | 1.00 | 5.76 |
| ATOM 738 | CG | LYS | A | 74 | −10.932 | 70.667 | 14.555 | 1.00 | 5.76 |
| ATOM 739 | CD | LYS | A | 74 | −11.479 | 69.544 | 13.669 | 1.00 | 5.76 |
| ATOM 740 | CE | LYS | A | 74 | −11.970 | 70.026 | 12.301 | 1.00 | 5.76 |
| ATOM 741 | NZ | LYS | A | 74 | −12.405 | 68.867 | 11.507 | 1.00 | 5.76 |
| ATOM 742 | H | LYS | A | 74 | −8.292 | 71.351 | 15.038 | 1.00 | 20.00 |
| ATOM 743 | 1HZ | LYS | A | 74 | −12.812 | 69.191 | 10.607 | 1.00 | 20.00 |
| ATOM 744 | 2HZ | LYS | A | 74 | −11.589 | 68.251 | 11.315 | 1.00 | 20.00 |
| ATOM 745 | 3HZ | LYS | A | 74 | −13.122 | 68.332 | 12.037 | 1.00 | 20.00 |
| ATOM 746 | N | TYR | A | 75 | −8.105 | 69.857 | 18.031 | 1.00 | 6.72 |
| ATOM 747 | CA | TYR | A | 75 | −7.641 | 69.230 | 19.267 | 1.00 | 6.72 |
| ATOM 748 | C | TYR | A | 75 | −6.326 | 69.787 | 19.785 | 1.00 | 6.72 |
| ATOM 749 | O | TYR | A | 75 | −5.300 | 69.730 | 19.126 | 1.00 | 6.72 |
| ATOM 750 | CB | TYR | A | 75 | −7.534 | 67.706 | 19.076 | 1.00 | 6.72 |
| ATOM 751 | CG | TYR | A | 75 | −7.403 | 66.932 | 20.380 | 1.00 | 6.72 |
| ATOM 752 | CD1 | TYR | A | 75 | −8.155 | 67.305 | 21.516 | 1.00 | 6.72 |
| ATOM 753 | CD2 | TYR | A | 75 | −6.537 | 65.821 | 20.414 | 1.00 | 6.72 |
| ATOM 754 | CE1 | TYR | A | 75 | −8.017 | 66.581 | 22.712 | 1.00 | 6.72 |
| ATOM 755 | CE2 | TYR | A | 75 | −6.429 | 65.069 | 21.597 | 1.00 | 6.72 |
| ATOM 756 | CZ | TYR | A | 75 | −7.156 | 65.466 | 22.738 | 1.00 | 6.72 |
| ATOM 757 | OH | TYR | A | 75 | −7.022 | 64.749 | 23.912 | 1.00 | 6.72 |
| ATOM 758 | H | TYR | A | 75 | −7.582 | 69.779 | 17.184 | 1.00 | 20.00 |
| ATOM 759 | HH | TYR | A | 75 | −6.405 | 64.032 | 23.778 | 1.00 | 20.00 |
| ATOM 760 | N | PRO | A | 76 | −6.378 | 70.278 | 21.045 | 1.00 | 6.84 |
| ATOM 761 | CA | PRO | A | 76 | −5.153 | 70.658 | 21.763 | 1.00 | 6.84 |
| ATOM 762 | C | PRO | A | 76 | −3.945 | 69.705 | 21.801 | 1.00 | 6.84 |
| ATOM 763 | O | PRO | A | 76 | −2.869 | 70.140 | 22.193 | 1.00 | 6.84 |
| ATOM 764 | CB | PRO | A | 76 | −5.675 | 71.047 | 23.158 | 1.00 | 6.84 |
| ATOM 765 | CG | PRO | A | 76 | −7.110 | 70.527 | 23.259 | 1.00 | 6.84 |
| ATOM 766 | CD | PRO | A | 76 | −7.589 | 70.543 | 21.817 | 1.00 | 6.84 |
| ATOM 767 | N | GLN | A | 77 | −4.130 | 68.421 | 21.422 | 1.00 | 4.75 |
| ATOM 768 | CA | GLN | A | 77 | −2.970 | 67.527 | 21.497 | 1.00 | 4.75 |
| ATOM 769 | C | GLN | A | 77 | −2.429 | 67.111 | 20.144 | 1.00 | 4.75 |
| ATOM 770 | O | GLN | A | 77 | −3.069 | 67.256 | 19.109 | 1.00 | 4.75 |
| ATOM 771 | CB | GLN | A | 77 | −3.276 | 66.243 | 22.268 | 1.00 | 4.75 |
| ATOM 772 | CG | GLN | A | 77 | −3.691 | 66.406 | 23.728 | 1.00 | 4.75 |
| ATOM 773 | CD | GLN | A | 77 | −4.116 | 65.052 | 24.270 | 1.00 | 4.75 |
| ATOM 774 | OE1 | GLN | A | 77 | −4.261 | 64.063 | 23.563 | 1.00 | 4.75 |
| ATOM 775 | NE2 | GLN | A | 77 | −4.362 | 65.046 | 25.582 | 1.00 | 4.75 |
| ATOM 776 | H | GLN | A | 77 | −4.940 | 68.125 | 20.921 | 1.00 | 20.00 |
| ATOM 777 | 1HE2 | GLN | A | 77 | −4.294 | 65.866 | 26.147 | 1.00 | 20.00 |
| ATOM 778 | 2HE2 | GLN | A | 77 | −4.643 | 64.173 | 25.977 | 1.00 | 20.00 |
| ATOM 779 | N | ASP | A | 78 | −1.225 | 66.532 | 20.243 | 1.00 | 4.94 |
| ATOM 780 | CA | ASP | A | 78 | −0.574 | 65.976 | 19.064 | 1.00 | 4.94 |
| ATOM 781 | C | ASP | A | 78 | −0.997 | 64.531 | 18.849 | 1.00 | 4.94 |
| ATOM 782 | O | ASP | A | 78 | −0.648 | 63.627 | 19.600 | 1.00 | 4.94 |
| ATOM 783 | CB | ASP | A | 78 | 0.958 | 66.079 | 19.192 | 1.00 | 4.94 |
| ATOM 784 | CG | ASP | A | 78 | 1.494 | 67.505 | 19.367 | 1.00 | 4.94 |
| ATOM 785 | OD1 | ASP | A | 78 | 0.727 | 68.446 | 19.569 | 1.00 | 4.94 |
| ATOM 786 | OD2 | ASP | A | 78 | 2.711 | 67.673 | 19.306 | 1.00 | 4.94 |
| ATOM 787 | H | ASP | A | 78 | −0.741 | 66.515 | 21.114 | 1.00 | 20.00 |
| ATOM 788 | N | LEU | A | 79 | −1.793 | 64.355 | 17.786 | 1.00 | 4.95 |
| ATOM 789 | CA | LEU | A | 79 | −2.205 | 62.999 | 17.414 | 1.00 | 4.95 |
| ATOM 790 | C | LEU | A | 79 | −1.076 | 62.291 | 16.694 | 1.00 | 4.95 |
| ATOM 791 | O | LEU | A | 79 | −0.197 | 62.926 | 16.126 | 1.00 | 4.95 |
| ATOM 792 | CB | LEU | A | 79 | −3.389 | 62.965 | 16.436 | 1.00 | 4.95 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 793 | CG | LEU A | 79 | −4.762 | 63.586 | 16.735 | 1.00 | 4.95 |
| ATOM 794 | CD1 | LEU A | 79 | −4.774 | 65.114 | 16.862 | 1.00 | 4.95 |
| ATOM 795 | CD2 | LEU A | 79 | −5.740 | 63.157 | 15.636 | 1.00 | 4.95 |
| ATOM 796 | H | LEU A | 79 | −1.974 | 65.160 | 17.219 | 1.00 | 20.00 |
| ATOM 797 | N | VAL A | 80 | −1.157 | 60.953 | 16.686 | 1.00 | 4.14 |
| ATOM 798 | CA | VAL A | 80 | −0.198 | 60.297 | 15.808 | 1.00 | 4.14 |
| ATOM 799 | C | VAL A | 80 | −0.829 | 59.810 | 14.523 | 1.00 | 4.14 |
| ATOM 800 | O | VAL A | 80 | −1.731 | 58.978 | 14.497 | 1.00 | 4.14 |
| ATOM 801 | CB | VAL A | 80 | 0.564 | 59.169 | 16.502 | 1.00 | 4.14 |
| ATOM 802 | CG1 | VAL A | 80 | 1.853 | 58.906 | 15.725 | 1.00 | 4.14 |
| ATOM 803 | CG2 | VAL A | 80 | 0.853 | 59.476 | 17.974 | 1.00 | 4.14 |
| ATOM 804 | H | VAL A | 80 | −1.867 | 60.439 | 17.164 | 1.00 | 20.00 |
| ATOM 805 | N | MET A | 81 | −0.298 | 60.402 | 13.444 | 1.00 | 4.15 |
| ATOM 806 | CA | MET A | 81 | −0.756 | 60.001 | 12.119 | 1.00 | 4.15 |
| ATOM 807 | C | MET A | 81 | −0.141 | 58.682 | 11.708 | 1.00 | 4.15 |
| ATOM 808 | O | MET A | 81 | −0.810 | 57.727 | 11.336 | 1.00 | 4.15 |
| ATOM 809 | CB | MET A | 81 | −0.410 | 61.085 | 11.095 | 1.00 | 4.15 |
| ATOM 810 | CG | MET A | 81 | −0.941 | 62.451 | 11.517 | 1.00 | 4.15 |
| ATOM 811 | SD | MET A | 81 | −0.314 | 63.804 | 10.514 | 1.00 | 4.15 |
| ATOM 812 | CE | MET A | 81 | −1.208 | 63.435 | 9.007 | 1.00 | 4.15 |
| ATOM 813 | H | MET A | 81 | 0.500 | 60.999 | 13.566 | 1.00 | 20.00 |
| ATOM 814 | N | MET A | 82 | 1.200 | 58.683 | 11.789 | 1.00 | 5.02 |
| ATOM 815 | CA | MET A | 82 | 1.919 | 57.508 | 11.307 | 1.00 | 5.02 |
| ATOM 816 | C | MET A | 82 | 3.104 | 57.195 | 12.187 | 1.00 | 5.02 |
| ATOM 817 | O | MET A | 82 | 3.784 | 58.086 | 12.672 | 1.00 | 5.02 |
| ATOM 818 | CB | MET A | 82 | 2.399 | 57.723 | 9.873 | 1.00 | 5.02 |
| ATOM 819 | CG | MET A | 82 | 1.292 | 57.743 | 8.819 | 1.00 | 5.02 |
| ATOM 820 | SD | MET A | 82 | 1.937 | 58.016 | 7.169 | 1.00 | 5.02 |
| ATOM 821 | CE | MET A | 82 | 2.667 | 59.632 | 7.451 | 1.00 | 5.02 |
| ATOM 822 | H | MET A | 82 | 1.694 | 59.472 | 12.167 | 1.00 | 20.00 |
| ATOM 823 | N | GLU A | 83 | 3.327 | 55.888 | 12.366 | 1.00 | 4.99 |
| ATOM 824 | CA | GLU A | 83 | 4.413 | 55.493 | 13.261 | 1.00 | 4.99 |
| ATOM 825 | C | GLU A | 83 | 5.275 | 54.450 | 12.650 | 1.00 | 4.99 |
| ATOM 826 | O | GLU A | 83 | 4.736 | 53.553 | 12.025 | 1.00 | 4.99 |
| ATOM 827 | CB | GLU A | 83 | 3.889 | 54.756 | 14.457 | 1.00 | 4.99 |
| ATOM 828 | CG | GLU A | 83 | 3.089 | 55.618 | 15.382 | 1.00 | 4.99 |
| ATOM 829 | CD | GLU A | 83 | 3.773 | 55.640 | 16.726 | 1.00 | 4.99 |
| ATOM 830 | OE1 | GLU A | 83 | 4.446 | 54.677 | 17.122 | 1.00 | 4.99 |
| ATOM 831 | OE2 | GLU A | 83 | 3.627 | 56.648 | 17.397 | 1.00 | 4.99 |
| ATOM 832 | H | GLU A | 83 | 2.737 | 55.195 | 11.955 | 1.00 | 20.00 |
| ATOM 833 | N | GLY A | 84 | 6.580 | 54.558 | 12.923 | 1.00 | 3.83 |
| ATOM 834 | CA | GLY A | 84 | 7.526 | 53.514 | 12.559 | 1.00 | 3.83 |
| ATOM 835 | C | GLY A | 84 | 8.373 | 53.054 | 13.724 | 1.00 | 3.83 |
| ATOM 836 | O | GLY A | 84 | 9.097 | 53.839 | 14.314 | 1.00 | 3.83 |
| ATOM 837 | H | GLY A | 84 | 6.904 | 55.409 | 13.340 | 1.00 | 20.00 |
| ATOM 838 | N | LYS A | 85 | 8.269 | 51.751 | 14.030 | 1.00 | 5.40 |
| ATOM 839 | CA | LYS A | 85 | 9.204 | 51.217 | 15.017 | 1.00 | 5.40 |
| ATOM 840 | C | LYS A | 85 | 10.119 | 50.200 | 14.395 | 1.00 | 5.40 |
| ATOM 841 | O | LYS A | 85 | 9.685 | 49.201 | 13.833 | 1.00 | 5.40 |
| ATOM 842 | CB | LYS A | 85 | 8.492 | 50.533 | 16.176 | 1.00 | 5.40 |
| ATOM 843 | CG | LYS A | 85 | 7.538 | 51.436 | 16.942 | 1.00 | 5.40 |
| ATOM 844 | CD | LYS A | 85 | 6.814 | 50.636 | 18.015 | 1.00 | 5.40 |
| ATOM 845 | CE | LYS A | 85 | 5.815 | 51.489 | 18.788 | 1.00 | 5.40 |
| ATOM 846 | NZ | LYS A | 85 | 5.158 | 50.615 | 19.763 | 1.00 | 5.40 |
| ATOM 847 | H | LYS A | 85 | 7.645 | 51.137 | 13.554 | 1.00 | 20.00 |
| ATOM 848 | 1HZ | LYS A | 85 | 4.477 | 51.153 | 20.340 | 1.00 | 20.00 |
| ATOM 849 | 2HZ | LYS A | 85 | 4.658 | 49.860 | 19.252 | 1.00 | 20.00 |
| ATOM 850 | 3HZ | LYS A | 85 | 5.853 | 50.191 | 20.406 | 1.00 | 20.00 |
| ATOM 851 | N | MET A | 86 | 11.410 | 50.491 | 14.536 | 1.00 | 17.02 |
| ATOM 852 | CA | MET A | 86 | 12.372 | 49.480 | 14.142 | 1.00 | 17.02 |
| ATOM 853 | C | MET A | 86 | 13.285 | 49.154 | 15.294 | 1.00 | 17.02 |
| ATOM 854 | O | MET A | 86 | 14.205 | 49.889 | 15.621 | 1.00 | 17.02 |
| ATOM 855 | CB | MET A | 86 | 13.173 | 49.922 | 12.912 | 1.00 | 17.02 |
| ATOM 856 | CG | MET A | 86 | 12.308 | 50.081 | 11.658 | 1.00 | 17.02 |
| ATOM 857 | SD | MET A | 86 | 11.506 | 48.548 | 11.152 | 1.00 | 17.02 |
| ATOM 858 | CE | MET A | 86 | 12.959 | 47.697 | 10.523 | 1.00 | 17.02 |
| ATOM 859 | H | MET A | 86 | 11.698 | 51.351 | 14.962 | 1.00 | 20.00 |
| ATOM 860 | N | MET A | 87 | 13.039 | 47.975 | 15.882 | 1.00 | 29.14 |
| ATOM 861 | CA | MET A | 87 | 14.077 | 47.534 | 16.819 | 1.00 | 29.14 |
| ATOM 862 | C | MET A | 87 | 15.137 | 46.684 | 16.139 | 1.00 | 29.14 |
| ATOM 863 | O | MET A | 87 | 15.631 | 45.671 | 16.614 | 1.00 | 29.14 |
| ATOM 864 | CB | MET A | 87 | 13.486 | 46.853 | 18.054 | 1.00 | 29.14 |
| ATOM 865 | CG | MET A | 87 | 14.428 | 47.021 | 19.249 | 1.00 | 29.14 |
| ATOM 866 | SD | MET A | 87 | 13.931 | 46.100 | 20.705 | 1.00 | 29.14 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 867 | CE | MET A | 87 | 15.308 | 46.529 | 21.781 | 1.00 | 29.14 |
| ATOM 868 | H | MET A | 87 | 12.292 | 47.397 | 15.551 | 1.00 | 20.00 |
| ATOM 869 | N | SER A | 88 | 15.438 | 47.156 | 14.930 | 1.00 | 17.75 |
| ATOM 870 | CA | SER A | 88 | 16.291 | 46.381 | 14.060 | 1.00 | 17.75 |
| ATOM 871 | C | SER A | 88 | 17.673 | 46.973 | 13.968 | 1.00 | 17.75 |
| ATOM 872 | O | SER A | 88 | 18.220 | 47.231 | 12.907 | 1.00 | 17.75 |
| ATOM 873 | CB | SER A | 88 | 15.610 | 46.322 | 12.716 | 1.00 | 17.75 |
| ATOM 874 | OG | SER A | 88 | 16.348 | 45.494 | 11.820 | 1.00 | 17.75 |
| ATOM 875 | H | SER A | 88 | 15.116 | 48.050 | 14.630 | 1.00 | 20.00 |
| ATOM 876 | HG | SER A | 88 | 16.557 | 46.092 | 11.120 | 1.00 | 20.00 |
| ATOM 877 | N | TYR A | 89 | 18.231 | 47.164 | 15.158 | 1.00 | 19.14 |
| ATOM 878 | CA | TYR A | 89 | 19.673 | 47.374 | 15.157 | 1.00 | 19.14 |
| ATOM 879 | C | TYR A | 89 | 20.375 | 46.042 | 14.875 | 1.00 | 19.14 |
| ATOM 880 | O | TYR A | 89 | 19.781 | 45.118 | 14.327 | 1.00 | 19.14 |
| ATOM 881 | CB | TYR A | 89 | 20.080 | 48.072 | 16.468 | 1.00 | 19.14 |
| ATOM 882 | CG | TYR A | 89 | 19.571 | 47.288 | 17.655 | 1.00 | 19.14 |
| ATOM 883 | CD1 | TYR A | 89 | 18.320 | 47.611 | 18.217 | 1.00 | 19.14 |
| ATOM 884 | CD2 | TYR A | 89 | 20.356 | 46.231 | 18.149 | 1.00 | 19.14 |
| ATOM 885 | CE1 | TYR A | 89 | 17.828 | 46.823 | 19.266 | 1.00 | 19.14 |
| ATOM 886 | CE2 | TYR A | 89 | 19.868 | 45.444 | 19.198 | 1.00 | 19.14 |
| ATOM 887 | CZ | TYR A | 89 | 18.604 | 45.746 | 19.736 | 1.00 | 19.14 |
| ATOM 888 | OH | TYR A | 89 | 18.115 | 44.967 | 20.761 | 1.00 | 19.14 |
| ATOM 889 | H | TYR A | 89 | 17.720 | 46.902 | 15.975 | 1.00 | 20.00 |
| ATOM 890 | HH | TYR A | 89 | 18.859 | 44.678 | 21.287 | 1.00 | 20.00 |
| ATOM 891 | N | CYS A | 90 | 21.651 | 45.956 | 15.252 | 1.00 | 32.37 |
| ATOM 892 | CA | CYS A | 90 | 22.299 | 44.667 | 15.015 | 1.00 | 32.37 |
| ATOM 893 | C | CYS A | 90 | 22.823 | 44.026 | 16.287 | 1.00 | 32.37 |
| ATOM 894 | O | CYS A | 90 | 22.546 | 44.478 | 17.389 | 1.00 | 32.37 |
| ATOM 895 | CB | CYS A | 90 | 23.385 | 44.854 | 13.957 | 1.00 | 32.37 |
| ATOM 896 | SG | CYS A | 90 | 24.212 | 46.439 | 14.170 | 1.00 | 32.37 |
| ATOM 897 | H | CYS A | 90 | 22.147 | 46.712 | 15.679 | 1.00 | 20.00 |
| ATOM 898 | N | THR A | 91 | 23.605 | 42.962 | 16.086 | 1.00 | 22.92 |
| ATOM 899 | CA | THR A | 91 | 24.339 | 42.363 | 17.196 | 1.00 | 22.92 |
| ATOM 900 | C | THR A | 91 | 25.818 | 42.616 | 16.939 | 1.00 | 22.92 |
| ATOM 901 | O | THR A | 91 | 26.149 | 43.587 | 16.278 | 1.00 | 22.92 |
| ATOM 902 | CB | THR A | 91 | 23.988 | 40.882 | 17.199 | 1.00 | 22.92 |
| ATOM 903 | OG1 | THR A | 91 | 24.115 | 40.369 | 15.866 | 1.00 | 22.92 |
| ATOM 904 | CG2 | THR A | 91 | 22.563 | 40.647 | 17.710 | 1.00 | 22.92 |
| ATOM 905 | H | THR A | 91 | 23.795 | 42.572 | 15.187 | 1.00 | 20.00 |
| ATOM 906 | HG1 | THR A | 91 | 24.137 | 39.424 | 15.940 | 1.00 | 20.00 |
| ATOM 907 | N | THR A | 92 | 26.708 | 41.721 | 17.400 | 1.00 | 5.61 |
| ATOM 908 | CA | THR A | 92 | 28.086 | 41.853 | 16.913 | 1.00 | 5.61 |
| ATOM 909 | C | THR A | 92 | 28.213 | 41.890 | 15.392 | 1.00 | 5.61 |
| ATOM 910 | O | THR A | 92 | 27.912 | 40.922 | 14.704 | 1.00 | 5.61 |
| ATOM 911 | CB | THR A | 92 | 28.926 | 40.714 | 17.486 | 1.00 | 5.61 |
| ATOM 912 | OG1 | THR A | 92 | 28.595 | 40.529 | 18.867 | 1.00 | 5.61 |
| ATOM 913 | CG2 | THR A | 92 | 30.430 | 40.943 | 17.305 | 1.00 | 5.61 |
| ATOM 914 | H | THR A | 92 | 26.508 | 40.997 | 18.059 | 1.00 | 20.00 |
| ATOM 915 | HG1 | THR A | 92 | 29.235 | 39.918 | 19.211 | 1.00 | 20.00 |
| ATOM 916 | N | GLY A | 93 | 28.658 | 43.058 | 14.909 | 1.00 | 3.78 |
| ATOM 917 | CA | GLY A | 93 | 28.732 | 43.206 | 13.464 | 1.00 | 3.78 |
| ATOM 918 | C | GLY A | 93 | 29.306 | 44.546 | 13.070 | 1.00 | 3.78 |
| ATOM 919 | O | GLY A | 93 | 29.678 | 45.364 | 13.903 | 1.00 | 3.78 |
| ATOM 920 | H | GLY A | 93 | 28.829 | 43.853 | 15.492 | 1.00 | 20.00 |
| ATOM 921 | N | GLN A | 94 | 29.357 | 44.705 | 11.739 | 1.00 | 15.42 |
| ATOM 922 | CA | GLN A | 94 | 29.825 | 45.959 | 11.157 | 1.00 | 15.42 |
| ATOM 923 | C | GLN A | 94 | 28.774 | 47.056 | 11.240 | 1.00 | 15.42 |
| ATOM 924 | O | GLN A | 94 | 27.854 | 47.009 | 12.047 | 1.00 | 15.42 |
| ATOM 925 | CB | GLN A | 94 | 30.255 | 45.687 | 9.710 | 1.00 | 15.42 |
| ATOM 926 | CG | GLN A | 94 | 31.542 | 44.868 | 9.579 | 1.00 | 15.42 |
| ATOM 927 | CD | GLN A | 94 | 32.724 | 45.680 | 10.075 | 1.00 | 15.42 |
| ATOM 928 | OE1 | GLN A | 94 | 33.261 | 45.475 | 11.152 | 1.00 | 15.42 |
| ATOM 929 | NE2 | GLN A | 94 | 33.116 | 46.632 | 9.222 | 1.00 | 15.42 |
| ATOM 930 | H | GLN A | 94 | 28.969 | 43.993 | 11.158 | 1.00 | 20.00 |
| ATOM 931 | 1HE2 | GLN A | 94 | 32.648 | 46.789 | 8.353 | 1.00 | 20.00 |
| ATOM 932 | 2HE2 | GLN A | 94 | 33.914 | 47.171 | 9.484 | 1.00 | 20.00 |
| ATOM 933 | N | MET A | 95 | 28.930 | 48.044 | 10.337 | 1.00 | 18.74 |
| ATOM 934 | CA | MET A | 95 | 27.843 | 49.006 | 10.176 | 1.00 | 18.74 |
| ATOM 935 | C | MET A | 95 | 26.493 | 48.376 | 9.859 | 1.00 | 18.74 |
| ATOM 936 | O | MET A | 95 | 26.386 | 47.301 | 9.281 | 1.00 | 18.74 |
| ATOM 937 | CB | MET A | 95 | 28.211 | 50.069 | 9.127 | 1.00 | 18.74 |
| ATOM 938 | CG | MET A | 95 | 28.503 | 49.492 | 7.737 | 1.00 | 18.74 |
| ATOM 939 | SD | MET A | 95 | 28.762 | 50.723 | 6.449 | 1.00 | 18.74 |
| ATOM 940 | CE | MET A | 95 | 29.080 | 49.589 | 5.084 | 1.00 | 18.74 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 941 | H | MET A | 95 | 29.733 | 48.091 | 9.751 | 1.00 | 20.00 |
| ATOM 942 | N | TRP A | 96 | 25.463 | 49.120 | 10.262 | 1.00 | 3.87 |
| ATOM 943 | CA | TRP A | 96 | 24.112 | 48.694 | 9.925 | 1.00 | 3.87 |
| ATOM 944 | C | TRP A | 96 | 23.339 | 49.887 | 9.430 | 1.00 | 3.87 |
| ATOM 945 | O | TRP A | 96 | 23.504 | 50.978 | 9.955 | 1.00 | 3.87 |
| ATOM 946 | CB | TRP A | 96 | 23.421 | 48.062 | 11.142 | 1.00 | 3.87 |
| ATOM 947 | CG | TRP A | 96 | 23.354 | 49.035 | 12.303 | 1.00 | 3.87 |
| ATOM 948 | CD1 | TRP A | 96 | 24.333 | 49.259 | 13.283 | 1.00 | 3.87 |
| ATOM 949 | CD2 | TRP A | 96 | 22.280 | 49.934 | 12.644 | 1.00 | 3.87 |
| ATOM 950 | NE1 | TRP A | 96 | 23.943 | 50.198 | 14.181 | 1.00 | 3.87 |
| ATOM 951 | CE2 | TRP A | 96 | 22.674 | 50.647 | 13.825 | 1.00 | 3.87 |
| ATOM 952 | CE3 | TRP A | 96 | 21.028 | 50.190 | 12.049 | 1.00 | 3.87 |
| ATOM 953 | CZ2 | TRP A | 96 | 21.806 | 51.609 | 14.383 | 1.00 | 3.87 |
| ATOM 954 | CZ3 | TRP A | 96 | 20.172 | 51.154 | 12.617 | 1.00 | 3.87 |
| ATOM 955 | CH2 | TRP A | 96 | 20.557 | 51.857 | 13.777 | 1.00 | 3.87 |
| ATOM 956 | H | TRP A | 96 | 25.635 | 49.947 | 10.803 | 1.00 | 20.00 |
| ATOM 957 | HE1 | TRP A | 96 | 24.476 | 50.477 | 14.958 | 1.00 | 20.00 |
| ATOM 958 | N | ALA A | 97 | 22.498 | 49.640 | 8.418 | 1.00 | 3.76 |
| ATOM 959 | CA | ALA A | 97 | 21.642 | 50.732 | 7.978 | 1.00 | 3.76 |
| ATOM 960 | C | ALA A | 97 | 20.211 | 50.269 | 7.857 | 1.00 | 3.76 |
| ATOM 961 | O | ALA A | 97 | 19.943 | 49.221 | 7.277 | 1.00 | 3.76 |
| ATOM 962 | CB | ALA A | 97 | 22.111 | 51.295 | 6.636 | 1.00 | 3.76 |
| ATOM 963 | H | ALA A | 97 | 22.433 | 48.732 | 8.009 | 1.00 | 20.00 |
| ATOM 964 | N | ARG A | 98 | 19.322 | 51.073 | 8.467 | 1.00 | 11.69 |
| ATOM 965 | CA | ARG A | 98 | 17.895 | 50.758 | 8.389 | 1.00 | 11.69 |
| ATOM 966 | C | ARG A | 98 | 17.113 | 51.920 | 7.835 | 1.00 | 11.69 |
| ATOM 967 | O | ARG A | 98 | 17.389 | 53.074 | 8.138 | 1.00 | 11.69 |
| ATOM 968 | CB | ARG A | 98 | 17.282 | 50.406 | 9.749 | 1.00 | 11.69 |
| ATOM 969 | CG | ARG A | 98 | 18.026 | 49.325 | 10.519 | 1.00 | 11.69 |
| ATOM 970 | CD | ARG A | 98 | 18.214 | 48.043 | 9.724 | 1.00 | 11.69 |
| ATOM 971 | NE | ARG A | 98 | 19.092 | 47.120 | 10.438 | 1.00 | 11.69 |
| ATOM 972 | CZ | ARG A | 98 | 18.895 | 45.804 | 10.316 | 1.00 | 11.69 |
| ATOM 973 | NH1 | ARG A | 98 | 19.725 | 44.923 | 10.868 | 1.00 | 11.69 |
| ATOM 974 | NH2 | ARG A | 98 | 17.862 | 45.392 | 9.604 | 1.00 | 11.69 |
| ATOM 975 | H | ARG A | 98 | 19.647 | 51.921 | 8.896 | 1.00 | 20.00 |
| ATOM 976 | HE | ARG A | 98 | 19.795 | 47.481 | 11.051 | 1.00 | 20.00 |
| ATOM 977 | 1HH1 | ARG A | 98 | 19.644 | 43.944 | 10.682 | 1.00 | 20.00 |
| ATOM 978 | 2HH2 | ARG A | 98 | 20.449 | 45.230 | 11.485 | 1.00 | 20.00 |
| ATOM 979 | 1HH2 | ARG A | 98 | 17.815 | 44.424 | 9.344 | 1.00 | 20.00 |
| ATOM 980 | 2HH2 | ARG A | 98 | 17.183 | 46.019 | 9.228 | 1.00 | 20.00 |
| ATOM 981 | N | SER A | 99 | 16.112 | 51.568 | 7.023 | 1.00 | 7.28 |
| ATOM 982 | CA | SER A | 99 | 15.251 | 52.651 | 6.579 | 1.00 | 7.28 |
| ATOM 983 | C | SER A | 99 | 13.819 | 52.537 | 7.045 | 1.00 | 7.28 |
| ATOM 984 | O | SER A | 99 | 13.218 | 51.468 | 7.051 | 1.00 | 7.28 |
| ATOM 985 | CB | SER A | 99 | 15.326 | 52.777 | 5.062 | 1.00 | 7.28 |
| ATOM 986 | OG | SER A | 99 | 14.993 | 51.548 | 4.407 | 1.00 | 7.28 |
| ATOM 987 | H | SER A | 99 | 15.937 | 50.634 | 6.715 | 1.00 | 20.00 |
| ATOM 988 | HG | SER A | 99 | 15.592 | 51.447 | 3.679 | 1.00 | 20.00 |
| ATOM 989 | N | SER A | 100 | 13.291 | 53.712 | 7.406 | 1.00 | 2.73 |
| ATOM 990 | CA | SER A | 100 | 11.865 | 53.753 | 7.707 | 1.00 | 2.73 |
| ATOM 991 | C | SER A | 100 | 11.154 | 54.722 | 6.785 | 1.00 | 2.73 |
| ATOM 992 | O | SER A | 100 | 11.559 | 55.866 | 6.644 | 1.00 | 2.73 |
| ATOM 993 | CB | SER A | 100 | 11.645 | 54.133 | 9.173 | 1.00 | 2.73 |
| ATOM 994 | OG | SER A | 100 | 12.260 | 53.161 | 10.026 | 1.00 | 2.73 |
| ATOM 995 | H | SER A | 100 | 13.847 | 54.548 | 7.414 | 1.00 | 20.00 |
| ATOM 996 | HG | SER A | 100 | 12.324 | 53.557 | 10.887 | 1.00 | 20.00 |
| ATOM 997 | N | TYR A | 101 | 10.081 | 54.205 | 6.157 | 1.00 | 2.72 |
| ATOM 998 | CA | TYR A | 101 | 9.290 | 55.066 | 5.268 | 1.00 | 2.72 |
| ATOM 999 | C | TYR A | 101 | 7.839 | 55.064 | 5.678 | 1.00 | 2.72 |
| ATOM 1000 | O | TYR A | 101 | 7.281 | 54.003 | 5.901 | 1.00 | 2.72 |
| ATOM 1001 | CB | TYR A | 101 | 9.380 | 54.580 | 3.816 | 1.00 | 2.72 |
| ATOM 1002 | CG | TYR A | 101 | 8.532 | 55.444 | 2.905 | 1.00 | 2.72 |
| ATOM 1003 | CD1 | TYR A | 101 | 9.050 | 56.650 | 2.391 | 1.00 | 2.72 |
| ATOM 1004 | CD2 | TYR A | 101 | 7.223 | 55.019 | 2.613 | 1.00 | 2.72 |
| ATOM 1005 | CE1 | TYR A | 101 | 8.244 | 57.444 | 1.559 | 1.00 | 2.72 |
| ATOM 1006 | CE2 | TYR A | 101 | 6.413 | 55.818 | 1.795 | 1.00 | 2.72 |
| ATOM 1007 | CZ | TYR A | 101 | 6.940 | 57.004 | 1.255 | 1.00 | 2.72 |
| ATOM 1008 | OH | TYR A | 101 | 6.153 | 57.736 | 0.390 | 1.00 | 2.72 |
| ATOM 1009 | H | TYR A | 101 | 9.831 | 53.250 | 6.305 | 1.00 | 20.00 |
| ATOM 1010 | HH | TYR A | 101 | 5.326 | 57.292 | 0.259 | 1.00 | 20.00 |
| ATOM 1011 | N | LEU A | 102 | 7.253 | 56.255 | 5.767 | 1.00 | 17.88 |
| ATOM 1012 | CA | LEU A | 102 | 5.860 | 56.384 | 6.183 | 1.00 | 17.88 |
| ATOM 1013 | C | LEU A | 102 | 5.100 | 57.129 | 5.097 | 1.00 | 17.88 |
| ATOM 1014 | O | LEU A | 102 | 5.688 | 57.936 | 4.388 | 1.00 | 17.88 |

TABLE 1-continued

Atomic coordinates of the higher-order structure of Fas ligand

| Atom species | Amino acid residues | | | # | X | Y | Z | OCC | B |
|---|---|---|---|---|---|---|---|---|---|
| ATOM 1015 | CB | LEU | A | 102 | 5.803 | 57.140 | 7.519 | 1.00 | 17.88 |
| ATOM 1016 | CG | LEU | A | 102 | 5.972 | 56.301 | 8.801 | 1.00 | 17.88 |
| ATOM 1017 | CD1 | LEU | A | 102 | 4.868 | 55.256 | 8.909 | 1.00 | 17.88 |
| ATOM 1018 | CD2 | LEU | A | 102 | 7.353 | 55.674 | 9.006 | 1.00 | 17.88 |
| ATOM 1019 | H | LEU | A | 102 | 7.742 | 57.061 | 5.433 | 1.00 | 20.00 |
| ATOM 1020 | N | GLY | A | 103 | 3.798 | 56.824 | 4.975 | 1.00 | 5.34 |
| ATOM 1021 | CA | GLY | A | 103 | 3.053 | 57.518 | 3.923 | 1.00 | 5.34 |
| ATOM 1022 | C | GLY | A | 103 | 1.577 | 57.172 | 3.900 | 1.00 | 5.34 |
| ATOM 1023 | O | GLY | A | 103 | 1.227 | 56.000 | 3.874 | 1.00 | 5.34 |
| ATOM 1024 | H | GLY | A | 103 | 3.334 | 56.161 | 5.562 | 1.00 | 20.00 |
| ATOM 1025 | N | ALA | A | 104 | 0.734 | 58.226 | 3.923 | 1.00 | 6.66 |
| ATOM 1026 | CA | ALA | A | 104 | −0.713 | 57.984 | 3.938 | 1.00 | 6.66 |
| ATOM 1027 | C | ALA | A | 104 | −1.551 | 59.223 | 3.656 | 1.00 | 6.66 |
| ATOM 1028 | O | ALA | A | 104 | −1.029 | 60.330 | 3.607 | 1.00 | 6.66 |
| ATOM 1029 | CB | ALA | A | 104 | −1.133 | 57.414 | 5.287 | 1.00 | 6.66 |
| ATOM 1030 | H | ALA | A | 104 | 1.093 | 59.164 | 3.962 | 1.00 | 20.00 |
| ATOM 1031 | N | VAL | A | 105 | −2.867 | 58.989 | 3.460 | 1.00 | 2.80 |
| ATOM 1032 | CA | VAL | A | 105 | −3.752 | 60.117 | 3.148 | 1.00 | 2.80 |
| ATOM 1033 | C | VAL | A | 105 | −4.645 | 60.533 | 4.296 | 1.00 | 2.80 |
| ATOM 1034 | O | VAL | A | 105 | −5.287 | 59.720 | 4.950 | 1.00 | 2.80 |
| ATOM 1035 | CB | VAL | A | 105 | −4.602 | 59.805 | 1.914 | 1.00 | 2.80 |
| ATOM 1036 | CG1 | VAL | A | 105 | −5.572 | 60.920 | 1.528 | 1.00 | 2.80 |
| ATOM 1037 | CG2 | VAL | A | 105 | −3.673 | 59.526 | 0.754 | 1.00 | 2.80 |
| ATOM 1038 | H | VAL | A | 105 | −3.265 | 58.071 | 3.522 | 1.00 | 20.00 |
| ATOM 1039 | N | PHE | A | 106 | −4.654 | 61.859 | 4.497 | 1.00 | 2.81 |
| ATOM 1040 | CA | PHE | A | 106 | −5.386 | 62.398 | 5.637 | 1.00 | 2.81 |
| ATOM 1041 | C | PHE | A | 106 | −6.159 | 63.659 | 5.250 | 1.00 | 2.81 |
| ATOM 1042 | O | PHE | A | 106 | −5.778 | 64.341 | 4.308 | 1.00 | 2.81 |
| ATOM 1043 | CB | PHE | A | 106 | −4.376 | 62.653 | 6.766 | 1.00 | 2.81 |
| ATOM 1044 | CG | PHE | A | 106 | −3.693 | 61.370 | 7.221 | 1.00 | 2.81 |
| ATOM 1045 | CD1 | PHE | A | 106 | −2.354 | 61.109 | 6.859 | 1.00 | 2.81 |
| ATOM 1046 | CD2 | PHE | A | 106 | −4.396 | 60.457 | 8.033 | 1.00 | 2.81 |
| ATOM 1047 | CE1 | PHE | A | 106 | −1.702 | 59.974 | 7.380 | 1.00 | 2.81 |
| ATOM 1048 | CE2 | PHE | A | 106 | −3.758 | 59.319 | 8.556 | 1.00 | 2.81 |
| ATOM 1049 | CZ | PHE | A | 106 | −2.402 | 59.105 | 8.245 | 1.00 | 2.81 |
| ATOM 1050 | H | PHE | A | 106 | −4.116 | 62.456 | 3.895 | 1.00 | 20.00 |
| ATOM 1051 | N | ASN | A | 107 | −7.255 | 63.955 | 5.988 | 1.00 | 6.84 |
| ATOM 1052 | CA | ASN | A | 107 | −7.863 | 65.278 | 5.759 | 1.00 | 6.84 |
| ATOM 1053 | C | ASN | A | 107 | −7.295 | 66.277 | 6.714 | 1.00 | 6.84 |
| ATOM 1054 | O | ASN | A | 107 | −7.481 | 66.185 | 7.922 | 1.00 | 6.84 |
| ATOM 1055 | CB | ASN | A | 107 | −9.369 | 65.410 | 5.997 | 1.00 | 6.84 |
| ATOM 1056 | CG | ASN | A | 107 | −10.175 | 64.699 | 4.954 | 1.00 | 6.84 |
| ATOM 1057 | OD1 | ASN | A | 107 | −10.677 | 65.231 | 3.975 | 1.00 | 6.84 |
| ATOM 1058 | ND2 | ASN | A | 107 | −10.299 | 63.426 | 5.256 | 1.00 | 6.84 |
| ATOM 1059 | H | ASN | A | 107 | −7.478 | 63.414 | 6.795 | 1.00 | 20.00 |
| ATOM 1060 | 1HD2 | ASN | A | 107 | −9.850 | 63.061 | 6.071 | 1.00 | 20.00 |
| ATOM 1061 | 2HD2 | ASN | A | 107 | −10.834 | 62.817 | 4.673 | 1.00 | 20.00 |
| ATOM 1062 | N | LEU | A | 108 | −6.609 | 67.239 | 6.111 | 1.00 | 5.08 |
| ATOM 1063 | CA | LEU | A | 108 | −6.140 | 68.308 | 6.973 | 1.00 | 5.08 |
| ATOM 1064 | C | LEU | A | 108 | −7.006 | 69.538 | 6.833 | 1.00 | 5.08 |
| ATOM 1065 | O | LEU | A | 108 | −7.826 | 69.648 | 5.923 | 1.00 | 5.08 |
| ATOM 1066 | CB | LEU | A | 108 | −4.661 | 68.566 | 6.699 | 1.00 | 5.08 |
| ATOM 1067 | CG | LEU | A | 108 | −3.832 | 67.297 | 6.932 | 1.00 | 5.08 |
| ATOM 1068 | CD1 | LEU | A | 108 | −2.413 | 67.423 | 6.391 | 1.00 | 5.08 |
| ATOM 1069 | CD2 | LEU | A | 108 | −3.845 | 66.857 | 8.396 | 1.00 | 5.08 |
| ATOM 1070 | H | LEU | A | 108 | −6.553 | 67.274 | 5.111 | 1.00 | 20.00 |
| ATOM 1071 | N | THR | A | 109 | −6.793 | 70.436 | 7.797 | 1.00 | 3.97 |
| ATOM 1072 | CA | THR | A | 109 | −7.583 | 71.659 | 7.816 | 1.00 | 3.97 |
| ATOM 1073 | C | THR | A | 109 | −6.596 | 72.809 | 7.748 | 1.00 | 3.97 |
| ATOM 1074 | O | THR | A | 109 | −5.409 | 72.624 | 7.969 | 1.00 | 3.97 |
| ATOM 1075 | CB | THR | A | 109 | −8.413 | 71.698 | 9.115 | 1.00 | 3.97 |
| ATOM 1076 | OG1 | THR | A | 109 | −9.031 | 70.427 | 9.358 | 1.00 | 3.97 |
| ATOM 1077 | CG2 | THR | A | 109 | −9.489 | 72.790 | 9.136 | 1.00 | 3.97 |
| ATOM 1078 | H | THR | A | 109 | −6.022 | 70.350 | 8.436 | 1.00 | 20.00 |
| ATOM 1079 | HG1 | THR | A | 109 | −9.492 | 70.529 | 10.177 | 1.00 | 20.00 |
| ATOM 1080 | N | SER | A | 110 | −7.090 | 74.019 | 7.467 | 1.00 | 5.78 |
| ATOM 1081 | CA | SER | A | 110 | −6.181 | 75.132 | 7.727 | 1.00 | 5.78 |
| ATOM 1082 | C | SER | A | 110 | −5.717 | 75.216 | 9.180 | 1.00 | 5.78 |
| ATOM 1083 | O | SER | A | 110 | −6.457 | 74.892 | 10.103 | 1.00 | 5.78 |
| ATOM 1084 | CB | SER | A | 110 | −6.858 | 76.425 | 7.292 | 1.00 | 5.78 |
| ATOM 1085 | OG | SER | A | 110 | −7.383 | 76.244 | 5.972 | 1.00 | 5.78 |
| ATOM 1086 | H | SER | A | 110 | −8.020 | 74.186 | 7.139 | 1.00 | 20.00 |
| ATOM 1087 | HG | SER | A | 110 | −6.722 | 76.600 | 5.381 | 1.00 | 20.00 |
| ATOM 1088 | N | ALA | A | 111 | −4.456 | 75.673 | 9.307 | 1.00 | 23.23 |

TABLE 1-continued

Atomic coordinates of the higher-order structure of Fas ligand

| Atom species | Amino acid residues | | | # | X | Y | Z | OCC | B |
|---|---|---|---|---|---|---|---|---|---|
| ATOM 1089 | CA | ALA | A | 111 | −3.794 | 76.025 | 10.569 | 1.00 | 23.23 |
| ATOM 1090 | C | ALA | A | 111 | −3.149 | 74.915 | 11.374 | 1.00 | 23.23 |
| ATOM 1091 | O | ALA | A | 111 | −2.361 | 75.193 | 12.274 | 1.00 | 23.23 |
| ATOM 1092 | CB | ALA | A | 111 | −4.675 | 76.865 | 11.508 | 1.00 | 23.23 |
| ATOM 1093 | H | ALA | A | 111 | −3.916 | 75.702 | 8.463 | 1.00 | 20.00 |
| ATOM 1094 | N | ASP | A | 112 | −3.484 | 73.655 | 11.047 | 1.00 | 12.39 |
| ATOM 1095 | CA | ASP | A | 112 | −2.809 | 72.652 | 11.861 | 1.00 | 12.39 |
| ATOM 1096 | C | ASP | A | 112 | −1.360 | 72.396 | 11.493 | 1.00 | 12.39 |
| ATOM 1097 | O | ASP | A | 112 | −0.903 | 72.732 | 10.405 | 1.00 | 12.39 |
| ATOM 1098 | CB | ASP | A | 112 | −3.661 | 71.388 | 12.018 | 1.00 | 12.39 |
| ATOM 1099 | CG | ASP | A | 112 | −3.767 | 70.469 | 10.816 | 1.00 | 12.39 |
| ATOM 1100 | OD1 | ASP | A | 112 | −3.607 | 69.267 | 11.004 | 1.00 | 12.39 |
| ATOM 1101 | OD2 | ASP | A | 112 | −4.052 | 70.934 | 9.720 | 1.00 | 12.39 |
| ATOM 1102 | H | ASP | A | 112 | −4.067 | 73.372 | 10.281 | 1.00 | 20.00 |
| ATOM 1103 | N | HIS | A | 113 | −0.645 | 71.849 | 12.492 | 1.00 | 16.60 |
| ATOM 1104 | CA | HIS | A | 113 | 0.771 | 71.584 | 12.259 | 1.00 | 16.60 |
| ATOM 1105 | C | HIS | A | 113 | 1.049 | 70.105 | 12.141 | 1.00 | 16.60 |
| ATOM 1106 | O | HIS | A | 113 | 0.514 | 69.306 | 12.898 | 1.00 | 16.60 |
| ATOM 1107 | CB | HIS | A | 113 | 1.655 | 72.098 | 13.395 | 1.00 | 16.60 |
| ATOM 1108 | CG | HIS | A | 113 | 1.693 | 73.602 | 13.508 | 1.00 | 16.60 |
| ATOM 1109 | ND1 | HIS | A | 113 | 0.738 | 74.324 | 14.117 | 1.00 | 16.60 |
| ATOM 1110 | CD2 | HIS | A | 113 | 2.700 | 74.466 | 13.066 | 1.00 | 16.60 |
| ATOM 1111 | CE1 | HIS | A | 113 | 1.128 | 75.635 | 14.067 | 1.00 | 16.60 |
| ATOM 1112 | NE2 | HIS | A | 113 | 2.336 | 75.725 | 13.423 | 1.00 | 16.60 |
| ATOM 1113 | H | HIS | A | 113 | −1.107 | 71.541 | 13.328 | 1.00 | 20.00 |
| ATOM 1114 | HD1 | HIS | A | 113 | −0.092 | 73.977 | 14.506 | 1.00 | 20.00 |
| ATOM 1115 | N | LEU | A | 114 | 1.949 | 69.777 | 11.205 | 1.00 | 5.46 |
| ATOM 1116 | CA | LEU | A | 114 | 2.475 | 68.413 | 11.254 | 1.00 | 5.46 |
| ATOM 1117 | C | LEU | A | 114 | 3.926 | 68.404 | 11.683 | 1.00 | 5.46 |
| ATOM 1118 | O | LEU | A | 114 | 4.682 | 69.309 | 11.346 | 1.00 | 5.46 |
| ATOM 1119 | CB | LEU | A | 114 | 2.348 | 67.678 | 9.916 | 1.00 | 5.46 |
| ATOM 1120 | CG | LEU | A | 114 | 0.964 | 67.659 | 9.261 | 1.00 | 5.46 |
| ATOM 1121 | CD1 | LEU | A | 114 | 0.945 | 66.690 | 8.088 | 1.00 | 5.46 |
| ATOM 1122 | CD2 | LEU | A | 114 | −0.182 | 67.343 | 10.213 | 1.00 | 5.46 |
| ATOM 1123 | H | LEU | A | 114 | 2.297 | 70.482 | 10.585 | 1.00 | 20.00 |
| ATOM 1124 | N | TYR | A | 115 | 4.274 | 67.352 | 12.444 | 1.00 | 8.89 |
| ATOM 1125 | CA | TYR | A | 115 | 5.662 | 67.210 | 12.894 | 1.00 | 8.89 |
| ATOM 1126 | C | TYR | A | 115 | 6.174 | 65.820 | 12.623 | 1.00 | 8.89 |
| ATOM 1127 | O | TYR | A | 115 | 5.412 | 64.863 | 12.610 | 1.00 | 8.89 |
| ATOM 1128 | CB | TYR | A | 115 | 5.814 | 67.473 | 14.394 | 1.00 | 8.89 |
| ATOM 1129 | CG | TYR | A | 115 | 5.461 | 68.900 | 14.726 | 1.00 | 8.89 |
| ATOM 1130 | CD1 | TYR | A | 115 | 6.421 | 69.912 | 14.523 | 1.00 | 8.89 |
| ATOM 1131 | CD2 | TYR | A | 115 | 4.176 | 69.174 | 15.231 | 1.00 | 8.89 |
| ATOM 1132 | CE1 | TYR | A | 115 | 6.073 | 71.243 | 14.807 | 1.00 | 8.89 |
| ATOM 1133 | CE2 | TYR | A | 115 | 3.831 | 70.503 | 15.515 | 1.00 | 8.89 |
| ATOM 1134 | CZ | TYR | A | 115 | 4.777 | 71.522 | 15.280 | 1.00 | 8.89 |
| ATOM 1135 | OH | TYR | A | 115 | 4.414 | 72.834 | 15.511 | 1.00 | 8.89 |
| ATOM 1136 | H | TYR | A | 115 | 3.583 | 66.661 | 12.676 | 1.00 | 20.00 |
| ATOM 1137 | HH | TYR | A | 115 | 3.481 | 72.871 | 15.676 | 1.00 | 20.00 |
| ATOM 1138 | N | VAL | A | 116 | 7.494 | 65.743 | 12.391 | 1.00 | 5.15 |
| ATOM 1139 | CA | VAL | A | 116 | 8.070 | 64.434 | 12.085 | 1.00 | 5.15 |
| ATOM 1140 | C | VAL | A | 116 | 9.369 | 64.215 | 12.824 | 1.00 | 5.15 |
| ATOM 1141 | O | VAL | A | 116 | 10.402 | 64.765 | 12.464 | 1.00 | 5.15 |
| ATOM 1142 | CB | VAL | A | 116 | 8.284 | 64.281 | 10.577 | 1.00 | 5.15 |
| ATOM 1143 | CG1 | VAL | A | 116 | 8.984 | 62.982 | 10.210 | 1.00 | 5.15 |
| ATOM 1144 | CG2 | VAL | A | 116 | 6.955 | 64.328 | 9.653 | 1.00 | 5.15 |
| ATOM 1145 | H | VAL | A | 116 | 8.066 | 66.562 | 12.404 | 1.00 | 20.00 |
| ATOM 1146 | N | ASN | A | 117 | 9.263 | 63.388 | 13.872 | 1.00 | 8.77 |
| ATOM 1147 | CA | ASN | A | 117 | 10.485 | 63.210 | 14.650 | 1.00 | 8.77 |
| ATOM 1148 | C | ASN | A | 117 | 10.937 | 61.767 | 14.713 | 1.00 | 8.77 |
| ATOM 1149 | O | ASN | A | 117 | 10.154 | 60.829 | 14.595 | 1.00 | 8.77 |
| ATOM 1150 | CB | ASN | A | 117 | 10.350 | 63.800 | 16.061 | 1.00 | 8.77 |
| ATOM 1151 | CG | ASN | A | 117 | 10.177 | 65.309 | 16.010 | 1.00 | 8.77 |
| ATOM 1152 | OD1 | ASN | A | 117 | 10.707 | 66.013 | 15.164 | 1.00 | 8.77 |
| ATOM 1153 | ND2 | ASN | A | 117 | 9.376 | 65.790 | 16.966 | 1.00 | 8.77 |
| ATOM 1154 | H | ASN | A | 117 | 8.418 | 62.875 | 14.048 | 1.00 | 20.00 |
| ATOM 1155 | 1HD2 | ASN | A | 117 | 8.981 | 65.202 | 17.668 | 1.00 | 20.00 |
| ATOM 1156 | 2HD2 | ASN | A | 117 | 9.194 | 66.772 | 16.957 | 1.00 | 20.00 |
| ATOM 1157 | N | VAL | A | 118 | 12.261 | 61.657 | 14.908 | 1.00 | 2.80 |
| ATOM 1158 | CA | VAL | A | 118 | 12.889 | 60.363 | 15.168 | 1.00 | 2.80 |
| ATOM 1159 | C | VAL | A | 118 | 13.317 | 60.341 | 16.623 | 1.00 | 2.80 |
| ATOM 1160 | O | VAL | A | 118 | 13.598 | 61.390 | 17.189 | 1.00 | 2.80 |
| ATOM 1161 | CB | VAL | A | 118 | 14.106 | 60.198 | 14.240 | 1.00 | 2.80 |
| ATOM 1162 | CG1 | VAL | A | 118 | 14.931 | 58.932 | 14.486 | 1.00 | 2.80 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 1163 | CG2 | VAL A | 118 | 13.686 | 60.300 | 12.780 | 1.00 | 2.80 |
| ATOM 1164 | H | VAL A | 118 | 12.814 | 62.483 | 15.015 | 1.00 | 20.00 |
| ATOM 1165 | N | SER A | 119 | 13.364 | 59.128 | 17.200 | 1.00 | 3.07 |
| ATOM 1166 | CA | SER A | 119 | 13.914 | 59.016 | 18.551 | 1.00 | 3.07 |
| ATOM 1167 | C | SER A | 119 | 15.367 | 59.474 | 18.716 | 1.00 | 3.07 |
| ATOM 1168 | O | SER A | 119 | 15.669 | 60.363 | 19.502 | 1.00 | 3.07 |
| ATOM 1169 | CB | SER A | 119 | 13.686 | 57.589 | 19.052 | 1.00 | 3.07 |
| ATOM 1170 | OG | SER A | 119 | 14.115 | 56.654 | 18.053 | 1.00 | 3.07 |
| ATOM 1171 | H | SER A | 119 | 13.064 | 58.308 | 16.706 | 1.00 | 20.00 |
| ATOM 1172 | HG | SER A | 119 | 14.876 | 56.209 | 18.450 | 1.00 | 20.00 |
| ATOM 1173 | N | GLU A | 120 | 16.257 | 58.852 | 17.922 | 1.00 | 12.56 |
| ATOM 1174 | CA | GLU A | 120 | 17.662 | 59.245 | 18.058 | 1.00 | 12.56 |
| ATOM 1175 | C | GLU A | 120 | 18.245 | 59.835 | 16.796 | 1.00 | 12.56 |
| ATOM 1176 | O | GLU A | 120 | 18.428 | 59.174 | 15.782 | 1.00 | 12.56 |
| ATOM 1177 | CB | GLU A | 120 | 18.576 | 58.093 | 18.498 | 1.00 | 12.56 |
| ATOM 1178 | CG | GLU A | 120 | 18.296 | 57.424 | 19.851 | 1.00 | 12.56 |
| ATOM 1179 | CD | GLU A | 120 | 17.012 | 56.613 | 19.830 | 1.00 | 12.56 |
| ATOM 1180 | OE1 | GLU A | 120 | 16.676 | 56.047 | 18.790 | 1.00 | 12.56 |
| ATOM 1181 | OE2 | GLU A | 120 | 16.340 | 56.562 | 20.857 | 1.00 | 12.56 |
| ATOM 1182 | H | GLU A | 120 | 15.973 | 58.071 | 17.365 | 1.00 | 20.00 |
| ATOM 1183 | N | LEU A | 121 | 18.572 | 61.127 | 16.897 | 1.00 | 16.20 |
| ATOM 1184 | CA | LEU A | 121 | 19.092 | 61.724 | 15.669 | 1.00 | 16.20 |
| ATOM 1185 | C | LEU A | 121 | 20.555 | 61.434 | 15.374 | 1.00 | 16.20 |
| ATOM 1186 | O | LEU A | 121 | 21.031 | 61.580 | 14.255 | 1.00 | 16.20 |
| ATOM 1187 | CB | LEU A | 121 | 18.721 | 63.205 | 15.560 | 1.00 | 16.20 |
| ATOM 1188 | CG | LEU A | 121 | 17.226 | 63.441 | 15.290 | 1.00 | 16.20 |
| ATOM 1189 | CD1 | LEU A | 121 | 16.729 | 62.549 | 14.164 | 1.00 | 16.20 |
| ATOM 1190 | CD2 | LEU A | 121 | 16.310 | 63.322 | 16.510 | 1.00 | 16.20 |
| ATOM 1191 | H | LEU A | 121 | 18.412 | 61.651 | 17.733 | 1.00 | 20.00 |
| ATOM 1192 | N | SER A | 122 | 21.227 | 60.893 | 16.409 | 1.00 | 8.33 |
| ATOM 1193 | CA | SER A | 122 | 22.535 | 60.272 | 16.188 | 1.00 | 8.33 |
| ATOM 1194 | C | SER A | 122 | 22.568 | 59.195 | 15.112 | 1.00 | 8.33 |
| ATOM 1195 | O | SER A | 122 | 23.584 | 58.940 | 14.479 | 1.00 | 8.33 |
| ATOM 1196 | CB | SER A | 122 | 23.045 | 59.687 | 17.500 | 1.00 | 8.33 |
| ATOM 1197 | OG | SER A | 122 | 22.731 | 60.587 | 18.567 | 1.00 | 8.33 |
| ATOM 1198 | H | SER A | 122 | 20.883 | 60.940 | 17.347 | 1.00 | 20.00 |
| ATOM 1199 | HG | SER A | 122 | 23.155 | 60.237 | 19.341 | 1.00 | 20.00 |
| ATOM 1200 | N | LEU A | 123 | 21.385 | 58.577 | 14.931 | 1.00 | 10.07 |
| ATOM 1201 | CA | LEU A | 123 | 21.259 | 57.556 | 13.894 | 1.00 | 10.07 |
| ATOM 1202 | C | LEU A | 123 | 21.336 | 58.072 | 12.471 | 1.00 | 10.07 |
| ATOM 1203 | O | LEU A | 123 | 21.589 | 57.318 | 11.540 | 1.00 | 10.07 |
| ATOM 1204 | CB | LEU A | 123 | 19.918 | 56.851 | 14.007 | 1.00 | 10.07 |
| ATOM 1205 | CG | LEU A | 123 | 19.596 | 56.197 | 15.341 | 1.00 | 10.07 |
| ATOM 1206 | CD1 | LEU A | 123 | 18.093 | 55.945 | 15.449 | 1.00 | 10.07 |
| ATOM 1207 | CD2 | LEU A | 123 | 20.438 | 54.948 | 15.593 | 1.00 | 10.07 |
| ATOM 1208 | H | LEU A | 123 | 20.574 | 58.842 | 15.457 | 1.00 | 20.00 |
| ATOM 1209 | N | VAL A | 124 | 21.025 | 59.371 | 12.325 | 1.00 | 5.90 |
| ATOM 1210 | CA | VAL A | 124 | 20.726 | 59.799 | 10.964 | 1.00 | 5.90 |
| ATOM 1211 | C | VAL A | 124 | 21.921 | 59.840 | 10.046 | 1.00 | 5.90 |
| ATOM 1212 | O | VAL A | 124 | 22.982 | 60.387 | 10.323 | 1.00 | 5.90 |
| ATOM 1213 | CB | VAL A | 124 | 19.940 | 61.116 | 10.948 | 1.00 | 5.90 |
| ATOM 1214 | CG1 | VAL A | 124 | 19.532 | 61.582 | 9.546 | 1.00 | 5.90 |
| ATOM 1215 | CG2 | VAL A | 124 | 18.682 | 60.926 | 11.782 | 1.00 | 5.90 |
| ATOM 1216 | H | VAL A | 124 | 21.015 | 60.016 | 13.092 | 1.00 | 20.00 |
| ATOM 1217 | N | ASN A | 125 | 21.657 | 59.217 | 8.896 | 1.00 | 5.82 |
| ATOM 1218 | CA | ASN A | 125 | 22.640 | 59.347 | 7.835 | 1.00 | 5.82 |
| ATOM 1219 | C | ASN A | 125 | 22.475 | 60.654 | 7.120 | 1.00 | 5.82 |
| ATOM 1220 | O | ASN A | 125 | 21.375 | 61.039 | 6.750 | 1.00 | 5.82 |
| ATOM 1221 | CB | ASN A | 125 | 22.501 | 58.207 | 6.835 | 1.00 | 5.82 |
| ATOM 1222 | CG | ASN A | 125 | 22.928 | 56.936 | 7.511 | 1.00 | 5.82 |
| ATOM 1223 | OD1 | ASN A | 125 | 23.689 | 56.957 | 8.463 | 1.00 | 5.82 |
| ATOM 1224 | ND2 | ASN A | 125 | 22.402 | 55.826 | 6.977 | 1.00 | 5.82 |
| ATOM 1225 | H | ASN A | 125 | 20.748 | 58.818 | 8.760 | 1.00 | 20.00 |
| ATOM 1226 | 1HD2 | ASN A | 125 | 21.811 | 55.874 | 6.174 | 1.00 | 20.00 |
| ATOM 1227 | 2HD2 | ASN A | 125 | 22.587 | 54.944 | 7.409 | 1.00 | 20.00 |
| ATOM 1228 | N | PHE A | 126 | 23.629 | 61.297 | 6.914 | 1.00 | 7.35 |
| ATOM 1229 | CA | PHE A | 126 | 23.582 | 62.373 | 5.934 | 1.00 | 7.35 |
| ATOM 1230 | C | PHE A | 126 | 24.544 | 62.117 | 4.810 | 1.00 | 7.35 |
| ATOM 1231 | O | PHE A | 126 | 25.128 | 63.023 | 4.233 | 1.00 | 7.35 |
| ATOM 1232 | CB | PHE A | 126 | 23.870 | 63.740 | 6.546 | 1.00 | 7.35 |
| ATOM 1233 | CG | PHE A | 126 | 22.917 | 64.028 | 7.676 | 1.00 | 7.35 |
| ATOM 1234 | CD1 | PHE A | 126 | 23.359 | 63.811 | 8.997 | 1.00 | 7.35 |
| ATOM 1235 | CD2 | PHE A | 126 | 21.621 | 64.520 | 7.402 | 1.00 | 7.35 |
| ATOM 1236 | CE1 | PHE A | 126 | 22.510 | 64.136 | 10.070 | 1.00 | 7.35 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM | 1237 | CE2 | PHE | A | 126 | 20.773 | 64.851 | 8.476 | 1.00 | 7.35 |
| ATOM | 1238 | CZ | PHE | A | 126 | 21.236 | 64.676 | 9.798 | 1.00 | 7.35 |
| ATOM | 1239 | H | PHE | A | 126 | 24.485 | 61.035 | 7.360 | 1.00 | 20.00 |
| ATOM | 1240 | N | GLU | A | 127 | 24.688 | 60.812 | 4.511 | 1.00 | 24.73 |
| ATOM | 1241 | CA | GLU | A | 127 | 25.455 | 60.561 | 3.297 | 1.00 | 24.73 |
| ATOM | 1242 | C | GLU | A | 127 | 24.765 | 61.137 | 2.073 | 1.00 | 24.73 |
| ATOM | 1243 | O | GLU | A | 127 | 25.389 | 61.707 | 1.189 | 1.00 | 24.73 |
| ATOM | 1244 | CB | GLU | A | 127 | 25.725 | 59.072 | 3.104 | 1.00 | 24.73 |
| ATOM | 1245 | CG | GLU | A | 127 | 26.677 | 58.837 | 1.922 | 1.00 | 24.73 |
| ATOM | 1246 | CD | GLU | A | 127 | 27.964 | 58.218 | 2.414 | 1.00 | 24.73 |
| ATOM | 1247 | OE1 | GLU | A | 127 | 28.272 | 57.109 | 1.979 | 1.00 | 24.73 |
| ATOM | 1248 | OE2 | GLU | A | 127 | 28.632 | 58.829 | 3.245 | 1.00 | 24.73 |
| ATOM | 1249 | H | GLU | A | 127 | 24.181 | 60.106 | 5.002 | 1.00 | 20.00 |
| ATOM | 1250 | N | GLU | A | 128 | 23.431 | 60.945 | 2.079 | 1.00 | 23.04 |
| ATOM | 1251 | CA | GLU | A | 128 | 22.694 | 61.261 | 0.861 | 1.00 | 23.04 |
| ATOM | 1252 | C | GLU | A | 128 | 21.313 | 61.807 | 1.171 | 1.00 | 23.04 |
| ATOM | 1253 | O | GLU | A | 128 | 20.947 | 61.971 | 2.328 | 1.00 | 23.04 |
| ATOM | 1254 | CB | GLU | A | 128 | 22.615 | 59.987 | 0.045 | 1.00 | 23.04 |
| ATOM | 1255 | CG | GLU | A | 128 | 23.910 | 59.607 | −0.685 | 1.00 | 23.04 |
| ATOM | 1256 | CD | GLU | A | 128 | 23.939 | 60.144 | −2.103 | 1.00 | 23.04 |
| ATOM | 1257 | OE1 | GLU | A | 128 | 22.997 | 60.832 | −2.510 | 1.00 | 23.04 |
| ATOM | 1258 | OE2 | GLU | A | 128 | 24.913 | 59.852 | −2.798 | 1.00 | 23.04 |
| ATOM | 1259 | H | GLU | A | 128 | 22.928 | 60.568 | 2.862 | 1.00 | 20.00 |
| ATOM | 1260 | N | SER | A | 129 | 20.537 | 62.056 | 0.099 | 1.00 | 19.86 |
| ATOM | 1261 | CA | SER | A | 129 | 19.298 | 62.850 | 0.216 | 1.00 | 19.86 |
| ATOM | 1262 | C | SER | A | 129 | 18.103 | 62.253 | 0.958 | 1.00 | 19.86 |
| ATOM | 1263 | O | SER | A | 129 | 17.013 | 62.805 | 1.032 | 1.00 | 19.86 |
| ATOM | 1264 | CB | SER | A | 129 | 18.861 | 63.281 | −1.184 | 1.00 | 19.86 |
| ATOM | 1265 | OG | SER | A | 129 | 20.026 | 63.459 | −1.996 | 1.00 | 19.86 |
| ATOM | 1266 | H | SER | A | 129 | 20.885 | 61.864 | −0.824 | 1.00 | 20.00 |
| ATOM | 1267 | HG | SER | A | 129 | 19.718 | 63.707 | −2.867 | 1.00 | 20.00 |
| ATOM | 1268 | N | GLN | A | 130 | 18.363 | 61.056 | 1.484 | 1.00 | 15.57 |
| ATOM | 1269 | CA | GLN | A | 130 | 17.353 | 60.136 | 1.992 | 1.00 | 15.57 |
| ATOM | 1270 | C | GLN | A | 130 | 16.283 | 60.634 | 2.962 | 1.00 | 15.57 |
| ATOM | 1271 | O | GLN | A | 130 | 15.133 | 60.216 | 2.905 | 1.00 | 15.57 |
| ATOM | 1272 | CB | GLN | A | 130 | 18.125 | 58.956 | 2.558 | 1.00 | 15.57 |
| ATOM | 1273 | CG | GLN | A | 130 | 19.140 | 59.328 | 3.657 | 1.00 | 15.57 |
| ATOM | 1274 | CD | GLN | A | 130 | 20.572 | 58.937 | 3.305 | 1.00 | 15.57 |
| ATOM | 1275 | OE1 | GLN | A | 130 | 21.535 | 59.345 | 3.944 | 1.00 | 15.57 |
| ATOM | 1276 | NE2 | GLN | A | 130 | 20.710 | 58.067 | 2.295 | 1.00 | 15.57 |
| ATOM | 1277 | H | GLN | A | 130 | 19.321 | 60.784 | 1.462 | 1.00 | 20.00 |
| ATOM | 1278 | 1HE2 | GLN | A | 130 | 20.003 | 57.812 | 1.637 | 1.00 | 20.00 |
| ATOM | 1279 | 2HE2 | GLN | A | 130 | 21.612 | 57.658 | 2.183 | 1.00 | 20.00 |
| ATOM | 1280 | N | THR | A | 131 | 16.719 | 61.510 | 3.877 | 1.00 | 3.96 |
| ATOM | 1281 | CA | THR | A | 131 | 15.791 | 61.902 | 4.933 | 1.00 | 3.96 |
| ATOM | 1282 | C | THR | A | 131 | 14.970 | 63.131 | 4.590 | 1.00 | 3.96 |
| ATOM | 1283 | O | THR | A | 131 | 15.474 | 64.245 | 4.469 | 1.00 | 3.96 |
| ATOM | 1284 | CB | THR | A | 131 | 16.558 | 62.045 | 6.253 | 1.00 | 3.96 |
| ATOM | 1285 | OG1 | THR | A | 131 | 17.098 | 60.768 | 6.631 | 1.00 | 3.96 |
| ATOM | 1286 | CG2 | THR | A | 131 | 15.726 | 62.628 | 7.400 | 1.00 | 3.96 |
| ATOM | 1287 | H | THR | A | 131 | 17.641 | 61.887 | 3.823 | 1.00 | 20.00 |
| ATOM | 1288 | HG1 | THR | A | 131 | 17.691 | 60.951 | 7.349 | 1.00 | 20.00 |
| ATOM | 1289 | N | PHE | A | 132 | 13.667 | 62.845 | 4.442 | 1.00 | 6.06 |
| ATOM | 1290 | CA | PHE | A | 132 | 12.752 | 63.873 | 3.965 | 1.00 | 6.06 |
| ATOM | 1291 | C | PHE | A | 132 | 11.362 | 63.754 | 4.556 | 1.00 | 6.06 |
| ATOM | 1292 | O | PHE | A | 132 | 10.972 | 62.693 | 5.022 | 1.00 | 6.06 |
| ATOM | 1293 | CB | PHE | A | 132 | 12.702 | 63.885 | 2.427 | 1.00 | 6.06 |
| ATOM | 1294 | CG | PHE | A | 132 | 12.234 | 62.575 | 1.829 | 1.00 | 6.06 |
| ATOM | 1295 | CD1 | PHE | A | 132 | 10.884 | 62.175 | 1.949 | 1.00 | 6.06 |
| ATOM | 1296 | CD2 | PHE | A | 132 | 13.169 | 61.778 | 1.136 | 1.00 | 6.06 |
| ATOM | 1297 | CE1 | PHE | A | 132 | 10.467 | 60.957 | 1.382 | 1.00 | 6.06 |
| ATOM | 1298 | CE2 | PHE | A | 132 | 12.753 | 60.561 | 0.563 | 1.00 | 6.06 |
| ATOM | 1299 | CZ | PHE | A | 132 | 11.407 | 60.162 | 0.695 | 1.00 | 6.06 |
| ATOM | 1300 | H | PHE | A | 132 | 13.343 | 61.917 | 4.647 | 1.00 | 20.00 |
| ATOM | 1301 | N | PHE | A | 133 | 10.628 | 64.873 | 4.477 | 1.00 | 7.15 |
| ATOM | 1302 | CA | PHE | A | 133 | 9.214 | 64.866 | 4.855 | 1.00 | 7.15 |
| ATOM | 1303 | C | PHE | A | 133 | 8.445 | 65.768 | 3.918 | 1.00 | 7.15 |
| ATOM | 1304 | O | PHE | A | 133 | 8.868 | 66.881 | 3.647 | 1.00 | 7.15 |
| ATOM | 1305 | CB | PHE | A | 133 | 9.052 | 65.335 | 6.310 | 1.00 | 7.15 |
| ATOM | 1306 | CG | PHE | A | 133 | 7.611 | 65.586 | 6.714 | 1.00 | 7.15 |
| ATOM | 1307 | CD1 | PHE | A | 133 | 6.609 | 64.626 | 6.446 | 1.00 | 7.15 |
| ATOM | 1308 | CD2 | PHE | A | 133 | 7.299 | 66.794 | 7.375 | 1.00 | 7.15 |
| ATOM | 1309 | CE1 | PHE | A | 133 | 5.281 | 64.876 | 6.837 | 1.00 | 7.15 |
| ATOM | 1310 | CE2 | PHE | A | 133 | 5.972 | 67.039 | 7.779 | 1.00 | 7.15 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM 1311 | CZ | PHE | A | 133 | 4.975 | 66.081 | 7.503 | 1.00 | 7.15 |
| ATOM 1312 | H | PHE | A | 133 | 11.065 | 65.710 | 4.134 | 1.00 | 20.00 |
| ATOM 1313 | N | GLY | A | 134 | 7.306 | 65.265 | 3.432 | 1.00 | 4.00 |
| ATOM 1314 | CA | GLY | A | 134 | 6.587 | 66.141 | 2.523 | 1.00 | 4.00 |
| ATOM 1315 | C | GLY | A | 134 | 5.111 | 65.853 | 2.424 | 1.00 | 4.00 |
| ATOM 1316 | O | GLY | A | 134 | 4.638 | 64.774 | 2.764 | 1.00 | 4.00 |
| ATOM 1317 | H | GLY | A | 134 | 6.958 | 64.355 | 3.670 | 1.00 | 20.00 |
| ATOM 1318 | N | LEU | A | 135 | 4.410 | 66.893 | 1.946 | 1.00 | 5.48 |
| ATOM 1319 | CA | LEU | A | 135 | 2.963 | 66.783 | 1.775 | 1.00 | 5.48 |
| ATOM 1320 | C | LEU | A | 135 | 2.573 | 67.208 | 0.387 | 1.00 | 5.48 |
| ATOM 1321 | O | LEU | A | 135 | 3.311 | 67.919 | −0.285 | 1.00 | 5.48 |
| ATOM 1322 | CB | LEU | A | 135 | 2.154 | 67.712 | 2.683 | 1.00 | 5.48 |
| ATOM 1323 | CG | LEU | A | 135 | 2.479 | 67.767 | 4.168 | 1.00 | 5.48 |
| ATOM 1324 | CD1 | LEU | A | 135 | 1.468 | 68.655 | 4.892 | 1.00 | 5.48 |
| ATOM 1325 | CD2 | LEU | A | 135 | 2.584 | 66.394 | 4.809 | 1.00 | 5.48 |
| ATOM 1326 | H | LEU | A | 135 | 4.910 | 67.671 | 1.560 | 1.00 | 20.00 |
| ATOM 1327 | N | TYR | A | 136 | 1.345 | 66.809 | 0.030 | 1.00 | 5.12 |
| ATOM 1328 | CA | TYR | A | 136 | 0.694 | 67.444 | −1.113 | 1.00 | 5.12 |
| ATOM 1329 | C | TYR | A | 136 | −0.799 | 67.241 | −1.096 | 1.00 | 5.12 |
| ATOM 1330 | O | TYR | A | 136 | −1.284 | 66.190 | −0.703 | 1.00 | 5.12 |
| ATOM 1331 | CB | TYR | A | 136 | 1.278 | 66.980 | −2.454 | 1.00 | 5.12 |
| ATOM 1332 | CG | TYR | A | 136 | 1.350 | 65.477 | −2.571 | 1.00 | 5.12 |
| ATOM 1333 | CD1 | TYR | A | 136 | 2.412 | 64.790 | −1.951 | 1.00 | 5.12 |
| ATOM 1334 | CD2 | TYR | A | 136 | 0.372 | 64.808 | −3.330 | 1.00 | 5.12 |
| ATOM 1335 | CE1 | TYR | A | 136 | 2.541 | 63.408 | −2.156 | 1.00 | 5.12 |
| ATOM 1336 | CE2 | TYR | A | 136 | 0.509 | 63.428 | −3.543 | 1.00 | 5.12 |
| ATOM 1337 | CZ | TYR | A | 136 | 1.609 | 62.754 | −2.982 | 1.00 | 5.12 |
| ATOM 1338 | OH | TYR | A | 136 | 1.767 | 61.412 | −3.258 | 1.00 | 5.12 |
| ATOM 1339 | H | TYR | A | 136 | 0.911 | 66.058 | 0.534 | 1.00 | 20.00 |
| ATOM 1340 | HH | TYR | A | 136 | 0.909 | 61.010 | −3.263 | 1.00 | 20.00 |
| ATOM 1341 | N | LYS | A | 137 | −1.507 | 68.291 | −1.538 | 1.00 | 11.54 |
| ATOM 1342 | CA | LYS | A | 137 | −2.953 | 68.117 | −1.654 | 1.00 | 11.54 |
| ATOM 1343 | C | LYS | A | 137 | −3.344 | 67.290 | −2.869 | 1.00 | 11.54 |
| ATOM 1344 | O | LYS | A | 137 | −2.754 | 67.419 | −3.936 | 1.00 | 11.54 |
| ATOM 1345 | CB | LYS | A | 137 | −3.665 | 69.482 | −1.621 | 1.00 | 11.54 |
| ATOM 1346 | CG | LYS | A | 137 | −5.187 | 69.346 | −1.504 | 1.00 | 11.54 |
| ATOM 1347 | CD | LYS | A | 137 | −5.992 | 70.630 | −1.322 | 1.00 | 11.54 |
| ATOM 1348 | CE | LYS | A | 137 | −7.486 | 70.304 | −1.403 | 1.00 | 11.54 |
| ATOM 1349 | NZ | LYS | A | 137 | −8.302 | 71.450 | −0.976 | 1.00 | 11.54 |
| ATOM 1350 | H | LYS | A | 137 | −1.020 | 69.113 | −1.839 | 1.00 | 20.00 |
| ATOM 1351 | HZ | LYS | A | 137 | −9.308 | 71.233 | −1.116 | 1.00 | 20.00 |
| ATOM 1352 | 2HZ | LYS | A | 137 | −8.173 | 71.604 | 0.050 | 1.00 | 20.00 |
| ATOM 1353 | 3HZ | LYS | A | 137 | −8.047 | 72.322 | −1.482 | 1.00 | 20.00 |
| ATOM 1354 | N | LEU | A | 138 | −4.353 | 66.438 | −2.633 | 1.00 | 2.56 |
| ATOM 1355 | CA | LEU | A | 138 | −4.970 | 65.690 | −3.725 | 1.00 | 2.56 |
| ATOM 1356 | C | LEU | A | 138 | −6.144 | 66.433 | −4.378 | 1.00 | 2.56 |
| ATOM 1357 | O | LEU | A | 138 | −6.847 | 65.833 | −5.193 | 1.00 | 2.56 |
| ATOM 1358 | CB | LEU | A | 138 | −5.401 | 64.309 | −3.210 | 1.00 | 2.56 |
| ATOM 1359 | CG | LEU | A | 138 | −4.306 | 63.538 | −2.464 | 1.00 | 2.56 |
| ATOM 1360 | CD1 | LEU | A | 138 | −4.866 | 62.281 | −1.807 | 1.00 | 2.56 |
| ATOM 1361 | CD2 | LEU | A | 138 | −3.096 | 63.225 | −3.345 | 1.00 | 2.56 |
| ATOM 1362 | OXT | LEU | A | 138 | −6.365 | 67.610 | −4.073 | 1.00 | 2.56 |
| ATOM 1363 | H | LEU | A | 138 | −4.752 | 66.418 | −1.714 | 1.00 | 20.00 |
| ATOM 1364 | N | ARG | B | 1 | −2.937 | 62.603 | −15.335 | 1.00 | 5.73 |
| ATOM 1365 | CA | ARG | B | 1 | −2.035 | 63.134 | −16.365 | 1.00 | 5.73 |
| ATOM 1366 | C | ARG | B | 1 | −0.958 | 62.103 | −16.634 | 1.00 | 5.73 |
| ATOM 1367 | O | ARG | B | 1 | −1.307 | 60.944 | −16.804 | 1.00 | 5.73 |
| ATOM 1368 | CB | ARG | B | 1 | −1.504 | 64.518 | −15.977 | 1.00 | 5.73 |
| ATOM 1369 | CG | ARG | B | 1 | −2.513 | 65.637 | −16.220 | 1.00 | 5.73 |
| ATOM 1370 | CD | ARG | B | 1 | −1.898 | 67.011 | −15.960 | 1.00 | 5.73 |
| ATOM 1371 | NE | ARG | B | 1 | −2.866 | 68.071 | −16.230 | 1.00 | 5.73 |
| ATOM 1372 | CZ | ARG | B | 1 | −3.105 | 69.035 | −15.314 | 1.00 | 5.73 |
| ATOM 1373 | NH1 | ARG | B | 1 | −3.990 | 69.989 | −15.599 | 1.00 | 5.73 |
| ATOM 1374 | NH2 | ARG | B | 1 | −2.471 | 69.032 | −14.139 | 1.00 | 5.73 |
| ATOM 1375 | 1H | ARG | B | 1 | −3.784 | 63.195 | −15.230 | 1.00 | 20.00 |
| ATOM 1376 | 2H | ARG | B | 1 | −3.197 | 61.641 | −15.643 | 1.00 | 20.00 |
| ATOM 1377 | 3H | ARG | B | 1 | −2.432 | 62.534 | −14.428 | 1.00 | 20.00 |
| ATOM 1378 | HE | ARG | B | 1 | −3.320 | 68.068 | −17.123 | 1.00 | 20.00 |
| ATOM 1379 | 1HH1 | ARG | B | 1 | −4.193 | 70.723 | −14.951 | 1.00 | 20.00 |
| ATOM 1380 | 2HH1 | ARG | B | 1 | −4.476 | 69.987 | −16.474 | 1.00 | 20.00 |
| ATOM 1381 | 1HH2 | ARG | B | 1 | −2.614 | 69.754 | −13.462 | 1.00 | 20.00 |
| ATOM 1382 | 2HH2 | ARG | B | 1 | −1.839 | 68.293 | −13.898 | 1.00 | 20.00 |
| ATOM 1383 | N | LYS | B | 2 | 0.318 | 62.537 | −16.655 | 1.00 | 19.49 |
| ATOM 1384 | CA | LYS | B | 2 | 1.393 | 61.594 | −16.965 | 1.00 | 19.49 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 1385 | C | LYS B | 2 | 1.627 | 60.661 | −15.819 | 1.00 | 19.49 |
| ATOM 1386 | O | LYS B | 2 | 1.798 | 61.091 | −14.695 | 1.00 | 19.49 |
| ATOM 1387 | CB | LYS B | 2 | 2.732 | 62.274 | −17.247 | 1.00 | 19.49 |
| ATOM 1388 | CG | LYS B | 2 | 2.778 | 63.147 | −18.491 | 1.00 | 19.49 |
| ATOM 1389 | CD | LYS B | 2 | 2.066 | 64.470 | −18.286 | 1.00 | 19.49 |
| ATOM 1390 | CE | LYS B | 2 | 2.193 | 65.340 | −19.507 | 1.00 | 19.49 |
| ATOM 1391 | NZ | LYS B | 2 | 1.180 | 65.110 | −20.544 | 1.00 | 19.49 |
| ATOM 1392 | H | LYS B | 2 | 0.597 | 63.447 | −16.360 | 1.00 | 20.00 |
| ATOM 1393 | 1HZ | LYS B | 2 | 1.214 | 65.974 | −21.140 | 1.00 | 20.00 |
| ATOM 1394 | 2HZ | LYS B | 2 | 1.405 | 64.257 | −21.095 | 1.00 | 20.00 |
| ATOM 1395 | 3HZ | LYS B | 2 | 0.233 | 65.037 | −20.128 | 1.00 | 20.00 |
| ATOM 1396 | N | VAL B | 3 | 1.581 | 59.377 | −16.177 | 1.00 | 4.59 |
| ATOM 1397 | CA | VAL B | 3 | 1.753 | 58.335 | −15.177 | 1.00 | 4.59 |
| ATOM 1398 | C | VAL B | 3 | 2.608 | 57.262 | −15.816 | 1.00 | 4.59 |
| ATOM 1399 | O | VAL B | 3 | 2.582 | 57.072 | −17.030 | 1.00 | 4.59 |
| ATOM 1400 | CB | VAL B | 3 | 0.379 | 57.792 | −14.718 | 1.00 | 4.59 |
| ATOM 1401 | CG1 | VAL B | 3 | 0.475 | 56.648 | −13.705 | 1.00 | 4.59 |
| ATOM 1402 | CG2 | VAL B | 3 | −0.487 | 58.909 | −14.131 | 1.00 | 4.59 |
| ATOM 1403 | H | VAL B | 3 | 1.494 | 59.105 | −17.136 | 1.00 | 20.00 |
| ATOM 1404 | N | ALA B | 4 | 3.368 | 56.603 | −14.938 | 1.00 | 5.22 |
| ATOM 1405 | CA | ALA B | 4 | 4.135 | 55.432 | −15.315 | 1.00 | 5.22 |
| ATOM 1406 | C | ALA B | 4 | 4.150 | 54.517 | −14.117 | 1.00 | 5.22 |
| ATOM 1407 | O | ALA B | 4 | 4.200 | 54.973 | −12.981 | 1.00 | 5.22 |
| ATOM 1408 | CB | ALA B | 4 | 5.576 | 55.815 | −15.653 | 1.00 | 5.22 |
| ATOM 1409 | H | ALA B | 4 | 3.349 | 56.867 | −13.969 | 1.00 | 20.00 |
| ATOM 1410 | N | HIS B | 5 | 4.111 | 53.221 | −14.421 | 1.00 | 4.76 |
| ATOM 1411 | CA | HIS B | 5 | 4.349 | 52.235 | −13.371 | 1.00 | 4.76 |
| ATOM 1412 | C | HIS B | 5 | 4.993 | 51.074 | −14.063 | 1.00 | 4.76 |
| ATOM 1413 | O | HIS B | 5 | 4.331 | 50.490 | −14.896 | 1.00 | 4.76 |
| ATOM 1414 | CB | HIS B | 5 | 3.032 | 51.774 | −12.730 | 1.00 | 4.76 |
| ATOM 1415 | CG | HIS B | 5 | 3.317 | 50.760 | −11.644 | 1.00 | 4.76 |
| ATOM 1416 | ND1 | HIS B | 5 | 3.511 | 51.104 | −10.365 | 1.00 | 4.76 |
| ATOM 1417 | CD2 | HIS B | 5 | 3.455 | 49.372 | −11.763 | 1.00 | 4.76 |
| ATOM 1418 | CE1 | HIS B | 5 | 3.773 | 49.951 | −9.680 | 1.00 | 4.76 |
| ATOM 1419 | NE2 | HIS B | 5 | 3.740 | 48.886 | −10.533 | 1.00 | 4.76 |
| ATOM 1420 | H | HIS B | 5 | 3.968 | 52.930 | −15.371 | 1.00 | 20.00 |
| ATOM 1421 | HD1 | HIS B | 5 | 3.469 | 52.017 | −10.008 | 1.00 | 20.00 |
| ATOM 1422 | N | LEU B | 6 | 6.259 | 50.801 | −13.732 | 1.00 | 6.04 |
| ATOM 1423 | CA | LEU B | 6 | 7.023 | 49.785 | −14.455 | 1.00 | 6.04 |
| ATOM 1424 | C | LEU B | 6 | 7.455 | 48.665 | −13.559 | 1.00 | 6.04 |
| ATOM 1425 | O | LEU B | 6 | 7.694 | 48.882 | −12.380 | 1.00 | 6.04 |
| ATOM 1426 | CB | LEU B | 6 | 8.319 | 50.358 | −14.995 | 1.00 | 6.04 |
| ATOM 1427 | CG | LEU B | 6 | 8.147 | 51.555 | −15.901 | 1.00 | 6.04 |
| ATOM 1428 | CD1 | LEU B | 6 | 9.510 | 52.012 | −16.382 | 1.00 | 6.04 |
| ATOM 1429 | CD2 | LEU B | 6 | 7.204 | 51.258 | −17.060 | 1.00 | 6.04 |
| ATOM 1430 | H | LEU B | 6 | 6.704 | 51.325 | −13.009 | 1.00 | 20.00 |
| ATOM 1431 | N | THR B | 7 | 7.595 | 47.482 | −14.168 | 1.00 | 3.03 |
| ATOM 1432 | CA | THR B | 7 | 8.116 | 46.387 | −13.358 | 1.00 | 3.03 |
| ATOM 1433 | C | THR B | 7 | 9.485 | 45.927 | −13.817 | 1.00 | 3.03 |
| ATOM 1434 | O | THR B | 7 | 9.911 | 46.196 | −14.935 | 1.00 | 3.03 |
| ATOM 1435 | CB | THR B | 7 | 7.112 | 45.234 | −13.336 | 1.00 | 3.03 |
| ATOM 1436 | OG1 | THR B | 7 | 6.655 | 44.949 | −14.663 | 1.00 | 3.03 |
| ATOM 1437 | CG2 | THR B | 7 | 5.923 | 45.549 | −12.423 | 1.00 | 3.03 |
| ATOM 1438 | H | THR B | 7 | 7.403 | 47.340 | −15.143 | 1.00 | 20.00 |
| ATOM 1439 | HG1 | THR B | 7 | 6.334 | 44.057 | −14.655 | 1.00 | 20.00 |
| ATOM 1440 | N | GLY B | 8 | 10.169 | 45.241 | −12.885 | 1.00 | 3.29 |
| ATOM 1441 | CA | GLY B | 8 | 11.479 | 44.700 | −13.245 | 1.00 | 3.29 |
| ATOM 1442 | C | GLY B | 8 | 11.416 | 43.393 | −14.016 | 1.00 | 3.29 |
| ATOM 1443 | O | GLY B | 8 | 10.604 | 42.517 | −13.740 | 1.00 | 3.29 |
| ATOM 1444 | H | GLY B | 8 | 9.769 | 45.109 | −11.974 | 1.00 | 20.00 |
| ATOM 1445 | N | LYS B | 9 | 12.331 | 43.292 | −14.996 | 1.00 | 6.71 |
| ATOM 1446 | CA | LYS B | 9 | 12.359 | 42.070 | −15.801 | 1.00 | 6.71 |
| ATOM 1447 | C | LYS B | 9 | 12.776 | 40.805 | −15.075 | 1.00 | 6.71 |
| ATOM 1448 | O | LYS B | 9 | 13.951 | 40.545 | −14.840 | 1.00 | 6.71 |
| ATOM 1449 | CB | LYS B | 9 | 13.256 | 42.205 | −17.028 | 1.00 | 6.71 |
| ATOM 1450 | CG | LYS B | 9 | 12.803 | 43.248 | −18.036 | 1.00 | 6.71 |
| ATOM 1451 | CD | LYS B | 9 | 13.558 | 43.111 | −19.356 | 1.00 | 6.71 |
| ATOM 1452 | CE | LYS B | 9 | 13.034 | 44.076 | −20.419 | 1.00 | 6.71 |
| ATOM 1453 | NZ | LYS B | 9 | 14.003 | 44.169 | −21.520 | 1.00 | 6.71 |
| ATOM 1454 | H | LYS B | 9 | 12.937 | 44.069 | −15.182 | 1.00 | 20.00 |
| ATOM 1455 | 1HZ | LYS B | 9 | 13.760 | 44.969 | −22.136 | 1.00 | 20.00 |
| ATOM 1456 | 2HZ | LYS B | 9 | 14.946 | 44.419 | −21.127 | 1.00 | 20.00 |
| ATOM 1457 | 3HZ | LYS B | 9 | 14.076 | 43.284 | −22.051 | 1.00 | 20.00 |
| ATOM 1458 | N | SER B | 10 | 11.747 | 39.985 | −14.810 | 1.00 | 13.61 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM | 1459 | CA | SER | B | 10 | 11.964 | 38.612 | −14.334 | 1.00 | 13.61 |
| ATOM | 1460 | C | SER | B | 10 | 13.071 | 37.832 | −15.017 | 1.00 | 13.61 |
| ATOM | 1461 | O | SER | B | 10 | 13.970 | 37.261 | −14.409 | 1.00 | 13.61 |
| ATOM | 1462 | CB | SER | B | 10 | 10.673 | 37.804 | −14.424 | 1.00 | 13.61 |
| ATOM | 1463 | OG | SER | B | 10 | 9.604 | 38.576 | −13.884 | 1.00 | 13.61 |
| ATOM | 1464 | H | SER | B | 10 | 10.839 | 40.413 | −14.779 | 1.00 | 20.00 |
| ATOM | 1465 | HG | SER | B | 10 | 8.872 | 37.982 | −13.776 | 1.00 | 20.00 |
| ATOM | 1466 | N | ASN | B | 11 | 12.970 | 37.830 | −16.352 | 1.00 | 8.64 |
| ATOM | 1467 | CA | ASN | B | 11 | 14.102 | 37.232 | −17.049 | 1.00 | 8.64 |
| ATOM | 1468 | C | ASN | B | 11 | 15.041 | 38.261 | −17.633 | 1.00 | 8.64 |
| ATOM | 1469 | O | ASN | B | 11 | 15.192 | 38.429 | −18.836 | 1.00 | 8.64 |
| ATOM | 1470 | CB | ASN | B | 11 | 13.657 | 36.153 | −18.048 | 1.00 | 8.64 |
| ATOM | 1471 | CG | ASN | B | 11 | 13.192 | 34.864 | −17.360 | 1.00 | 8.64 |
| ATOM | 1472 | OD1 | ASN | B | 11 | 12.646 | 33.972 | −17.994 | 1.00 | 8.64 |
| ATOM | 1473 | ND2 | ASN | B | 11 | 13.420 | 34.765 | −16.037 | 1.00 | 8.64 |
| ATOM | 1474 | H | ASN | B | 11 | 12.213 | 38.284 | −16.820 | 1.00 | 20.00 |
| ATOM | 1475 | 1HD2 | ASN | B | 11 | 13.855 | 35.461 | −15.458 | 1.00 | 20.00 |
| ATOM | 1476 | 2HD2 | ASN | B | 11 | 13.115 | 33.917 | −15.609 | 1.00 | 20.00 |
| ATOM | 1477 | N | SER | B | 12 | 15.692 | 38.936 | −16.679 | 1.00 | 14.76 |
| ATOM | 1478 | CA | SER | B | 12 | 16.852 | 39.723 | −17.067 | 1.00 | 14.76 |
| ATOM | 1479 | C | SER | B | 12 | 18.084 | 39.073 | −16.486 | 1.00 | 14.76 |
| ATOM | 1480 | O | SER | B | 12 | 18.003 | 38.271 | −15.563 | 1.00 | 14.76 |
| ATOM | 1481 | CB | SER | B | 12 | 16.722 | 41.173 | −16.597 | 1.00 | 14.76 |
| ATOM | 1482 | OG | SER | B | 12 | 17.626 | 41.998 | −17.338 | 1.00 | 14.76 |
| ATOM | 1483 | H | SER | B | 12 | 15.500 | 38.780 | −15.708 | 1.00 | 20.00 |
| ATOM | 1484 | HG | SER | B | 12 | 17.326 | 42.893 | −17.220 | 1.00 | 20.00 |
| ATOM | 1485 | N | ARG | B | 13 | 19.233 | 39.424 | −17.081 | 1.00 | 14.62 |
| ATOM | 1486 | CA | ARG | B | 13 | 20.459 | 38.887 | −16.492 | 1.00 | 14.62 |
| ATOM | 1487 | C | ARG | B | 13 | 20.732 | 39.464 | −15.113 | 1.00 | 14.62 |
| ATOM | 1488 | O | ARG | B | 13 | 20.252 | 40.533 | −14.771 | 1.00 | 14.62 |
| ATOM | 1489 | CB | ARG | B | 13 | 21.651 | 39.127 | −17.421 | 1.00 | 14.62 |
| ATOM | 1490 | CG | ARG | B | 13 | 21.465 | 38.479 | −18.792 | 1.00 | 14.62 |
| ATOM | 1491 | CD | ARG | B | 13 | 22.723 | 38.571 | −19.661 | 1.00 | 14.62 |
| ATOM | 1492 | NE | ARG | B | 13 | 22.569 | 37.794 | −20.893 | 1.00 | 14.62 |
| ATOM | 1493 | CZ | ARG | B | 13 | 22.814 | 36.463 | −20.915 | 1.00 | 14.62 |
| ATOM | 1494 | NH1 | ARG | B | 13 | 22.591 | 35.776 | −22.032 | 1.00 | 14.62 |
| ATOM | 1495 | NH2 | ARG | B | 13 | 23.270 | 35.837 | −19.829 | 1.00 | 14.62 |
| ATOM | 1496 | H | ARG | B | 13 | 19.207 | 40.156 | −17.765 | 1.00 | 20.00 |
| ATOM | 1497 | HE | ARG | B | 13 | 22.226 | 38.279 | −21.699 | 1.00 | 20.00 |
| ATOM | 1498 | 1HH1 | ARG | B | 13 | 22.754 | 34.790 | −22.080 | 1.00 | 20.00 |
| ATOM | 1499 | 2HH1 | ARG | B | 13 | 22.251 | 36.238 | −22.852 | 1.00 | 20.00 |
| ATOM | 1500 | 1HH2 | ARG | B | 13 | 23.434 | 34.851 | −19.812 | 1.00 | 20.00 |
| ATOM | 1501 | 2HH2 | ARG | B | 13 | 23.457 | 36.362 | −18.998 | 1.00 | 20.00 |
| ATOM | 1502 | N | SER | B | 14 | 21.549 | 38.731 | −14.340 | 1.00 | 5.58 |
| ATOM | 1503 | CA | SER | B | 14 | 21.812 | 39.197 | −12.977 | 1.00 | 5.58 |
| ATOM | 1504 | C | SER | B | 14 | 22.520 | 40.535 | −12.807 | 1.00 | 5.58 |
| ATOM | 1505 | O | SER | B | 14 | 22.519 | 41.117 | −11.732 | 1.00 | 5.58 |
| ATOM | 1506 | CB | SER | B | 14 | 22.559 | 38.112 | −12.209 | 1.00 | 5.58 |
| ATOM | 1507 | OG | SER | B | 14 | 22.065 | 36.832 | −12.622 | 1.00 | 5.58 |
| ATOM | 1508 | H | SER | B | 14 | 21.798 | 37.787 | −14.558 | 1.00 | 20.00 |
| ATOM | 1509 | HG | SER | B | 14 | 22.136 | 36.270 | −11.860 | 1.00 | 20.00 |
| ATOM | 1510 | N | MET | B | 15 | 23.138 | 40.993 | −13.914 | 1.00 | 11.01 |
| ATOM | 1511 | CA | MET | B | 15 | 23.705 | 42.340 | −13.849 | 1.00 | 11.01 |
| ATOM | 1512 | C | MET | B | 15 | 22.714 | 43.511 | −13.896 | 1.00 | 11.01 |
| ATOM | 1513 | O | MET | B | 15 | 22.716 | 44.325 | −12.986 | 1.00 | 11.01 |
| ATOM | 1514 | CB | MET | B | 15 | 24.874 | 42.528 | −14.832 | 1.00 | 11.01 |
| ATOM | 1515 | CG | MET | B | 15 | 25.998 | 41.498 | −14.706 | 1.00 | 11.01 |
| ATOM | 1516 | SD | MET | B | 15 | 27.322 | 41.796 | −15.892 | 1.00 | 11.01 |
| ATOM | 1517 | CE | MET | B | 15 | 27.838 | 43.418 | −15.302 | 1.00 | 11.01 |
| ATOM | 1518 | H | MET | B | 15 | 23.109 | 40.463 | −14.757 | 1.00 | 20.00 |
| ATOM | 1519 | N | PRO | B | 16 | 21.872 | 43.632 | −14.966 | 1.00 | 6.76 |
| ATOM | 1520 | CA | PRO | B | 16 | 20.965 | 44.786 | −14.986 | 1.00 | 6.76 |
| ATOM | 1521 | C | PRO | B | 16 | 19.665 | 44.616 | −14.206 | 1.00 | 6.76 |
| ATOM | 1522 | O | PRO | B | 16 | 19.076 | 43.549 | −14.101 | 1.00 | 6.76 |
| ATOM | 1523 | CB | PRO | B | 16 | 20.716 | 44.959 | −16.485 | 1.00 | 6.76 |
| ATOM | 1524 | CG | PRO | B | 16 | 20.694 | 43.532 | −17.028 | 1.00 | 6.76 |
| ATOM | 1525 | CD | PRO | B | 16 | 21.773 | 42.846 | −16.199 | 1.00 | 6.76 |
| ATOM | 1526 | N | LEU | B | 17 | 19.206 | 45.781 | −13.720 | 1.00 | 6.37 |
| ATOM | 1527 | CA | LEU | B | 17 | 17.781 | 45.908 | −13.424 | 1.00 | 6.37 |
| ATOM | 1528 | C | LEU | B | 17 | 17.143 | 46.560 | −14.627 | 1.00 | 6.37 |
| ATOM | 1529 | O | LEU | B | 17 | 17.528 | 47.653 | −15.017 | 1.00 | 6.37 |
| ATOM | 1530 | CB | LEU | B | 17 | 17.564 | 46.791 | −12.191 | 1.00 | 6.37 |
| ATOM | 1531 | CG | LEU | B | 17 | 16.128 | 46.859 | −11.658 | 1.00 | 6.37 |
| ATOM | 1532 | CD1 | LEU | B | 17 | 15.573 | 45.486 | −11.265 | 1.00 | 6.37 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 1533 | CD2 | LEU B | 17 | 16.021 | 47.859 | −10.505 | 1.00 | 6.37 |
| ATOM 1534 | H | LEU B | 17 | 19.764 | 46.605 | −13.794 | 1.00 | 20.00 |
| ATOM 1535 | N | GLU B | 18 | 16.186 | 45.843 | −15.221 | 1.00 | 14.08 |
| ATOM 1536 | CA | GLU B | 18 | 15.596 | 46.473 | −16.394 | 1.00 | 14.08 |
| ATOM 1537 | C | GLU B | 18 | 14.112 | 46.640 | −16.190 | 1.00 | 14.08 |
| ATOM 1538 | O | GLU B | 18 | 13.490 | 45.838 | −15.505 | 1.00 | 14.08 |
| ATOM 1539 | CB | GLU B | 18 | 15.912 | 45.659 | −17.648 | 1.00 | 14.08 |
| ATOM 1540 | CG | GLU B | 18 | 16.059 | 46.515 | −18.916 | 1.00 | 14.08 |
| ATOM 1541 | CD | GLU B | 18 | 16.075 | 45.650 | −20.167 | 1.00 | 14.08 |
| ATOM 1542 | OE1 | GLU B | 18 | 16.395 | 44.465 | −20.108 | 1.00 | 14.08 |
| ATOM 1543 | OE2 | GLU B | 18 | 15.688 | 46.124 | −21.232 | 1.00 | 14.08 |
| ATOM 1544 | H | GLU B | 18 | 15.837 | 44.981 | −14.855 | 1.00 | 20.00 |
| ATOM 1545 | N | TRP B | 19 | 13.583 | 47.722 | −16.774 | 1.00 | 6.20 |
| ATOM 1546 | CA | TRP B | 19 | 12.151 | 47.934 | −16.600 | 1.00 | 6.20 |
| ATOM 1547 | C | TRP B | 19 | 11.337 | 47.428 | −17.775 | 1.00 | 6.20 |
| ATOM 1548 | O | TRP B | 19 | 11.859 | 47.205 | −18.862 | 1.00 | 6.20 |
| ATOM 1549 | CB | TRP B | 19 | 11.865 | 49.412 | −16.339 | 1.00 | 6.20 |
| ATOM 1550 | CG | TRP B | 19 | 12.506 | 49.881 | −15.052 | 1.00 | 6.20 |
| ATOM 1551 | CD1 | TRP B | 19 | 13.518 | 50.846 | −14.929 | 1.00 | 6.20 |
| ATOM 1552 | CD2 | TRP B | 19 | 12.237 | 49.442 | −13.701 | 1.00 | 6.20 |
| ATOM 1553 | NE1 | TRP B | 19 | 13.879 | 51.019 | −13.629 | 1.00 | 6.20 |
| ATOM 1554 | CE2 | TRP B | 19 | 13.115 | 50.173 | −12.833 | 1.00 | 6.20 |
| ATOM 1555 | CE3 | TRP B | 19 | 11.337 | 48.504 | −13.154 | 1.00 | 6.20 |
| ATOM 1556 | CZ2 | TRP B | 19 | 13.085 | 49.938 | −11.441 | 1.00 | 6.20 |
| ATOM 1557 | CZ3 | TRP B | 19 | 11.313 | 48.280 | −11.763 | 1.00 | 6.20 |
| ATOM 1558 | CH2 | TRP B | 19 | 12.185 | 48.991 | −10.909 | 1.00 | 6.20 |
| ATOM 1559 | H | TRP B | 19 | 14.125 | 48.305 | −17.378 | 1.00 | 20.00 |
| ATOM 1560 | HE1 | TRP B | 19 | 14.576 | 51.627 | −13.305 | 1.00 | 20.00 |
| ATOM 1561 | N | GLU B | 20 | 10.034 | 47.266 | −17.500 | 1.00 | 5.13 |
| ATOM 1562 | CA | GLU B | 20 | 9.142 | 46.757 | −18.537 | 1.00 | 5.13 |
| ATOM 1563 | C | GLU B | 20 | 7.800 | 47.449 | −18.566 | 1.00 | 5.13 |
| ATOM 1564 | O | GLU B | 20 | 7.310 | 47.882 | −17.530 | 1.00 | 5.13 |
| ATOM 1565 | CB | GLU B | 20 | 8.919 | 45.262 | −18.340 | 1.00 | 5.13 |
| ATOM 1566 | CG | GLU B | 20 | 9.485 | 44.456 | −19.508 | 1.00 | 5.13 |
| ATOM 1567 | CD | GLU B | 20 | 9.237 | 42.972 | −19.312 | 1.00 | 5.13 |
| ATOM 1568 | OE1 | GLU B | 20 | 8.122 | 42.600 | −18.951 | 1.00 | 5.13 |
| ATOM 1569 | OE2 | GLU B | 20 | 10.158 | 42.187 | −19.534 | 1.00 | 5.13 |
| ATOM 1570 | H | GLU B | 20 | 9.712 | 47.331 | −16.553 | 1.00 | 20.00 |
| ATOM 1571 | N | ASP B | 21 | 7.248 | 47.482 | −19.802 | 1.00 | 13.73 |
| ATOM 1572 | CA | ASP B | 21 | 5.954 | 48.123 | −20.064 | 1.00 | 13.73 |
| ATOM 1573 | C | ASP B | 21 | 4.760 | 47.192 | −20.205 | 1.00 | 13.73 |
| ATOM 1574 | O | ASP B | 21 | 3.641 | 47.477 | −19.793 | 1.00 | 13.73 |
| ATOM 1575 | CB | ASP B | 21 | 5.995 | 49.036 | −21.295 | 1.00 | 13.73 |
| ATOM 1576 | CG | ASP B | 21 | 7.170 | 49.993 | −21.267 | 1.00 | 13.73 |
| ATOM 1577 | OD1 | ASP B | 21 | 7.639 | 50.358 | −22.342 | 1.00 | 13.73 |
| ATOM 1578 | OD2 | ASP B | 21 | 7.623 | 50.366 | −20.186 | 1.00 | 13.73 |
| ATOM 1579 | H | ASP B | 21 | 7.815 | 47.200 | −20.571 | 1.00 | 20.00 |
| ATOM 1580 | N | THR B | 22 | 5.024 | 46.037 | −20.816 | 1.00 | 11.65 |
| ATOM 1581 | CA | THR B | 22 | 3.851 | 45.207 | −21.073 | 1.00 | 11.65 |
| ATOM 1582 | C | THR B | 22 | 3.541 | 44.196 | −19.981 | 1.00 | 11.65 |
| ATOM 1583 | O | THR B | 22 | 3.677 | 42.987 | −20.122 | 1.00 | 11.65 |
| ATOM 1584 | CB | THR B | 22 | 3.953 | 44.603 | −22.475 | 1.00 | 11.65 |
| ATOM 1585 | OG1 | THR B | 22 | 4.317 | 45.647 | −23.389 | 1.00 | 11.65 |
| ATOM 1586 | CG2 | THR B | 22 | 2.654 | 43.933 | −22.940 | 1.00 | 11.65 |
| ATOM 1587 | H | THR B | 22 | 5.938 | 45.799 | −21.132 | 1.00 | 20.00 |
| ATOM 1588 | HG1 | THR B | 22 | 4.335 | 45.272 | −24.258 | 1.00 | 20.00 |
| ATOM 1589 | N | TYR B | 23 | 3.094 | 44.781 | −18.861 | 1.00 | 6.57 |
| ATOM 1590 | CA | TYR B | 23 | 2.693 | 43.947 | −17.734 | 1.00 | 6.57 |
| ATOM 1591 | C | TYR B | 23 | 1.345 | 44.418 | −17.222 | 1.00 | 6.57 |
| ATOM 1592 | O | TYR B | 23 | 0.938 | 45.543 | −17.481 | 1.00 | 6.57 |
| ATOM 1593 | CB | TYR B | 23 | 3.798 | 43.961 | −16.660 | 1.00 | 6.57 |
| ATOM 1594 | CG | TYR B | 23 | 3.492 | 43.041 | −15.496 | 1.00 | 6.57 |
| ATOM 1595 | CD1 | TYR B | 23 | 3.030 | 43.598 | −14.284 | 1.00 | 6.57 |
| ATOM 1596 | CD2 | TYR B | 23 | 3.665 | 41.652 | −15.659 | 1.00 | 6.57 |
| ATOM 1597 | CE1 | TYR B | 23 | 2.702 | 42.740 | −13.222 | 1.00 | 6.57 |
| ATOM 1598 | CE2 | TYR B | 23 | 3.344 | 40.795 | −14.593 | 1.00 | 6.57 |
| ATOM 1599 | CZ | TYR B | 23 | 2.853 | 41.350 | −13.394 | 1.00 | 6.57 |
| ATOM 1600 | OH | TYR B | 23 | 2.500 | 40.513 | −12.356 | 1.00 | 6.57 |
| ATOM 1601 | H | TYR B | 23 | 2.973 | 45.780 | −18.851 | 1.00 | 20.00 |
| ATOM 1602 | HH | TYR B | 23 | 2.824 | 39.635 | −12.510 | 1.00 | 20.00 |
| ATOM 1603 | N | GLY B | 24 | 0.670 | 43.497 | −16.498 | 1.00 | 5.63 |
| ATOM 1604 | CA | GLY B | 24 | −0.703 | 43.702 | −16.025 | 1.00 | 5.63 |
| ATOM 1605 | C | GLY B | 24 | −1.050 | 45.118 | −15.618 | 1.00 | 5.63 |
| ATOM 1606 | O | GLY B | 24 | −1.892 | 45.777 | −16.217 | 1.00 | 5.63 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM | 1607 | H | GLY | B | 24 | 1.118 | 42.621 | −16.332 | 1.00 | 20.00 |
| ATOM | 1608 | N | ILE | B | 25 | −0.341 | 45.579 | −14.574 | 1.00 | 5.38 |
| ATOM | 1609 | CA | ILE | B | 25 | −0.527 | 47.010 | −14.405 | 1.00 | 5.38 |
| ATOM | 1610 | C | ILE | B | 25 | 0.742 | 47.811 | −14.553 | 1.00 | 5.38 |
| ATOM | 1611 | O | ILE | B | 25 | 1.286 | 48.396 | −13.627 | 1.00 | 5.38 |
| ATOM | 1612 | CB | ILE | B | 25 | −1.321 | 47.376 | −13.153 | 1.00 | 5.38 |
| ATOM | 1613 | CG1 | ILE | B | 25 | −2.448 | 46.363 | −12.908 | 1.00 | 5.38 |
| ATOM | 1614 | CG2 | ILE | B | 25 | −1.881 | 48.780 | −13.392 | 1.00 | 5.38 |
| ATOM | 1615 | CD1 | ILE | B | 25 | −2.995 | 46.321 | −11.485 | 1.00 | 5.38 |
| ATOM | 1616 | H | ILE | B | 25 | 0.309 | 45.038 | −14.040 | 1.00 | 20.00 |
| ATOM | 1617 | N | VAL | B | 26 | 1.167 | 47.811 | −15.818 | 1.00 | 4.68 |
| ATOM | 1618 | CA | VAL | B | 26 | 2.240 | 48.716 | −16.181 | 1.00 | 4.68 |
| ATOM | 1619 | C | VAL | B | 26 | 1.778 | 49.691 | −17.243 | 1.00 | 4.68 |
| ATOM | 1620 | O | VAL | B | 26 | 1.171 | 49.339 | −18.246 | 1.00 | 4.68 |
| ATOM | 1621 | CB | VAL | B | 26 | 3.479 | 47.926 | −16.590 | 1.00 | 4.68 |
| ATOM | 1622 | CG1 | VAL | B | 26 | 4.515 | 48.837 | −17.216 | 1.00 | 4.68 |
| ATOM | 1623 | CG2 | VAL | B | 26 | 4.090 | 47.225 | −15.379 | 1.00 | 4.68 |
| ATOM | 1624 | H | VAL | B | 26 | 0.734 | 47.247 | −16.526 | 1.00 | 20.00 |
| ATOM | 1625 | N | LEU | B | 27 | 2.034 | 50.966 | −16.911 | 1.00 | 5.09 |
| ATOM | 1626 | CA | LEU | B | 27 | 1.449 | 52.017 | −17.739 | 1.00 | 5.09 |
| ATOM | 1627 | C | LEU | B | 27 | 2.401 | 53.101 | −18.118 | 1.00 | 5.09 |
| ATOM | 1628 | O | LEU | B | 27 | 3.452 | 53.289 | −17.513 | 1.00 | 5.09 |
| ATOM | 1629 | CB | LEU | B | 27 | 0.305 | 52.723 | −17.039 | 1.00 | 5.09 |
| ATOM | 1630 | CG | LEU | B | 27 | −0.552 | 51.709 | −16.329 | 1.00 | 5.09 |
| ATOM | 1631 | CD1 | LEU | B | 27 | −0.966 | 52.266 | −14.972 | 1.00 | 5.09 |
| ATOM | 1632 | CD2 | LEU | B | 27 | −1.581 | 51.067 | −17.269 | 1.00 | 5.09 |
| ATOM | 1633 | H | LEU | B | 27 | 2.571 | 51.146 | −16.086 | 1.00 | 20.00 |
| ATOM | 1634 | N | LEU | B | 28 | 1.884 | 53.824 | −19.126 | 1.00 | 7.30 |
| ATOM | 1635 | CA | LEU | B | 28 | 2.567 | 54.936 | −19.752 | 1.00 | 7.30 |
| ATOM | 1636 | C | LEU | B | 28 | 1.549 | 55.965 | −20.212 | 1.00 | 7.30 |
| ATOM | 1637 | O | LEU | B | 28 | 0.592 | 55.617 | −20.892 | 1.00 | 7.30 |
| ATOM | 1638 | CB | LEU | B | 28 | 3.319 | 54.376 | −20.958 | 1.00 | 7.30 |
| ATOM | 1639 | CG | LEU | B | 28 | 4.099 | 55.444 | −21.707 | 1.00 | 7.30 |
| ATOM | 1640 | CD1 | LEU | B | 28 | 4.988 | 56.179 | −20.723 | 1.00 | 7.30 |
| ATOM | 1641 | CD2 | LEU | B | 28 | 4.860 | 54.900 | −22.915 | 1.00 | 7.30 |
| ATOM | 1642 | H | LEU | B | 28 | 1.013 | 53.559 | −19.540 | 1.00 | 20.00 |
| ATOM | 1643 | N | SER | B | 29 | 1.837 | 57.231 | −19.862 | 1.00 | 16.57 |
| ATOM | 1644 | CA | SER | B | 29 | 1.051 | 58.324 | −20.438 | 1.00 | 16.57 |
| ATOM | 1645 | C | SER | B | 29 | 1.894 | 59.556 | −20.704 | 1.00 | 16.57 |
| ATOM | 1646 | O | SER | B | 29 | 2.071 | 60.393 | −19.831 | 1.00 | 16.57 |
| ATOM | 1647 | CB | SER | B | 29 | −0.113 | 58.706 | −19.518 | 1.00 | 16.57 |
| ATOM | 1648 | OG | SER | B | 29 | −0.892 | 57.552 | −19.197 | 1.00 | 16.57 |
| ATOM | 1649 | H | SER | B | 29 | 2.516 | 57.368 | −19.138 | 1.00 | 20.00 |
| ATOM | 1650 | HG | SER | B | 29 | −1.574 | 57.830 | −18.604 | 1.00 | 20.00 |
| ATOM | 1651 | N | GLY | B | 30 | 2.433 | 59.646 | −21.934 | 1.00 | 4.20 |
| ATOM | 1652 | CA | GLY | B | 30 | 3.245 | 60.833 | −22.238 | 1.00 | 4.20 |
| ATOM | 1653 | C | GLY | B | 30 | 4.710 | 60.762 | −21.821 | 1.00 | 4.20 |
| ATOM | 1654 | O | GLY | B | 30 | 5.582 | 61.427 | −22.363 | 1.00 | 4.20 |
| ATOM | 1655 | H | GLY | B | 30 | 2.315 | 58.915 | −22.606 | 1.00 | 20.00 |
| ATOM | 1656 | N | VAL | B | 31 | 4.957 | 59.904 | −20.823 | 1.00 | 3.10 |
| ATOM | 1657 | CA | VAL | B | 31 | 6.350 | 59.619 | −20.483 | 1.00 | 3.10 |
| ATOM | 1658 | C | VAL | B | 31 | 6.927 | 58.775 | −21.622 | 1.00 | 3.10 |
| ATOM | 1659 | O | VAL | B | 31 | 6.182 | 58.264 | −22.451 | 1.00 | 3.10 |
| ATOM | 1660 | CB | VAL | B | 31 | 6.350 | 58.914 | −19.102 | 1.00 | 3.10 |
| ATOM | 1661 | CG1 | VAL | B | 31 | 7.718 | 58.487 | −18.560 | 1.00 | 3.10 |
| ATOM | 1662 | CG2 | VAL | B | 31 | 5.614 | 59.780 | −18.077 | 1.00 | 3.10 |
| ATOM | 1663 | H | VAL | B | 31 | 4.226 | 59.313 | −20.495 | 1.00 | 20.00 |
| ATOM | 1664 | N | LYS | B | 32 | 8.253 | 58.643 | −21.656 | 1.00 | 18.46 |
| ATOM | 1665 | CA | LYS | B | 32 | 8.752 | 57.633 | −22.580 | 1.00 | 18.46 |
| ATOM | 1666 | C | LYS | B | 32 | 9.828 | 56.828 | −21.904 | 1.00 | 18.46 |
| ATOM | 1667 | O | LYS | B | 32 | 10.568 | 57.346 | −21.080 | 1.00 | 18.46 |
| ATOM | 1668 | CB | LYS | B | 32 | 9.251 | 58.285 | −23.874 | 1.00 | 18.46 |
| ATOM | 1669 | CG | LYS | B | 32 | 9.612 | 57.287 | −24.980 | 1.00 | 18.46 |
| ATOM | 1670 | CD | LYS | B | 32 | 10.032 | 57.977 | −26.273 | 1.00 | 18.46 |
| ATOM | 1671 | CE | LYS | B | 32 | 11.231 | 58.903 | −26.084 | 1.00 | 18.46 |
| ATOM | 1672 | NZ | LYS | B | 32 | 11.475 | 59.598 | −27.353 | 1.00 | 18.46 |
| ATOM | 1673 | H | LYS | B | 32 | 8.846 | 59.148 | −21.026 | 1.00 | 20.00 |
| ATOM | 1674 | 1HZ | LYS | B | 32 | 12.267 | 60.261 | −27.240 | 1.00 | 20.00 |
| ATOM | 1675 | 2HZ | LYS | B | 32 | 11.692 | 58.899 | −28.092 | 1.00 | 20.00 |
| ATOM | 1676 | 3HZ | LYS | B | 32 | 10.617 | 60.124 | −27.617 | 1.00 | 20.00 |
| ATOM | 1677 | N | TYR | B | 33 | 9.880 | 55.545 | −22.275 | 1.00 | 6.60 |
| ATOM | 1678 | CA | TYR | B | 33 | 10.983 | 54.766 | −21.735 | 1.00 | 6.60 |
| ATOM | 1679 | C | TYR | B | 33 | 12.116 | 54.735 | −22.717 | 1.00 | 6.60 |
| ATOM | 1680 | O | TYR | B | 33 | 11.920 | 54.625 | −23.922 | 1.00 | 6.60 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 1681 | CB | TYR B | 33 | 10.512 | 53.362 | −21.366 | 1.00 | 6.60 |
| ATOM 1682 | CG | TYR B | 33 | 9.247 | 53.516 | −20.563 | 1.00 | 6.60 |
| ATOM 1683 | CD1 | TYR B | 33 | 8.019 | 53.173 | −21.156 | 1.00 | 6.60 |
| ATOM 1684 | CD2 | TYR B | 33 | 9.329 | 54.041 | −19.261 | 1.00 | 6.60 |
| ATOM 1685 | CE1 | TYR B | 33 | 6.839 | 53.358 | −20.423 | 1.00 | 6.60 |
| ATOM 1686 | CE2 | TYR B | 33 | 8.147 | 54.265 | −18.545 | 1.00 | 6.60 |
| ATOM 1687 | CZ | TYR B | 33 | 6.922 | 53.921 | −19.135 | 1.00 | 6.60 |
| ATOM 1688 | OH | TYR B | 33 | 5.770 | 54.173 | −18.423 | 1.00 | 6.60 |
| ATOM 1689 | H | TYR B | 33 | 9.269 | 55.151 | −22.961 | 1.00 | 20.00 |
| ATOM 1690 | HH | TYR B | 33 | 5.709 | 53.591 | −17.673 | 1.00 | 20.00 |
| ATOM 1691 | N | LYS B | 34 | 13.313 | 54.882 | −22.152 | 1.00 | 11.73 |
| ATOM 1692 | CA | LYS B | 34 | 14.439 | 54.807 | −23.066 | 1.00 | 11.73 |
| ATOM 1693 | C | LYS B | 34 | 15.414 | 53.710 | −22.667 | 1.00 | 11.73 |
| ATOM 1694 | O | LYS B | 34 | 15.039 | 52.549 | −22.586 | 1.00 | 11.73 |
| ATOM 1695 | CB | LYS B | 34 | 15.026 | 56.211 | −23.263 | 1.00 | 11.73 |
| ATOM 1696 | CG | LYS B | 34 | 15.784 | 56.336 | −24.585 | 1.00 | 11.73 |
| ATOM 1697 | CD | LYS B | 34 | 16.356 | 57.731 | −24.803 | 1.00 | 11.73 |
| ATOM 1698 | CE | LYS B | 34 | 17.181 | 57.796 | −26.085 | 1.00 | 11.73 |
| ATOM 1699 | NZ | LYS B | 34 | 17.616 | 59.180 | −26.307 | 1.00 | 11.73 |
| ATOM 1700 | H | LYS B | 34 | 13.379 | 55.065 | −21.167 | 1.00 | 20.00 |
| ATOM 1701 | 1HZ | LYS B | 34 | 18.227 | 59.223 | −27.148 | 1.00 | 20.00 |
| ATOM 1702 | 2HZ | LYS B | 34 | 16.779 | 59.777 | −26.456 | 1.00 | 20.00 |
| ATOM 1703 | 3HZ | LYS B | 34 | 18.135 | 59.523 | −25.473 | 1.00 | 20.00 |
| ATOM 1704 | N | LYS B | 35 | 16.673 | 54.091 | −22.389 | 1.00 | 6.70 |
| ATOM 1705 | CA | LYS B | 35 | 17.605 | 53.057 | −21.948 | 1.00 | 6.70 |
| ATOM 1706 | C | LYS B | 35 | 17.466 | 52.778 | −20.461 | 1.00 | 6.70 |
| ATOM 1707 | O | LYS B | 35 | 18.296 | 53.161 | −19.650 | 1.00 | 6.70 |
| ATOM 1708 | CB | LYS B | 35 | 19.032 | 53.471 | −22.317 | 1.00 | 6.70 |
| ATOM 1709 | CG | LYS B | 35 | 19.220 | 53.710 | −23.819 | 1.00 | 6.70 |
| ATOM 1710 | CD | LYS B | 35 | 20.602 | 54.284 | −24.139 | 1.00 | 6.70 |
| ATOM 1711 | CE | LYS B | 35 | 20.825 | 54.515 | −25.635 | 1.00 | 6.70 |
| ATOM 1712 | NZ | LYS B | 35 | 22.139 | 55.142 | −25.835 | 1.00 | 6.70 |
| ATOM 1713 | H | LYS B | 35 | 16.959 | 55.046 | −22.366 | 1.00 | 20.00 |
| ATOM 1714 | 1HZ | LYS B | 35 | 22.324 | 55.256 | −26.853 | 1.00 | 20.00 |
| ATOM 1715 | 2HZ | LYS B | 35 | 22.157 | 56.071 | −25.369 | 1.00 | 20.00 |
| ATOM 1716 | 3HZ | LYS B | 35 | 22.875 | 54.537 | −25.418 | 1.00 | 20.00 |
| ATOM 1717 | N | GLY B | 36 | 16.335 | 52.120 | −20.147 | 1.00 | 3.55 |
| ATOM 1718 | CA | GLY B | 36 | 16.037 | 51.813 | −18.746 | 1.00 | 3.55 |
| ATOM 1719 | C | GLY B | 36 | 15.702 | 53.015 | −17.871 | 1.00 | 3.55 |
| ATOM 1720 | O | GLY B | 36 | 15.893 | 53.006 | −16.662 | 1.00 | 3.55 |
| ATOM 1721 | H | GLY B | 36 | 15.712 | 51.860 | −20.890 | 1.00 | 20.00 |
| ATOM 1722 | N | GLY B | 37 | 15.191 | 54.060 | −18.542 | 1.00 | 4.03 |
| ATOM 1723 | CA | GLY B | 37 | 14.923 | 55.271 | −17.774 | 1.00 | 4.03 |
| ATOM 1724 | C | GLY B | 37 | 13.723 | 56.023 | −18.283 | 1.00 | 4.03 |
| ATOM 1725 | O | GLY B | 37 | 13.267 | 55.800 | −19.402 | 1.00 | 4.03 |
| ATOM 1726 | H | GLY B | 37 | 15.022 | 54.024 | −19.524 | 1.00 | 20.00 |
| ATOM 1727 | N | LEU B | 38 | 13.227 | 56.901 | −17.396 | 1.00 | 5.45 |
| ATOM 1728 | CA | LEU B | 38 | 11.996 | 57.610 | −17.747 | 1.00 | 5.45 |
| ATOM 1729 | C | LEU B | 38 | 12.278 | 58.998 | −18.260 | 1.00 | 5.45 |
| ATOM 1730 | O | LEU B | 38 | 12.997 | 59.757 | −17.630 | 1.00 | 5.45 |
| ATOM 1731 | CB | LEU B | 38 | 11.023 | 57.759 | −16.568 | 1.00 | 5.45 |
| ATOM 1732 | CG | LEU B | 38 | 10.741 | 56.537 | −15.691 | 1.00 | 5.45 |
| ATOM 1733 | CD1 | LEU B | 38 | 9.403 | 56.672 | −14.972 | 1.00 | 5.45 |
| ATOM 1734 | CD2 | LEU B | 38 | 10.781 | 55.213 | −16.431 | 1.00 | 5.45 |
| ATOM 1735 | H | LEU B | 38 | 13.712 | 57.058 | −16.531 | 1.00 | 20.00 |
| ATOM 1736 | N | LEU B | 39 | 11.664 | 59.299 | −19.411 | 1.00 | 2.74 |
| ATOM 1737 | CA | VAL B | 39 | 11.708 | 60.675 | −19.903 | 1.00 | 2.74 |
| ATOM 1738 | C | VAL B | 39 | 10.461 | 61.426 | −19.476 | 1.00 | 2.74 |
| ATOM 1739 | O | VAL B | 39 | 9.345 | 60.988 | −19.735 | 1.00 | 2.74 |
| ATOM 1740 | CB | VAL B | 39 | 11.821 | 60.711 | −21.435 | 1.00 | 2.74 |
| ATOM 1741 | CG1 | VAL B | 39 | 12.109 | 62.130 | −21.937 | 1.00 | 2.74 |
| ATOM 1742 | CG2 | VAL B | 39 | 12.842 | 59.704 | −21.966 | 1.00 | 2.74 |
| ATOM 1743 | H | VAL B | 39 | 11.116 | 58.595 | −19.864 | 1.00 | 20.00 |
| ATOM 1744 | N | ILE B | 40 | 10.691 | 62.572 | −18.818 | 1.00 | 15.04 |
| ATOM 1745 | CA | ILE B | 40 | 9.525 | 63.344 | −18.386 | 1.00 | 15.04 |
| ATOM 1746 | C | ILE B | 40 | 8.975 | 64.260 | −19.476 | 1.00 | 15.04 |
| ATOM 1747 | O | ILE B | 40 | 9.686 | 65.007 | −20.136 | 1.00 | 15.04 |
| ATOM 1748 | CB | ILE B | 40 | 9.823 | 64.084 | −17.062 | 1.00 | 15.04 |
| ATOM 1749 | CG1 | ILE B | 40 | 9.938 | 63.084 | −15.905 | 1.00 | 15.04 |
| ATOM 1750 | CG2 | ILE B | 40 | 8.721 | 65.079 | −16.692 | 1.00 | 15.04 |
| ATOM 1751 | CD1 | ILE B | 40 | 11.290 | 62.394 | −15.729 | 1.00 | 15.04 |
| ATOM 1752 | H | ILE B | 40 | 11.634 | 62.859 | −18.616 | 1.00 | 20.00 |
| ATOM 1753 | N | ASN B | 41 | 7.644 | 64.142 | −19.638 | 1.00 | 16.19 |
| ATOM 1754 | CA | ASN B | 41 | 6.938 | 64.933 | −20.650 | 1.00 | 16.19 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 1755 | C | ASN B | 41 | 6.778 | 66.408 | −20.315 | 1.00 | 16.19 |
| ATOM 1756 | O | ASN B | 41 | 6.972 | 67.278 | −21.154 | 1.00 | 16.19 |
| ATOM 1757 | CB | ASN B | 41 | 5.561 | 64.308 | −20.911 | 1.00 | 16.19 |
| ATOM 1758 | CG | ASN B | 41 | 4.884 | 64.784 | −22.196 | 1.00 | 16.19 |
| ATOM 1759 | OD1 | ASN B | 41 | 4.669 | 64.029 | −23.129 | 1.00 | 16.19 |
| ATOM 1760 | ND2 | ASN B | 41 | 4.456 | 66.052 | −22.196 | 1.00 | 16.19 |
| ATOM 1761 | H | ASN B | 41 | 7.170 | 63.468 | −19.075 | 1.00 | 20.00 |
| ATOM 1762 | 1HD2 | ASN B | 41 | 4.608 | 66.715 | −21.465 | 1.00 | 20.00 |
| ATOM 1763 | 2HD2 | ASN B | 41 | 3.974 | 66.360 | −23.014 | 1.00 | 20.00 |
| ATOM 1764 | N | GLU B | 42 | 6.338 | 66.662 | −19.074 | 1.00 | 4.33 |
| ATOM 1765 | CA | GLU B | 42 | 5.914 | 68.031 | −18.787 | 1.00 | 4.33 |
| ATOM 1766 | C | GLU B | 42 | 6.497 | 68.543 | −17.496 | 1.00 | 4.33 |
| ATOM 1767 | O | GLU B | 42 | 6.958 | 67.793 | −16.648 | 1.00 | 4.33 |
| ATOM 1768 | CB | GLU B | 42 | 4.386 | 68.120 | −18.726 | 1.00 | 4.33 |
| ATOM 1769 | CG | GLU B | 42 | 3.711 | 68.762 | −19.948 | 1.00 | 4.33 |
| ATOM 1770 | CD | GLU B | 42 | 2.214 | 68.473 | −19.919 | 1.00 | 4.33 |
| ATOM 1771 | OE1 | GLU B | 42 | 1.572 | 68.756 | −18.903 | 1.00 | 4.33 |
| ATOM 1772 | OE2 | GLU B | 42 | 1.699 | 67.914 | −20.897 | 1.00 | 4.33 |
| ATOM 1773 | H | GLU B | 42 | 6.316 | 65.982 | −18.339 | 1.00 | 20.00 |
| ATOM 1774 | N | THR B | 43 | 6.421 | 69.869 | −17.368 | 1.00 | 2.66 |
| ATOM 1775 | CA | THR B | 43 | 6.788 | 70.427 | −16.075 | 1.00 | 2.66 |
| ATOM 1776 | C | THR B | 43 | 5.698 | 70.214 | −15.037 | 1.00 | 2.66 |
| ATOM 1777 | O | THR B | 43 | 4.499 | 70.270 | −15.318 | 1.00 | 2.66 |
| ATOM 1778 | CB | THR B | 43 | 7.133 | 71.908 | −16.261 | 1.00 | 2.66 |
| ATOM 1779 | OG1 | THR B | 43 | 8.013 | 72.045 | −17.382 | 1.00 | 2.66 |
| ATOM 1780 | CG2 | THR B | 43 | 7.750 | 72.562 | −15.020 | 1.00 | 2.66 |
| ATOM 1781 | H | THR B | 43 | 6.113 | 70.458 | −18.114 | 1.00 | 20.00 |
| ATOM 1782 | HG1 | THR B | 43 | 8.287 | 72.953 | −17.402 | 1.00 | 20.00 |
| ATOM 1783 | N | GLY B | 44 | 6.166 | 69.962 | −13.813 | 1.00 | 2.64 |
| ATOM 1784 | CA | GLY B | 44 | 5.217 | 69.955 | −12.712 | 1.00 | 2.64 |
| ATOM 1785 | C | GLY B | 44 | 5.668 | 69.028 | −11.619 | 1.00 | 2.64 |
| ATOM 1786 | O | GLY B | 44 | 6.769 | 68.494 | −11.641 | 1.00 | 2.64 |
| ATOM 1787 | H | GLY B | 44 | 7.146 | 69.796 | −13.661 | 1.00 | 20.00 |
| ATOM 1788 | N | LEU B | 45 | 4.751 | 68.860 | −10.662 | 1.00 | 5.33 |
| ATOM 1789 | CA | LEU B | 45 | 5.085 | 67.931 | −9.596 | 1.00 | 5.33 |
| ATOM 1790 | C | LEU B | 45 | 4.807 | 66.510 | −9.993 | 1.00 | 5.33 |
| ATOM 1791 | O | LEU B | 45 | 3.782 | 66.188 | −10.577 | 1.00 | 5.33 |
| ATOM 1792 | CB | LEU B | 45 | 4.323 | 68.311 | −8.339 | 1.00 | 5.33 |
| ATOM 1793 | CG | LEU B | 45 | 4.818 | 69.669 | −7.859 | 1.00 | 5.33 |
| ATOM 1794 | CD1 | LEU B | 45 | 3.733 | 70.465 | −7.151 | 1.00 | 5.33 |
| ATOM 1795 | CD2 | LEU B | 45 | 6.104 | 69.539 | −7.048 | 1.00 | 5.33 |
| ATOM 1796 | H | LEU B | 45 | 3.838 | 69.256 | −10.719 | 1.00 | 20.00 |
| ATOM 1797 | N | TYR B | 46 | 5.787 | 65.684 | −9.652 | 1.00 | 3.53 |
| ATOM 1798 | CA | TYR B | 46 | 5.579 | 64.264 | −9.838 | 1.00 | 3.53 |
| ATOM 1799 | C | TYR B | 46 | 5.808 | 63.591 | −8.512 | 1.00 | 3.53 |
| ATOM 1800 | O | TYR B | 46 | 6.676 | 63.979 | −7.736 | 1.00 | 3.53 |
| ATOM 1801 | CB | TYR B | 46 | 6.525 | 63.703 | −10.907 | 1.00 | 3.53 |
| ATOM 1802 | CG | TYR B | 46 | 6.153 | 64.174 | −12.299 | 1.00 | 3.53 |
| ATOM 1803 | CD1 | TYR B | 46 | 6.502 | 65.475 | −12.725 | 1.00 | 3.53 |
| ATOM 1804 | CD2 | TYR B | 46 | 5.469 | 63.281 | −13.148 | 1.00 | 3.53 |
| ATOM 1805 | CE1 | TYR B | 46 | 6.153 | 65.894 | −14.020 | 1.00 | 3.53 |
| ATOM 1806 | CE2 | TYR B | 46 | 5.126 | 63.695 | −14.445 | 1.00 | 3.53 |
| ATOM 1807 | CZ | TYR B | 46 | 5.468 | 64.997 | −14.866 | 1.00 | 3.53 |
| ATOM 1808 | OH | TYR B | 46 | 5.116 | 65.393 | −16.144 | 1.00 | 3.53 |
| ATOM 1809 | H | TYR B | 46 | 6.616 | 66.022 | −9.201 | 1.00 | 20.00 |
| ATOM 1810 | HH | TYR B | 46 | 4.694 | 64.668 | −16.581 | 1.00 | 20.00 |
| ATOM 1811 | N | PHE B | 47 | 4.987 | 62.563 | −8.294 | 1.00 | 3.38 |
| ATOM 1812 | CA | PHE B | 47 | 5.343 | 61.642 | −7.232 | 1.00 | 3.38 |
| ATOM 1813 | C | PHE B | 47 | 6.117 | 60.500 | −7.842 | 1.00 | 3.38 |
| ATOM 1814 | O | PHE B | 47 | 5.688 | 59.851 | −8.791 | 1.00 | 3.38 |
| ATOM 1815 | CB | PHE B | 47 | 4.093 | 61.173 | −6.491 | 1.00 | 3.38 |
| ATOM 1816 | CG | PHE B | 47 | 4.436 | 60.359 | −5.261 | 1.00 | 3.38 |
| ATOM 1817 | CD1 | PHE B | 47 | 4.694 | 61.025 | −4.046 | 1.00 | 3.38 |
| ATOM 1818 | CD2 | PHE B | 47 | 4.473 | 58.950 | −5.337 | 1.00 | 3.38 |
| ATOM 1819 | CE1 | PHE B | 47 | 4.965 | 60.279 | −2.883 | 1.00 | 3.38 |
| ATOM 1820 | CE2 | PHE B | 47 | 4.742 | 58.199 | −4.177 | 1.00 | 3.38 |
| ATOM 1821 | CZ | PHE B | 47 | 4.976 | 58.871 | −2.959 | 1.00 | 3.38 |
| ATOM 1822 | H | PHE B | 47 | 4.276 | 62.339 | −8.962 | 1.00 | 20.00 |
| ATOM 1823 | N | VAL B | 48 | 7.306 | 60.352 | −7.259 | 1.00 | 2.79 |
| ATOM 1824 | CA | VAL B | 48 | 8.243 | 59.330 | −7.693 | 1.00 | 2.79 |
| ATOM 1825 | C | VAL B | 48 | 8.276 | 58.245 | −6.641 | 1.00 | 2.79 |
| ATOM 1826 | O | VAL B | 48 | 8.586 | 58.519 | −5.489 | 1.00 | 2.79 |
| ATOM 1827 | CB | VAL B | 48 | 9.624 | 59.984 | −7.845 | 1.00 | 2.79 |
| ATOM 1828 | CG1 | VAL B | 48 | 10.687 | 59.002 | −8.336 | 1.00 | 2.79 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 1829 | CG2 | VAL B | 48 | 9.542 | 61.234 | −8.726 | 1.00 | 2.79 |
| ATOM 1830 | H | VAL B | 48 | 7.543 | 60.947 | −6.488 | 1.00 | 20.00 |
| ATOM 1831 | N | TYR B | 49 | 7.943 | 57.021 | −7.067 | 1.00 | 3.73 |
| ATOM 1832 | CA | TYR B | 49 | 8.012 | 55.927 | −6.102 | 1.00 | 3.73 |
| ATOM 1833 | C | TYR B | 49 | 8.701 | 54.721 | −6.690 | 1.00 | 3.73 |
| ATOM 1834 | O | TYR B | 49 | 8.713 | 54.528 | −7.899 | 1.00 | 3.73 |
| ATOM 1835 | CB | TYR B | 49 | 6.620 | 55.541 | −5.576 | 1.00 | 3.73 |
| ATOM 1836 | CG | TYR B | 49 | 5.711 | 55.073 | −6.692 | 1.00 | 3.73 |
| ATOM 1837 | CD1 | TYR B | 49 | 5.725 | 53.714 | −7.069 | 1.00 | 3.73 |
| ATOM 1838 | CD2 | TYR B | 49 | 4.882 | 56.014 | −7.332 | 1.00 | 3.73 |
| ATOM 1839 | CE1 | TYR B | 49 | 4.911 | 53.292 | −8.130 | 1.00 | 3.73 |
| ATOM 1840 | CE2 | TYR B | 49 | 4.067 | 55.591 | −8.392 | 1.00 | 3.73 |
| ATOM 1841 | CZ | TYR B | 49 | 4.093 | 54.237 | −8.777 | 1.00 | 3.73 |
| ATOM 1842 | OH | TYR B | 49 | 3.291 | 53.816 | −9.819 | 1.00 | 3.73 |
| ATOM 1843 | H | TYR B | 49 | 7.677 | 56.848 | −8.020 | 1.00 | 20.00 |
| ATOM 1844 | HH | TYR B | 49 | 3.118 | 54.550 | −10.406 | 1.00 | 20.00 |
| ATOM 1845 | N | SER B | 50 | 9.248 | 53.906 | −5.783 | 1.00 | 5.02 |
| ATOM 1846 | CA | SER B | 50 | 9.844 | 52.663 | −6.257 | 1.00 | 5.02 |
| ATOM 1847 | C | SER B | 50 | 9.951 | 51.664 | −5.133 | 1.00 | 5.02 |
| ATOM 1848 | O | SER B | 50 | 10.089 | 52.034 | −3.973 | 1.00 | 5.02 |
| ATOM 1849 | CB | SER B | 50 | 11.212 | 52.937 | −6.889 | 1.00 | 5.02 |
| ATOM 1850 | OG | SER B | 50 | 11.819 | 51.710 | −7.302 | 1.00 | 5.02 |
| ATOM 1851 | H | SER B | 50 | 9.239 | 54.138 | −4.805 | 1.00 | 20.00 |
| ATOM 1852 | HG | SER B | 50 | 12.405 | 51.902 | −8.020 | 1.00 | 20.00 |
| ATOM 1853 | N | LYS B | 51 | 9.876 | 50.386 | −5.521 | 1.00 | 6.04 |
| ATOM 1854 | CA | LYS B | 51 | 10.122 | 49.364 | −4.517 | 1.00 | 6.04 |
| ATOM 1855 | C | LYS B | 51 | 10.911 | 48.207 | −5.077 | 1.00 | 6.04 |
| ATOM 1856 | O | LYS B | 51 | 10.713 | 47.791 | −6.211 | 1.00 | 6.04 |
| ATOM 1857 | CB | LYS B | 51 | 8.821 | 48.885 | −3.871 | 1.00 | 6.04 |
| ATOM 1858 | CG | LYS B | 51 | 9.132 | 48.324 | −2.491 | 1.00 | 6.04 |
| ATOM 1859 | CD | LYS B | 51 | 7.946 | 48.007 | −1.603 | 1.00 | 6.04 |
| ATOM 1860 | CE | LYS B | 51 | 8.484 | 47.686 | −0.212 | 1.00 | 6.04 |
| ATOM 1861 | NZ | LYS B | 51 | 7.398 | 47.117 | 0.581 | 1.00 | 6.04 |
| ATOM 1862 | H | LYS B | 51 | 9.811 | 50.160 | −6.497 | 1.00 | 20.00 |
| ATOM 1863 | 1HZ | LYS B | 51 | 7.682 | 46.966 | 1.564 | 1.00 | 20.00 |
| ATOM 1864 | 2HZ | LYS B | 51 | 6.604 | 47.786 | 0.545 | 1.00 | 20.00 |
| ATOM 1865 | 3HZ | LYS B | 51 | 7.086 | 46.220 | 0.165 | 1.00 | 20.00 |
| ATOM 1866 | N | VAL B | 52 | 11.823 | 47.721 | −4.221 | 1.00 | 4.38 |
| ATOM 1867 | CA | VAL B | 52 | 12.590 | 46.529 | −4.566 | 1.00 | 4.38 |
| ATOM 1868 | C | VAL B | 52 | 12.647 | 45.555 | −3.423 | 1.00 | 4.38 |
| ATOM 1869 | O | VAL B | 52 | 12.506 | 45.898 | −2.250 | 1.00 | 4.38 |
| ATOM 1870 | CB | VAL B | 52 | 14.021 | 46.856 | −4.973 | 1.00 | 4.38 |
| ATOM 1871 | CG1 | VAL B | 52 | 14.076 | 47.461 | −6.371 | 1.00 | 4.38 |
| ATOM 1872 | CG2 | VAL B | 52 | 14.701 | 47.698 | −3.894 | 1.00 | 4.38 |
| ATOM 1873 | H | VAL B | 52 | 11.935 | 48.148 | −3.320 | 1.00 | 20.00 |
| ATOM 1874 | N | TYR B | 53 | 12.865 | 44.305 | −3.848 | 1.00 | 6.58 |
| ATOM 1875 | CA | TYR B | 53 | 12.999 | 43.242 | −2.868 | 1.00 | 6.58 |
| ATOM 1876 | C | TYR B | 53 | 14.224 | 42.432 | −3.113 | 1.00 | 6.58 |
| ATOM 1877 | O | TYR B | 53 | 14.646 | 42.174 | −4.236 | 1.00 | 6.58 |
| ATOM 1878 | CB | TYR B | 53 | 11.808 | 42.293 | −2.864 | 1.00 | 6.58 |
| ATOM 1879 | CG | TYR B | 53 | 10.620 | 42.980 | −2.253 | 1.00 | 6.58 |
| ATOM 1880 | CD1 | TYR B | 53 | 10.088 | 42.461 | −1.062 | 1.00 | 6.58 |
| ATOM 1881 | CD2 | TYR B | 53 | 10.085 | 44.118 | −2.886 | 1.00 | 6.58 |
| ATOM 1882 | CE1 | TYR B | 53 | 8.999 | 43.123 | −0.487 | 1.00 | 6.58 |
| ATOM 1883 | CE2 | TYR B | 53 | 9.003 | 44.778 | −2.312 | 1.00 | 6.58 |
| ATOM 1884 | CZ | TYR B | 53 | 8.477 | 44.264 | −1.122 | 1.00 | 6.58 |
| ATOM 1885 | OH | TYR B | 53 | 7.387 | 44.900 | −0.577 | 1.00 | 6.58 |
| ATOM 1886 | H | TYR B | 53 | 12.906 | 44.099 | −4.827 | 1.00 | 20.00 |
| ATOM 1887 | HH | TYR B | 53 | 6.681 | 44.721 | −1.206 | 1.00 | 20.00 |
| ATOM 1888 | N | PHE B | 54 | 14.760 | 42.045 | −1.963 | 1.00 | 6.05 |
| ATOM 1889 | CA | PHE B | 54 | 16.004 | 41.312 | −1.998 | 1.00 | 6.05 |
| ATOM 1890 | C | PHE B | 54 | 15.823 | 40.024 | −1.260 | 1.00 | 6.05 |
| ATOM 1891 | O | PHE B | 54 | 15.083 | 39.964 | −0.285 | 1.00 | 6.05 |
| ATOM 1892 | CB | PHE B | 54 | 17.105 | 42.100 | −1.304 | 1.00 | 6.05 |
| ATOM 1893 | CG | PHE B | 54 | 17.166 | 43.518 | −1.812 | 1.00 | 6.05 |
| ATOM 1894 | CD1 | PHE B | 54 | 16.982 | 44.571 | −0.893 | 1.00 | 6.05 |
| ATOM 1895 | CD2 | PHE B | 54 | 17.422 | 43.768 | −3.176 | 1.00 | 6.05 |
| ATOM 1896 | CE1 | PHE B | 54 | 17.131 | 45.899 | −1.331 | 1.00 | 6.05 |
| ATOM 1897 | CE2 | PHE B | 54 | 17.566 | 45.093 | −3.614 | 1.00 | 6.05 |
| ATOM 1898 | CZ | PHE B | 54 | 17.459 | 46.143 | −2.680 | 1.00 | 6.05 |
| ATOM 1899 | H | PHE B | 54 | 14.344 | 42.270 | −1.079 | 1.00 | 20.00 |
| ATOM 1900 | N | ARG B | 55 | 16.526 | 39.015 | −1.765 | 1.00 | 19.70 |
| ATOM 1901 | CA | ARG B | 55 | 16.603 | 37.727 | −1.098 | 1.00 | 19.70 |
| ATOM 1902 | C | ARG B | 55 | 18.021 | 37.259 | −1.120 | 1.00 | 19.70 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 1903 | O | ARG B | 55 | 18.864 | 37.720 | −1.878 | 1.00 | 19.70 |
| ATOM 1904 | CB | ARG B | 55 | 15.869 | 36.631 | −1.875 | 1.00 | 19.70 |
| ATOM 1905 | CG | ARG B | 55 | 14.605 | 36.029 | −1.265 | 1.00 | 19.70 |
| ATOM 1906 | CD | ARG B | 55 | 13.722 | 35.199 | −2.191 | 1.00 | 19.70 |
| ATOM 1907 | NE | ARG B | 55 | 14.354 | 34.010 | −2.725 | 1.00 | 19.70 |
| ATOM 1908 | CZ | ARG B | 55 | 13.407 | 33.083 | −3.011 | 1.00 | 19.70 |
| ATOM 1909 | NH1 | ARG B | 55 | 13.834 | 31.913 | −3.459 | 1.00 | 19.70 |
| ATOM 1910 | NH2 | ARG B | 55 | 12.082 | 33.279 | −2.883 | 1.00 | 19.70 |
| ATOM 1911 | H | ARG B | 55 | 16.851 | 39.058 | −2.711 | 1.00 | 20.00 |
| ATOM 1912 | HE | ARG B | 55 | 15.340 | 33.798 | −2.649 | 1.00 | 20.00 |
| ATOM 1913 | 1HH1 | ARG B | 55 | 14.211 | 31.927 | −4.367 | 1.00 | 20.00 |
| ATOM 1914 | 2HH1 | ARG B | 55 | 13.827 | 31.014 | −2.997 | 1.00 | 20.00 |
| ATOM 1915 | 1HH2 | ARG B | 55 | 11.486 | 32.457 | −2.945 | 1.00 | 20.00 |
| ATOM 1916 | 2HH2 | ARG B | 55 | 11.707 | 34.227 | −2.766 | 1.00 | 20.00 |
| ATOM 1917 | N | GLY B | 56 | 18.187 | 36.218 | −0.312 | 1.00 | 3.53 |
| ATOM 1918 | CA | GLY B | 56 | 19.319 | 35.361 | −0.579 | 1.00 | 3.53 |
| ATOM 1919 | C | GLY B | 56 | 19.209 | 34.163 | 0.307 | 1.00 | 3.53 |
| ATOM 1920 | O | GLY B | 56 | 18.407 | 34.109 | 1.234 | 1.00 | 3.53 |
| ATOM 1921 | H | GLY B | 56 | 17.503 | 35.955 | 0.372 | 1.00 | 20.00 |
| ATOM 1922 | N | GLN B | 57 | 20.060 | 33.208 | −0.036 | 1.00 | 16.13 |
| ATOM 1923 | CA | GLN B | 57 | 20.209 | 32.098 | 0.872 | 1.00 | 16.13 |
| ATOM 1924 | C | GLN B | 57 | 21.595 | 32.176 | 1.461 | 1.00 | 16.13 |
| ATOM 1925 | O | GLN B | 57 | 22.529 | 32.523 | 0.747 | 1.00 | 16.13 |
| ATOM 1926 | CB | GLN B | 57 | 19.964 | 30.836 | 0.074 | 1.00 | 16.13 |
| ATOM 1927 | CG | GLN B | 57 | 19.750 | 29.677 | 1.023 | 1.00 | 16.13 |
| ATOM 1928 | CD | GLN B | 57 | 19.263 | 28.515 | 0.211 | 1.00 | 16.13 |
| ATOM 1929 | OE1 | GLN B | 57 | 19.868 | 28.041 | −0.737 | 1.00 | 16.13 |
| ATOM 1930 | NE2 | GLN B | 57 | 18.090 | 28.083 | 0.623 | 1.00 | 16.13 |
| ATOM 1931 | H | GLU B | 57 | 20.692 | 33.287 | −0.806 | 1.00 | 20.00 |
| ATOM 1932 | 1HE2 | GLN B | 57 | 17.528 | 28.462 | 1.360 | 1.00 | 20.00 |
| ATOM 1933 | 2HE2 | GLN B | 57 | 17.709 | 27.342 | 0.078 | 1.00 | 20.00 |
| ATOM 1934 | N | SER B | 58 | 21.672 | 31.894 | 2.779 | 1.00 | 30.56 |
| ATOM 1935 | CA | SER B | 58 | 22.937 | 32.099 | 3.488 | 1.00 | 30.56 |
| ATOM 1936 | C | SER B | 58 | 23.348 | 33.560 | 3.488 | 1.00 | 30.56 |
| ATOM 1937 | O | SER B | 58 | 22.668 | 34.423 | 2.936 | 1.00 | 30.56 |
| ATOM 1938 | CB | SER B | 58 | 24.052 | 31.188 | 2.952 | 1.00 | 30.56 |
| ATOM 1939 | OG | SER B | 58 | 23.563 | 29.846 | 2.851 | 1.00 | 30.56 |
| ATOM 1940 | H | SER B | 58 | 20.856 | 31.697 | 3.319 | 1.00 | 20.00 |
| ATOM 1941 | HG | SER B | 58 | 24.153 | 29.391 | 2.263 | 1.00 | 20.00 |
| ATOM 1942 | N | CYS B | 59 | 24.473 | 33.821 | 4.168 | 1.00 | 24.24 |
| ATOM 1943 | CA | CYS B | 59 | 24.721 | 35.240 | 4.358 | 1.00 | 24.24 |
| ATOM 1944 | C | CYS B | 59 | 26.179 | 35.604 | 4.410 | 1.00 | 24.24 |
| ATOM 1945 | O | CYS B | 59 | 26.993 | 34.974 | 5.074 | 1.00 | 24.24 |
| ATOM 1946 | CB | CYS B | 59 | 24.017 | 35.730 | 5.610 | 1.00 | 24.24 |
| ATOM 1947 | SG | CYS B | 59 | 22.424 | 34.925 | 5.943 | 1.00 | 24.24 |
| ATOM 1948 | H | CYS B | 59 | 25.047 | 33.142 | 4.623 | 1.00 | 20.00 |
| ATOM 1949 | N | ASN B | 60 | 26.445 | 36.674 | 3.655 | 1.00 | 8.07 |
| ATOM 1950 | CA | ASN B | 60 | 27.803 | 37.181 | 3.505 | 1.00 | 8.07 |
| ATOM 1951 | C | ASN B | 60 | 27.712 | 38.679 | 3.715 | 1.00 | 8.07 |
| ATOM 1952 | O | ASN B | 60 | 26.626 | 39.204 | 3.926 | 1.00 | 8.07 |
| ATOM 1953 | CB | ASN B | 60 | 28.348 | 36.873 | 2.101 | 1.00 | 8.07 |
| ATOM 1954 | CG | ASN B | 60 | 28.566 | 35.385 | 1.862 | 1.00 | 8.07 |
| ATOM 1955 | OD1 | ASN B | 60 | 27.762 | 34.525 | 2.191 | 1.00 | 8.07 |
| ATOM 1956 | ND2 | ASN B | 60 | 29.712 | 35.110 | 1.230 | 1.00 | 8.07 |
| ATOM 1957 | H | ASN B | 60 | 25.694 | 37.178 | 3.230 | 1.00 | 20.00 |
| ATOM 1958 | 1HD2 | ASN B | 60 | 30.349 | 35.821 | 0.941 | 1.00 | 20.00 |
| ATOM 1959 | 2HD2 | ASN B | 60 | 29.904 | 34.149 | 1.039 | 1.00 | 20.00 |
| ATOM 1960 | N | ASN B | 61 | 28.864 | 39.359 | 3.639 | 1.00 | 15.42 |
| ATOM 1961 | CA | ASN B | 61 | 28.756 | 40.807 | 3.837 | 1.00 | 15.42 |
| ATOM 1962 | C | ASN B | 61 | 28.540 | 41.551 | 2.535 | 1.00 | 15.42 |
| ATOM 1963 | O | ASN B | 61 | 29.457 | 41.673 | 1.734 | 1.00 | 15.42 |
| ATOM 1964 | CB | ASN B | 61 | 29.990 | 41.379 | 4.541 | 1.00 | 15.42 |
| ATOM 1965 | CG | ASN B | 61 | 30.169 | 40.772 | 5.918 | 1.00 | 15.42 |
| ATOM 1966 | OD1 | ASN B | 61 | 29.305 | 40.820 | 6.782 | 1.00 | 15.42 |
| ATOM 1967 | ND2 | ASN B | 61 | 31.360 | 40.190 | 6.090 | 1.00 | 15.42 |
| ATOM 1968 | H | ASN B | 61 | 29.712 | 38.924 | 3.343 | 1.00 | 20.00 |
| ATOM 1969 | 1HD2 | ASN B | 61 | 32.042 | 40.177 | 5.361 | 1.00 | 20.00 |
| ATOM 1970 | 2HD2 | ASN B | 61 | 31.552 | 39.770 | 6.975 | 1.00 | 20.00 |
| ATOM 1971 | N | LEU B | 62 | 27.296 | 42.037 | 2.365 | 1.00 | 19.58 |
| ATOM 1972 | CA | LEU B | 62 | 26.949 | 42.800 | 1.158 | 1.00 | 19.58 |
| ATOM 1973 | C | LEU B | 62 | 25.910 | 43.872 | 1.451 | 1.00 | 19.58 |
| ATOM 1974 | O | LEU B | 62 | 24.813 | 43.581 | 1.907 | 1.00 | 19.58 |
| ATOM 1975 | CB | LEU B | 62 | 26.404 | 41.888 | 0.050 | 1.00 | 19.58 |
| ATOM 1976 | CG | LEU B | 62 | 27.456 | 41.075 | −0.713 | 1.00 | 19.58 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 1977 | CD1 | LEU B | 62 | 26.808 | 40.058 | −1.652 | 1.00 | 19.58 |
| ATOM 1978 | CD2 | LEU B | 62 | 28.453 | 41.971 | −1.451 | 1.00 | 19.58 |
| ATOM 1979 | H | LEU B | 62 | 26.591 | 41.845 | 3.048 | 1.00 | 20.00 |
| ATOM 1980 | N | PRO B | 63 | 26.292 | 45.145 | 1.194 | 1.00 | 9.44 |
| ATOM 1981 | CA | PRO B | 63 | 25.327 | 46.240 | 1.359 | 1.00 | 9.44 |
| ATOM 1982 | C | PRO B | 63 | 24.362 | 46.327 | 0.187 | 1.00 | 9.44 |
| ATOM 1983 | O | PRO B | 63 | 24.732 | 46.155 | −0.963 | 1.00 | 9.44 |
| ATOM 1984 | CB | PRO B | 63 | 26.254 | 47.453 | 1.455 | 1.00 | 9.44 |
| ATOM 1985 | CG | PRO B | 63 | 27.442 | 47.106 | 0.553 | 1.00 | 9.44 |
| ATOM 1986 | CD | PRO B | 63 | 27.612 | 45.604 | 0.765 | 1.00 | 9.44 |
| ATOM 1987 | N | LEU B | 64 | 23.098 | 46.610 | 0.523 | 1.00 | 5.10 |
| ATOM 1988 | CA | LEU B | 64 | 22.149 | 46.685 | −0.586 | 1.00 | 5.10 |
| ATOM 1989 | C | LEU B | 64 | 21.731 | 48.123 | −0.793 | 1.00 | 5.10 |
| ATOM 1990 | O | LEU B | 64 | 21.449 | 48.822 | 0.175 | 1.00 | 5.10 |
| ATOM 1991 | CB | LEU B | 64 | 20.913 | 45.821 | −0.305 | 1.00 | 5.10 |
| ATOM 1992 | CG | LEU B | 64 | 21.125 | 44.624 | 0.639 | 1.00 | 5.10 |
| ATOM 1993 | CD1 | LEU B | 64 | 19.793 | 44.030 | 1.081 | 1.00 | 5.10 |
| ATOM 1994 | CD2 | LEU B | 64 | 22.076 | 43.551 | 0.107 | 1.00 | 5.10 |
| ATOM 1995 | H | LEU B | 64 | 22.795 | 46.760 | 1.466 | 1.00 | 20.00 |
| ATOM 1996 | N | SER B | 65 | 21.696 | 48.556 | −2.057 | 1.00 | 3.51 |
| ATOM 1997 | CA | SER B | 65 | 21.241 | 49.929 | −2.224 | 1.00 | 3.51 |
| ATOM 1998 | C | SER B | 65 | 20.139 | 50.073 | −3.245 | 1.00 | 3.51 |
| ATOM 1999 | O | SER B | 65 | 20.023 | 49.294 | −4.182 | 1.00 | 3.51 |
| ATOM 2000 | CB | SER B | 65 | 22.418 | 50.866 | −2.518 | 1.00 | 3.51 |
| ATOM 2001 | OG | SER B | 65 | 22.900 | 50.675 | −3.851 | 1.00 | 3.51 |
| ATOM 2002 | H | SER B | 65 | 22.020 | 48.015 | −2.839 | 1.00 | 20.00 |
| ATOM 2003 | HG | SER B | 65 | 23.809 | 50.944 | −3.862 | 1.00 | 20.00 |
| ATOM 2004 | N | HIS B | 66 | 19.330 | 51.113 | −3.009 | 1.00 | 11.85 |
| ATOM 2005 | CA | HIS B | 66 | 18.265 | 51.404 | −3.954 | 1.00 | 11.85 |
| ATOM 2006 | C | HIS B | 66 | 18.102 | 52.890 | −4.158 | 1.00 | 11.85 |
| ATOM 2007 | O | HIS B | 66 | 17.670 | 53.607 | −3.263 | 1.00 | 11.85 |
| ATOM 2008 | CB | HIS B | 66 | 16.957 | 50.808 | −3.463 | 1.00 | 11.85 |
| ATOM 2009 | CG | HIS B | 66 | 15.926 | 51.036 | −4.531 | 1.00 | 11.85 |
| ATOM 2010 | ND1 | HIS B | 66 | 14.974 | 51.976 | −4.456 | 1.00 | 11.85 |
| ATOM 2011 | CD2 | HIS B | 66 | 15.795 | 50.347 | −5.732 | 1.00 | 11.85 |
| ATOM 2012 | CE1 | HIS B | 66 | 14.232 | 51.876 | −5.592 | 1.00 | 11.85 |
| ATOM 2013 | NE2 | HIS B | 66 | 14.735 | 50.874 | −6.376 | 1.00 | 11.85 |
| ATOM 2014 | H | HIS B | 66 | 19.438 | 51.641 | −2.165 | 1.00 | 20.00 |
| ATOM 2015 | HD1 | HIS B | 66 | 14.870 | 52.654 | −3.764 | 1.00 | 20.00 |
| ATOM 2016 | N | LYS B | 67 | 18.490 | 53.327 | −5.359 | 1.00 | 4.98 |
| ATOM 2017 | CA | LYS B | 67 | 18.563 | 54.774 | −5.512 | 1.00 | 4.98 |
| ATOM 2018 | C | LYS B | 67 | 17.905 | 55.256 | −6.792 | 1.00 | 4.98 |
| ATOM 2019 | O | LYS B | 67 | 18.078 | 54.678 | −7.861 | 1.00 | 4.98 |
| ATOM 2020 | CB | LYS B | 67 | 20.027 | 55.217 | −5.434 | 1.00 | 4.98 |
| ATOM 2021 | CG | LYS B | 67 | 20.811 | 54.729 | −4.205 | 1.00 | 4.98 |
| ATOM 2022 | CD | LYS B | 67 | 22.318 | 54.883 | −4.410 | 1.00 | 4.98 |
| ATOM 2023 | CE | LYS B | 67 | 23.203 | 54.587 | −3.199 | 1.00 | 4.98 |
| ATOM 2024 | NZ | LYS B | 67 | 24.111 | 55.731 | −3.002 | 1.00 | 4.98 |
| ATOM 2025 | H | LYS B | 67 | 18.772 | 52.703 | −6.096 | 1.00 | 20.00 |
| ATOM 2026 | 1HZ | LYS B | 67 | 24.581 | 55.693 | −2.081 | 1.00 | 20.00 |
| ATOM 2027 | 2HZ | LYS B | 67 | 24.793 | 55.826 | −3.779 | 1.00 | 20.00 |
| ATOM 2028 | 3HZ | LYS B | 67 | 23.529 | 56.599 | −2.969 | 1.00 | 20.00 |
| ATOM 2029 | N | VAL B | 68 | 17.134 | 56.341 | −6.618 | 1.00 | 3.61 |
| ATOM 2030 | CA | VAL B | 68 | 16.534 | 57.023 | −7.761 | 1.00 | 3.61 |
| ATOM 2031 | C | VAL B | 68 | 17.318 | 58.284 | −8.064 | 1.00 | 3.61 |
| ATOM 2032 | O | VAL B | 68 | 17.558 | 59.108 | −7.186 | 1.00 | 3.61 |
| ATOM 2033 | CB | VAL B | 68 | 15.063 | 57.366 | −7.480 | 1.00 | 3.61 |
| ATOM 2034 | CG1 | VAL B | 68 | 14.377 | 58.002 | −8.696 | 1.00 | 3.61 |
| ATOM 2035 | CG2 | VAL B | 68 | 14.303 | 56.142 | −6.962 | 1.00 | 3.61 |
| ATOM 2036 | H | VAL B | 68 | 17.091 | 56.765 | −5.713 | 1.00 | 20.00 |
| ATOM 2037 | N | TYR B | 69 | 17.710 | 58.374 | −9.339 | 1.00 | 4.98 |
| ATOM 2038 | CA | TYR B | 69 | 18.533 | 59.487 | −9.792 | 1.00 | 4.98 |
| ATOM 2039 | C | TYR B | 69 | 17.818 | 60.297 | −10.848 | 1.00 | 4.98 |
| ATOM 2040 | O | TYR B | 69 | 16.970 | 59.784 | −11.570 | 1.00 | 4.98 |
| ATOM 2041 | CB | TYR B | 69 | 19.840 | 58.992 | −10.413 | 1.00 | 4.98 |
| ATOM 2042 | CG | TYR B | 69 | 20.583 | 58.031 | −9.518 | 1.00 | 4.98 |
| ATOM 2043 | CD1 | TYR B | 69 | 21.419 | 58.533 | −8.501 | 1.00 | 4.98 |
| ATOM 2044 | CD2 | TYR B | 69 | 20.440 | 56.650 | −9.757 | 1.00 | 4.98 |
| ATOM 2045 | CE1 | TYR B | 69 | 22.183 | 57.629 | −7.745 | 1.00 | 4.98 |
| ATOM 2046 | CE2 | TYR B | 69 | 21.200 | 55.747 | −9.000 | 1.00 | 4.98 |
| ATOM 2047 | CZ | TYR B | 69 | 22.082 | 56.252 | −8.024 | 1.00 | 4.98 |
| ATOM 2048 | OH | TYR B | 69 | 22.874 | 55.363 | −7.328 | 1.00 | 4.98 |
| ATOM 2049 | H | TYR B | 69 | 17.400 | 57.688 | −9.996 | 1.00 | 20.00 |
| ATOM 2050 | HH | TYR B | 69 | 22.509 | 54.491 | −7.405 | 1.00 | 20.00 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 2051 | N | MET B | 70 | 18.227 | 61.571 | −10.926 | 1.00 | 14.09 |
| ATOM 2052 | CA | MET B | 70 | 17.730 | 62.380 | −12.034 | 1.00 | 14.09 |
| ATOM 2053 | C | MET B | 70 | 18.838 | 62.969 | −12.878 | 1.00 | 14.09 |
| ATOM 2054 | O | MET B | 70 | 19.700 | 63.696 | −12.404 | 1.00 | 14.09 |
| ATOM 2055 | CB | MET B | 70 | 16.781 | 63.483 | −11.550 | 1.00 | 14.09 |
| ATOM 2056 | CG | MET B | 70 | 17.382 | 64.452 | −10.537 | 1.00 | 14.09 |
| ATOM 2057 | SD | MET B | 70 | 16.248 | 65.699 | −9.921 | 1.00 | 14.09 |
| ATOM 2058 | CE | MET B | 70 | 15.800 | 66.467 | −11.481 | 1.00 | 14.09 |
| ATOM 2059 | H | MET B | 70 | 18.923 | 61.907 | −10.286 | 1.00 | 20.00 |
| ATOM 2060 | N | ARG B | 71 | 18.763 | 62.643 | −14.169 | 1.00 | 7.41 |
| ATOM 2061 | CA | ARG B | 71 | 19.595 | 63.405 | −15.088 | 1.00 | 7.41 |
| ATOM 2062 | C | ARG B | 71 | 18.783 | 64.520 | −15.707 | 1.00 | 7.41 |
| ATOM 2063 | O | ARG B | 71 | 18.037 | 64.319 | −16.661 | 1.00 | 7.41 |
| ATOM 2064 | CB | ARG B | 71 | 20.201 | 62.514 | −16.168 | 1.00 | 7.41 |
| ATOM 2065 | CG | ARG B | 71 | 21.244 | 63.289 | −16.974 | 1.00 | 7.41 |
| ATOM 2066 | CD | ARG B | 71 | 21.943 | 62.439 | −18.028 | 1.00 | 7.41 |
| ATOM 2067 | NE | ARG B | 71 | 22.965 | 63.233 | −18.704 | 1.00 | 7.41 |
| ATOM 2068 | CZ | ARG B | 71 | 23.825 | 62.664 | −19.570 | 1.00 | 7.41 |
| ATOM 2069 | NH1 | ARG B | 71 | 23.771 | 61.354 | −19.809 | 1.00 | 7.41 |
| ATOM 2070 | NH2 | ARG B | 71 | 24.728 | 63.424 | −20.183 | 1.00 | 7.41 |
| ATOM 2071 | H | ARG B | 71 | 18.020 | 62.049 | −14.480 | 1.00 | 20.00 |
| ATOM 2072 | HE | ARG B | 71 | 23.010 | 64.206 | −18.467 | 1.00 | 20.00 |
| ATOM 2073 | 1HH1 | ARG B | 71 | 24.383 | 60.907 | −20.458 | 1.00 | 20.00 |
| ATOM 2074 | 2HH1 | ARG B | 71 | 23.104 | 60.794 | −19.314 | 1.00 | 20.00 |
| ATOM 2075 | 1HH2 | ARG B | 71 | 25.376 | 63.044 | −20.843 | 1.00 | 20.00 |
| ATOM 2076 | 2HH2 | ARG B | 71 | 24.772 | 64.402 | −19.980 | 1.00 | 20.00 |
| ATOM 2077 | N | ASN B | 72 | 18.944 | 65.697 | −15.084 | 1.00 | 8.42 |
| ATOM 2078 | CA | ASN B | 72 | 18.118 | 66.811 | −15.540 | 1.00 | 8.42 |
| ATOM 2079 | C | ASN B | 72 | 18.669 | 67.504 | −16.777 | 1.00 | 8.42 |
| ATOM 2080 | O | ASN B | 72 | 19.847 | 67.410 | −17.089 | 1.00 | 8.42 |
| ATOM 2081 | CB | ASN B | 72 | 17.843 | 67.773 | −14.375 | 1.00 | 8.42 |
| ATOM 2082 | CG | ASN B | 72 | 16.681 | 68.700 | −14.696 | 1.00 | 8.42 |
| ATOM 2083 | OD1 | ASN B | 72 | 16.871 | 69.829 | −15.127 | 1.00 | 8.42 |
| ATOM 2084 | ND2 | ASN B | 72 | 15.466 | 68.182 | −14.493 | 1.00 | 8.42 |
| ATOM 2085 | H | ASN B | 72 | 19.670 | 65.789 | −14.399 | 1.00 | 20.00 |
| ATOM 2086 | 1HD2 | ASN B | 72 | 15.295 | 67.230 | −14.208 | 1.00 | 20.00 |
| ATOM 2087 | 2HD2 | ASN B | 72 | 14.644 | 68.719 | −14.666 | 1.00 | 20.00 |
| ATOM 2088 | N | SER B | 73 | 17.772 | 68.216 | −17.479 | 1.00 | 5.16 |
| ATOM 2089 | CA | SER B | 73 | 18.254 | 69.002 | −18.614 | 1.00 | 5.16 |
| ATOM 2090 | C | SER B | 73 | 19.172 | 70.146 | −18.207 | 1.00 | 5.16 |
| ATOM 2091 | O | SER B | 73 | 20.171 | 70.451 | −18.846 | 1.00 | 5.16 |
| ATOM 2092 | CB | SER B | 73 | 17.047 | 69.529 | −19.386 | 1.00 | 5.16 |
| ATOM 2093 | OG | SER B | 73 | 16.136 | 70.134 | −18.460 | 1.00 | 5.16 |
| ATOM 2094 | H | SER B | 73 | 16.814 | 68.316 | −17.202 | 1.00 | 20.00 |
| ATOM 2095 | HG | SER B | 73 | 15.436 | 70.509 | −18.981 | 1.00 | 20.00 |
| ATOM 2096 | N | LYS B | 74 | 18.775 | 70.760 | −17.078 | 1.00 | 5.76 |
| ATOM 2097 | CA | LYS B | 74 | 19.557 | 71.877 | −16.547 | 1.00 | 5.76 |
| ATOM 2098 | C | LYS B | 74 | 20.972 | 71.502 | −16.131 | 1.00 | 5.76 |
| ATOM 2099 | O | LYS B | 74 | 21.926 | 72.239 | −16.340 | 1.00 | 5.76 |
| ATOM 2100 | CB | LYS B | 74 | 18.819 | 72.519 | −15.370 | 1.00 | 5.76 |
| ATOM 2101 | CG | LYS B | 74 | 17.413 | 73.020 | −15.716 | 1.00 | 5.76 |
| ATOM 2102 | CD | LYS B | 74 | 16.639 | 73.446 | −14.465 | 1.00 | 5.76 |
| ATOM 2103 | CE | LYS B | 74 | 15.212 | 73.910 | −14.763 | 1.00 | 5.76 |
| ATOM 2104 | NZ | LYS B | 74 | 14.530 | 74.225 | −13.498 | 1.00 | 5.76 |
| ATOM 2105 | H | LYS B | 74 | 17.915 | 70.461 | −16.653 | 1.00 | 20.00 |
| ATOM 2106 | 1HZ | LYS B | 74 | 13.585 | 74.611 | −13.697 | 1.00 | 20.00 |
| ATOM 2107 | 2HZ | LYS B | 74 | 14.437 | 73.360 | −12.928 | 1.00 | 20.00 |
| ATOM 2108 | 3HZ | LYS B | 74 | 15.085 | 74.927 | −12.968 | 1.00 | 20.00 |
| ATOM 2109 | N | TYR B | 75 | 21.052 | 70.308 | −15.517 | 1.00 | 6.72 |
| ATOM 2110 | CA | TYR B | 75 | 22.355 | 69.866 | −15.029 | 1.00 | 6.72 |
| ATOM 2111 | C | TYR B | 75 | 22.884 | 68.605 | −15.692 | 1.00 | 6.72 |
| ATOM 2112 | O | TYR B | 75 | 22.288 | 67.541 | −15.621 | 1.00 | 6.72 |
| ATOM 2113 | CB | TYR B | 75 | 22.304 | 69.691 | −13.501 | 1.00 | 6.72 |
| ATOM 2114 | CG | TYR B | 75 | 23.684 | 69.575 | −12.877 | 1.00 | 6.72 |
| ATOM 2115 | CD1 | TYR B | 75 | 24.731 | 70.423 | −13.298 | 1.00 | 6.72 |
| ATOM 2116 | CD2 | TYR B | 75 | 23.883 | 68.612 | −11.868 | 1.00 | 6.72 |
| ATOM 2117 | CE1 | TYR B | 75 | 26.013 | 70.269 | −12.746 | 1.00 | 6.72 |
| ATOM 2118 | CE2 | TYR B | 75 | 25.155 | 68.485 | −11.286 | 1.00 | 6.72 |
| ATOM 2119 | CZ | TYR B | 75 | 26.211 | 69.299 | −11.745 | 1.00 | 6.72 |
| ATOM 2120 | CH | TYR B | 75 | 27.472 | 69.145 | −11.200 | 1.00 | 6.72 |
| ATOM 2121 | H | TYR B | 75 | 20.243 | 69.735 | −15.404 | 1.00 | 20.00 |
| ATOM 2122 | HH | TYR B | 75 | 27.446 | 68.497 | −10.498 | 1.00 | 20.00 |
| ATOM 2123 | N | PRO B | 76 | 24.086 | 68.747 | −16.300 | 1.00 | 6.84 |
| ATOM 2124 | CA | PRO B | 76 | 24.816 | 67.585 | −16.827 | 1.00 | 6.84 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 2125 | C | PRO B | 76 | 25.006 | 66.326 | −15.966 | 1.00 | 6.84 |
| ATOM 2126 | O | PRO B | 76 | 25.395 | 65.299 | −16.509 | 1.00 | 6.84 |
| ATOM 2127 | CB | PRO B | 76 | 26.141 | 68.197 | −17.316 | 1.00 | 6.84 |
| ATOM 2128 | CG | PRO B | 76 | 26.233 | 69.598 | −16.710 | 1.00 | 6.84 |
| ATOM 2129 | CD | PRO B | 76 | 24.776 | 70.006 | −16.566 | 1.00 | 6.84 |
| ATOM 2130 | N | GLN B | 77 | 24.760 | 66.415 | −14.641 | 1.00 | 4.75 |
| ATOM 2131 | CA | GLN B | 77 | 24.972 | 65.200 | −13.848 | 1.00 | 4.75 |
| ATOM 2132 | C | GLN B | 77 | 23.695 | 64.568 | −13.339 | 1.00 | 4.75 |
| ATOM 2133 | O | GLN B | 77 | 22.623 | 65.162 | −13.333 | 1.00 | 4.75 |
| ATOM 2134 | CB | GLN B | 77 | 25.861 | 65.447 | −12.629 | 1.00 | 4.75 |
| ATOM 2135 | CG | GLN B | 77 | 27.283 | 65.926 | −12.910 | 1.00 | 4.75 |
| ATOM 2136 | CD | GLN B | 77 | 27.941 | 66.295 | −11.592 | 1.00 | 4.75 |
| ATOM 2137 | OE1 | GLN B | 77 | 27.336 | 66.341 | −10.529 | 1.00 | 4.75 |
| ATOM 2138 | NE2 | GLN B | 77 | 29.232 | 66.613 | −11.703 | 1.00 | 4.75 |
| ATOM 2139 | H | GLN B | 77 | 24.261 | 67.181 | −14.242 | 1.00 | 20.00 |
| ATOM 2140 | 1HE2 | GLN B | 77 | 29.703 | 66.647 | −12.582 | 1.00 | 20.00 |
| ATOM 2141 | 2HE2 | GLN B | 77 | 29.708 | 66.843 | −10.855 | 1.00 | 20.00 |
| ATOM 2142 | N | ASP B | 78 | 23.908 | 63.336 | −12.860 | 1.00 | 4.94 |
| ATOM 2143 | CA | ASP B | 78 | 22.824 | 62.590 | −12.233 | 1.00 | 4.94 |
| ATOM 2144 | C | ASP B | 78 | 22.750 | 62.909 | −10.749 | 1.00 | 4.94 |
| ATOM 2145 | O | ASP B | 78 | 23.609 | 62.544 | −9.955 | 1.00 | 4.94 |
| ATOM 2146 | CB | ASP B | 78 | 23.007 | 61.077 | −12.459 | 1.00 | 4.94 |
| ATOM 2147 | CG | ASP B | 78 | 23.049 | 60.650 | −13.931 | 1.00 | 4.94 |
| ATOM 2148 | OD1 | ASP B | 78 | 23.096 | 61.491 | −14.830 | 1.00 | 4.94 |
| ATOM 2149 | OD2 | ASP B | 78 | 23.042 | 59.446 | −14.181 | 1.00 | 4.94 |
| ATOM 2150 | H | ASP B | 78 | 24.799 | 62.900 | −12.960 | 1.00 | 20.00 |
| ATOM 2151 | N | LEU B | 79 | 21.678 | 63.638 | −10.411 | 1.00 | 4.95 |
| ATOM 2152 | CA | LEU B | 79 | 21.433 | 63.943 | −8.999 | 1.00 | 4.95 |
| ATOM 2153 | C | LEU B | 79 | 20.834 | 62.737 | −8.306 | 1.00 | 4.95 |
| ATOM 2154 | O | LEU B | 79 | 20.248 | 61.873 | −8.945 | 1.00 | 4.95 |
| ATOM 2155 | CB | LEU B | 79 | 20.417 | 65.076 | −8.786 | 1.00 | 4.95 |
| ATOM 2156 | CG | LEU B | 79 | 20.596 | 66.498 | −9.339 | 1.00 | 4.95 |
| ATOM 2157 | CD1 | LEU B | 79 | 20.566 | 66.614 | −10.868 | 1.00 | 4.95 |
| ATOM 2158 | CD2 | LEU B | 79 | 19.508 | 67.394 | −8.739 | 1.00 | 4.95 |
| ATOM 2159 | H | LEU B | 79 | 21.021 | 63.835 | −11.139 | 1.00 | 20.00 |
| ATOM 2160 | N | VAL B | 80 | 20.953 | 62.729 | −6.971 | 1.00 | 4.14 |
| ATOM 2161 | CA | VAL B | 80 | 20.194 | 61.682 | −6.300 | 1.00 | 4.14 |
| ATOM 2162 | C | VAL B | 80 | 18.944 | 62.215 | −5.635 | 1.00 | 4.14 |
| ATOM 2163 | O | VAL B | 80 | 18.974 | 63.051 | −4.738 | 1.00 | 4.14 |
| ATOM 2164 | CB | VAL B | 80 | 21.039 | 60.884 | −5.308 | 1.00 | 4.14 |
| ATOM 2165 | CG1 | VAL B | 80 | 20.353 | 59.543 | −5.042 | 1.00 | 4.14 |
| ATOM 2166 | CG2 | VAL B | 80 | 22.480 | 60.689 | −5.790 | 1.00 | 4.14 |
| ATOM 2167 | H | VAL B | 80 | 21.441 | 63.434 | −6.458 | 1.00 | 20.00 |
| ATOM 2168 | N | MET B | 81 | 17.828 | 61.680 | −6.152 | 1.00 | 4.15 |
| ATOM 2169 | CA | MET B | 81 | 16.536 | 62.049 | −5.584 | 1.00 | 4.15 |
| ATOM 2170 | C | MET B | 81 | 16.289 | 61.328 | −4.277 | 1.00 | 4.15 |
| ATOM 2171 | O | MET B | 81 | 15.990 | 61.914 | −3.245 | 1.00 | 4.15 |
| ATOM 2172 | CB | MET B | 81 | 15.418 | 61.732 | −6.580 | 1.00 | 4.15 |
| ATOM 2173 | CG | MET B | 81 | 15.667 | 62.383 | −7.938 | 1.00 | 4.15 |
| ATOM 2174 | SD | MET B | 81 | 14.554 | 61.808 | −9.225 | 1.00 | 4.15 |
| ATOM 2175 | CE | MET B | 81 | 13.053 | 62.577 | −8.623 | 1.00 | 4.15 |
| ATOM 2176 | H | MET B | 81 | 17.915 | 60.935 | −6.818 | 1.00 | 20.00 |
| ATOM 2177 | N | MET B | 82 | 16.424 | 59.995 | −4.382 | 1.00 | 5.02 |
| ATOM 2178 | CA | MET B | 82 | 16.100 | 59.176 | −3.218 | 1.00 | 5.02 |
| ATOM 2179 | C | MET B | 82 | 17.063 | 58.021 | −3.084 | 1.00 | 5.02 |
| ATOM 2180 | O | MET B | 82 | 17.486 | 57.434 | −4.068 | 1.00 | 5.02 |
| ATOM 2181 | CB | MET B | 82 | 14.671 | 58.643 | −3.322 | 1.00 | 5.02 |
| ATOM 2182 | CG | MET B | 82 | 13.577 | 59.700 | −3.168 | 1.00 | 5.02 |
| ATOM 2183 | SD | MET B | 82 | 11.933 | 59.007 | −3.335 | 1.00 | 5.02 |
| ATOM 2184 | CE | MET B | 82 | 12.094 | 58.382 | −5.010 | 1.00 | 5.02 |
| ATOM 2185 | H | MET B | 82 | 16.740 | 59.575 | −5.238 | 1.00 | 20.00 |
| ATOM 2186 | N | GLU B | 83 | 17.387 | 57.718 | −1.821 | 1.00 | 4.99 |
| ATOM 2187 | CA | GLU B | 83 | 18.381 | 56.671 | −1.585 | 1.00 | 4.99 |
| ATOM 2188 | C | GLU B | 83 | 17.901 | 55.708 | −0.561 | 1.00 | 4.99 |
| ATOM 2189 | O | GLU B | 83 | 17.326 | 56.154 | 0.417 | 1.00 | 4.99 |
| ATOM 2190 | CB | GLU B | 83 | 19.597 | 57.227 | −0.899 | 1.00 | 4.99 |
| ATOM 2191 | CG | GLU B | 83 | 20.427 | 58.122 | −1.769 | 1.00 | 4.99 |
| ATOM 2192 | CD | GLU B | 83 | 21.766 | 57.465 | −1.998 | 1.00 | 4.99 |
| ATOM 2193 | OE1 | GLU B | 83 | 22.287 | 56.750 | −1.129 | 1.00 | 4.99 |
| ATOM 2194 | OE2 | GLU B | 83 | 22.303 | 57.675 | −3.073 | 1.00 | 4.99 |
| ATOM 2195 | H | GLU B | 83 | 17.001 | 58.220 | −1.049 | 1.00 | 20.00 |
| ATOM 2196 | N | GLY B | 84 | 18.224 | 54.428 | −0.777 | 1.00 | 3.83 |
| ATOM 2197 | C | GLY B | 84 | 18.006 | 53.408 | 0.239 | 1.00 | 3.83 |
| ATOM 2198 | C | GLY B | 84 | 19.240 | 52.578 | 0.510 | 1.00 | 3.83 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 2199 | O | GLY B | 84 | 19.763 | 51.931 | −0.383 | 1.00 | 3.83 |
| ATOM 2200 | H | GLY B | 84 | 18.565 | 54.172 | −1.683 | 1.00 | 20.00 |
| ATOM 2201 | N | LYS B | 85 | 19.685 | 52.610 | 1.776 | 1.00 | 5.40 |
| ATOM 2202 | CA | LYS B | 85 | 20.759 | 51.687 | 2.133 | 1.00 | 5.40 |
| ATOM 2203 | C | LYS B | 85 | 20.283 | 50.677 | 3.139 | 1.00 | 5.40 |
| ATOM 2204 | O | LYS B | 85 | 19.809 | 51.019 | 4.216 | 1.00 | 5.40 |
| ATOM 2205 | CB | LYS B | 85 | 21.959 | 52.406 | 2.738 | 1.00 | 5.40 |
| ATOM 2206 | CG | LYS B | 85 | 22.574 | 53.465 | 1.834 | 1.00 | 5.40 |
| ATOM 2207 | CD | LYS B | 85 | 23.701 | 54.191 | 2.558 | 1.00 | 5.40 |
| ATOM 2208 | CE | LYS B | 85 | 24.309 | 55.303 | 1.710 | 1.00 | 5.40 |
| ATOM 2209 | NZ | LYS B | 85 | 25.353 | 55.954 | 2.506 | 1.00 | 5.40 |
| ATOM 2210 | H | LYS B | 85 | 19.252 | 53.165 | 2.482 | 1.00 | 20.00 |
| ATOM 2211 | 1HZ | LYS B | 85 | 25.825 | 56.703 | 1.954 | 1.00 | 20.00 |
| ATOM 2212 | 2HZ | LYS B | 85 | 24.920 | 56.371 | 3.354 | 1.00 | 20.00 |
| ATOM 2213 | 3HZ | LYS B | 85 | 26.082 | 55.271 | 2.784 | 1.00 | 20.00 |
| ATOM 2214 | N | MET B | 86 | 20.443 | 49.416 | 2.746 | 1.00 | 17.02 |
| ATOM 2215 | CA | MET B | 86 | 20.192 | 48.371 | 3.721 | 1.00 | 17.02 |
| ATOM 2216 | C | MET B | 86 | 21.403 | 47.488 | 3.860 | 1.00 | 17.02 |
| ATOM 2217 | O | MET B | 86 | 21.681 | 46.631 | 3.034 | 1.00 | 17.02 |
| ATOM 2218 | CB | MET B | 86 | 18.952 | 47.547 | 3.353 | 1.00 | 17.02 |
| ATOM 2219 | CG | MET B | 86 | 17.654 | 48.359 | 3.398 | 1.00 | 17.02 |
| ATOM 2220 | SD | MET B | 86 | 17.292 | 49.027 | 5.033 | 1.00 | 17.02 |
| ATOM 2221 | CE | MET B | 86 | 16.822 | 47.490 | 5.839 | 1.00 | 17.02 |
| ATOM 2222 | H | MET B | 66 | 20.790 | 49.206 | 1.829 | 1.00 | 20.00 |
| ATOM 2223 | N | MET B | 87 | 22.106 | 47.685 | 4.984 | 1.00 | 29.14 |
| ATOM 2224 | CA | MET B | 87 | 23.124 | 46.665 | 5.254 | 1.00 | 29.14 |
| ATOM 2225 | C | MET B | 87 | 22.576 | 45.528 | 6.101 | 1.00 | 29.14 |
| ATOM 2226 | O | MET B | 87 | 23.172 | 45.001 | 7.030 | 1.00 | 29.14 |
| ATOM 2227 | CB | MET B | 87 | 24.400 | 47.267 | 5.842 | 1.00 | 29.14 |
| ATOM 2228 | CG | MET B | 87 | 25.607 | 46.391 | 5.494 | 1.00 | 29.14 |
| ATOM 2229 | SD | MET B | 87 | 27.129 | 46.891 | 6.297 | 1.00 | 29.14 |
| ATOM 2230 | CE | MET B | 87 | 28.207 | 45.591 | 5.675 | 1.00 | 29.14 |
| ATOM 2231 | H | MET B | 87 | 21.810 | 48.376 | 5.643 | 1.00 | 20.00 |
| ATOM 2232 | N | SER B | 88 | 21.339 | 45.198 | 5.734 | 1.00 | 17.75 |
| ATOM 2233 | CA | SER B | 88 | 20.592 | 44.258 | 6.536 | 1.00 | 17.75 |
| ATOM 2234 | C | SER B | 88 | 20.486 | 42.917 | 5.860 | 1.00 | 17.75 |
| ATOM 2235 | O | SER B | 88 | 19.424 | 42.337 | 5.695 | 1.00 | 17.75 |
| ATOM 2236 | CB | SER B | 88 | 19.238 | 44.871 | 6.792 | 1.00 | 17.75 |
| ATOM 2237 | OG | SER B | 88 | 18.465 | 44.031 | 7.649 | 1.00 | 17.75 |
| ATOM 2238 | H | SER B | 88 | 20.935 | 45.558 | 4.896 | 1.00 | 20.00 |
| ATOM 2239 | HG | SER B | 88 | 17.736 | 43.798 | 7.096 | 1.00 | 20.00 |
| ATOM 2240 | N | TYR B | 89 | 21.665 | 42.435 | 5.485 | 1.00 | 19.14 |
| ATOM 2241 | CA | TYR B | 89 | 21.703 | 41.012 | 5.173 | 1.00 | 19.14 |
| ATOM 2242 | C | TYR B | 89 | 21.602 | 40.211 | 6.475 | 1.00 | 19.14 |
| ATOM 2243 | O | TYR B | 89 | 21.140 | 40.714 | 7.494 | 1.00 | 19.14 |
| ATOM 2244 | CB | TYR B | 89 | 22.947 | 40.721 | 4.315 | 1.00 | 19.14 |
| ATOM 2245 | CG | TYR B | 89 | 24.188 | 41.226 | 5.014 | 1.00 | 19.14 |
| ATOM 2246 | CD1 | TYR B | 89 | 24.671 | 42.518 | 4.730 | 1.00 | 19.14 |
| ATOM 2247 | CD2 | TYR B | 89 | 24.810 | 40.393 | 5.961 | 1.00 | 19.14 |
| ATOM 2248 | CE1 | TYR B | 89 | 25.772 | 42.999 | 5.450 | 1.00 | 19.14 |
| ATOM 2249 | CE2 | TYR B | 89 | 25.911 | 40.871 | 6.681 | 1.00 | 19.14 |
| ATOM 2250 | CZ | TYR B | 89 | 26.371 | 42.175 | 6.421 | 1.00 | 19.14 |
| ATOM 2251 | OH | TYR B | 89 | 27.446 | 42.654 | 7.135 | 1.00 | 19.14 |
| ATOM 2252 | H | TYR B | 89 | 22.485 | 42.969 | 5.683 | 1.00 | 20.00 |
| ATOM 2253 | HH | TYR B | 89 | 28.032 | 41.918 | 7.308 | 1.00 | 20.00 |
| ATOM 2254 | N | CYS B | 90 | 22.037 | 38.951 | 6.428 | 1.00 | 32.37 |
| ATOM 2255 | CA | CYS B | 90 | 21.963 | 38.207 | 7.684 | 1.00 | 32.37 |
| ATOM 2256 | C | CYS B | 90 | 23.314 | 37.701 | 8.156 | 1.00 | 32.37 |
| ATOM 2257 | O | CYS B | 90 | 24.354 | 38.064 | 7.627 | 1.00 | 32.37 |
| ATOM 2258 | CB | CYS B | 90 | 20.929 | 37.094 | 7.529 | 1.00 | 32.37 |
| ATOM 2259 | SG | CYS B | 90 | 21.007 | 36.374 | 5.881 | 1.00 | 32.37 |
| ATOM 2260 | H | CYS B | 90 | 22.397 | 38.527 | 5.596 | 1.00 | 20.00 |
| ATOM 2261 | N | THR B | 91 | 23.252 | 36.832 | 9.169 | 1.00 | 22.92 |
| ATOM 2262 | CA | THR B | 91 | 24.448 | 36.119 | 9.606 | 1.00 | 22.92 |
| ATOM 2263 | C | THR B | 91 | 24.228 | 34.649 | 9.285 | 1.00 | 22.92 |
| ATOM 2264 | O | THR B | 91 | 23.484 | 34.344 | 8.367 | 1.00 | 22.92 |
| ATOM 2265 | CB | THR B | 91 | 24.589 | 36.380 | 11.100 | 1.00 | 22.92 |
| ATOM 2266 | OG1 | THR B | 91 | 23.331 | 36.129 | 11.739 | 1.00 | 22.92 |
| ATOM 2267 | CG2 | THR B | 91 | 25.033 | 37.819 | 11.377 | 1.00 | 22.92 |
| ATOM 2268 | H | THR B | 91 | 22.403 | 36.564 | 9.621 | 1.00 | 20.00 |
| ATOM 2269 | HG1 | THR B | 91 | 23.509 | 36.058 | 12.668 | 1.00 | 20.00 |
| ATOM 2270 | N | THR B | 92 | 24.817 | 33.729 | 10.071 | 1.00 | 5.61 |
| ATOM 2271 | CA | THR B | 92 | 24.376 | 32.342 | 9.901 | 1.00 | 5.61 |
| ATOM 2272 | C | THR B | 92 | 22.875 | 32.158 | 10.014 | 1.00 | 5.61 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 2273 | O | THR B | 92 | 22.265 | 32.381 | 11.054 | 1.00 | 5.61 |
| ATOM 2274 | CB | THR B | 92 | 25.085 | 31.451 | 10.912 | 1.00 | 5.61 |
| ATOM 2275 | OG1 | THR B | 92 | 26.466 | 31.817 | 10.966 | 1.00 | 5.61 |
| ATOM 2276 | CG2 | THR B | 92 | 24.920 | 29.959 | 10.601 | 1.00 | 5.61 |
| ATOM 2277 | H | THR B | 92 | 25.535 | 33.916 | 10.738 | 1.00 | 20.00 |
| ATOM 2278 | HG1 | THR B | 92 | 26.892 | 31.160 | 11.501 | 1.00 | 20.00 |
| ATOM 2279 | N | GLY B | 93 | 22.314 | 31.756 | 8.877 | 1.00 | 3.78 |
| ATOM 2280 | CA | GLY B | 93 | 20.879 | 31.663 | 8.914 | 1.00 | 3.78 |
| ATOM 2281 | C | GLY B | 93 | 20.378 | 31.121 | 7.625 | 1.00 | 3.78 |
| ATOM 2282 | O | GLY B | 93 | 21.093 | 30.841 | 6.666 | 1.00 | 3.78 |
| ATOM 2283 | H | GLY B | 93 | 22.789 | 31.646 | 8.003 | 1.00 | 20.00 |
| ATOM 2284 | N | GLN B | 94 | 19.062 | 31.003 | 7.674 | 1.00 | 15.42 |
| ATOM 2285 | CA | GLN B | 94 | 18.408 | 30.650 | 6.454 | 1.00 | 15.42 |
| ATOM 2286 | C | GLN B | 94 | 18.502 | 31.773 | 5.453 | 1.00 | 15.42 |
| ATOM 2287 | O | GLN B | 94 | 19.242 | 32.743 | 5.553 | 1.00 | 15.42 |
| ATOM 2288 | CB | GLN B | 94 | 16.980 | 30.303 | 6.857 | 1.00 | 15.42 |
| ATOM 2289 | CG | GLN B | 94 | 16.940 | 28.953 | 7.556 | 1.00 | 15.42 |
| ATOM 2290 | CD | GLN B | 94 | 17.358 | 27.874 | 6.577 | 1.00 | 15.42 |
| ATOM 2291 | OE1 | GLN B | 94 | 18.301 | 27.136 | 6.819 | 1.00 | 15.42 |
| ATOM 2292 | NE2 | GLN B | 94 | 16.573 | 27.723 | 5.504 | 1.00 | 15.42 |
| ATOM 2293 | H | GLN B | 94 | 18.504 | 31.364 | 8.418 | 1.00 | 20.00 |
| ATOM 2294 | 1HE2 | GLN B | 94 | 15.682 | 28.163 | 5.350 | 1.00 | 20.00 |
| ATOM 2295 | 2HE2 | GLN B | 94 | 16.926 | 27.114 | 4.795 | 1.00 | 20.00 |
| ATOM 2296 | N | MET B | 95 | 17.640 | 31.566 | 4.484 | 1.00 | 18.74 |
| ATOM 2297 | CA | MET B | 95 | 17.266 | 32.637 | 3.570 | 1.00 | 18.74 |
| ATOM 2298 | C | MET B | 95 | 16.755 | 33.926 | 4.243 | 1.00 | 18.74 |
| ATOM 2299 | O | MET B | 95 | 16.209 | 33.910 | 5.341 | 1.00 | 18.74 |
| ATOM 2300 | CB | MET B | 95 | 16.186 | 32.044 | 2.692 | 1.00 | 18.74 |
| ATOM 2301 | CG | MET B | 95 | 15.061 | 31.664 | 3.652 | 1.00 | 18.74 |
| ATOM 2302 | SD | MET B | 95 | 13.472 | 31.178 | 3.039 | 1.00 | 18.74 |
| ATOM 2303 | CE | MET B | 95 | 12.867 | 30.943 | 4.699 | 1.00 | 18.74 |
| ATOM 2304 | H | MET B | 95 | 17.203 | 30.670 | 4.513 | 1.00 | 20.00 |
| ATOM 2305 | N | TRP B | 96 | 16.917 | 35.037 | 3.505 | 1.00 | 3.87 |
| ATOM 2306 | CA | TRP B | 96 | 16.528 | 36.338 | 4.053 | 1.00 | 3.87 |
| ATOM 2307 | C | TRP B | 96 | 15.869 | 37.182 | 2.987 | 1.00 | 3.87 |
| ATOM 2308 | O | TRP B | 96 | 16.243 | 37.094 | 1.825 | 1.00 | 3.87 |
| ATOM 2309 | CB | TRP B | 96 | 17.755 | 37.069 | 4.628 | 1.00 | 3.87 |
| ATOM 2310 | CG | TRP B | 96 | 18.818 | 37.286 | 3.565 | 1.00 | 3.87 |
| ATOM 2311 | CD1 | TRP B | 96 | 19.818 | 36.382 | 3.175 | 1.00 | 3.87 |
| ATOM 2312 | CD2 | TRP B | 96 | 19.025 | 38.445 | 2.730 | 1.00 | 3.87 |
| ATOM 2313 | NE1 | TRP B | 96 | 20.603 | 36.890 | 2.191 | 1.00 | 3.87 |
| ATOM 2314 | CE2 | TRP B | 96 | 20.146 | 38.165 | 1.876 | 1.00 | 3.87 |
| ATOM 2315 | CE3 | TRP B | 96 | 18.353 | 39.680 | 2.622 | 1.00 | 3.87 |
| ATOM 2316 | CZ2 | TRP B | 96 | 20.572 | 39.129 | 0.936 | 1.00 | 3.87 |
| ATOM 2317 | CZ3 | TRP B | 96 | 18.787 | 40.632 | 1.678 | 1.00 | 3.87 |
| ATOM 2318 | CH2 | TRP B | 96 | 19.888 | 40.358 | 0.839 | 1.00 | 3.87 |
| ATOM 2319 | H | TRP B | 96 | 17.365 | 34.971 | 2.607 | 1.00 | 20.00 |
| ATOM 2320 | HE1 | TRP B | 96 | 21.371 | 36.419 | 1.795 | 1.00 | 20.00 |
| ATOM 2321 | N | ALA B | 97 | 14.896 | 38.001 | 3.426 | 1.00 | 3.76 |
| ATOM 2322 | CA | ALA B | 97 | 14.310 | 38.918 | 2.450 | 1.00 | 3.76 |
| ATOM 2323 | C | ALA B | 97 | 14.183 | 40.311 | 3.025 | 1.00 | 3.76 |
| ATOM 2324 | O | ALA B | 97 | 13.706 | 40.486 | 4.142 | 1.00 | 3.76 |
| ATOM 2325 | CB | ALA B | 97 | 12.934 | 38.430 | 1.992 | 1.00 | 3.76 |
| ATOM 2326 | H | ALA B | 97 | 14.582 | 38.005 | 4.367 | 1.00 | 20.00 |
| ATOM 2327 | N | ARG B | 98 | 14.669 | 41.280 | 2.227 | 1.00 | 11.69 |
| ATOM 2328 | CA | ARG B | 98 | 14.570 | 42.677 | 2.651 | 1.00 | 11.69 |
| ATOM 2329 | C | ARG B | 98 | 13.868 | 43.511 | 1.612 | 1.00 | 11.69 |
| ATOM 2330 | O | ARG B | 98 | 14.072 | 43.340 | 0.417 | 1.00 | 11.69 |
| ATOM 2331 | CB | ARG B | 98 | 15.934 | 43.328 | 2.909 | 1.00 | 11.69 |
| ATOM 2332 | CG | ARG B | 98 | 16.838 | 42.551 | 3.856 | 1.00 | 11.69 |
| ATOM 2333 | CD | ARG B | 98 | 16.184 | 42.240 | 5.193 | 1.00 | 11.69 |
| ATOM 2334 | NE | ARG B | 98 | 17.015 | 41.329 | 5.974 | 1.00 | 11.69 |
| ATOM 2335 | CZ | ARG B | 98 | 17.025 | 41.432 | 7.306 | 1.00 | 11.69 |
| ATOM 2336 | NH1 | ARG B | 98 | 17.686 | 40.563 | 8.065 | 1.00 | 11.69 |
| ATOM 2337 | NH2 | ARG B | 98 | 16.333 | 42.411 | 7.860 | 1.00 | 11.69 |
| ATOM 2338 | H | ARG B | 98 | 15.016 | 41.031 | 1.318 | 1.00 | 20.00 |
| ATOM 2339 | HE | ARG B | 98 | 17.602 | 40.669 | 5.504 | 1.00 | 20.00 |
| ATOM 2340 | 1HH1 | ARG B | 98 | 17.606 | 40.574 | 9.062 | 1.00 | 20.00 |
| ATOM 2341 | 2HH1 | ARG B | 98 | 18.279 | 39.876 | 7.646 | 1.00 | 20.00 |
| ATOM 2342 | 1HH2 | ARG B | 98 | 16.182 | 42.387 | 8.852 | 1.00 | 20.00 |
| ATOM 2343 | 2HH2 | ARG B | 98 | 15.871 | 43.113 | 7.323 | 1.00 | 20.00 |
| ATOM 2344 | N | SER B | 99 | 13.044 | 44.436 | 2.114 | 1.00 | 7.28 |
| ATOM 2345 | CA | SER B | 99 | 12.448 | 45.344 | 1.148 | 1.00 | 7.28 |
| ATOM 2346 | C | SER B | 99 | 12.868 | 46.786 | 1.316 | 1.00 | 7.28 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 2347 | O | SER B | 99 | 12.959 | 47.316 | 2.417 | 1.00 | 7.28 |
| ATOM 2348 | CB | SER B | 99 | 10.932 | 45.207 | 1.188 | 1.00 | 7.28 |
| ATOM 2349 | OG | SER B | 99 | 10.412 | 45.436 | 2.502 | 1.00 | 7.28 |
| ATOM 2350 | H | SER B | 99 | 12.817 | 44.523 | 3.083 | 1.00 | 20.00 |
| ATOM 2351 | HG | SER B | 99 | 9.663 | 44.864 | 2.611 | 1.00 | 20.00 |
| ATOM 2352 | N | SER B | 100 | 13.086 | 47.407 | 0.151 | 1.00 | 2.73 |
| ATOM 2353 | CA | SER B | 100 | 13.319 | 48.845 | 0.182 | 1.00 | 2.73 |
| ATOM 2354 | C | SER B | 100 | 12.271 | 49.572 | −0.634 | 1.00 | 2.73 |
| ATOM 2355 | O | SER B | 100 | 12.017 | 49.224 | −1.778 | 1.00 | 2.73 |
| ATOM 2356 | CB | SER B | 100 | 14.726 | 49.165 | −0.330 | 1.00 | 2.73 |
| ATOM 2357 | OG | SER B | 100 | 15.704 | 48.535 | 0.504 | 1.00 | 2.73 |
| ATOM 2358 | H | SER B | 100 | 13.030 | 46.908 | −0.719 | 1.00 | 20.00 |
| ATOM 2359 | HG | SER B | 100 | 16.521 | 48.545 | 0.018 | 1.00 | 20.00 |
| ATOM 2360 | N | TYR B | 101 | 11.668 | 50.588 | 0.010 | 1.00 | 2.72 |
| ATOM 2361 | CA | TYR B | 101 | 10.661 | 51.388 | −0.699 | 1.00 | 2.72 |
| ATOM 2362 | C | TYR B | 101 | 11.006 | 52.854 | −0.634 | 1.00 | 2.72 |
| ATOM 2363 | O | TYR B | 101 | 11.325 | 53.348 | 0.434 | 1.00 | 2.72 |
| ATOM 2364 | CB | TYR B | 101 | 9.273 | 51.194 | −0.078 | 1.00 | 2.72 |
| ATOM 2365 | CG | TYR B | 101 | 8.242 | 52.053 | −0.781 | 1.00 | 2.72 |
| ATOM 2366 | CD1 | TYR B | 101 | 7.624 | 51.594 | −1.962 | 1.00 | 2.72 |
| ATOM 2367 | CD2 | TYR B | 101 | 7.944 | 53.315 | −0.235 | 1.00 | 2.72 |
| ATOM 2368 | CE1 | TYR B | 101 | 6.680 | 52.411 | −2.606 | 1.00 | 2.72 |
| ATOM 2369 | CE2 | TYR B | 101 | 7.015 | 54.137 | −0.885 | 1.00 | 2.72 |
| ATOM 2370 | CZ | TYR B | 101 | 6.372 | 53.666 | −2.044 | 1.00 | 2.72 |
| ATOM 2371 | OH | TYR B | 101 | 5.402 | 54.459 | −2.622 | 1.00 | 2.72 |
| ATOM 2372 | H | TYR B | 101 | 11.914 | 50.791 | 0.957 | 1.00 | 20.00 |
| ATOM 2373 | HH | TYR B | 101 | 5.286 | 55.245 | −2.107 | 1.00 | 20.00 |
| ATOM 2374 | N | LEU B | 102 | 10.935 | 53.525 | −1.781 | 1.00 | 17.88 |
| ATOM 2375 | CA | LEU B | 102 | 11.286 | 54.940 | −1.857 | 1.00 | 17.88 |
| ATOM 2376 | C | LEU B | 102 | 10.100 | 55.696 | −2.431 | 1.00 | 17.88 |
| ATOM 2377 | O | LEU B | 102 | 9.326 | 55.127 | −3.192 | 1.00 | 17.88 |
| ATOM 2378 | CB | LEU B | 102 | 12.530 | 55.098 | −2.745 | 1.00 | 17.88 |
| ATOM 2379 | CG | LEU B | 102 | 13.902 | 54.915 | −2.066 | 1.00 | 17.88 |
| ATOM 2380 | CD1 | LEU B | 102 | 14.099 | 55.948 | −0.964 | 1.00 | 17.88 |
| ATOM 2381 | CD2 | LEU B | 102 | 14.212 | 53.502 | −1.564 | 1.00 | 17.88 |
| ATOM 2382 | H | LEU B | 102 | 10.530 | 53.077 | −2.578 | 1.00 | 20.00 |
| ATOM 2383 | N | GLY B | 103 | 9.968 | 56.973 | −2.035 | 1.00 | 5.34 |
| ATOM 2384 | CA | GLY B | 103 | 8.821 | 57.714 | −2.565 | 1.00 | 5.34 |
| ATOM 2385 | C | GLY B | 103 | 8.775 | 59.160 | −2.114 | 1.00 | 5.34 |
| ATOM 2386 | O | GLY B | 103 | 8.857 | 59.429 | −0.923 | 1.00 | 5.34 |
| ATOM 2387 | H | GLY B | 103 | 10.609 | 57.423 | −1.413 | 1.00 | 20.00 |
| ATOM 2388 | N | ALA B | 104 | 8.653 | 60.074 | −3.102 | 1.00 | 6.66 |
| ATOM 2389 | CA | ALA B | 104 | 8.624 | 61.499 | −2.757 | 1.00 | 6.66 |
| ATOM 2390 | C | ALA B | 104 | 8.185 | 62.405 | −3.899 | 1.00 | 6.66 |
| ATOM 2391 | O | ALA B | 104 | 8.047 | 61.959 | −5.031 | 1.00 | 6.66 |
| ATOM 2392 | CB | ALA B | 104 | 9.999 | 61.951 | −2.285 | 1.00 | 6.66 |
| ATOM 2393 | H | ALA B | 104 | 8.612 | 59.782 | −4.062 | 1.00 | 20.00 |
| ATOM 2394 | N | VAL B | 105 | 7.958 | 63.691 | −3.550 | 1.00 | 2.80 |
| ATOM 2395 | CA | VAL B | 105 | 7.496 | 64.636 | −4.573 | 1.00 | 2.80 |
| ATOM 2396 | C | VAL B | 105 | 8.557 | 65.607 | −5.040 | 1.00 | 2.80 |
| ATOM 2397 | O | VAL B | 105 | 9.264 | 66.228 | −4.257 | 1.00 | 2.80 |
| ATOM 2398 | CB | VAL B | 105 | 6.268 | 65.403 | −4.079 | 1.00 | 2.80 |
| ATOM 2399 | CG1 | VAL B | 105 | 5.733 | 66.430 | −5.074 | 1.00 | 2.80 |
| ATOM 2400 | CG2 | VAL B | 105 | 5.180 | 64.402 | −3.756 | 1.00 | 2.80 |
| ATOM 2401 | H | VAL B | 105 | 8.094 | 64.027 | −2.616 | 1.00 | 20.00 |
| ATOM 2402 | N | PHE B | 106 | 8.619 | 65.708 | −6.376 | 1.00 | 2.81 |
| ATOM 2403 | CA | PHE B | 106 | 9.664 | 66.528 | −6.978 | 1.00 | 2.81 |
| ATOM 2404 | C | PHE B | 106 | 9.114 | 67.358 | −8.136 | 1.00 | 2.81 |
| ATOM 2405 | O | PHE B | 106 | 8.123 | 66.974 | −8.743 | 1.00 | 2.81 |
| ATOM 2406 | CB | PHE B | 106 | 10.802 | 65.593 | −7.415 | 1.00 | 2.81 |
| ATOM 2407 | CG | PHE B | 106 | 11.413 | 64.847 | −6.236 | 1.00 | 2.81 |
| ATOM 2408 | CD1 | PHE B | 106 | 11.117 | 63.482 | −6.026 | 1.00 | 2.81 |
| ATOM 2409 | CD2 | PHE B | 106 | 12.302 | 65.518 | −5.373 | 1.00 | 2.81 |
| ATOM 2410 | CE1 | PHE B | 106 | 11.778 | 62.779 | −4.999 | 1.00 | 2.81 |
| ATOM 2411 | CE2 | PHE B | 106 | 12.964 | 64.828 | −4.342 | 1.00 | 2.81 |
| ATOM 2412 | CZ | PHE B | 106 | 12.714 | 63.452 | −4.185 | 1.00 | 2.81 |
| ATOM 2413 | H | PHE B | 106 | 7.979 | 65.181 | −6.943 | 1.00 | 20.00 |
| ATOM 2414 | N | ASN B | 107 | 9.767 | 68.507 | −8.431 | 1.00 | 6.84 |
| ATOM 2415 | CA | ASN B | 107 | 9.373 | 69.186 | −9.678 | 1.00 | 6.84 |
| ATOM 2416 | C | ASN B | 107 | 10.243 | 68.732 | −10.805 | 1.00 | 6.84 |
| ATOM 2417 | O | ASN B | 107 | 11.443 | 68.979 | −10.825 | 1.00 | 6.84 |
| ATOM 2418 | CB | ASN B | 107 | 9.530 | 70.708 | −9.733 | 1.00 | 6.84 |
| ATOM 2419 | CG | ASN B | 107 | 8.548 | 71.417 | −8.851 | 1.00 | 6.84 |
| ATOM 2420 | OD1 | ASN B | 107 | 7.503 | 71.922 | −9.232 | 1.00 | 6.84 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 2421 | ND2 | ASN B | 107 | 8.985 | 71.454 | −7.612 | 1.00 | 6.84 |
| ATOM 2422 | H | ASN B | 107 | 10.618 | 68.734 | −7.963 | 1.00 | 20.00 |
| ATOM 2423 | 1HD2 | ASN B | 107 | 9.849 | 71.011 | −7.373 | 1.00 | 20.00 |
| ATOM 2424 | 2HD2 | ASN B | 107 | 8.455 | 71.916 | −6.904 | 1.00 | 20.00 |
| ATOM 2425 | N | LEU B | 108 | 9.577 | 68.073 | −11.744 | 1.00 | 5.08 |
| ATOM 2426 | CA | LEU B | 108 | 10.346 | 67.725 | −12.925 | 1.00 | 5.08 |
| ATOM 2427 | C | LEU B | 108 | 10.047 | 68.671 | −14.065 | 1.00 | 5.08 |
| ATOM 2428 | O | LEU B | 108 | 9.103 | 69.459 | −14.019 | 1.00 | 5.08 |
| ATOM 2429 | CB | LEU B | 108 | 10.108 | 66.257 | −13.267 | 1.00 | 5.08 |
| ATOM 2430 | CG | LEU B | 108 | 10.498 | 65.352 | −12.092 | 1.00 | 5.08 |
| ATOM 2431 | CD1 | LEU B | 108 | 9.994 | 63.925 | −12.266 | 1.00 | 5.08 |
| ATOM 2432 | CD2 | LEU B | 108 | 11.998 | 65.394 | −11.801 | 1.00 | 5.08 |
| ATOM 2433 | H | LEU B | 108 | 8.582 | 67.966 | −11.683 | 1.00 | 20.00 |
| ATOM 2434 | N | THR B | 109 | 10.917 | 68.562 | −15.072 | 1.00 | 3.97 |
| ATOM 2435 | CA | THR B | 109 | 10.774 | 69.430 | −16.233 | 1.00 | 3.97 |
| ATOM 2436 | C | THR B | 109 | 10.626 | 68.516 | −17.434 | 1.00 | 3.97 |
| ATOM 2437 | O | THR B | 109 | 10.912 | 67.332 | −17.352 | 1.00 | 3.97 |
| ATOM 2438 | CB | THR B | 109 | 12.026 | 70.323 | −16.345 | 1.00 | 3.97 |
| ATOM 2439 | OG1 | THR B | 109 | 12.366 | 70.880 | −15.068 | 1.00 | 3.97 |
| ATOM 2440 | CG2 | THR B | 109 | 11.893 | 71.460 | −17.365 | 1.00 | 3.97 |
| ATOM 2441 | H | THR B | 109 | 11.587 | 67.813 | −15.111 | 1.00 | 20.00 |
| ATOM 2442 | HG1 | THR B | 109 | 13.135 | 71.406 | −15.223 | 1.00 | 20.00 |
| ATOM 2443 | N | SER B | 110 | 10.201 | 69.070 | −18.575 | 1.00 | 5.78 |
| ATOM 2444 | CA | SER B | 110 | 10.374 | 68.239 | −19.764 | 1.00 | 5.78 |
| ATOM 2445 | C | SER B | 110 | 11.829 | 67.856 | −20.030 | 1.00 | 5.78 |
| ATOM 2446 | O | SER B | 110 | 12.747 | 68.622 | −19.753 | 1.00 | 5.78 |
| ATOM 2447 | CB | SER B | 110 | 9.770 | 68.967 | −20.960 | 1.00 | 5.78 |
| ATOM 2448 | OG | SER B | 110 | 8.459 | 69.426 | −20.608 | 1.00 | 5.78 |
| ATOM 2449 | H | SER B | 110 | 9.827 | 69.994 | −18.648 | 1.00 | 20.00 |
| ATOM 2450 | HG | SER B | 110 | 7.853 | 68.778 | −20.963 | 1.00 | 20.00 |
| ATOM 2451 | N | ALA B | 111 | 11.965 | 66.634 | −20.583 | 1.00 | 23.23 |
| ATOM 2452 | CA | ALA B | 111 | 13.211 | 66.062 | −21.107 | 1.00 | 23.23 |
| ATOM 2453 | C | ALA B | 111 | 14.150 | 65.377 | −20.133 | 1.00 | 23.23 |
| ATOM 2454 | O | ALA B | 111 | 15.034 | 64.639 | −20.556 | 1.00 | 23.23 |
| ATOM 2455 | CB | ALA B | 111 | 14.027 | 67.046 | −21.962 | 1.00 | 23.23 |
| ATOM 2456 | H | ALA B | 111 | 11.149 | 66.052 | −20.558 | 1.00 | 20.00 |
| ATOM 2457 | N | ASP B | 112 | 13.951 | 65.624 | −18.827 | 1.00 | 12.39 |
| ATOM 2458 | CA | ASP B | 112 | 14.887 | 64.918 | −17.960 | 1.00 | 12.39 |
| ATOM 2459 | C | ASP B | 112 | 14.602 | 63.441 | −17.774 | 1.00 | 12.39 |
| ATOM 2460 | O | ASP B | 112 | 13.496 | 62.963 | −18.011 | 1.00 | 12.39 |
| ATOM 2461 | CB | ASP B | 112 | 15.137 | 65.687 | −16.659 | 1.00 | 12.39 |
| ATOM 2462 | CG | ASP B | 112 | 14.027 | 65.684 | −15.626 | 1.00 | 12.39 |
| ATOM 2463 | OD1 | ASP B | 112 | 14.336 | 65.452 | −14.461 | 1.00 | 12.39 |
| ATOM 2464 | OD2 | ASP B | 112 | 12.883 | 65.956 | −15.963 | 1.00 | 12.39 |
| ATOM 2465 | H | ASP B | 112 | 13.204 | 66.161 | −18.428 | 1.00 | 20.00 |
| ATOM 2466 | N | HIS B | 113 | 15.683 | 62.734 | −17.404 | 1.00 | 16.60 |
| ATOM 2467 | CA | HIS B | 113 | 15.525 | 61.297 | −17.207 | 1.00 | 16.60 |
| ATOM 2468 | C | HIS B | 113 | 15.572 | 60.926 | −15.745 | 1.00 | 16.60 |
| ATOM 2469 | O | HIS B | 113 | 16.376 | 61.456 | −14.990 | 1.00 | 16.60 |
| ATOM 2470 | CB | HIS B | 113 | 16.626 | 60.489 | −17.893 | 1.00 | 16.60 |
| ATOM 2471 | CG | HIS B | 113 | 16.587 | 60.556 | −19.400 | 1.00 | 16.60 |
| ATOM 2472 | ND1 | HIS B | 113 | 17.096 | 61.577 | −20.109 | 1.00 | 16.60 |
| ATOM 2473 | CD2 | HIS B | 113 | 16.085 | 59.597 | −20.285 | 1.00 | 16.60 |
| ATOM 2474 | CE1 | HIS B | 113 | 16.924 | 61.276 | −21.433 | 1.00 | 16.60 |
| ATOM 2475 | NE2 | HIS B | 113 | 16.305 | 60.058 | −21.544 | 1.00 | 16.60 |
| ATOM 2476 | H | HIS B | 113 | 16.534 | 63.209 | −17.164 | 1.00 | 20.00 |
| ATOM 2477 | HD1 | HIS B | 113 | 17.498 | 62.393 | −19.744 | 1.00 | 20.00 |
| ATOM 2478 | N | LEU B | 114 | 14.723 | 59.954 | −15.388 | 1.00 | 5.46 |
| ATOM 2479 | CA | LEU B | 114 | 14.929 | 59.347 | −14.074 | 1.00 | 5.46 |
| ATOM 2480 | C | LEU B | 114 | 15.405 | 57.916 | −14.205 | 1.00 | 5.46 |
| ATOM 2481 | O | LEU B | 114 | 15.000 | 57.205 | −15.118 | 1.00 | 5.46 |
| ATOM 2482 | CB | LEU B | 114 | 13.670 | 59.370 | −13.203 | 1.00 | 5.46 |
| ATOM 2483 | CG | LEU B | 114 | 12.970 | 60.720 | −13.022 | 1.00 | 5.46 |
| ATOM 2484 | CD1 | LEU B | 114 | 11.903 | 60.623 | −11.942 | 1.00 | 5.46 |
| ATOM 2485 | CD2 | LEU B | 114 | 13.906 | 61.882 | −12.721 | 1.00 | 5.46 |
| ATOM 2586 | H | LEU B | 114 | 14.055 | 59.615 | −16.054 | 1.00 | 20.00 |
| ATOM 2487 | N | TYR B | 115 | 16.285 | 57.535 | −13.264 | 1.00 | 8.89 |
| ATOM 2488 | CA | TYR B | 115 | 16.799 | 56.162 | −13.264 | 1.00 | 8.89 |
| ATOM 2489 | C | TYR B | 115 | 16.701 | 55.548 | −11.893 | 1.00 | 8.89 |
| ATOM 2490 | O | TYR B | 115 | 16.762 | 56.244 | −10.890 | 1.00 | 8.89 |
| ATOM 2491 | CB | TYR B | 115 | 18.265 | 56.090 | −13.693 | 1.00 | 8.89 |
| ATOM 2492 | CG | TYR B | 115 | 18.430 | 56.555 | −15.116 | 1.00 | 8.89 |
| ATOM 2493 | CD1 | TYR B | 115 | 18.156 | 55.658 | −16.169 | 1.00 | 8.89 |
| ATOM 2494 | CD2 | TYR B | 115 | 18.853 | 57.878 | −15.346 | 1.00 | 8.89 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 2495 | CE1 | TYR B | 115 | 18.283 | 56.109 | −17.493 | 1.00 | 8.89 |
| ATOM 2496 | CE2 | TYR B | 115 | 18.980 | 58.325 | −16.668 | 1.00 | 8.89 |
| ATOM 2497 | CZ | TYR B | 115 | 18.674 | 57.443 | −17.724 | 1.00 | 8.89 |
| ATOM 2498 | OH | TYR B | 115 | 18.748 | 57.906 | −19.023 | 1.00 | 8.89 |
| ATOM 2499 | H | TYR B | 115 | 16.565 | 58.190 | −12.555 | 1.00 | 20.00 |
| ATOM 2500 | HH | TYR B | 115 | 18.874 | 58.845 | −19.007 | 1.00 | 20.00 |
| ATOM 2501 | N | VAL B | 116 | 16.532 | 54.216 | −11.885 | 1.00 | 5.15 |
| ATOM 2502 | CA | VAL B | 116 | 16.391 | 53.542 | −10.595 | 1.00 | 5.15 |
| ATOM 2503 | C | VAL B | 116 | 17.197 | 52.266 | −10.542 | 1.00 | 5.15 |
| ATOM 2504 | O | VAL B | 116 | 16.810 | 51.248 | −11.102 | 1.00 | 5.15 |
| ATOM 2505 | CB | VAL B | 116 | 14.918 | 53.250 | −10.302 | 1.00 | 5.15 |
| ATOM 2506 | CG1 | VAL B | 116 | 14.721 | 52.473 | −9.013 | 1.00 | 5.15 |
| ATOM 2507 | CG2 | VAL B | 116 | 14.139 | 54.543 | −10.200 | 1.00 | 5.15 |
| ATOM 2508 | H | VAL B | 116 | 16.478 | 53.701 | −12.740 | 1.00 | 20.00 |
| ATOM 2509 | N | ASN B | 117 | 18.333 | 52.372 | −9.843 | 1.00 | 8.77 |
| ATOM 2510 | CA | ASN B | 117 | 19.167 | 51.174 | −9.830 | 1.00 | 8.77 |
| ATOM 2511 | C | ASN B | 117 | 19.399 | 50.633 | −8.436 | 1.00 | 8.77 |
| ATOM 2512 | O | ASN B | 117 | 19.350 | 51.348 | −7.439 | 1.00 | 8.77 |
| ATOM 2513 | CB | ASN B | 117 | 20.500 | 51.404 | −10.555 | 1.00 | 8.77 |
| ATOM 2514 | CG | ASN B | 117 | 20.279 | 51.688 | −12.032 | 1.00 | 8.77 |
| ATOM 2515 | OD1 | ASN B | 117 | 19.378 | 51.179 | −12.681 | 1.00 | 8.77 |
| ATOM 2516 | ND2 | ASN B | 117 | 21.150 | 52.562 | −12.547 | 1.00 | 8.77 |
| ATOM 2517 | H | ASN B | 117 | 18.541 | 53.196 | −9.308 | 1.00 | 20.00 |
| ATOM 2518 | 1 HD2 | ASN B | 117 | 21.897 | 52.941 | −12.005 | 1.00 | 20.00 |
| ATOM 2519 | 2 HD2 | ASN B | 117 | 21.029 | 52.817 | −13.504 | 1.00 | 20.00 |
| ATOM 2520 | N | VAL B | 118 | 19.655 | 49.315 | −8.438 | 1.00 | 2.80 |
| ATOM 2521 | CA | VAL B | 118 | 20.075 | 48.618 | −7.224 | 1.00 | 2.80 |
| ATOM 2522 | C | VAL B | 118 | 21.538 | 48.250 | −7.381 | 1.00 | 2.80 |
| ATOM 2523 | O | VAL B | 118 | 21.997 | 48.046 | −8.497 | 1.00 | 2.80 |
| ATOM 2524 | CG1 | VAL B | 118 | 19.216 | 47.353 | −7.046 | 1.00 | 2.80 |
| ATOM 2525 | CG1 | VAL B | 118 | 19.631 | 46.461 | −5.874 | 1.00 | 2.80 |
| ATOM 2526 | CG2 | VAL B | 118 | 17.739 | 47.713 | −6.963 | 1.00 | 2.80 |
| ATOM 2527 | H | VAL B | 118 | 19.690 | 48.821 | −9.306 | 1.00 | 20.00 |
| ATOM 2528 | N | SER B | 119 | 22.244 | 48.163 | −6.241 | 1.00 | 3.07 |
| ATOM 2529 | CA | SER B | 119 | 23.620 | 47.667 | −6.305 | 1.00 | 3.07 |
| ATOM 2530 | C | SER B | 119 | 23.792 | 46.253 | −6.866 | 1.00 | 3.07 |
| ATOM 2531 | O | SER B | 119 | 24.505 | 46.037 | −7.838 | 1.00 | 3.07 |
| ATOM 2532 | CB | SER B | 119 | 24.264 | 47.836 | −4.928 | 1.00 | 3.07 |
| ATOM 2533 | OG | SER B | 119 | 23.390 | 47.315 | −3.918 | 1.00 | 3.07 |
| ATOM 2534 | H | SER B | 119 | 21.832 | 48.402 | −5.357 | 1.00 | 20.00 |
| ATOM 2535 | HG | SER B | 119 | 23.856 | 46.543 | −3.572 | 1.00 | 20.00 |
| ATOM 2536 | N | GLU B | 120 | 23.090 | 45.294 | −6.235 | 1.00 | 12.56 |
| ATOM 2537 | CA | GLU B | 120 | 23.241 | 43.924 | −6.733 | 1.00 | 12.56 |
| ATOM 2538 | C | GLU B | 120 | 21.951 | 43.320 | −7.233 | 1.00 | 12.56 |
| ATOM 2539 | O | GLU B | 120 | 21.020 | 43.039 | −6.489 | 1.00 | 12.56 |
| ATOM 2540 | CB | GLU B | 120 | 23.834 | 42.961 | −5.695 | 1.00 | 12.56 |
| ATOM 2541 | CG | GLU B | 120 | 25.244 | 43.250 | −5.162 | 1.00 | 12.56 |
| ATOM 2542 | CD | GLU B | 120 | 25.277 | 44.479 | −4.271 | 1.00 | 12.56 |
| ATOM 2543 | OE1 | GLU B | 120 | 24.290 | 44.756 | −3.591 | 1.00 | 12.56 |
| ATOM 2544 | OE2 | GLU B | 120 | 26.294 | 45.168 | −4.272 | 1.00 | 12.56 |
| ATOM 2545 | H | GLU B | 120 | 22.593 | 45.503 | −5.392 | 1.00 | 20.00 |
| ATOM 2546 | N | LEU B | 121 | 21.931 | 43.090 | −8.549 | 1.00 | 16.20 |
| ATOM 2547 | CA | LEU B | 121 | 20.674 | 42.546 | −9.053 | 1.00 | 16.20 |
| ATOM 2548 | C | LEU B | 121 | 20.477 | 41.055 | −8.837 | 1.00 | 16.20 |
| ATOM 2549 | O | LEU B | 121 | 19.372 | 40.533 | −8.905 | 1.00 | 16.20 |
| ATOM 2550 | CB | LEU B | 121 | 20.391 | 43.005 | −10.486 | 1.00 | 16.20 |
| ATOM 2551 | CG | LEU B | 121 | 20.038 | 44.497 | −10.587 | 1.00 | 16.20 |
| ATOM 2552 | CD1 | LEU B | 121 | 19.002 | 44.883 | −9.542 | 1.00 | 16.20 |
| ATOM 2553 | CD2 | LEU B | 121 | 21.227 | 45.458 | −10.542 | 1.00 | 16.20 |
| ATOM 2554 | H | LEU B | 121 | 22.699 | 43.329 | −9.143 | 1.00 | 20.00 |
| ATOM 2555 | N | SER B | 122 | 21.592 | 40.403 | −8.449 | 1.00 | 8.33 |
| ATOM 2556 | CA | SER B | 122 | 21.491 | 39.047 | −7.904 | 1.00 | 8.33 |
| ATOM 2557 | C | SER B | 122 | 20.531 | 38.891 | −6.732 | 1.00 | 8.33 |
| ATOM 2558 | O | SER B | 122 | 19.965 | 37.833 | −6.494 | 1.00 | 8.33 |
| ATOM 2559 | CB | SER B | 122 | 22.875 | 38.562 | −7.484 | 1.00 | 8.33 |
| ATOM 2560 | OG | SER B | 122 | 23.832 | 38.967 | −8.468 | 1.00 | 8.33 |
| ATOM 2561 | H | SER B | 122 | 22.503 | 40.801 | −8.558 | 1.00 | 20.00 |
| ATOM 2562 | HG | SER B | 122 | 24.651 | 38.552 | −8.225 | 1.00 | 20.00 |
| ATOM 2563 | N | LEU B | 123 | 20.371 | 40.017 | −6.012 | 1.00 | 10.07 |
| ATOM 2564 | CA | LEU B | 123 | 19.436 | 40.032 | −4.890 | 1.00 | 10.07 |
| ATOM 2565 | C | LEU B | 123 | 17.973 | 39.912 | −5.267 | 1.00 | 10.07 |
| ATOM 2566 | O | LEU B | 123 | 17.134 | 39.559 | −4.448 | 1.00 | 10.07 |
| ATOM 2567 | CB | LEU B | 123 | 19.562 | 41.335 | −4.118 | 1.00 | 10.07 |
| ATOM 2568 | CG | LEU B | 123 | 20.938 | 41.678 | −3.570 | 1.00 | 10.07 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM 2569 | CD1 | LEU | B | 123 | 21.015 | 43.169 | −3.242 | 1.00 | 10.07 |
| ATOM 2570 | CD2 | LEU | B | 123 | 21.330 | 40.782 | −2.398 | 1.00 | 10.07 |
| ATOM 2571 | H | LEU | B | 123 | 20.845 | 40.864 | −6.264 | 1.00 | 20.00 |
| ATOM 2572 | N | LEU | B | 124 | 17.680 | 40.300 | −6.519 | 1.00 | 5.90 |
| ATOM 2573 | CA | LEU | B | 124 | 16.267 | 40.546 | −6.784 | 1.00 | 5.90 |
| ATOM 2574 | C | LEU | B | 124 | 15.405 | 39.307 | −6.803 | 1.00 | 5.90 |
| ATOM 2575 | O | VAL | B | 124 | 15.683 | 38.288 | −7.425 | 1.00 | 5.90 |
| ATOM 2576 | CB | VAL | B | 124 | 16.078 | 41.404 | −8.043 | 1.00 | 5.90 |
| ATOM 2577 | CG1 | VAL | B | 124 | 14.619 | 41.768 | −8.338 | 1.00 | 5.90 |
| ATOM 2578 | CG2 | VAL | B | 124 | 16.871 | 42.690 | −7.865 | 1.00 | 5.90 |
| ATOM 2579 | H | VAL | B | 124 | 18.375 | 40.396 | −7.233 | 1.00 | 20.00 |
| ATOM 2580 | N | ASN | B | 125 | 14.303 | 39.483 | −6.070 | 1.00 | 5.82 |
| ATOM 2581 | CA | ASN | B | 125 | 13.268 | 38.466 | −6.159 | 1.00 | 5.82 |
| ATOM 2582 | C | ASN | B | 125 | 12.436 | 38.671 | −7.381 | 1.00 | 5.82 |
| ATOM 2583 | O | ASN | B | 125 | 11.998 | 39.778 | −7.656 | 1.00 | 5.82 |
| ATOM 2584 | CB | ASN | B | 125 | 12.354 | 38.519 | −4.943 | 1.00 | 5.82 |
| ATOM 2585 | CG | ASN | B | 125 | 13.162 | 37.999 | −3.808 | 1.00 | 5.82 |
| ATOM 2586 | OD1 | ASN | B | 125 | 14.077 | 37.236 | −4.056 | 1.00 | 5.82 |
| ATOM 2587 | ND2 | ASN | B | 125 | 12.807 | 38.450 | −2.591 | 1.00 | 5.82 |
| ATOM 2588 | H | ASN | B | 125 | 14.155 | 40.369 | −5.628 | 1.00 | 20.00 |
| ATOM 2589 | 1 HD2 | ASN | B | 125 | 12.024 | 39.059 | −2.498 | 1.00 | 20.00 |
| ATOM 2590 | 2 HD2 | ASN | B | 125 | 13.325 | 38.216 | −1.766 | 1.00 | 20.00 |
| ATOM 2591 | N | PHE | B | 126 | 12.207 | 37.549 | −8.072 | 1.00 | 7.35 |
| ATOM 2592 | CA | PHE | B | 126 | 11.119 | 37.606 | −9.041 | 1.00 | 7.35 |
| ATOM 2593 | C | PHE | B | 126 | 10.099 | 36.555 | −8.715 | 1.00 | 7.35 |
| ATOM 2594 | O | PHE | B | 126 | 9.564 | 35.843 | −9.555 | 1.00 | 7.35 |
| ATOM 2595 | CB | PHE | B | 126 | 11.595 | 37.426 | −10.476 | 1.00 | 7.35 |
| ATOM 2596 | CG | PHE | B | 126 | 12.638 | 38.457 | −10.804 | 1.00 | 7.35 |
| ATOM 2597 | CD1 | PHE | B | 126 | 13.993 | 38.081 | −10.727 | 1.00 | 7.35 |
| ATOM 2598 | CD2 | PHE | B | 126 | 12.248 | 39.758 | −11.192 | 1.00 | 7.35 |
| ATOM 2599 | CE1 | PHE | B | 126 | 14.984 | 39.008 | −11.092 | 1.00 | 7.35 |
| ATOM 2600 | CE2 | PHE | B | 126 | 13.239 | 40.685 | −11.564 | 1.00 | 7.35 |
| ATOM 2601 | CZ | PHE | B | 126 | 14.594 | 40.291 | −11.532 | 1.00 | 7.35 |
| ATOM 2602 | H | PHE | B | 126 | 12.688 | 36.693 | −7.882 | 1.00 | 20.00 |
| ATOM 2603 | N | GLU | B | 127 | 9.865 | 36.476 | −7.396 | 1.00 | 24.73 |
| ATOM 2604 | CA | GLU | B | 127 | 8.691 | 35.743 | −6.955 | 1.00 | 24.73 |
| ATOM 2605 | C | GLU | B | 127 | 7.431 | 36.370 | −7.515 | 1.00 | 24.73 |
| ATOM 2606 | O | GLU | B | 127 | 6.521 | 35.753 | −8.053 | 1.00 | 24.73 |
| ATOM 2607 | CB | GLU | B | 127 | 8.591 | 35.817 | −5.445 | 1.00 | 24.73 |
| ATOM 2608 | CG | GLU | B | 127 | 7.585 | 34.753 | −5.001 | 1.00 | 24.73 |
| ATOM 2609 | CD | GLU | B | 127 | 8.355 | 33.515 | −4.517 | 1.00 | 24.73 |
| ATOM 2610 | OE1 | GLU | B | 127 | 8.966 | 33.486 | −3.443 | 1.00 | 24.73 |
| ATOM 2611 | OE2 | GLU | B | 127 | 8.382 | 32.557 | −5.246 | 1.00 | 24.73 |
| ATOM 2612 | H | GLU | B | 127 | 10.416 | 36.983 | −6.739 | 1.00 | 20.00 |
| ATOM 2613 | N | GLU | B | 128 | 7.441 | 37.688 | −7.277 | 1.00 | 23.04 |
| ATOM 2614 | CA | GLU | B | 128 | 6.166 | 38.365 | −7.373 | 1.00 | 23.04 |
| ATOM 2615 | C | GLU | B | 128 | 6.353 | 39.772 | −7.856 | 1.00 | 23.04 |
| ATOM 2616 | O | GLU | B | 128 | 7.468 | 40.213 | −8.110 | 1.00 | 23.04 |
| ATOM 2617 | CB | GLU | B | 128 | 5.557 | 38.339 | −5.989 | 1.00 | 23.04 |
| ATOM 2618 | CG | GLU | B | 128 | 4.727 | 37.086 | −5.729 | 1.00 | 23.04 |
| ATOM 2619 | CD | GLU | B | 128 | 3.295 | 37.307 | −6.160 | 1.00 | 23.04 |
| ATOM 2620 | OE1 | GLU | B | 128 | 2.980 | 38.384 | −6.680 | 1.00 | 23.04 |
| ATOM 2621 | OE2 | GLU | B | 128 | 2.500 | 36.393 | −5.955 | 1.00 | 23.04 |
| ATOM 2622 | H | GLU | B | 128 | 8.219 | 38.174 | −6.866 | 1.00 | 20.00 |
| ATOM 2623 | N | SER | B | 129 | 5.217 | 40.479 | −7.935 | 1.00 | 19.86 |
| ATOM 2624 | CA | SER | B | 129 | 5.190 | 41.782 | −8.619 | 1.00 | 19.86 |
| ATOM 2625 | C | SER | B | 129 | 5.966 | 42.944 | −7.999 | 1.00 | 19.86 |
| ATOM 2626 | O | SER | B | 129 | 5.971 | 44.069 | −8.479 | 1.00 | 19.86 |
| ATOM 2627 | GB | SER | B | 129 | 3.737 | 42.203 | −8.827 | 1.00 | 19.86 |
| ATOM 2628 | OG | SER | B | 129 | 2.958 | 41.052 | −9.163 | 1.00 | 19.86 |
| ATOM 2629 | H | SER | B | 129 | 4.353 | 40.037 | −7.661 | 1.00 | 20.00 |
| ATOM 2630 | HG | SER | B | 129 | 2.038 | 41.313 | −9.105 | 1.00 | 20.00 |
| ATOM 2631 | N | GLN | B | 130 | 6.604 | 42.618 | −6.871 | 1.00 | 15.57 |
| ATOM 2632 | CA | GLN | B | 130 | 7.165 | 43.597 | −5.948 | 1.00 | 15.57 |
| ATOM 2633 | C | GLN | B | 130 | 8.061 | 44.718 | −6.469 | 1.00 | 15.57 |
| ATOM 2634 | O | GLN | B | 130 | 8.015 | 45.841 | −5.981 | 1.00 | 15.57 |
| ATOM 2635 | GB | GLN | B | 130 | 7.858 | 42.813 | −4.846 | 1.00 | 15.57 |
| ATOM 2636 | CG | GLN | B | 130 | 8.998 | 41.884 | −5.311 | 1.00 | 15.57 |
| ATOM 2637 | CD | GLN | B | 130 | 8.664 | 40.407 | −5.145 | 1.00 | 15.57 |
| ATOM 2638 | CE1 | GLN | B | 130 | 9.297 | 39.522 | −5.707 | 1.00 | 15.57 |
| ATOM 2639 | NE2 | GLN | B | 130 | 7.630 | 40.142 | −4.338 | 1.00 | 15.57 |
| ATOM 2640 | H | GLN | B | 130 | 6.616 | 41.649 | −6.641 | 1.00 | 20.00 |
| ATOM 2641 | 1 HE2 | GLN | B | 130 | 7.088 | 40.805 | −3.827 | 1.00 | 20.00 |
| ATOM 2642 | 2 HE2 | GLN | B | 130 | 7.346 | 39.189 | −4.262 | 1.00 | 20.00 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM 2643 | N | THR | B | 131 | 8.902 | 44.358 | −7.447 | 1.00 | 3.96 |
| ATOM 2644 | CA | THR | B | 131 | 9.869 | 45.355 | −7.893 | 1.00 | 3.96 |
| ATOM 2645 | C | THR | B | 131 | 9.359 | 46.228 | −9.023 | 1.00 | 3.96 |
| ATOM 2646 | O | THR | B | 131 | 9.134 | 45.786 | −10.147 | 1.00 | 3.96 |
| ATOM 2647 | CB | THR | B | 131 | 11.200 | 44.669 | −8.225 | 1.00 | 3.96 |
| ATOM 2648 | OG1 | THR | B | 131 | 11.738 | 44.065 | −7.038 | 1.00 | 3.96 |
| ATOM 2649 | CG2 | THR | B | 131 | 12.236 | 45.603 | −8.859 | 1.00 | 3.96 |
| ATOM 2650 | H | THR | B | 131 | 8.839 | 43.456 | −7.870 | 1.00 | 20.00 |
| ATOM 2651 | HG1 | THR | B | 131 | 12.465 | 43.535 | −7.339 | 1.00 | 20.00 |
| ATOM 2652 | N | PHE | B | 132 | 9.195 | 47.504 | −8.640 | 1.00 | 6.06 |
| ATOM 2653 | CA | PHE | B | 132 | 8.580 | 46.458 | −9.553 | 1.00 | 6.06 |
| ATOM 2654 | C | PHE | B | 132 | 9.126 | 49.862 | −9.396 | 1.00 | 6.06 |
| ATOM 2655 | O | PHE | B | 132 | 9.692 | 50.198 | −8.365 | 1.00 | 6.06 |
| ATOM 2656 | CB | PHE | B | 132 | 7.049 | 48.437 | −9.410 | 1.00 | 6.06 |
| ATOM 2657 | CG | PHE | B | 132 | 6.573 | 48.792 | −8.018 | 1.00 | 6.06 |
| ATOM 2658 | CD1 | PHE | B | 132 | 6.682 | 50.119 | −7.541 | 1.00 | 6.06 |
| ATOM 2659 | CD2 | PHE | B | 132 | 6.006 | 47.778 | −7.219 | 1.00 | 6.06 |
| ATOM 2660 | CE1 | PHE | B | 132 | 6.234 | 50.430 | −6.245 | 1.00 | 6.06 |
| ATOM 2661 | CE2 | PHE | B | 132 | 5.552 | 48.087 | −5.923 | 1.00 | 6.06 |
| ATOM 2662 | CZ | PHE | B | 132 | 5.675 | 49.409 | −5.448 | 1.00 | 6.06 |
| ATOM 2663 | H | PHE | B | 132 | 9.489 | 47.782 | −7.721 | 1.00 | 20.00 |
| ATOM 2664 | N | PHE | B | 133 | 8.893 | 50.667 | −10.443 | 1.00 | 7.15 |
| ATOM 2665 | CA | PHE | B | 133 | 9.216 | 52.094 | −10.375 | 1.00 | 7.15 |
| ATOM 2666 | C | PHE | B | 133 | 8.160 | 52.877 | −11.118 | 1.00 | 7.15 |
| ATOM 2667 | O | PHE | B | 133 | 7.790 | 52.516 | −12.224 | 1.00 | 7.15 |
| ATOM 2668 | CB | PHE | B | 133 | 10.603 | 52.353 | −10.983 | 1.00 | 7.15 |
| ATOM 2669 | CG | PHE | B | 133 | 10.922 | 53.825 | −11.169 | 1.00 | 7.15 |
| ATOM 2670 | CD1 | PHE | B | 133 | 10.718 | 54.745 | −10.116 | 1.00 | 7.15 |
| ATOM 2671 | CD2 | PHE | B | 133 | 11.440 | 54.250 | −12.412 | 1.00 | 7.15 |
| ATOM 2672 | CE1 | PHE | B | 133 | 11.031 | 56.104 | −10.306 | 1.00 | 7.15 |
| ATOM 2673 | CE2 | PHE | B | 133 | 11.766 | 55.607 | −12.599 | 1.00 | 7.15 |
| ATOM 2674 | CZ | PHE | B | 133 | 11.556 | 56.522 | −11.547 | 1.00 | 7.15 |
| ATOM 2675 | H | PHE | B | 133 | 8.474 | 50.273 | −11.267 | 1.00 | 20.00 |
| ATOM 2676 | N | GLY | B | 134 | 7.687 | 53.957 | −10.491 | 1.00 | 4.00 |
| ATOM 2677 | CA | GLY | B | 134 | 6.660 | 54.684 | −11.218 | 1.00 | 4.00 |
| ATOM 2678 | C | GLY | B | 134 | 6.524 | 56.129 | −10.814 | 1.00 | 4.00 |
| ATOM 2679 | O | GLY | B | 134 | 6.950 | 56.542 | −9.741 | 1.00 | 4.00 |
| ATOM 2680 | H | GLY | B | 134 | 8.007 | 54.259 | −9.590 | 1.00 | 20.00 |
| ATOM 2681 | N | LEU | B | 135 | 5.913 | 56.875 | −11.747 | 1.00 | 5.48 |
| ATOM 2682 | CA | LEU | B | 135 | 5.698 | 58.301 | −11.516 | 1.00 | 5.48 |
| ATOM 2683 | C | LEU | B | 135 | 4.262 | 58.657 | −11.780 | 1.00 | 5.48 |
| ATOM 2684 | O | LEU | B | 135 | 3.551 | 57.936 | −12.470 | 1.00 | 5.48 |
| ATOM 2685 | CB | LEU | B | 135 | 6.481 | 59.215 | −12.461 | 1.00 | 5.48 |
| ATOM 2686 | CG | LEU | B | 135 | 7.961 | 58.954 | −12.694 | 1.00 | 5.48 |
| ATOM 2687 | CD1 | LEU | B | 135 | 8.553 | 60.056 | −13.571 | 1.00 | 5.48 |
| ATOM 2688 | CD2 | LEU | B | 135 | 8.749 | 58.771 | −11.408 | 1.00 | 5.48 |
| ATOM 2689 | H | LEU | B | 135 | 5.468 | 56.411 | −12.517 | 1.00 | 20.00 |
| ATOM 2690 | N | TYR | B | 136 | 3.902 | 59.841 | −11.268 | 1.00 | 5.12 |
| ATOM 2691 | CA | TYR | B | 136 | 2.670 | 60.475 | −11.731 | 1.00 | 5.12 |
| ATOM 2692 | C | TYR | B | 136 | 2.647 | 61.949 | −11.422 | 1.00 | 5.12 |
| ATOM 2693 | O | TYR | B | 136 | 3.133 | 62.379 | −10.385 | 1.00 | 5.12 |
| ATOM 2694 | CB | TYR | B | 136 | 1.414 | 59.795 | −11.169 | 1.00 | 5.12 |
| ATOM 2695 | CG | TYR | B | 136 | 1.462 | 59.619 | −9.671 | 1.00 | 5.12 |
| ATOM 2696 | CD1 | TYR | B | 136 | 2.201 | 58.549 | −9.128 | 1.00 | 5.12 |
| ATOM 2697 | CD2 | TYR | B | 136 | 0.734 | 60.509 | −8.860 | 1.00 | 5.12 |
| ATOM 2698 | CE1 | TYR | B | 136 | 2.150 | 58.319 | −7.745 | 1.00 | 5.12 |
| ATOM 2699 | CE2 | TYR | B | 136 | 0.675 | 60.270 | −7.479 | 1.00 | 5.12 |
| ATOM 2700 | CZ | TYR | B | 136 | 1.355 | 59.160 | −6.945 | 1.00 | 5.12 |
| ATOM 2701 | OH | TYR | B | 136 | 1.232 | 58.901 | −5.596 | 1.00 | 5.12 |
| ATOM 2702 | H | TYR | B | 136 | 4.467 | 60.252 | −10.548 | 1.00 | 20.00 |
| ATOM 2703 | HH | TYR | B | 136 | 1.239 | 59.729 | −5.136 | 1.00 | 20.00 |
| ATOM 2704 | N | LYS | B | 137 | 2.064 | 62.706 | −12.363 | 1.00 | 11.54 |
| ATOM 2705 | CA | LYS | B | 137 | 1.910 | 64.129 | −12.070 | 1.00 | 11.54 |
| ATOM 2706 | C | LYS | B | 137 | 0.784 | 64.402 | −11.084 | 1.00 | 11.54 |
| ATOM 2707 | O | LYS | B | 137 | −0.262 | 63.763 | −11.129 | 1.00 | 11.54 |
| ATOM 2708 | CB | LYS | B | 137 | 1.758 | 64.935 | −13.373 | 1.00 | 11.54 |
| ATOM 2709 | CG | LYS | B | 137 | 1.835 | 66.448 | −13.139 | 1.00 | 11.54 |
| ATOM 2710 | CD | LYS | B | 137 | 1.837 | 67.348 | −14.372 | 1.00 | 11.54 |
| ATOM 2711 | CE | LYS | B | 137 | 1.746 | 68.811 | −13.928 | 1.00 | 11.54 |
| ATOM 2712 | Hz | LYS | B | 137 | 2.007 | 69.724 | −15.050 | 1.00 | 11.54 |
| ATOM 2713 | H | LYS | B | 137 | 1.698 | 62.264 | −13.184 | 1.00 | 20.00 |
| ATOM 2714 | 1 HZ | LYS | B | 137 | 1.867 | 70.705 | −14.740 | 1.00 | 20.00 |
| ATOM 2715 | 2 HZ | LYS | B | 137 | 3.010 | 69.645 | −15.337 | 1.00 | 20.00 |
| ATOM 2716 | 3 HZ | LYS | B | 137 | 1.404 | 69.516 | −15.872 | 1.00 | 20.00 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM | 2717 | N | LEU | B | 138 | 1.070 | 65.368 | −10.198 | 1.00 | 2.56 |
| ATOM | 2718 | CA | LEU | B | 138 | 0.042 | 65.880 | −9.295 | 1.00 | 2.56 |
| ATOM | 2719 | C | LEU | B | 138 | −0.736 | 67.067 | −9.876 | 1.00 | 2.56 |
| ATOM | 2720 | O | LEU | B | 138 | −1.506 | 67.689 | −9.144 | 1.00 | 2.56 |
| ATOM | 2721 | CB | LEU | B | 138 | 0.688 | 66.242 | −7.949 | 1.00 | 2.56 |
| ATOM | 2722 | CG | LEU | B | 138 | 1.557 | 65.135 | −7.341 | 1.00 | 2.56 |
| ATOM | 2723 | CD1 | LEU | B | 138 | 2.317 | 65.642 | −6.121 | 1.00 | 2.56 |
| ATOM | 2724 | CD2 | LEU | B | 138 | 0.766 | 63.865 | −7.029 | 1.00 | 2.56 |
| ATOM | 2725 | OXT | LEU | B | 138 | −0.574 | 67.379 | −11.062 | 1.00 | 2.56 |
| ATOM | 2726 | H | LEU | B | 138 | 1.965 | 65.813 | −10.253 | 1.00 | 20.00 |
| ATOM | 2727 | N | ARG | C | 1 | −11.122 | 63.107 | −5.160 | 1.00 | 5.73 |
| ATOM | 2728 | CA | ARG | C | 1 | −12.158 | 62.194 | −5.656 | 1.00 | 5.73 |
| ATOM | 2729 | C | ARG | C | 1 | −12.274 | 61.039 | −4.682 | 1.00 | 5.73 |
| ATOM | 2730 | O | ARG | C | 1 | −12.338 | 61.304 | −3.491 | 1.00 | 5.73 |
| ATOM | 2731 | CB | ARG | C | 1 | −11.889 | 61.777 | −7.105 | 1.00 | 5.73 |
| ATOM | 2732 | CG | ARG | C | 1 | −12.301 | 62.841 | −8.119 | 1.00 | 5.73 |
| ATOM | 2733 | CD | ARG | C | 1 | −12.165 | 62.329 | −9.552 | 1.00 | 5.73 |
| ATOM | 2734 | NE | ARG | C | 1 | −12.591 | 63.346 | −10.511 | 1.00 | 5.73 |
| ATOM | 2735 | CZ | ARG | C | 1 | −11.792 | 63.695 | −11.543 | 1.00 | 5.73 |
| ATOM | 2736 | NH1 | ARG | C | 1 | −12.217 | 64.618 | −12.404 | 1.00 | 5.73 |
| ATOM | 2737 | NH2 | ARG | C | 1 | −10.592 | 63.129 | −11.697 | 1.00 | 5.73 |
| ATOM | 2738 | 1H | ARG | C | 1 | −11.124 | 64.006 | −5.682 | 1.00 | 20.00 |
| ATOM | 2739 | 2H | ARG | C | 1 | −11.336 | 63.267 | −4.152 | 1.00 | 20.00 |
| ATOM | 2740 | 3H | ARG | C | 1 | −10.188 | 62.653 | −5.231 | 1.00 | 20.00 |
| ATOM | 2741 | HE | ARG | C | 1 | −13.500 | 63.748 | −10.389 | 1.00 | 20.00 |
| ATOM | 2742 | 1 HH1 | ARG | C | 1 | −11.658 | 64.901 | −13.184 | 1.00 | 20.00 |
| ATOM | 2743 | 2 HH1 | ARG | C | 1 | −13.111 | 65.052 | −12.285 | 1.00 | 20.00 |
| ATOM | 2744 | 1 HH2 | ARG | C | 1 | −9.999 | 63.354 | −12.471 | 1.00 | 20.00 |
| ATOM | 2745 | 2 HH2 | ARG | C | 1 | −10.245 | 62.467 | −11.031 | 1.00 | 20.00 |
| ATOM | 2746 | N | LYS | C | 2 | −12.286 | 59.794 | −5.199 | 1.00 | 19.49 |
| ATOM | 2747 | CA | LYS | C | 2 | −12.453 | 58.651 | −4.301 | 1.00 | 19.49 |
| ATOM | 2748 | C | LYS | C | 2 | −11.210 | 58.413 | −3.504 | 1.00 | 19.49 |
| ATOM | 2749 | O | LYS | C | 2 | −10.120 | 58.321 | −4.054 | 1.00 | 19.49 |
| ATOM | 2750 | CB | LYS | C | 2 | −12.747 | 57.342 | −5.032 | 1.00 | 19.49 |
| ATOM | 2751 | CG | LYS | C | 2 | −14.079 | 57.283 | −5.763 | 1.00 | 19.49 |
| ATOM | 2752 | CD | LYS | C | 2 | −14.062 | 58.092 | −7.045 | 1.00 | 19.49 |
| ATOM | 2753 | CE | LYS | C | 2 | −15.357 | 57.915 | −7.789 | 1.00 | 19.49 |
| ATOM | 2754 | NZ | LYS | C | 2 | −16.406 | 58.884 | −7.450 | 1.00 | 19.49 |
| ATOM | 2755 | H | LYS | C | 2 | −12.075 | 59.589 | −6.151 | 1.00 | 20.00 |
| ATOM | 2756 | 1 HZ | LYS | C | 2 | −17.050 | 58.874 | −8.282 | 1.00 | 20.00 |
| ATOM | 2757 | 2 HZ | LYS | C | 2 | −16.899 | 58.602 | −6.579 | 1.00 | 20.00 |
| ATOM | 2758 | 3 HZ | LYS | C | 2 | −16.014 | 59.840 | −7.355 | 1.00 | 20.00 |
| ATOM | 2759 | N | VAL | C | 3 | −11.437 | 58.360 | −2.191 | 1.00 | 4.59 |
| ATOM | 2760 | CA | VAL | C | 3 | −10.328 | 58.169 | −1.270 | 1.00 | 4.59 |
| ATOM | 2761 | C | VAL | C | 3 | −10.810 | 57.210 | −0.203 | 1.00 | 4.59 |
| ATOM | 2762 | O | VAL | C | 3 | −11.995 | 57.162 | 0.117 | 1.00 | 4.59 |
| ATOM | 2763 | CB | VAL | C | 3 | −9.876 | 59.524 | −0.679 | 1.00 | 4.59 |
| ATOM | 2764 | CG1 | VAL | C | 3 | −8.749 | 59.403 | 0.351 | 1.00 | 4.59 |
| ATOM | 2765 | CG2 | VAL | C | 3 | 9.443 | 60.490 | −1.784 | 1.00 | 4.59 |
| ATOM | 2766 | H | VAL | C | 3 | −12.366 | 58.386 | −1.821 | 1.00 | 20.00 |
| ATOM | 2767 | N | ALA | C | 4 | −9.833 | 56.450 | 0.299 | 1.00 | 5.22 |
| ATOM | 2768 | CA | ALA | C | 4 | −10.047 | 55.588 | 1.445 | 1.00 | 5.22 |
| ATOM | 2769 | C | ALA | C | 4 | −8.759 | 55.575 | 2.228 | 1.00 | 5.22 |
| ATOM | 2770 | O | ALA | C | 4 | −7.677 | 55.614 | 1.655 | 1.00 | 5.22 |
| ATOM | 2771 | CB | ALA | C | 4 | −10.359 | 54.160 | 0.998 | 1.00 | 5.22 |
| ATOM | 2772 | H | ALA | C | 4 | −8.902 | 56.534 | −0.066 | 1.00 | 20.00 |
| ATOM | 2773 | N | HIS | C | 5 | −8.926 | 55.512 | 3.548 | 1.00 | 4.76 |
| ATOM | 2774 | CA | HIS | C | 5 | −7.770 | 55.262 | 4.404 | 1.00 | 4.76 |
| ATOM | 2775 | C | HIS | C | 5 | −8.312 | 54.515 | 5.584 | 1.00 | 4.76 |
| ATOM | 2776 | O | HIS | C | 5 | −9.121 | 55.092 | 6.283 | 1.00 | 4.76 |
| ATOM | 2777 | CB | HIS | C | 5 | −7.137 | 51.578 | 4.880 | 1.00 | 4.76 |
| ATOM | 2778 | CG | HIS | C | 5 | −5.938 | 56.284 | 5.753 | 1.00 | 4.76 |
| ATOM | 2779 | ND1 | HIS | C | 5 | −4.695 | 56.176 | 5.267 | 1.00 | 4.76 |
| ATOM | 2780 | CD2 | HIS | C | 5 | −5.902 | 56.052 | 7.133 | 1.00 | 4.76 |
| ATOM | 2781 | CE1 | HIS | C | 5 | −3.881 | 55.876 | 6.322 | 1.00 | 4.76 |
| ATOM | 2782 | NE2 | HIS | C | 5 | −4.616 | 55.799 | 7.469 | 1.00 | 4.76 |
| ATOM | 2783 | H | HIS | C | 5 | −9.845 | 55.588 | 3.945 | 1.00 | 20.00 |
| ATOM | 2784 | HD1 | HIS | C | 5 | −4.439 | 56.295 | 4.327 | 1.00 | 20.00 |
| ATOM | 2785 | N | LEU | C | 6 | −7.889 | 53.257 | 5.746 | 1.00 | 6.04 |
| ATOM | 2786 | CA | LEU | C | 6 | −8.469 | 52.397 | 6.777 | 1.00 | 6.04 |
| ATOM | 2787 | C | LEU | C | 6 | −7.439 | 51.931 | 7.762 | 1.00 | 6.04 |
| ATOM | 2788 | O | LEU | C | 6 | −6.284 | 51.752 | 7.403 | 1.00 | 6.04 |
| ATOM | 2789 | CB | LEU | C | 6 | −9.028 | 51.122 | 6.176 | 1.00 | 6.04 |
| ATOM | 2790 | CG | LEU | C | 6 | −10.064 | 51.332 | 5.095 | 1.00 | 6.04 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 2791 | CD1 | LEU C | 6 | −10.532 | 49.982 | 4.586 | 1.00 | 6.04 |
| ATOM 2792 | CD2 | LEU C | 6 | −11.226 | 52.191 | 5.575 | 1.00 | 6.04 |
| ATOM 2793 | H | LEU C | 6 | −7.203 | 52.882 | 5.126 | 1.00 | 20.00 |
| ATOM 2794 | N | THR C | 7 | −7.908 | 51.695 | 8.993 | 1.00 | 3.03 |
| ATOM 2795 | CA | THR C | 7 | −6.966 | 51.140 | 9.959 | 1.00 | 3.03 |
| ATOM 2796 | C | THR C | 7 | −7.318 | 49.722 | 10.363 | 1.00 | 3.03 |
| ATOM 2797 | O | THR C | 7 | −8.439 | 49.261 | 10.178 | 1.00 | 3.03 |
| ATOM 2798 | CB | THR C | 7 | −6.867 | 52.062 | 11.173 | 1.00 | 3.03 |
| ATOM 2799 | OG1 | THR C | 7 | −8.176 | 52.445 | 11.612 | 1.00 | 3.03 |
| ATOM 2800 | CG2 | THR C | 7 | −6.030 | 53.305 | 10.659 | 1.00 | 3.03 |
| ATOM 2801 | H | THR C | 7 | −8.866 | 51.841 | 9.252 | 1.00 | 20.00 |
| ATOM 2802 | HG1 | THR C | 7 | −8.091 | 52.724 | 12.514 | 1.00 | 20.00 |
| ATOM 2803 | N | GLY C | 8 | −6.290 | 49.040 | 10.898 | 1.00 | 3.29 |
| ATOM 2804 | CA | GLY C | 8 | −6.531 | 47.675 | 11.365 | 1.00 | 3.29 |
| ATOM 2805 | C | GLY C | 8 | −7.155 | 47.598 | 12.747 | 1.00 | 3.29 |
| ATOM 2806 | O | GLY C | 8 | −6.839 | 48.372 | 13.644 | 1.00 | 3.29 |
| ATOM 2807 | H | GLY C | 8 | −5.388 | 49.475 | 10.962 | 1.00 | 20.00 |
| ATOM 2808 | N | LYS C | 9 | −8.054 | 46.609 | 12.887 | 1.00 | 6.71 |
| ATOM 2809 | CA | LYS C | 9 | −8.724 | 46.455 | 14.179 | 1.00 | 6.71 |
| ATOM 2810 | C | LYS C | 9 | −7.858 | 45.990 | 15.333 | 1.00 | 6.71 |
| ATOM 2811 | O | LYS C | 9 | 7.574 | 44.810 | 15.502 | 1.00 | 6.71 |
| ATOM 2812 | CB | LYS C | 9 | −9.923 | 45.517 | 14.099 | 1.00 | 6.71 |
| ATOM 2813 | CG | LYS C | 9 | −11.065 | 46.024 | 13.232 | 1.00 | 6.71 |
| ATOM 2814 | CD | LYS C | 9 | −12.326 | 45.188 | 13.433 | 1.00 | 6.71 |
| ATOM 2815 | CE | LYS C | 9 | −13.508 | 45.733 | 12.633 | 1.00 | 6.71 |
| ATOM 2816 | NZ | LYS C | 9 | −14.572 | 44.722 | 12.583 | 1.00 | 6.71 |
| ATOM 2817 | H | LYS C | 9 | −8.285 | 46.041 | 12.094 | 1.00 | 20.00 |
| ATOM 2818 | 1 HZ | LYS C | 9 | −15.268 | 44.980 | 11.857 | 1.00 | 20.00 |
| ATOM 2819 | 2 HZ | LYS C | 9 | −14.168 | 43.814 | 12.239 | 1.00 | 20.00 |
| ATOM 2820 | 3 HZ | LYS C | 9 | −15.015 | 44.575 | 13.506 | 1.00 | 20.00 |
| ATOM 2821 | N | SER C | 10 | −7.530 | 46.982 | 16.177 | 1.00 | 13.61 |
| ATOM 2822 | CA | SER C | 10 | −6.930 | 46.711 | 17.490 | 1.00 | 13.61 |
| ATOM 2823 | C | SER C | 10 | −7.500 | 45.534 | 18.260 | 1.00 | 13.61 |
| ATOM 2824 | O | SER C | 10 | −6.811 | 44.625 | 18.709 | 1.00 | 13.61 |
| ATOM 2825 | CB | SER C | 10 | −7.009 | 47.953 | 18.372 | 1.00 | 13.61 |
| ATOM 2826 | OG | SER C | 10 | −6.617 | 49.092 | 17.109 | 1.00 | 13.61 |
| ATOM 2827 | H | SER C | 10 | −7.560 | 47.914 | 15.805 | 1.00 | 20.00 |
| ATOM 2828 | HG | SER C | 10 | −6.513 | 49.803 | 18.230 | 1.00 | 20.00 |
| ATOM 2829 | N | ASN C | 11 | −8.831 | 45.583 | 18.399 | 1.00 | 8.64 |
| ATOM 2830 | CA | ASN C | 11 | −9.426 | 44.390 | 18.989 | 1.00 | 8.64 |
| ATOM 2831 | C | ASN C | 11 | −10.069 | 43.481 | 17.969 | 1.00 | 8.64 |
| ATOM 2832 | O | ASN C | 11 | −11.272 | 43.259 | 17.930 | 1.00 | 8.64 |
| ATOM 2833 | CB | ASN C | 11 | −10.342 | 44.728 | 20.173 | 1.00 | 8.64 |
| ATOM 2834 | CG | ASN C | 11 | −9.562 | 45.112 | 21.433 | 1.00 | 8.64 |
| ATOM 2835 | OD1 | ASN C | 11 | −10.138 | 45.560 | 22.414 | 1.00 | 8.64 |
| ATOM 2836 | ND2 | ASN C | 11 | −8.230 | 44.922 | 21.405 | 1.00 | 8.64 |
| ATOM 2837 | H | ASN C | 11 | −9.369 | 46.347 | 18.044 | 1.00 | 20.00 |
| ATOM 2838 | 1 HD2 | ASN C | 11 | −7.694 | 44.571 | 20.632 | 1.00 | 20.00 |
| ATOM 2839 | 2 HD2 | ASN C | 11 | −7.746 | 45.163 | 22.245 | 1.00 | 20.00 |
| ATOM 2840 | N | SER C | 12 | −9.167 | 42.939 | 17.144 | 1.00 | 14.76 |
| ATOM 2841 | CA | SER C | 12 | −9.586 | 41.802 | 16.339 | 1.00 | 14.76 |
| ATOM 2842 | C | SER C | 12 | −8.904 | 40.563 | 16.865 | 1.00 | 14.76 |
| ATOM 2843 | O | SER C | 12 | −7.930 | 40.637 | 17.606 | 1.00 | 14.76 |
| ATOM 2844 | CB | SER C | 12 | −9.272 | 42.024 | 14.859 | 1.00 | 14.76 |
| ATOM 2845 | OG | SER C | 12 | −10.060 | 41.134 | 14.062 | 1.00 | 14.76 |
| ATOM 2846 | H | SER C | 12 | −8.198 | 43.194 | 17.191 | 1.00 | 20.00 |
| ATOM 2847 | HG | SER C | 12 | −10.101 | 41.522 | 13.194 | 1.00 | 20.00 |
| ATOM 2848 | N | ARG C | 13 | −9.465 | 39.409 | 16.476 | 1.00 | 14.62 |
| ATOM 2849 | CA | ARG C | 13 | −8.762 | 38.197 | 16.886 | 1.00 | 14.62 |
| ATOM 2850 | C | ARG C | 13 | −7.415 | 38.113 | 16.185 | 1.00 | 14.62 |
| ATOM 2851 | O | ARG C | 13 | −7.237 | 38.658 | 15.107 | 1.00 | 14.62 |
| ATOM 2852 | CB | ARG C | 13 | −9.649 | 36.969 | 16.634 | 1.00 | 14.62 |
| ATOM 2853 | CG | ARG C | 13 | −10.958 | 37.042 | 17.429 | 1.00 | 14.62 |
| ATOM 2854 | CD | ARG C | 13 | −11.796 | 35.761 | 17.346 | 1.00 | 14.62 |
| ATOM 2855 | NE | ARG C | 13 | −12.945 | 35.813 | 18.255 | 1.00 | 14.62 |
| ATOM 2856 | CZ | ARG C | 13 | −12.821 | 35.476 | 19.560 | 1.00 | 14.62 |
| ATOM 2857 | NH1 | ARG C | 13 | −13.868 | 35.600 | 20.373 | 1.00 | 14.62 |
| ATOM 2858 | NH2 | ARG C | 13 | −11.660 | 35.027 | 20.039 | 1.00 | 14.62 |
| ATOM 2859 | H | ARG C | 13 | −10.181 | 39.450 | 15.778 | 1.00 | 20.00 |
| ATOM 2860 | HE | ARG C | 13 | −13.809 | 36.153 | 17.881 | 1.00 | 20.00 |
| ATOM 2861 | 1 HH1 | ARG C | 13 | −13.804 | 35.371 | 21.344 | 1.00 | 20.00 |
| ATOM 2862 | 2 HH1 | ARG C | 13 | −14.745 | 35.930 | 20.022 | 1.00 | 20.00 |
| ATOM 2863 | 1 HH2 | ARG C | 13 | −11.538 | 34.791 | 21.003 | 1.00 | 20.00 |
| ATOM 2864 | 2 HH2 | ARG C | 13 | −10.881 | 34.919 | 19.423 | 1.00 | 20.00 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM 2865 | N | SER | C | 14 | −6.474 | 37.379 | 16.812 | 1.00 | 5.58 |
| ATOM 2866 | CA | SER | C | 14 | −5.119 | 37.234 | 16.246 | 1.00 | 5.58 |
| ATOM 2867 | C | SER | C | 14 | −5.031 | 36.662 | 14.863 | 1.00 | 5.58 |
| ATOM 2868 | O | SER | C | 14 | −4.028 | 36.618 | 14.167 | 1.00 | 5.58 |
| ATOM 2869 | CB | SER | C | 14 | −4.293 | 36.320 | 17.124 | 1.00 | 5.58 |
| ATOM 2870 | OG | SER | C | 14 | −4.659 | 36.531 | 18.486 | 1.00 | 5.58 |
| ATOM 2871 | H | SER | C | 14 | −6.642 | 36.896 | 17.668 | 1.00 | 20.00 |
| ATOM 2872 | HG | SER | C | 14 | −3.837 | 36.636 | 18.947 | 1.00 | 20.00 |
| ATOM 2873 | N | MET | C | 15 | −6.184 | 36.171 | 14.535 | 1.00 | 11.01 |
| ATOM 2874 | CA | MET | C | 15 | −6.374 | 35.586 | 13.259 | 1.00 | 11.01 |
| ATOM 2875 | C | MET | C | 15 | −6.693 | 36.528 | 12.088 | 1.00 | 11.01 |
| ATOM 2876 | O | MET | C | 15 | −5.846 | 36.537 | 11.212 | 1.00 | 11.01 |
| ATOM 2877 | CB | MET | C | 15 | −7.437 | 34.564 | 13.481 | 1.00 | 11.01 |
| ATOM 2878 | CG | MET | C | 15 | −7.404 | 33.532 | 14.569 | 1.00 | 11.01 |
| ATOM 2879 | SD | MET | C | 15 | −8.931 | 32.670 | 14.158 | 1.00 | 11.01 |
| ATOM 2880 | CE | MET | C | 15 | −9.999 | 33.725 | 13.122 | 1.00 | 11.01 |
| ATOM 2881 | H | MET | C | 15 | −6.889 | 36.187 | 15.229 | 1.00 | 20.00 |
| ATOM 2882 | N | PRO | C | 16 | −7.852 | 37.294 | 11.986 | 1.00 | 6.76 |
| ATOM 2883 | CA | PRO | C | 16 | −7.930 | 38.151 | 10.789 | 1.00 | 6.76 |
| ATOM 2884 | C | PRO | C | 16 | −7.180 | 39.476 | 10.950 | 1.00 | 6.76 |
| ATOM 2885 | O | PRO | C | 16 | −6.989 | 40.010 | 12.036 | 1.00 | 6.76 |
| ATOM 2886 | CB | PRO | C | 16 | −9.435 | 38.379 | 10.638 | 1.00 | 6.76 |
| ATOM 2887 | CG | PRO | C | 16 | −9.925 | 38.490 | 12.082 | 1.00 | 6.76 |
| ATOM 2888 | CD | PRO | C | 16 | −9.037 | 37.494 | 12.840 | 1.00 | 6.76 |
| ATOM 2889 | N | LEU | C | 17 | −6.817 | 40.019 | 9.779 | 1.00 | 6.37 |
| ATOM 2890 | CA | LEU | C | 17 | −6.599 | 41.462 | 9.727 | 1.00 | 6.37 |
| ATOM 2891 | C | LEU | C | 17 | −7.895 | 42.076 | 9.257 | 1.00 | 6.37 |
| ATOM 2892 | O | LEU | C | 17 | −8.391 | 41.740 | 8.191 | 1.00 | 6.37 |
| ATOM 2893 | CB | LEU | C | 17 | −5.479 | 41.803 | 8.742 | 1.00 | 6.37 |
| ATOM 2894 | CG | LEU | C | 17 | −5.026 | 43.267 | 8.733 | 1.00 | 6.37 |
| ATOM 2895 | CD1 | LEU | C | 17 | −4.530 | 43.745 | 10.102 | 1.00 | 6.37 |
| ATOM 2896 | CD2 | LEU | C | 17 | −3.983 | 43.501 | 7.639 | 1.00 | 6.37 |
| ATOM 2897 | H | LEU | C | 17 | −6.948 | 39.513 | 8.930 | 1.00 | 20.00 |
| ATOM 2898 | N | GLU | C | 18 | −8.446 | 42.951 | 10.101 | 1.00 | 14.08 |
| ATOM 2899 | CA | GLU | C | 18 | −9.702 | 43.528 | 9.645 | 1.00 | 14.08 |
| ATOM 2900 | C | GLU | C | 18 | −9.574 | 45.029 | 9.569 | 1.00 | 14.08 |
| ATOM 2901 | O | GLU | C | 18 | −8.831 | 45.628 | 10.338 | 1.00 | 14.08 |
| ATOM 2902 | CB | GLU | C | 18 | −10.847 | 43.100 | 10.561 | 1.00 | 14.08 |
| ATOM 2903 | CG | GLU | C | 18 | −12.185 | 42.922 | 9.829 | 1.00 | 14.08 |
| ATOM 2904 | CD | GLU | C | 18 | −13.334 | 42.810 | 10.818 | 1.00 | 14.08 |
| ATOM 2905 | OE1 | GLU | C | 18 | −13.140 | 42.401 | 11.960 | 1.00 | 14.08 |
| ATOM 2906 | OE2 | GLU | C | 18 | −14.450 | 43.208 | 10.492 | 1.00 | 14.08 |
| ATOM 2907 | H | GLU | C | 18 | −8.002 | 43.255 | 10.944 | 1.00 | 20.00 |
| ATOM 2908 | N | TRP | C | 19 | −10.296 | 45.601 | 8.598 | 1.00 | 6.20 |
| ATOM 2909 | CA | TRP | C | 19 | −10.197 | 47.049 | 8.465 | 1.00 | 6.20 |
| ATOM 2910 | C | TRP | C | 19 | −11.343 | 47.773 | 9.141 | 1.00 | 6.20 |
| ATOM 2911 | O | TRP | C | 19 | −12.379 | 47.189 | 9.439 | 1.00 | 6.20 |
| ATOM 2912 | CB | TRP | C | 19 | −10.106 | 47.441 | 6.991 | 1.00 | 6.20 |
| ATOM 2913 | CG | TRP | C | 19 | −8.853 | 46.885 | 6.352 | 1.00 | 6.20 |
| ATOM 2914 | CD1 | TRP | C | 19 | −8.795 | 45.941 | 5.314 | 1.00 | 6.20 |
| ATOM 2915 | CD2 | TRP | C | 19 | −7.474 | 47.195 | 6.660 | 1.00 | 6.20 |
| ATOM 2916 | NE1 | TRP | C | 19 | −7.507 | 45.654 | 4.982 | 1.00 | 6.20 |
| ATOM 2917 | CE2 | TRP | C | 19 | −6.655 | 46.395 | 5.794 | 1.00 | 6.20 |
| ATOM 2918 | CE3 | TRP | C | 19 | −6.866 | 48.054 | 7.601 | 1.00 | 6.20 |
| ATOM 2919 | CZ2 | TRP | C | 19 | −5.247 | 46.481 | 5.878 | 1.00 | 6.20 |
| ATOM 2920 | CZ3 | TRP | C | 19 | −5.459 | 48.130 | 7.676 | 1.00 | 6.20 |
| ATOM 2921 | CH2 | TRP | C | 19 | −4.653 | 47.342 | 6.824 | 1.00 | 6.20 |
| ATOM 2922 | H | TRP | C | 19 | −10.942 | 45.070 | 8.052 | 1.00 | 20.00 |
| ATOM 2923 | HE1 | TRP | C | 19 | −7.222 | 45.005 | 4.305 | 1.00 | 20.00 |
| ATOM 2924 | N | GLU | C | 20 | −11.103 | 49.074 | 9.364 | 1.00 | 5.13 |
| ATOM 2925 | CA | GLU | C | 20 | −12.119 | 49.871 | 10.042 | 1.00 | 5.13 |
| ATOM 2926 | C | GLU | C | 20 | −12.285 | 51.257 | 9.464 | 1.00 | 5.13 |
| ATOM 2927 | O | GLU | C | 20 | −11.330 | 51.830 | 8.954 | 1.00 | 5.13 |
| ATOM 2928 | CB | GLU | C | 20 | −11.781 | 49.982 | 11.524 | 1.00 | 5.13 |
| ATOM 2929 | CG | GLU | C | 20 | −12.881 | 49.370 | 12.390 | 1.00 | 5.13 |
| ATOM 2930 | CD | GLU | C | 20 | −12.543 | 49.511 | 13.862 | 1.00 | 5.13 |
| ATOM 2931 | OE1 | GLU | C | 20 | −12.218 | 50.617 | 14.289 | 1.00 | 5.13 |
| ATOM 2932 | OE2 | GLU | C | 20 | −12.620 | 48.516 | 14.582 | 1.00 | 5.13 |
| ATOM 2933 | H | GLU | C | 20 | −10.183 | 49.447 | 9.224 | 1.00 | 20.00 |
| ATOM 2934 | N | ASF | C | 21 | −13.538 | 51.745 | 9.612 | 1.00 | 13.73 |
| ATOM 2935 | CA | ASF | C | 21 | −13.925 | 53.060 | 9.089 | 1.00 | 13.73 |
| ATOM 2936 | C | ASP | C | 21 | −14.013 | 54.183 | 10.109 | 1.00 | 13.73 |
| ATOM 2937 | O | ASP | C | 21 | −13.694 | 55.339 | 9.855 | 1.00 | 13.73 |
| ATOM 2938 | CB | ASP | C | 21 | −15.246 | 53.010 | 8.312 | 1.00 | 13.73 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM 2939 | CG | ASP | C | 21 | −15.275 | 51.896 | 7.282 | 1.00 | 13.73 |
| ATOM 2940 | OD1 | ASP | C | 21 | −16.364 | 51.402 | 7.002 | 1.00 | 13.73 |
| ATOM 2941 | OD2 | ASP | C | 21 | −14.223 | 51.517 | 6.768 | 1.00 | 13.73 |
| ATOM 2942 | H | ASP | C | 21 | −14.244 | 51.127 | 9.948 | 1.00 | 20.00 |
| ATOM 2943 | N | THR | C | 22 | −14.467 | 53.815 | 11.308 | 1.00 | 11.65 |
| ATOM 2944 | CA | THR | C | 22 | −14.684 | 54.918 | 12.238 | 1.00 | 11.65 |
| ATOM 2945 | C | THR | C | 22 | −13.502 | 55.223 | 13.145 | 1.00 | 11.65 |
| ATOM 2946 | O | THR | C | 22 | −13.506 | 55.015 | 14.351 | 1.00 | 11.65 |
| ATOM 2947 | CB | THR | C | 22 | −16.006 | 54.707 | 12.979 | 1.00 | 11.65 |
| ATOM 2948 | OG1 | THR | C | 22 | −17.011 | 54.362 | 12.015 | 1.00 | 11.65 |
| ATOM 2949 | CG2 | THR | C | 22 | −16.454 | 55.936 | 13.781 | 1.00 | 11.65 |
| ATOM 2950 | H | THR | C | 22 | −14.702 | 52.870 | 11.523 | 1.00 | 20.00 |
| ATOM 2951 | HG1 | THR | C | 22 | −17.830 | 54.261 | 12.480 | 1.00 | 20.00 |
| ATOM 2952 | N | TYR | C | 23 | −12.472 | 55.754 | 12.473 | 1.00 | 6.57 |
| ATOM 2953 | CA | TYR | C | 23 | −11.280 | 56.165 | 13.207 | 1.00 | 6.57 |
| ATOM 2954 | C | TYR | C | 23 | −10.882 | 57.564 | 12.776 | 1.00 | 6.57 |
| ATOM 2955 | O | TYR | C | 23 | −11.265 | 58.019 | 11.707 | 1.00 | 6.57 |
| ATOM 2956 | CB | TYR | C | 23 | −10.164 | 55.122 | 13.006 | 1.00 | 6.57 |
| ATOM 2957 | CG | TYR | C | 23 | −8.920 | 55.433 | 13.811 | 1.00 | 6.57 |
| ATOM 2958 | CD1 | TYR | C | 23 | −7.789 | 55.957 | 13.149 | 1.00 | 6.57 |
| ATOM 2959 | CD2 | TYR | C | 23 | −8.927 | 55.200 | 15.201 | 1.00 | 6.57 |
| ATOM 2960 | CE1 | TYR | C | 23 | −6.647 | 56.277 | 13.901 | 1.00 | 6.57 |
| ATOM 2961 | CE2 | TYR | C | 23 | −7.782 | 55.514 | 15.951 | 1.00 | 6.57 |
| ATOM 2962 | CZ | TYR | C | 23 | −6.660 | 56.057 | 15.293 | 1.00 | 6.57 |
| ATOM 2963 | OH | TYR | C | 23 | −5.540 | 56.393 | 16.025 | 1.00 | 6.57 |
| ATOM 2964 | H | TYR | C | 23 | −12.573 | 55.927 | 11.487 | 1.00 | 20.00 |
| ATOM 2965 | HH | TYR | C | 23 | −5.604 | 56.042 | 16.904 | 1.00 | 20.00 |
| ATOM 2966 | N | GLY | C | 24 | −10.108 | 58.222 | 13.667 | 1.00 | 5.63 |
| ATOM 2967 | CA | GLY | C | 24 | −9.714 | 59.625 | 13.501 | 1.00 | 5.63 |
| ATOM 2968 | C | GLY | C | 24 | −9.473 | 60.080 | 12.077 | 1.00 | 5.63 |
| ATOM 2969 | O | GLY | C | 24 | −10.171 | 60.934 | 11.543 | 1.00 | 5.63 |
| ATOM 2970 | H | GLY | C | 24 | −9.854 | 57.735 | 14.501 | 1.00 | 20.00 |
| ATOM 2971 | N | ILE | C | 25 | −8.454 | 59.456 | 11.464 | 1.00 | 5.38 |
| ATOM 2972 | CA | ILE | C | 25 | −8.434 | 59.750 | 10.041 | 1.00 | 5.38 |
| ATOM 2973 | C | ILE | C | 25 | −8.615 | 58.538 | 9.161 | 1.00 | 5.38 |
| ATOM 2974 | O | ILE | C | 25 | −7.741 | 58.094 | 8.430 | 1.00 | 5.38 |
| ATOM 2975 | CB | ILE | C | 25 | −7.254 | 60.623 | 9.618 | 1.00 | 5.38 |
| ATOM 2976 | CG1 | ILE | C | 25 | −6.921 | 61.660 | 10.699 | 1.00 | 5.38 |
| ATOM 2977 | CG2 | ILE | C | 25 | −7.670 | 61.298 | 8.310 | 1.00 | 5.38 |
| ATOM 2978 | CD1 | ILE | C | 25 | −5.541 | 62.297 | 10.587 | 1.00 | 5.38 |
| ATOM 2979 | H | ILE | C | 25 | −7.838 | 58.799 | 11.901 | 1.00 | 20.00 |
| ATOM 2980 | N | VAL | C | 26 | −9.849 | 58.042 | 9.273 | 1.00 | 4.68 |
| ATOM 2981 | CA | VAL | C | 26 | −10.267 | 57.013 | 8.342 | 1.00 | 4.68 |
| ATOM 2982 | C | VAL | C | 26 | −11.447 | 57.485 | 7.520 | 1.00 | 4.68 |
| ATOM 2983 | O | VAL | C | 26 | −12.430 | 58.020 | 8.017 | 1.00 | 4.68 |
| ATOM 2984 | CB | VAL | C | 26 | −10.539 | 55.710 | 9.086 | 1.00 | 4.68 |
| ATOM 2985 | CG1 | VAL | C | 26 | −11.229 | 54.705 | 8.186 | 1.00 | 4.68 |
| ATOM 2986 | CG2 | VAL | C | 26 | −9.233 | 55.113 | 9.605 | 1.00 | 4.68 |
| ATOM 2987 | H | VAL | C | 26 | −10.506 | 58.396 | 9.945 | 1.00 | 20.00 |
| ATOM 2988 | N | LEU | C | 27 | −11.244 | 57.327 | 6.202 | 1.00 | 5.09 |
| ATOM 2989 | CA | LEU | C | 27 | −12.194 | 57.944 | 5.282 | 1.00 | 5.09 |
| ATOM 2990 | C | LEU | C | 27 | −12.657 | 57.046 | 4.182 | 1.00 | 5.09 |
| ATOM 2991 | O | LEU | C | 27 | −12.047 | 56.030 | 3.863 | 1.00 | 5.09 |
| ATOM 2992 | CB | LEU | C | 27 | −11.602 | 59.160 | 4.596 | 1.00 | 5.09 |
| ATOM 2993 | CG | LEU | C | 27 | −10.839 | 59.981 | 5.603 | 1.00 | 5.09 |
| ATOM 2994 | CD1 | LEU | C | 27 | −9.551 | 60.492 | 4.968 | 1.00 | 5.09 |
| ATOM 2995 | CD2 | LEU | C | 27 | −11.756 | 60.922 | 6.397 | 1.00 | 5.09 |
| ATOM 2996 | H | LEU | C | 27 | −10.422 | 56.842 | 5.903 | 1.00 | 20.00 |
| ATOM 2997 | N | LEU | C | 28 | −13.754 | 57.566 | 3.606 | 1.00 | 7.30 |
| ATOM 2998 | CA | LEU | C | 28 | −14.469 | 56.924 | 2.525 | 1.00 | 7.30 |
| ATOM 2999 | C | LEU | C | 28 | −15.080 | 57.978 | 1.618 | 1.00 | 7.30 |
| ATOM 3000 | O | LEU | C | 28 | −15.783 | 58.861 | 2.091 | 1.00 | 7.30 |
| ATOM 3001 | CB | LEU | C | 28 | −15.574 | 56.077 | 3.156 | 1.00 | 7.30 |
| ATOM 3002 | CG | LEU | C | 28 | −16.415 | 55.343 | 2.124 | 1.00 | 7.30 |
| ATOM 3003 | CD1 | LEU | C | 28 | −15.498 | 54.547 | 1.215 | 1.00 | 7.30 |
| ATOM 3004 | CD2 | LEU | C | 28 | −17.526 | 54.498 | 2.745 | 1.00 | 7.30 |
| ATOM 3005 | H | LEU | C | 28 | −14.169 | 58.398 | 3.975 | 1.00 | 20.00 |
| ATOM 3006 | N | SER | C | 29 | −14.830 | 57.802 | 0.310 | 1.00 | 16.57 |
| ATOM 3007 | CA | SER | C | 29 | −15.560 | 58.618 | −0.661 | 1.00 | 16.57 |
| ATOM 3008 | C | SER | C | 29 | −15.927 | 57.838 | −1.909 | 1.00 | 16.57 |
| ATOM 3009 | O | SER | C | 29 | −15.149 | 57.761 | −2.849 | 1.00 | 16.57 |
| ATOM 3010 | CB | SER | C | 29 | −14.747 | 59.853 | −1.060 | 1.00 | 16.57 |
| ATOM 3011 | CG | SER | C | 29 | −14.301 | 60.551 | 0.105 | 1.00 | 16.57 |
| ATOM 3012 | H | SER | C | 29 | −14.073 | 57.193 | 0.058 | 1.00 | 20.00 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM 3013 | HG | SER | C | 29 | −13.788 | 61.289 | −0.191 | 1.00 | 20.00 |
| ATOM 3014 | N | GLY | C | 30 | −17.133 | 57.242 | −1.899 | 1.00 | 4.20 |
| ATOM 3015 | CA | GLY | C | 30 | −17.540 | 56.505 | −3.103 | 1.00 | 4.20 |
| ATOM 3016 | C | GLY | C | 30 | −17.068 | 55.057 | −3.192 | 1.00 | 4.20 |
| ATOM 3017 | O | GLY | C | 30 | −17.661 | 54.210 | −3.845 | 1.00 | 4.20 |
| ATOM 3018 | H | GLY | C | 30 | −17.718 | 57.271 | −1.087 | 1.00 | 20.00 |
| ATOM 3019 | N | VAL | C | 31 | −15.961 | 54.797 | −2.483 | 1.00 | 3.10 |
| ATOM 3020 | CA | VAL | C | 31 | −15.540 | 53.404 | −2.331 | 1.00 | 3.10 |
| ATOM 3021 | C | VAL | C | 31 | −16.559 | 52.715 | −1.420 | 1.00 | 3.10 |
| ATOM 3022 | O | VAL | C | 31 | −17.358 | 53.381 | −0.772 | 1.00 | 3.10 |
| ATOM 3023 | CB | VAL | C | 31 | −14.095 | 53.422 | −1.769 | 1.00 | 3.10 |
| ATOM 3024 | CG1 | VAL | C | 31 | −13.457 | 52.056 | −1.499 | 1.00 | 3.10 |
| ATOM 3025 | CG2 | VAL | C | 31 | −13.194 | 54.261 | −2.679 | 1.00 | 3.10 |
| ATOM 3026 | H | VAL | C | 31 | −15.577 | 55.509 | −1.903 | 1.00 | 20.00 |
| ATOM 3027 | N | LYS | C | 32 | −16.526 | 51.382 | −1.382 | 1.00 | 18.46 |
| ATOM 3028 | CA | LYS | C | 32 | −17.316 | 50.776 | −0.318 | 1.00 | 18.46 |
| ATOM 3029 | C | LYS | C | 32 | −16.521 | 49.683 | 0.344 | 1.00 | 18.46 |
| ATOM 3030 | O | LYS | C | 32 | −15.732 | 49.009 | −0.303 | 1.00 | 18.46 |
| ATOM 3031 | CB | LYS | C | 32 | −18.653 | 50.264 | −0.861 | 1.00 | 18.46 |
| ATOM 3032 | CG | LYS | C | 32 | −19.634 | 49.808 | 0.224 | 1.00 | 18.46 |
| ATOM 3033 | CD | LYS | C | 32 | −20.977 | 49.373 | −0.353 | 1.00 | 18.46 |
| ATOM 3034 | CE | LYS | C | 32 | −20.842 | 48.234 | −1.360 | 1.00 | 18.46 |
| ATOM 3035 | NZ | LYS | C | 32 | −22.165 | 47.978 | −1.939 | 1.00 | 18.46 |
| ATOM 3036 | H | LYS | C | 32 | −15.934 | 50.855 | −1.996 | 1.00 | 20.00 |
| ATOM 3037 | 1 HZ | LYS | C | 32 | −22.091 | 47.237 | −2.663 | 1.00 | 20.00 |
| ATOM 3038 | 2 HZ | LYS | C | 32 | −22.819 | 47.681 | −1.186 | 1.00 | 20.00 |
| ATOM 3039 | 3 HZ | LYS | C | 32 | −22.516 | 48.855 | −2.374 | 1.00 | 20.00 |
| ATOM 3040 | N | TYR | C | 33 | −16.750 | 49.537 | 1.652 | 1.00 | 6.60 |
| ATOM 3041 | CA | TYR | C | 33 | −16.085 | 48.415 | 2.297 | 1.00 | 6.60 |
| ATOM 3042 | C | TYR | C | 33 | −17.008 | 47.232 | 2.352 | 1.00 | 6.60 |
| ATOM 3043 | 0 | TYR | C | 33 | −18.202 | 47.359 | 2.600 | 1.00 | 6.60 |
| ATOM 3044 | CB | TYR | C | 33 | −15.590 | 48.819 | 3.685 | 1.00 | 6.60 |
| ATOM 3045 | CG | TYR | C | 33 | −14.855 | 50.126 | 3.535 | 1.00 | 6.60 |
| ATOM 3046 | CD1 | TYR | C | 33 | −15.445 | 51.301 | 4.037 | 1.00 | 6.60 |
| ATOM 3047 | 2 | TYR | C | 33 | −13.623 | 50.139 | 2.857 | 1.00 | 6.60 |
| ATOM 3048 | CE1 | TYR | C | 33 | −14.780 | 52.522 | 3.855 | 1.00 | 6.60 |
| ATOM 3049 | CE2 | TYR | C | 33 | −12.980 | 51.364 | 2.640 | 1.00 | 6.60 |
| ATOM 3050 | CZ | TYR | C | 33 | −13.568 | 52.536 | 3.138 | 1.00 | 6.60 |
| ATOM 3051 | OH | TYR | C | 33 | −12.933 | 53.732 | 2.886 | 1.00 | 6.60 |
| ATOM 3052 | H | TYR | C | 33 | −17.413 | 50.092 | 2.154 | 1.00 | 20.00 |
| ATOM 3053 | HH | TYR | C | 33 | −12.187 | 53.844 | 3.467 | 1.00 | 20.00 |
| ATOM 3054 | N | LYS | C | 34 | −16.411 | 46.075 | 2.067 | 1.00 | 11.73 |
| ATOM 3055 | CA | LYS | C | 34 | −17.262 | 44.901 | 2.159 | 1.00 | 11.73 |
| ATOM 3056 | C | LYS | C | 34 | −16.705 | 43.878 | 3.137 | 1.00 | 11.73 |
| ATOM 3057 | O | LYS | C | 34 | −16.525 | 44.178 | 4.310 | 1.00 | 11.73 |
| ATOM 3058 | CB | LYS | C | 34 | −17.587 | 44.396 | 0.747 | 1.00 | 11.73 |
| ATOM 3059 | CG | LYS | C | 34 | −18.886 | 43.591 | 0.707 | 1.00 | 11.73 |
| ATOM 3060 | CD | LYS | C | 34 | −19.229 | 43.105 | −0.697 | 1.00 | 11.73 |
| ATOM 3061 | CE | LYS | C | 34 | −20.485 | 42.237 | −0.693 | 1.00 | 11.73 |
| ATOM 3062 | NZ | LYS | C | 34 | −20.821 | 41.872 | −2.075 | 1.00 | 11.73 |
| ATOM 3063 | H | LYS | C | 34 | −15.450 | 46.067 | 1.778 | 1.00 | 20.00 |
| ATOM 3064 | 1 HZ | LYS | C | 34 | −21.636 | 41.226 | −2.078 | 1.00 | 20.00 |
| ATOM 3065 | 2 HZ | LYS | C | 34 | −21.060 | 42.734 | −2.605 | 1.00 | 20.00 |
| ATOM 3066 | 3 HZ | LYS | C | 34 | −20.004 | 41.413 | −2.526 | 1.00 | 20.00 |
| ATOM 3067 | N | LYS | C | 35 | −16.406 | 42.665 | 2.640 | 1.00 | 6.70 |
| ATOM 3068 | CA | LYS | C | 35 | −15.822 | 41.689 | 3.557 | 1.00 | 6.70 |
| ATOM 3069 | C | LYS | C | 35 | −14.321 | 41.878 | 3.697 | 1.00 | 6.70 |
| ATOM 3070 | O | LYS | C | 35 | −13.521 | 41.110 | 3.184 | 1.00 | 6.70 |
| ATOM 3071 | CB | LYS | C | 35 | −16.175 | 40.276 | 3.087 | 1.00 | 6.70 |
| ATOM 3072 | CG | LYS | C | 35 | −17.685 | 40.034 | 2.995 | 1.00 | 6.70 |
| ATOM 3073 | CD | LYS | C | 35 | −18.011 | 38.676 | 2.372 | 1.00 | 6.70 |
| ATOM 3074 | CE | LYS | C | 35 | −19.513 | 38.403 | 2.282 | 1.00 | 6.70 |
| ATOM 3075 | NZ | LYS | C | 35 | −19.727 | 37.118 | 1.600 | 1.00 | 6.70 |
| ATOM 3076 | H | LYS | C | 35 | −16.468 | 42.447 | 1.669 | 1.00 | 20.00 |
| ATOM 3077 | 1 HZ | LYS | C | 35 | −20.743 | 36.895 | 1.580 | 1.00 | 20.00 |
| ATOM 3078 | 2 HZ | LYS | C | 35 | −19.362 | 37.178 | 0.628 | 1.00 | 20.00 |
| ATOM 3079 | 3 HZ | LYS | C | 35 | −19.217 | 36.370 | 2.112 | 1.00 | 20.00 |
| ATOM 3080 | N | GLY | C | 36 | −13.989 | 42.981 | 4.392 | 1.00 | 3.55 |
| ATOM 3081 | CA | GLY | C | 36 | −12.577 | 43.326 | 4.576 | 1.00 | 3.55 |
| ATOM 3082 | C | GLY | C | 36 | −11.851 | 43.783 | 3.317 | 1.00 | 3.55 |
| ATOM 3083 | O | GLY | C | 36 | −10.642 | 43.652 | 3.185 | 1.00 | 3.55 |
| ATOM 3084 | H | GLY | C | 36 | −14.727 | 43.549 | 4.767 | 1.00 | 20.00 |
| ATOM 3085 | N | GLY | C | 37 | −12.652 | 44.331 | 2.388 | 1.00 | 4.03 |
| ATOM 3086 | CA | GLY | C | 37 | −12.034 | 44.710 | 1.123 | 1.00 | 4.03 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3087 | C | GLY C | 37 | −12.679 | 45.921 | 0.506 | 1.00 | 4.03 |
| ATOM 3088 | O | GLY C | 37 | −13.788 | 46.300 | 0.872 | 1.00 | 4.03 |
| ATOM 3089 | H | GLY C | 37 | −13.628 | 44.459 | 2.543 | 1.00 | 20.00 |
| ATOM 3090 | N | LEU C | 38 | −11.915 | 46.516 | −0.425 | 1.00 | 5.45 |
| ATOM 3091 | CA | LEU C | 38 | −12.392 | 47.771 | −1.003 | 1.00 | 5.45 |
| ATOM 3092 | C | LEU C | 38 | −13.036 | 47.562 | −2.349 | 1.00 | 5.45 |
| ATOM 3093 | O | LEU C | 38 | −12.464 | 46.930 | −3.222 | 1.00 | 5.45 |
| ATOM 3094 | CB | LEU C | 38 | −11.280 | 48.813 | −1.199 | 1.00 | 5.45 |
| ATOM 3095 | CG | LEU C | 38 | −10.282 | 49.055 | −0.062 | 1.00 | 5.45 |
| ATOM 3096 | CD1 | LEU C | 38 | −9.653 | 50.439 | −0.174 | 1.00 | 5.45 |
| ATOM 3097 | CD2 | LEU C | 38 | −10.857 | 48.872 | 1.331 | 1.00 | 5.45 |
| ATOM 3098 | H | LEU C | 38 | −11.052 | 46.088 | −0.705 | 1.00 | 20.00 |
| ATOM 3099 | N | VAL C | 39 | −14.234 | 48.139 | −2.483 | 1.00 | 2.74 |
| ATOM 3100 | CA | VAL C | 39 | −14.872 | 48.161 | −3.798 | 1.00 | 2.74 |
| ATOM 3101 | C | VAL C | 39 | −14.585 | 49.475 | −4.500 | 1.00 | 2.74 |
| ATOM 3102 | O | VAL C | 39 | −14.854 | 50.545 | −3.963 | 1.00 | 2.74 |
| ATOM 3103 | CB | VAL C | 39 | −16.392 | 47.973 | −3.676 | 1.00 | 2.74 |
| ATOM 3104 | CG1 | VAL C | 39 | −17.034 | 47.749 | −5.049 | 1.00 | 2.74 |
| ATOM 3105 | CG2 | VAL C | 39 | −16.763 | 46.864 | −2.691 | 1.00 | 2.74 |
| ATOM 3106 | H | VAL C | 39 | −14.628 | 48.615 | −1.697 | 1.00 | 20.00 |
| ATOM 3107 | N | ILE C | 40 | −14.035 | 49.356 | −5.717 | 1.00 | 15.04 |
| ATOM 3108 | CA | ILE C | 40 | −13.733 | 50.589 | −6.445 | 1.00 | 15.04 |
| ATOM 3109 | C | ILE C | 40 | −14.933 | 51.146 | −7.206 | 1.00 | 15.04 |
| ATOM 3110 | O | ILE C | 40 | −15.637 | 50.454 | −7.931 | 1.00 | 15.04 |
| ATOM 3111 | CB | ILE C | 40 | −12.482 | 50.404 | −7.334 | 1.00 | 15.04 |
| ATOM 3112 | CG1 | ILE C | 40 | −11.224 | 50.269 | −6.468 | 1.00 | 15.04 |
| ATOM 3113 | CG2 | ILE C | 40 | −12.258 | 51.589 | −8.277 | 1.00 | 15.04 |
| ATOM 3114 | CD1 | ILE C | 40 | −10.921 | 48.875 | −5.921 | 1.00 | 15.04 |
| ATOM 3115 | H | ILE C | 40 | −13.823 | 48.444 | −6.087 | 1.00 | 20.00 |
| ATOM 3116 | N | ASN C | 41 | −15.136 | 52.457 | −6.980 | 1.00 | 16.19 |
| ATOM 3117 | CA | ASN C | 41 | −16.258 | 53.161 | −7.609 | 1.00 | 16.19 |
| ATOM 3118 | C | ASN C | 41 | −16.095 | 53.432 | −9.097 | 1.00 | 16.19 |
| ATOM 3119 | O | ASN C | 41 | −17.018 | 53.256 | −9.881 | 1.00 | 16.19 |
| ATOM 3120 | CB | ASN C | 41 | −16.510 | 54.481 | −6.867 | 1.00 | 16.19 |
| ATOM 3121 | CG | ASN C | 41 | −17.861 | 55.130 | −7.167 | 1.00 | 16.19 |
| ATOM 3122 | OD1 | ASN C | 41 | −18.713 | 55.266 | −6.306 | 1.00 | 16.19 |
| ATOM 3123 | ND2 | ASN C | 41 | −18.015 | 55.628 | −8.401 | 1.00 | 16.19 |
| ATOM 3124 | H | ASN C | 41 | −14.522 | 52.913 | −6.338 | 1.00 | 20.00 |
| ATOM 3125 | 1 HD2 | ASN C | 41 | −17.360 | 55.540 | −9.150 | 1.00 | 20.00 |
| ATOM 3126 | 2 HD2 | ASN C | 41 | −18.876 | 56.096 | −8.588 | 1.00 | 29.00 |
| ATOM 3127 | N | GLU C | 42 | −14.907 | 53.944 | −9.454 | 1.00 | 4.33 |
| ATOM 3128 | CA | GLU C | 42 | −14.787 | 54.466 | −10.814 | 1.00 | 4.33 |
| ATOM 3129 | C | GLU C | 42 | −13.534 | 53.977 | −11.493 | 1.00 | 4.33 |
| ATOM 3130 | O | GLU C | 42 | −12.595 | 53.510 | −10.865 | 1.00 | 4.33 |
| ATOM 3131 | CB | GLU C | 42 | −14.792 | 55.998 | −10.804 | 1.00 | 4.33 |
| ATOM 3132 | CG | GLU C | 42 | −16.101 | 56.666 | −11.259 | 1.00 | 4.33 |
| ATOM 3133 | CD | GLU C | 42 | −16.092 | 58.138 | −10.857 | 1.00 | 4.33 |
| ATOM 3134 | OE1 | GLU C | 42 | −15.141 | 58.844 | −11.202 | 1.00 | 4.33 |
| ATOM 3135 | OE2 | GLU C | 42 | −17.018 | 58.566 | −10.153 | 1.00 | 4.33 |
| ATOM 3136 | H | GLU C | 42 | −14.103 | 53.956 | −8.857 | 1.00 | 20.00 |
| ATOM 3137 | N | THR C | 43 | −13.547 | 54.141 | −12.818 | 1.00 | 2.66 |
| ATOM 3138 | CA | THR C | 43 | −12.307 | 53.867 | −13.530 | 1.00 | 2.66 |
| ATOM 3139 | C | THR C | 43 | −11.293 | 54.986 | −13.353 | 1.00 | 2.66 |
| ATOM 3140 | O | THR C | 43 | −11.627 | 56.171 | −13.294 | 1.00 | 2.66 |
| ATOM 3141 | CB | THR C | 43 | −12.638 | 53.612 | −15.004 | 1.00 | 2.66 |
| ATOM 3142 | CG1 | THR C | 43 | −13.743 | 52.704 | −15.085 | 1.00 | 2.66 |
| ATOM 3143 | CG2 | THR C | 43 | −11.456 | 53.083 | −15.823 | 1.00 | 2.66 |
| ATOM 3144 | H | THR C | 43 | −14.362 | 54.449 | −13.307 | 1.00 | 20.00 |
| ATOM 3145 | HG1 | THR C | 43 | −13.856 | 52.497 | −16.004 | 1.00 | 20.00 |
| ATOM 3146 | N | GLY C | 44 | −10.030 | 54.561 | −13.267 | 1.00 | 2.64 |
| ATOM 3147 | CA | GLY C | 44 | −8.975 | 55.561 | −13.314 | 1.00 | 2.64 |
| ATOM 3148 | C | GLY C | 44 | −7.771 | 55.114 | −12.534 | 1.00 | 2.64 |
| ATOM 3149 | O | GLY C | 44 | −7.686 | 53.985 | −12.070 | 1.00 | 2.64 |
| ATOM 3150 | H | GLY C | 44 | −9.822 | 53.580 | −13.185 | 1.00 | 20.00 |
| ATOM 3151 | N | LEU C | 45 | −6.843 | 56.067 | −12.406 | 1.00 | 5.33 |
| ATOM 3152 | CA | LEU C | 45 | −5.669 | 55.735 | −11.616 | 1.00 | 5.33 |
| ATOM 3153 | C | LEU C | 45 | −5.924 | 55.899 | −10.146 | 1.00 | 5.33 |
| ATOM 3154 | O | LEU C | 45 | −6.508 | 56.873 | −9.692 | 1.00 | 5.33 |
| ATOM 3155 | CB | LEU C | 45 | −4.498 | 56.590 | −12.069 | 1.00 | 5.33 |
| ATOM 3156 | CG | LEU C | 45 | −4.141 | 56.211 | −13.500 | 1.00 | 5.33 |
| ATOM 3157 | CD1 | LEU C | 45 | −3.565 | 57.381 | −14.282 | 1.00 | 5.33 |
| ATOM 3158 | CD2 | LEU C | 45 | −3.268 | 54.960 | −13.545 | 1.00 | 5.33 |
| ATOM 3159 | H | LEU C | 45 | −6.982 | 56.997 | −12.739 | 1.00 | 20.00 |
| ATOM 3160 | N | TYR C | 46 | −5.461 | 54.881 | −9.431 | 1.00 | 3.53 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3161 | CA | TYR C | 46 | −5.502 | 54.984 | −7.987 | 1.00 | 3.53 |
| ATOM 3162 | C | TYR C | 46 | −4.104 | 54.772 | −7.471 | 1.00 | 3.53 |
| ATOM 3163 | O | TYR C | 46 | −3.348 | 53.953 | −7.983 | 1.00 | 3.53 |
| ATOM 3164 | CB | TYR C | 46 | −6.466 | 53.953 | −7.388 | 1.00 | 3.53 |
| ATOM 3165 | CG | TYR C | 46 | −7.916 | 54.293 | −7.678 | 1.00 | 3.53 |
| ATOM 3166 | CD1 | TYR C | 46 | −8.468 | 54.022 | −8.949 | 1.00 | 3.53 |
| ATOM 3167 | CD2 | TYR C | 46 | −8.686 | 54.869 | −6.648 | 1.00 | 3.53 |
| ATOM 3168 | CE1 | TYR C | 46 | −9.815 | 54.340 | −9.198 | 1.00 | 3.53 |
| ATOM 3169 | CE2 | TYR C | 46 | −10.033 | 55.180 | −6.893 | 1.00 | 3.53 |
| ATOM 3170 | CZ | TYR C | 46 | −10.582 | 54.916 | −8.164 | 1.00 | 3.53 |
| ATOM 3171 | OH | TYR C | 46 | −11.908 | 55.237 | −8.393 | 1.00 | 3.53 |
| ATOM 3172 | H | TYR C | 46 | −5.022 | 54.096 | −9.783 | 1.00 | 20.00 |
| ATOM 3173 | HH | TYR C | 46 | −12.277 | 55.583 | −7.594 | 1.00 | 20.00 |
| ATOM 3174 | N | PHE C | 47 | −3.802 | 55.550 | −6.430 | 1.00 | 3.38 |
| ATOM 3175 | CA | PHE C | 47 | −2.638 | 55.184 | −5.645 | 1.00 | 3.38 |
| ATOM 3176 | C | PHE C | 47 | −3.095 | 54.309 | −4.503 | 1.00 | 3.38 |
| ATOM 3177 | O | PHE C | 47 | −3.990 | 54.649 | −3.735 | 1.00 | 3.38 |
| ATOM 3178 | CB | PHE C | 47 | −1.899 | 56.433 | −5.168 | 1.00 | 3.38 |
| ATOM 3179 | CG | PHE C | 47 | −0.578 | 56.093 | −4.512 | 1.00 | 3.38 |
| ATOM 3180 | CD1 | PHE C | 47 | 0.570 | 55.933 | −5.316 | 1.00 | 3.38 |
| ATOM 3181 | CD2 | PHE C | 47 | −0.503 | 55.958 | −3.108 | 1.00 | 3.38 |
| ATOM 3182 | CE1 | PHE C | 47 | 1.814 | 55.663 | −4.715 | 1.00 | 3.38 |
| ATOM 3183 | CE2 | PHE C | 47 | 0.740 | 55.689 | −2.502 | 1.00 | 3.38 |
| ATOM 3184 | CZ | PHE C | 47 | 1.887 | 55.553 | −3.311 | 1.00 | 3.38 |
| ATOM 3185 | H | PHE C | 47 | −4.462 | 56.226 | −6.100 | 1.00 | 20.00 |
| ATOM 3186 | N | VAL C | 48 | −2.448 | 53.144 | −4.494 | 1.00 | 2.79 |
| ATOM 3187 | CA | VAL C | 48 | −2.731 | 52.119 | −3.504 | 1.00 | 2.79 |
| ATOM 3188 | C | VAL C | 48 | −1.569 | 52.062 | −2.537 | 1.00 | 2.79 |
| ATOM 3189 | O | VAL C | 48 | −0.440 | 51.828 | −2.948 | 1.00 | 2.79 |
| ATOM 3190 | CB | VAL C | 48 | −2.895 | 50.780 | −4.237 | 1.00 | 2.79 |
| ATOM 3191 | CG1 | VAL C | 48 | −3.237 | 49.630 | −3.289 | 1.00 | 2.79 |
| ATOM 3192 | CG2 | VAL C | 48 | −3.903 | 50.902 | −5.383 | 1.00 | 2.79 |
| ATOM 3193 | H | VAL C | 48 | −1.733 | 52.986 | −5.178 | 1.00 | 20.00 |
| ATOM 3194 | N | TYR C | 49 | −1.878 | 52.291 | −1.255 | 1.00 | 3.73 |
| ATOM 3195 | CA | TYR C | 49 | −0.801 | 52.202 | −0.273 | 1.00 | 3.73 |
| ATOM 3196 | C | TYR C | 49 | −1.226 | 51.413 | 0.939 | 1.00 | 3.73 |
| ATOM 3197 | O | TYR C | 49 | −2.404 | 51.338 | 1.262 | 1.00 | 3.73 |
| ATOM 3198 | CB | TYR C | 49 | −0.295 | 53.593 | 0.146 | 1.00 | 3.73 |
| ATOM 3199 | CG | TYR C | 49 | −1.390 | 54.417 | 0.789 | 1.00 | 3.73 |
| ATOM 3200 | CD1 | TYR C | 49 | −1.607 | 54.309 | 2.178 | 1.00 | 3.73 |
| ATOM 3201 | CD2 | TYR C | 49 | −2.169 | 55.264 | −0.023 | 1.00 | 3.73 |
| ATOM 3202 | CE1 | TYR C | 49 | −2.648 | 55.044 | 2.764 | 1.00 | 3.73 |
| ATOM 3203 | CE2 | TYR C | 49 | −3.209 | 55.999 | 0.564 | 1.00 | 3.73 |
| ATOM 3204 | CZ | TYR C | 49 | −3.435 | 55.878 | 1.948 | 1.00 | 3.73 |
| ATOM 3205 | OH | TYR C | 49 | −4.458 | 56.599 | 2.532 | 1.00 | 3.73 |
| ATOM 3206 | H | TYR C | 49 | −2.819 | 52.496 | −0.967 | 1.00 | 20.00 |
| ATOM 3207 | HH | TYR C | 49 | −5.137 | 56.775 | 1.882 | 1.00 | 20.00 |
| ATOM 3208 | N | SER C | 50 | −0.215 | 50.852 | 1.611 | 1.00 | 5.02 |
| ATOM 3209 | CA | SER C | 50 | −0.526 | 50.156 | 2.852 | 1.00 | 5.02 |
| ATOM 3210 | C | SER C | 50 | 0.703 | 50.043 | 3.719 | 1.00 | 5.02 |
| ATOM 3211 | O | SER C | 50 | 1.823 | 50.001 | 3.222 | 1.00 | 5.02 |
| ATOM 3212 | CB | SER C | 50 | −1.125 | 48.778 | 2.553 | 1.00 | 5.02 |
| ATOM 3213 | OG | SER C | 50 | −1.384 | 48.081 | 3.773 | 1.00 | 5.02 |
| ATOM 3214 | H | SER C | 50 | 0.730 | 50.917 | 1.277 | 1.00 | 20.00 |
| ATOM 3215 | HG | SER C | 50 | −2.105 | 47.485 | 3.620 | 1.00 | 20.00 |
| ATOM 3216 | N | LYS C | 51 | 0.451 | 50.004 | 5.032 | 1.00 | 6.04 |
| ATOM 3217 | CA | LYS C | 51 | 1.566 | 49.747 | 5.928 | 1.00 | 6.04 |
| ATOM 3218 | C | LYS C | 51 | 1.168 | 48.864 | 7.085 | 1.00 | 6.04 |
| ATOM 3219 | O | LYS C | 51 | 0.081 | 48.988 | 7.634 | 1.00 | 6.04 |
| ATOM 3220 | CB | LYS C | 51 | 2.204 | 51.046 | 6.419 | 1.00 | 6.04 |
| ATOM 3221 | CG | LYS C | 51 | 3.649 | 50.767 | 6.806 | 1.00 | 6.04 |
| ATOM 3222 | CD | LYS C | 51 | 4.515 | 51.970 | 7.118 | 1.00 | 6.04 |
| ATOM 3223 | CE | LYS C | 51 | 5.951 | 51.473 | 7.261 | 1.00 | 6.04 |
| ATOM 3224 | NZ | LYS C | 51 | 6.762 | 52.551 | 7.819 | 1.00 | 6.04 |
| ATOM 3225 | H | LYS C | 51 | −0.498 | 50.000 | 5.359 | 1.00 | 20.00 |
| ATOM 3226 | 1 HZ | LYS C | 51 | 7.767 | 52.303 | 7.829 | 1.00 | 20.00 |
| ATOM 3227 | 2 HZ | LYS C | 51 | 6.618 | 53.390 | 7.222 | 1.00 | 20.00 |
| ATOM 3228 | 3 HZ | LYS C | 51 | 6.445 | 52.779 | 8.779 | 1.00 | 20.00 |
| ATOM 3229 | N | VAL C | 52 | 2.106 | 47.962 | 7.414 | 1.00 | 4.38 |
| ATOM 3230 | CA | VAL C | 52 | 1.919 | 47.105 | 8.580 | 1.00 | 4.38 |
| ATOM 3231 | C | VAL C | 52 | 3.163 | 47.030 | 9.425 | 1.00 | 4.38 |
| ATOM 3232 | O | VAL C | 52 | 4.288 | 47.236 | 8.969 | 1.00 | 4.38 |
| ATOM 3233 | CB | VAL C | 52 | 1.526 | 45.684 | 8.196 | 1.00 | 4.38 |
| ATOM 3234 | CG1 | VAL C | 52 | 0.075 | 45.610 | 7.735 | 1.00 | 4.38 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3235 | CG2 | VAL C | 52 | 2.532 | 45.109 | 7.199 | 1.00 | 4.38 |
| ATOM 3236 | H | VAL C | 52 | 2.955 | 47.914 | 6.882 | 1.00 | 20.00 |
| ATOM 3237 | N | TYR C | 53 | 2.885 | 46.722 | 10.698 | 1.00 | 6.58 |
| ATOM 3238 | CA | TYR C | 53 | 3.982 | 46.563 | 11.640 | 1.00 | 6.58 |
| ATOM 3239 | C | TYR C | 53 | 3.874 | 45.285 | 12.404 | 1.00 | 6.58 |
| ATOM 3240 | O | TYR C | 53 | 2.802 | 44.814 | 12.771 | 1.00 | 6.58 |
| ATOM 3241 | CB | TYR C | 53 | 4.053 | 47.702 | 12.650 | 1.00 | 6.58 |
| ATOM 3242 | CG | TYR C | 53 | 4.540 | 48.956 | 11.979 | 1.00 | 6.58 |
| ATOM 3243 | CD1 | TYR C | 53 | 5.754 | 49.515 | 12.410 | 1.00 | 6.58 |
| ATOM 3244 | CD2 | TYR C | 53 | 3.772 | 49.528 | 10.946 | 1.00 | 6.58 |
| ATOM 3245 | CE1 | TYR C | 53 | 6.205 | 50.675 | 11.774 | 1.00 | 6.58 |
| ATOM 3246 | CE2 | TYR C | 53 | 4.222 | 50.682 | 10.313 | 1.00 | 6.58 |
| ATOM 3247 | CZ | TYR C | 53 | 5.430 | 51.241 | 10.747 | 1.00 | 6.58 |
| ATOM 3248 | OH | TYR C | 53 | 5.846 | 52.408 | 10.152 | 1.00 | 6.58 |
| ATOM 3249 | H | TYR C | 53 | 1.934 | 46.638 | 11.003 | 1.00 | 20.00 |
| ATOM 3250 | HH | TYR C | 53 | 5.227 | 53.067 | 10.477 | 1.00 | 20.00 |
| ATOM 3251 | N | PHE C | 54 | 5.075 | 44.765 | 12.622 | 1.00 | 6.05 |
| ATOM 3252 | CA | PHE C | 54 | 5.170 | 43.485 | 13.288 | 1.00 | 6.05 |
| ATOM 3253 | C | PHE C | 54 | 6.023 | 43.652 | 14.513 | 1.00 | 6.05 |
| ATOM 3254 | O | PHE C | 54 | 7.011 | 44.378 | 14.484 | 1.00 | 6.05 |
| ATOM 3255 | CB | PHE C | 54 | 5.816 | 42.470 | 12.343 | 1.00 | 6.05 |
| ATOM 3256 | CG | PHE C | 54 | 5.174 | 42.482 | 10.971 | 1.00 | 6.05 |
| ATOM 3257 | CD1 | PHE C | 54 | 5.975 | 42.770 | 9.844 | 1.00 | 6.05 |
| ATOM 3258 | CD2 | PHE C | 54 | 3.800 | 42.190 | 10.829 | 1.00 | 6.05 |
| ATOM 3259 | CE1 | PHE C | 54 | 5.413 | 42.696 | 8.555 | 1.00 | 6.05 |
| ATOM 3260 | CE2 | PHE C | 54 | 3.236 | 42.120 | 9.543 | 1.00 | 6.05 |
| ATOM 3261 | CZ | PHE C | 54 | 4.057 | 42.337 | 8.418 | 1.00 | 6.05 |
| ATOM 3262 | H | PHE C | 54 | 5.907 | 45.228 | 12.310 | 1.00 | 20.00 |
| ATOM 3263 | N | ARG C | 55 | 5.622 | 42.952 | 15.570 | 1.00 | 19.70 |
| ATOM 3264 | CA | ARG C | 55 | 6.572 | 42.757 | 16.651 | 1.00 | 19.70 |
| ATOM 3265 | C | ARG C | 55 | 6.573 | 41.317 | 17.086 | 1.00 | 19.70 |
| ATOM 3266 | O | ARG C | 55 | 5.775 | 40.502 | 16.642 | 1.00 | 19.70 |
| ATOM 3267 | CB | ARG C | 55 | 6.247 | 43.628 | 17.856 | 1.00 | 19.70 |
| ATOM 3268 | CG | ARG C | 55 | 7.422 | 44.314 | 18.542 | 1.00 | 19.70 |
| ATOM 3269 | CD | ARG C | 55 | 6.974 | 44.923 | 19.852 | 1.00 | 19.70 |
| ATOM 3270 | NE | ARG C | 55 | 6.518 | 43.926 | 20.818 | 1.00 | 19.70 |
| ATOM 3271 | CZ | ARG C | 55 | 5.435 | 44.370 | 21.486 | 1.00 | 19.70 |
| ATOM 3272 | NH1 | ARG C | 55 | 5.476 | 44.387 | 22.819 | 1.00 | 19.70 |
| ATOM 3273 | NH2 | ARG C | 55 | 4.366 | 44.819 | 20.807 | 1.00 | 19.70 |
| ATOM 3274 | H | ARG C | 55 | 4.731 | 42.491 | 15.582 | 1.00 | 20.00 |
| ATOM 3275 | HE | ARG C | 55 | 7.217 | 43.332 | 21.219 | 1.00 | 20.00 |
| ATOM 3276 | 1 HH1 | ARG C | 55 | 4.720 | 44.761 | 23.357 | 1.00 | 20.00 |
| ATOM 3277 | 2 HH1 | ARG C | 55 | 6.280 | 44.044 | 23.311 | 1.00 | 20.00 |
| ATOM 3278 | 1 HH2 | ARG C | 55 | 3.562 | 45.210 | 21.263 | 1.00 | 20.00 |
| ATOM 3279 | 2 HH2 | ARG C | 55 | 4.349 | 44.751 | 19.798 | 1.00 | 20.00 |
| ATOM 3280 | N | GLY C | 56 | 7.479 | 41.063 | 18.026 | 1.00 | 3.53 |
| ATOM 3281 | CA | GLY C | 56 | 7.387 | 39.825 | 18.773 | 1.00 | 3.53 |
| ATOM 3282 | C | GLY C | 56 | 8.374 | 39.905 | 19.899 | 1.00 | 3.53 |
| ATOM 3283 | 0 | GLY C | 56 | 9.263 | 40.752 | 19.911 | 1.00 | 3.53 |
| ATOM 3284 | H | GLY C | 56 | 8.224 | 41.708 | 18.207 | 1.00 | 20.00 |
| ATOM 3285 | N | GLN C | 57 | 8.161 | 38.991 | 20.841 | 1.00 | 16.13 |
| ATOM 3286 | CA | GLN C | 57 | 9.200 | 38.805 | 21.831 | 1.00 | 16.13 |
| ATOM 3287 | C | GLN C | 57 | 9.825 | 37.456 | 21.568 | 1.00 | 16.13 |
| ATOM 3288 | O | GLN C | 57 | 9.117 | 36.520 | 21.210 | 1.00 | 16.13 |
| ATOM 3289 | CB | GLN C | 57 | 8.567 | 38.938 | 23.211 | 1.00 | 16.13 |
| ATOM 3290 | CG | GLN C | 57 | 9.600 | 39.118 | 24.315 | 1.00 | 16.13 |
| ATOM 3291 | CD | GLN C | 57 | 8.893 | 39.628 | 25.547 | 1.00 | 16.13 |
| ATOM 3292 | OE1 | GLN C | 57 | 7.925 | 39.070 | 26.040 | 1.00 | 16.13 |
| ATOM 3293 | NE2 | GLN C | 57 | 9.418 | 40.761 | 26.016 | 1.00 | 16.13 |
| ATOM 3294 | H | GLN C | 57 | 7.420 | 38.322 | 20.786 | 1.00 | 20.00 |
| ATOM 3295 | 1 HE2 | GLN C | 57 | 10.181 | 41.219 | 25.564 | 1.00 | 20.00 |
| ATOM 3296 | 2 HE2 | GLN C | 57 | 8.999 | 41.118 | 26.849 | 1.00 | 20.00 |
| ATOM 3297 | N | SER C | 58 | 11.166 | 37.423 | 21.705 | 1.00 | 30.56 |
| ATOM 3298 | CA | SER C | 58 | 11.908 | 36.219 | 21.328 | 1.00 | 30.56 |
| ATOM 3299 | C | SER C | 58 | 11.762 | 35.901 | 19.850 | 1.00 | 30.56 |
| ATOM 3300 | O | SER C | 58 | 11.079 | 36.601 | 19.104 | 1.00 | 30.56 |
| ATOM 3301 | CB | SER C | 58 | 11.538 | 35.026 | 22.221 | 1.00 | 30.56 |
| ATOM 3302 | OG | SER C | 58 | 11.501 | 35.453 | 23.588 | 1.00 | 30.56 |
| ATOM 3303 | H | SER C | 58 | 11.683 | 38.246 | 21.931 | 1.00 | 20.00 |
| ATOM 3304 | HG | SER C | 58 | 11.062 | 34.765 | 24.069 | 1.00 | 20.00 |
| ATOM 3305 | N | CYS C | 59 | 12.462 | 34.836 | 19.435 | 1.00 | 24.24 |
| ATOM 3306 | CA | CYS C | 59 | 12.501 | 34.696 | 17.990 | 1.00 | 24.24 |
| ATOM 3307 | C | CYS C | 59 | 12.570 | 33.269 | 17.515 | 1.00 | 24.24 |
| ATOM 3308 | O | CYS C | 59 | 13.336 | 32.450 | 18.008 | 1.00 | 24.24 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3309 | CB | CYS C | 59 | 13.659 | 35.496 | 17.418 | 1.00 | 24.24 |
| ATOM 3310 | SG | CYS C | 59 | 14.016 | 37.043 | 18.301 | 1.00 | 24.24 |
| ATOM 3311 | H | CYS C | 59 | 13.019 | 34.245 | 20.017 | 1.00 | 20.00 |
| ATOM 3312 | N | ASN C | 60 | 11.707 | 33.035 | 16.519 | 1.00 | 8.07 |
| ATOM 3313 | CA | ASN C | 60 | 11.551 | 31.704 | 15.937 | 1.00 | 8.07 |
| ATOM 3314 | C | ASN C | 60 | 11.572 | 31.893 | 14.433 | 1.00 | 8.07 |
| ATOM 3315 | O | ASN C | 60 | 11.625 | 33.026 | 13.966 | 1.00 | 8.07 |
| ATOM 3316 | CB | ASN C | 60 | 10.214 | 31.075 | 16.357 | 1.00 | 8.07 |
| ATOM 3317 | CG | ASN C | 60 | 10.146 | 30.760 | 17.845 | 1.00 | 8.07 |
| ATOM 3318 | OD1 | ASN C | 60 | 10.511 | 31.536 | 18.717 | 1.00 | 8.07 |
| ATOM 3319 | ND2 | ASN C | 60 | 9.619 | 29.563 | 18.106 | 1.00 | 8.07 |
| ATOM 3320 | H | ASN C | 60 | 11.195 | 33.797 | 16.126 | 1.00 | 20.00 |
| ATOM 3321 | 1HD2 | ASN C | 60 | 9.294 | 28.953 | 17.382 | 1.00 | 20.00 |
| ATOM 3322 | 2 HD2 | ASN C | 60 | 9.532 | 29.302 | 19.066 | 1.00 | 20.00 |
| ATOM 3323 | N | ASN C | 61 | 11.514 | 30.780 | 13.682 | 1.00 | 15.42 |
| ATOM 3324 | CA | ASN C | 61 | 11.545 | 31.001 | 12.234 | 1.00 | 15.42 |
| ATOM 3325 | C | ASN C | 61 | 10.163 | 31.214 | 11.638 | 1.00 | 15.42 |
| ATOM 3326 | O | ASN C | 61 | 9.386 | 30.282 | 11.485 | 1.00 | 15.42 |
| ATOM 3327 | CB | ASN C | 61 | 12.265 | 29.860 | 11.501 | 1.00 | 15.42 |
| ATOM 3328 | CG | ASN C | 61 | 13.704 | 29.717 | 11.967 | 1.00 | 15.42 |
| ATOM 3329 | OD1 | ASN C | 61 | 14.510 | 30.636 | 11.888 | 1.00 | 15.42 |
| ATOM 3330 | ND2 | ASN C | 61 | 14.013 | 28.504 | 12.436 | 1.00 | 15.42 |
| ATOM 3331 | H | ASN C | 61 | 11.388 | 29.854 | 14.049 | 1.00 | 20.90 |
| ATOM 3332 | 1 HD2 | ASN C | 61 | 13.314 | 27.781 | 12.549 | 1.00 | 20.00 |
| ATOM 3333 | 2 HD2 | ASN C | 61 | 14.937 | 28.289 | 12.741 | 1.00 | 20.00 |
| ATOM 3334 | N | LEU C | 62 | 9.893 | 32.490 | 11.299 | 1.00 | 19.58 |
| ATOM 3335 | CA | LEU C | 62 | 8.602 | 32.835 | 10.690 | 1.00 | 19.58 |
| ATOM 3336 | C | LEU C | 62 | 8.741 | 33.958 | 9.677 | 1.00 | 19.58 |
| ATOM 3337 | O | LEU C | 62 | 9.193 | 35.050 | 9.995 | 1.00 | 19.58 |
| ATOM 3338 | CB | LEU C | 62 | 7.570 | 33.260 | 11.744 | 1.00 | 19.58 |
| ATOM 3339 | CG | LEU C | 62 | 6.938 | 32.121 | 12.549 | 1.00 | 19.58 |
| ATOM 3340 | CD1 | LEU C | 62 | 6.093 | 32.657 | 13.704 | 1.00 | 19.58 |
| ATOM 3341 | CD2 | LEU C | 62 | 6.140 | 31.158 | 11.664 | 1.00 | 19.58 |
| ATOM 3342 | H | LEU C | 62 | 10.560 | 33.207 | 11.502 | 1.00 | 20.00 |
| ATOM 3343 | N | PRO C | 63 | 8.351 | 33.655 | 8.417 | 1.00 | 9.44 |
| ATOM 3344 | CA | PRO C | 63 | 8.377 | 34.686 | 7.373 | 1.00 | 9.44 |
| ATOM 3345 | C | PRO C | 63 | 7.154 | 35.586 | 7.454 | 1.00 | 9.44 |
| ATOM 3346 | O | PRO C | 63 | 6.041 | 35.142 | 7.686 | 1.00 | 9.44 |
| ATOM 3347 | CB | PRO C | 63 | 8.373 | 33.832 | 6.108 | 1.00 | 9.44 |
| ATOM 3348 | CG | PRO C | 63 | 7.481 | 32.650 | 6.483 | 1.00 | 9.44 |
| ATOM 3349 | CD | PRO C | 63 | 7.877 | 32.365 | 7.927 | 1.00 | 9.44 |
| ATOM 3350 | N | LEU C | 64 | 7.405 | 36.879 | 7.242 | 1.00 | 5.10 |
| ATOM 3351 | CA | LEU C | 64 | 6.257 | 37.775 | 7.346 | 1.00 | 5.10 |
| ATOM 3352 | C | LEU C | 64 | 5.886 | 38.278 | 5.969 | 1.00 | 5.10 |
| ATOM 3353 | O | LEU C | 64 | 6.764 | 38.658 | 5.202 | 1.00 | 5.10 |
| ATOM 3354 | CB | LEU C | 64 | 6.582 | 38.963 | 8.261 | 1.00 | 5.10 |
| ATOM 3355 | CG | LEU C | 64 | 7.669 | 38.718 | 9.324 | 1.00 | 5.10 |
| ATOM 3356 | CD1 | LEU C | 64 | 8.140 | 40.030 | 9.940 | 1.00 | 5.10 |
| ATOM 3357 | CD2 | LEU C | 64 | 7.298 | 37.688 | 10.392 | 1.00 | 5.10 |
| ATOM 3358 | H | LEU C | 64 | 8.319 | 37.228 | 7.026 | 1.00 | 20.00 |
| ATOM 3359 | N | SER C | 65 | 4.586 | 38.273 | 5.666 | 1.00 | 3.51 |
| ATOM 3360 | CA | SER C | 65 | 4.250 | 38.805 | 4.354 | 1.00 | 3.51 |
| ATOM 3361 | C | SER C | 65 | 3.172 | 39.859 | 4.405 | 1.00 | 3.51 |
| ATOM 3362 | O | SER C | 65 | 2.328 | 39.873 | 5.292 | 1.00 | 3.51 |
| ATOM 3363 | CB | SER C | 65 | 3.902 | 37.678 | 3.377 | 1.00 | 3.51 |
| ATOM 3364 | OG | SER C | 65 | 2.619 | 37.124 | 3.681 | 1.00 | 3.51 |
| ATOM 3365 | H | SER C | 65 | 3.881 | 37.873 | 6.257 | 1.00 | 20.00 |
| ATOM 3366 | HG | SER C | 65 | 2.613 | 36.234 | 3.355 | 1.00 | 20.00 |
| ATOM 3367 | N | HIS C | 66 | 3.253 | 40.745 | 3.405 | 1.00 | 11.85 |
| ATOM 3368 | CA | HIS C | 66 | 2.241 | 41.783 | 3.293 | 1.00 | 11.85 |
| ATOM 3369 | C | HIS C | 66 | 1.873 | 42.036 | 1.853 | 1.00 | 11.85 |
| ATOM 3370 | O | HIS C | 66 | 2.665 | 42.562 | 1.079 | 1.00 | 11.85 |
| ATOM 3371 | CB | HIS C | 66 | 2.741 | 43.071 | 3.924 | 1.00 | 11.85 |
| ATOM 3372 | CG | HIS C | 66 | 1.617 | 44.067 | 3.872 | 1.00 | 11.85 |
| ATOM 3373 | ND1 | HIS C | 66 | 1.564 | 45.081 | 2.998 | 1.00 | 11.85 |
| ATOM 3374 | CD2 | HIS C | 66 | 0.485 | 44.099 | 4.680 | 1.00 | 11.85 |
| ATOM 3375 | CE1 | HIS C | 66 | 0.416 | 45.764 | 3.256 | 1.00 | 11.85 |
| ATOM 3376 | NE2 | HIS C | 66 | −0.247 | 45.162 | 4.290 | 1.00 | 11.85 |
| ATOM 3377 | H | HIS C | 66 | 4.033 | 40.708 | 2.779 | 1.00 | 20.00 |
| ATOM 3378 | HD1 | HIS C | 66 | 2.184 | 45.259 | 2.266 | 1.00 | 20.00 |
| ATOM 3379 | N | LYS C | 67 | 0.651 | 41.623 | 1.518 | 1.00 | 4.98 |
| ATOM 3380 | CA | LYS C | 67 | 0.363 | 41.645 | 0.093 | 1.00 | 4.98 |
| ATOM 3381 | C | LYS C | 67 | −0.988 | 42.273 | −0.208 | 1.00 | 4.98 |
| ATOM 3382 | O | LYS C | 67 | −1.971 | 42.048 | 0.490 | 1.00 | 4.98 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3383 | CB | LYS C | 67 | 0.482 | 40.216 | −0.443 | 1.00 | 4.98 |
| ATOM 3384 | CG | LYS C | 67 | 1.767 | 39.429 | −0.119 | 1.00 | 4.98 |
| ATOM 3385 | CD | LYS C | 67 | 1.594 | 37.922 | −0.344 | 1.00 | 4.98 |
| ATOM 3386 | CE | LYS C | 67 | 2.815 | 37.009 | −0.253 | 1.00 | 4.98 |
| ATOM 3387 | NZ | LYS C | 67 | 2.939 | 36.229 | −1.501 | 1.00 | 4.98 |
| ATOM 3388 | H | LYS C | 67 | −0.009 | 41.255 | 2.182 | 1.00 | 20.00 |
| ATOM 3389 | 1 HZ | LYS C | 67 | 3.886 | 35.825 | −1.586 | 1.00 | 20.00 |
| ATOM 3390 | 2 HZ | LYS C | 67 | 2.213 | 35.493 | −1.635 | 1.00 | 20.00 |
| ATOM 3391 | 3 HZ | LYS C | 67 | 2.868 | 36.897 | −2.300 | 1.00 | 20.00 |
| ATOM 3392 | N | VAL C | 68 | −0.975 | 43.094 | −1.269 | 1.00 | 3.61 |
| ATOM 3393 | CA | VAL C | 68 | −2.210 | 43.689 | −1.772 | 1.00 | 3.61 |
| ATOM 3394 | C | VAL C | 68 | −2.621 | 42.989 | −3.048 | 1.00 | 3.61 |
| ATOM 3395 | O | VAL C | 68 | −1.832 | 42.861 | −3.981 | 1.00 | 3.61 |
| ATOM 3396 | CB | VAL C | 68 | −2.021 | 45.189 | −2.044 | 1.00 | 3.61 |
| ATOM 3397 | CG1 | VAL C | 68 | −3.322 | 45.864 | −2.501 | 1.00 | 3.61 |
| ATOM 3398 | CG2 | VAL C | 68 | −1.395 | 45.894 | −0.838 | 1.00 | 3.61 |
| ATOM 3399 | H | VAL C | 68 | −0.127 | 43.195 | −1.787 | 1.00 | 20.00 |
| ATOM 3400 | N | TYR C | 69 | −3.883 | 42.554 | −3.043 | 1.00 | 4.98 |
| ATOM 3401 | CA | TYR C | 69 | −4.378 | 41.828 | −4.200 | 1.00 | 4.98 |
| ATOM 3402 | C | TYR C | 69 | −5.590 | 42.489 | −4.806 | 1.00 | 4.98 |
| ATOM 3403 | O | 'TYR C | 69 | −6.297 | 43.255 | −4.159 | 1.00 | 4.98 |
| ATOM 3404 | CB | TYR C | 69 | −4.730 | 40.394 | −3.819 | 1.00 | 4.98 |
| ATOM 3405 | CG | TYR C | 69 | −3.641 | 39.788 | −2.979 | 1.00 | 4.98 |
| ATOM 3406 | CD1 | TYR C | 69 | −2.565 | 39.154 | −3.617 | 1.00 | 4.98 |
| ATOM 3407 | CD2 | TYR C | 69 | −3.753 | 39.850 | −1.580 | 1.00 | 4.98 |
| ATOM 3408 | CE1 | TYR C | 69 | −1.664 | 38.427 | −2.831 | 1.00 | 4.98 |
| ATOM 3409 | CE2 | TYR C | 69 | −2.867 | 39.110 | −0.790 | 1.00 | 4.98 |
| ATOM 3410 | CZ | TYR C | 69 | −1.896 | 38.336 | −1.448 | 1.00 | 4.98 |
| ATOM 3411 | OH | TYR C | 69 | −1.164 | 37.436 | −0.713 | 1.00 | 4.98 |
| ATOM 3412 | H | TYR C | 69 | −4.476 | 42.714 | −2.251 | 1.00 | 20.00 |
| ATOM 3413 | HH | TYR C | 69 | −1.483 | 37.470 | 0.176 | 1.00 | 20.00 |
| ATOM 3414 | N | MET C | 70 | −5.799 | 42.145 | −6.080 | 1.00 | 14.09 |
| ATOM 3415 | CA | MET C | 70 | −7.000 | 42.649 | −6.734 | 1.00 | 14.09 |
| ATOM 3416 | C | MET C | 70 | −7.850 | 41.544 | −7.309 | 1.00 | 14.09 |
| ATOM 3417 | O | MET C | 70 | −7.422 | 40.761 | −8.147 | 1.00 | 14.09 |
| ATOM 3418 | CB | MET C | 70 | −6.664 | 43.692 | −7.807 | 1.00 | 14.09 |
| ATOM 3419 | CG | MET C | 70 | −5.727 | 43.206 | −8.908 | 1.00 | 14.09 |
| ATOM 3420 | SD | MET C | 70 | −5.286 | 44.450 | −10.124 | 1.00 | 14.09 |
| ATOM 3421 | CE | MET C | 70 | −6.932 | 44.872 | −10.703 | 1.00 | 14.09 |
| ATOM 3422 | H | MET C | 70 | −5.168 | 41.501 | −6.519 | 1.00 | 20.00 |
| ATOM 3423 | N | ARG C | 71 | −9.097 | 41.534 | −6.839 | 1.00 | 7.41 |
| ATOM 3424 | CA | ARG C | 71 | −10.059 | 40.714 | −7.557 | 1.00 | 7.41 |
| ATOM 3425 | C | ARG C | 71 | −10.825 | 41.567 | −8.541 | 1.00 | 7.41 |
| ATOM 3426 | O | ARG C | 71 | −11.781 | 42.256 | −8.194 | 1.00 | 7.41 |
| ATOM 3427 | CB | ARG C | 71 | −11.005 | 39.999 | −6.599 | 1.00 | 7.41 |
| ATOM 3428 | CG | ARG C | 71 | −11.847 | 38.974 | −7.358 | 1.00 | 7.41 |
| ATOM 3429 | CD | ARG C | 71 | −12.761 | 38.162 | −6.451 | 1.00 | 7.41 |
| ATOM 3430 | NE | ARG C | 71 | −13.474 | 37.162 | −7.242 | 1.00 | 7.41 |
| ATOM 3431 | CZ | ARG C | 71 | −14.237 | 36.227 | −6.646 | 1.00 | 7.41 |
| ATOM 3432 | NH1 | ARG C | 71 | −14.334 | 36.183 | −5.317 | 1.00 | 7.41 |
| ATOM 3433 | NH2 | ARG C | 71 | −14.891 | 35.348 | −7.400 | 1.00 | 7.41 |
| ATOM 3434 | H | ARG C | 71 | −9.365 | 42.213 | −6.154 | 1.00 | 20.00 |
| ATOM 3435 | HE | ARG C | 71 | −13.335 | 37.194 | −8.233 | 1.00 | 20.00 |
| ATOM 3436 | 1 HH1 | ARG C | 71 | −14.902 | 35.511 | −4.846 | 1.00 | 20.00 |
| ATOM 3437 | 2 HH1 | ARG C | 71 | −13.810 | 36.837 | −4.769 | 1.00 | 20.00 |
| ATOM 3438 | 1 HH2 | ARG C | 71 | −15.482 | 34.647 | −7.002 | 1.00 | 20.00 |
| ATOM 3439 | 2 HH2 | ARG C | 71 | −14.790 | 35.378 | −8.395 | 1.00 | 20.00 |
| ATOM 3440 | N | ASN C | 72 | −10.325 | 41.510 | −9.784 | 1.00 | 8.42 |
| ATOM 3441 | CA | ASN C | 72 | −10.929 | 42.380 | −10.789 | 1.00 | 8.42 |
| ATOM 3442 | C | ASN C | 72 | −12.207 | 41.812 | −11.386 | 1.00 | 8.42 |
| ATOM 3443 | O | ASN C | 72 | −12.456 | 40.616 | −11.342 | 1.00 | 8.42 |
| ATOM 3444 | CB | ASN C | 72 | −9.882 | 42.767 | −11.844 | 1.00 | 8.42 |
| ATOM 3445 | CG | ASN C | 72 | −10.343 | 43.970 | −12.652 | 1.00 | 8.42 |
| ATOM 3446 | OD1 | ASN C | 72 | −10.878 | 43.836 | −13.744 | 1.00 | 8.42 |
| ATOM 3447 | ND2 | ASN C | 72 | −10.137 | 45.157 | −12.071 | 1.00 | 8.42 |
| ATOM 3448 | H | ASN C | 72 | −9.622 | 40.825 | −9.988 | 1.00 | 20.00 |
| ATOM 3449 | 1 HD2 | ASN C | 72 | −9.766 | 45.276 | −11.141 | 1.00 | 20.00 |
| ATOM 3450 | 2 HD2 | ASN C | 72 | −10.392 | 46.004 | −12.532 | 1.00 | 20.00 |
| ATOM 3451 | N | SER C | 73 | −13.017 | 42.718 | −11.959 | 1.00 | 5.16 |
| ATOM 3452 | CA | SER C | 73 | −14.205 | 42.232 | −12.657 | 1.00 | 5.16 |
| ATOM 3453 | C | SER C | 73 | −13.882 | 41.409 | −13.897 | 1.00 | 5.16 |
| ATOM 3454 | O | SER C | 73 | −14.517 | 40.412 | −14.211 | 1.00 | 5.16 |
| ATOM 3455 | CB | SER C | 73 | −15.079 | 43.432 | −13.011 | 1.00 | 5.16 |
| ATOM 3456 | OG | SER C | 73 | −14.258 | 44.440 | −13.616 | 1.00 | 5.16 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM | 3457 | H | SER | C | 73 | −12.794 | 43.692 | −12.031 | 1.00 | 20.00 |
| ATOM | 3458 | HG | SER | C | 73 | −14.840 | 45.151 | −13.860 | 1.00 | 20.00 |
| ATOM | 3459 | N | LYS | C | 74 | −12.832 | 41.886 | −14.586 | 1.00 | 5.76 |
| ATOM | 3460 | CA | LYS | C | 74 | −12.403 | 41.214 | −15.812 | 1.00 | 5.76 |
| ATOM | 3461 | C | LYS | C | 74 | −11.907 | 39.791 | −15.607 | 1.00 | 5.76 |
| ATOM | 3462 | O | LYS | C | 74 | −12.165 | 38.901 | −16.406 | 1.00 | 5.76 |
| ATOM | 3463 | CB | LYS | C | 74 | −11.330 | 42.049 | −16.513 | 1.00 | 5.76 |
| ATOM | 3464 | CG | LYS | C | 74 | −11.792 | 43.465 | −16.874 | 1.00 | 5.76 |
| ATOM | 3465 | CD | LYS | C | 74 | −10.635 | 44.332 | −17.377 | 1.00 | 5.76 |
| ATOM | 3466 | CE | LYS | C | 74 | −11.038 | 45.774 | −17.696 | 1.00 | 5.76 |
| ATOM | 3467 | NZ | LYS | C | 74 | −9.843 | 46.532 | −18.098 | 1.00 | 5.76 |
| ATOM | 3468 | H | LYS | C | 74 | −12.417 | 42.746 | −14.275 | 1.00 | 20.00 |
| ATOM | 3469 | 1 HZ | LYS | C | 74 | −10.120 | 47.489 | −18.394 | 1.00 | 20.00 |
| ATOM | 3470 | 2 HZ | LYS | C | 74 | −9.183 | 46.597 | −17.296 | 1.00 | 20.00 |
| ATOM | 3471 | 3 HZ | LYS | C | 74 | −9.372 | 46.050 | −18.890 | 1.00 | 20.00 |
| ATOM | 3472 | N | TYR | C | 75 | −11.171 | 39.617 | −14.495 | 1.00 | 6.72 |
| ATOM | 3473 | CA | TYR | C | 75 | −10.638 | 38.280 | −14.249 | 1.00 | 6.72 |
| ATOM | 3474 | C | TYR | C | 75 | −11.066 | 37.699 | −12.920 | 1.00 | 6.72 |
| ATOM | 3475 | O | TYR | C | 75 | −10.772 | 38.246 | −11.869 | 1.00 | 6.72 |
| ATOM | 3476 | CB | TYR | C | 75 | −9.105 | 38.308 | −14.319 | 1.00 | 6.72 |
| ATOM | 3477 | CG | TYR | C | 75 | −8.440 | 36.943 | −14.287 | 1.00 | 6.72 |
| ATOM | 3478 | CD1 | TYR | C | 75 | −8.963 | 35.858 | −15.024 | 1.00 | 6.72 |
| ATOM | 3479 | CD2 | TYR | C | 75 | −7.267 | 36.814 | −13.518 | 1.00 | 6.72 |
| ATOM | 3480 | CE1 | TYR | C | 75 | −8.306 | 34.617 | −14.970 | 1.00 | 6.72 |
| ATOM | 3481 | CE2 | TYR | C | 75 | −6.593 | 35.582 | −13.488 | 1.00 | 6.72 |
| ATOM | 3482 | CZ | TYR | C | 75 | −7.124 | 34.492 | −14.207 | 1.00 | 6.72 |
| ATOM | 3483 | OH | TYR | C | 75 | −6.482 | 33.265 | −14.174 | 1.00 | 6.72 |
| ATOM | 3484 | H | TYR | C | 75 | −10.987 | 40.361 | −13.852 | 1.00 | 20.00 |
| ATOM | 3485 | HH | TYR | C | 75 | −5.693 | 33.285 | −13.631 | 1.00 | 20.00 |
| ATOM | 3486 | N | PRO | C | 76 | −11.714 | 36.515 | −13.012 | 1.00 | 6.84 |
| ATOM | 3487 | CA | PRO | C | 76 | −12.025 | 35.690 | −11.833 | 1.00 | 6.84 |
| ATOM | 3488 | C | PRO | C | 76 | −11.014 | 35.468 | −10.696 | 1.00 | 6.84 |
| ATOM | 3489 | O | PRO | C | 76 | −11.428 | 35.007 | −9.640 | 1.00 | 6.84 |
| ATOM | 3490 | CB | PRO | C | 76 | −12.531 | 34.374 | −12.448 | 1.00 | 6.84 |
| ATOM | 3491 | CG | PRO | C | 76 | −12.231 | 34.433 | −13.948 | 1.00 | 6.84 |
| ATOM | 3492 | CD | PRO | C | 76 | −12.214 | 35.922 | −14.250 | 1.00 | 6.84 |
| ATOM | 3493 | N | GLN | C | 77 | −9.716 | 35.758 | −10.921 | 1.00 | 4.75 |
| ATOM | 3494 | CA | GLN | C | 77 | −8.765 | 35.501 | −9.840 | 1.00 | 4.75 |
| ATOM | 3495 | C | GLN | C | 77 | −8.246 | 36.758 | −9.189 | 1.00 | 4.75 |
| ATOM | 3496 | O | GLN | C | 77 | −8.371 | 37.866 | −9.699 | 1.00 | 4.75 |
| ATOM | 3497 | CB | GLN | C | 77 | −7.552 | 34.724 | −10.328 | 1.00 | 4.75 |
| ATOM | 3498 | CG | GLN | C | 77 | −7.832 | 33.291 | −10.761 | 1.00 | 4.75 |
| ATOM | 3499 | CD | GLN | C | 77 | −6.554 | 32.722 | −11.343 | 1.00 | 4.75 |
| ATOM | 3500 | OE1 | GLN | C | 77 | −5.532 | 33.383 | −11.471 | 1.00 | 4.75 |
| ATOM | 3501 | NE2 | GLN | C | 77 | −6.653 | 31.456 | −11.751 | 1.00 | 4.75 |
| ATOM | 3502 | H | GLN | C | 77 | −9.415 | 36.320 | −11.686 | 1.00 | 20.00 |
| ATOM | 3503 | 1 HE2 | GLN | C | 77 | −7.507 | 30.941 | −11.721 | 1.00 | 20.00 |
| ATOM | 3504 | 2 HE2 | GLN | C | 77 | −5.814 | 31.054 | −12.113 | 1.00 | 20.00 |
| ATOM | 3505 | N | ASP | C | 78 | −7.604 | 36.490 | −8.049 | 1.00 | 4.94 |
| ATOM | 3506 | CA | ASP | C | 78 | −6.988 | 37.584 | −7.322 | 1.00 | 4.94 |
| ATOM | 3507 | C | ASP | C | 78 | −5.543 | 37.751 | −7.745 | 1.00 | 4.94 |
| ATOM | 3508 | O | ASP | C | 78 | −4.675 | 36.920 | −7.507 | 1.00 | 4.94 |
| ATOM | 3509 | CB | ASP | C | 78 | −7.137 | 37.369 | −5.809 | 1.00 | 4.94 |
| ATOM | 3510 | CG | ASP | C | 78 | −8.590 | 37.333 | −5.326 | 1.00 | 4.94 |
| ATOM | 3511 | OD1 | ASP | C | 78 | −9.492 | 36.990 | −6.093 | 1.00 | 4.94 |
| ATOM | 3512 | OD2 | ASP | C | 78 | −8.822 | 37.650 | −4.160 | 1.00 | 4.94 |
| ATOM | 3513 | H | ASP | C | 78 | −7.663 | 35.592 | −7.618 | 1.00 | 20.00 |
| ATOM | 3514 | N | LEU | C | 79 | −5.336 | 38.879 | −8.431 | 1.00 | 4.95 |
| ATOM | 3515 | CA | LEU | C | 79 | −3.977 | 39.208 | −8.865 | 1.00 | 4.95 |
| ATOM | 3516 | C | LEU | C | 79 | −3.188 | 39.759 | −7.698 | 1.00 | 4.95 |
| ATOM | 3517 | 0 | LEU | C | 79 | −3.760 | 40.270 | −6.747 | 1.00 | 4.95 |
| ATOM | 3518 | CB | LEU | C | 79 | −3.930 | 40.309 | −9.933 | 1.00 | 4.95 |
| ATOM | 3519 | CG | LEU | C | 79 | −4.627 | 40.199 | −11.297 | 1.00 | 4.95 |
| ATOM | 3520 | CD1 | LEU | C | 79 | −6.160 | 40.174 | −11.253 | 1.00 | 4.95 |
| ATOM | 3521 | CD2 | LEU | C | 79 | −4.160 | 41.367 | −12.169 | 1.00 | 4.95 |
| ATOM | 3522 | H | LEU | C | 79 | −6.111 | 39.509 | −8.505 | 1.00 | 20.00 |
| ATOM | 3523 | N | VAL | C | 80 | −1.858 | 39.696 | −7.827 | 1.00 | 4.14 |
| ATOM | 3524 | CA | VAL | C | 80 | −1.108 | 40.425 | −6.814 | 1.00 | 4.14 |
| ATOM | 3525 | C | VAL | C | 80 | −0.562 | 41.739 | −7.329 | 1.00 | 4.14 |
| ATOM | 3526 | O | VAL | C | 80 | 0.236 | 41.816 | −8.259 | 1.00 | 4.14 |
| ATOM | 3527 | CB | VAL | C | 80 | 0.009 | 39.588 | −6.196 | 1.00 | 4.14 |
| ATOM | 3528 | CG1 | VAL | C | 80 | 0.437 | 40.220 | −4.868 | 1.00 | 4.14 |
| ATOM | 3529 | CG2 | VAL | C | 80 | −0.375 | 38.110 | −6.068 | 1.00 | 4.14 |
| ATOM | 3530 | H | VAL | C | 80 | −1.406 | 39.260 | −8.604 | 1.00 | 20.00 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM | 3531 | N | MET | C | 81 | −1.062 | 42.786 | −6.659 | 1.00 | 4.15 |
| ATOM | 3532 | CA | MET | C | 81 | −0.591 | 44.126 | −6.993 | 1.00 | 4.15 |
| ATOM | 3533 | C | MET | C | 81 | 0.776 | 44.387 | −6.400 | 1.00 | 4.15 |
| ATOM | 3534 | O | MET | C | 81 | 1.723 | 44.782 | −7.067 | 1.00 | 4.15 |
| ATOM | 3535 | CB | MET | C | 81 | −1.591 | 45.171 | −6.492 | 1.00 | 4.15 |
| ATOM | 3536 | CG | MET | C | 81 | −3.003 | 44.888 | −6.998 | 1.00 | 4.15 |
| ATOM | 3537 | SD | MET | C | 81 | −4.263 | 45.898 | −6.212 | 1.00 | 4.15 |
| ATOM | 3538 | CE | MET | C | 81 | −3.831 | 47.468 | −6.958 | 1.00 | 4.15 |
| ATOM | 3539 | H | MET | C | 81 | −1.634 | 42.611 | −5.854 | 1.00 | 20.00 |
| ATOM | 3540 | N | MET | C | 82 | 0.823 | 44.151 | −5.078 | 1.00 | 5.02 |
| ATOM | 3541 | CA | MET | C | 82 | 2.053 | 44.479 | −4.364 | 1.00 | 5.02 |
| ATOM | 3542 | C | MET | C | 82 | 2.351 | 43.463 | −3.289 | 1.00 | 5.02 |
| ATOM | 3543 | O | MET | C | 82 | 1.456 | 42.968 | −2.622 | 1.00 | 5.02 |
| ATOM | 3544 | CB | MET | C | 82 | 1.951 | 45.865 | −3.728 | 1.00 | 5.02 |
| ATOM | 3545 | CG | MET | C | 82 | 1.957 | 47.031 | −4.716 | 1.00 | 5.02 |
| ATOM | 3546 | SD | MET | C | 82 | 1.820 | 48.615 | −3.889 | 1.00 | 5.02 |
| ATOM | 3547 | CE | MET | C | 82 | 0.217 | 48.358 | −3.121 | 1.00 | 5.02 |
| ATOM | 3548 | H | MET | C | 82 | 0.031 | 43.765 | −4.595 | 1.00 | 20.00 |
| ATOM | 3549 | N | GLU | C | 83 | 3.650 | 43.181 | −3.141 | 1.00 | 4.99 |
| ATOM | 3550 | CA | GLU | C | 83 | 4.031 | 42.168 | −2.159 | 1.00 | 4.99 |
| ATOM | 3551 | C | GLU | C | 83 | 5.134 | 42.647 | −1.289 | 1.00 | 4.99 |
| ATOM | 3552 | O | GLU | C | 83 | 6.027 | 43.296 | −1.805 | 1.00 | 4.99 |
| ATOM | 3553 | CB | GLU | C | 83 | 4.703 | 41.001 | −2.815 | 1.00 | 4.99 |
| ATOM | 3554 | CG | GLU | C | 83 | 3.789 | 40.181 | −3.667 | 1.00 | 4.99 |
| ATOM | 3555 | CD | GLU | C | 83 | 3.711 | 38.793 | −3.086 | 1.00 | 4.99 |
| ATOM | 3556 | OE1 | GLU | C | 83 | 4.676 | 38.279 | −2.501 | 1.00 | 4.99 |
| ATOM | 3557 | OE2 | GLU | C | 83 | 2.651 | 38.212 | −3.228 | 1.00 | 4.99 |
| ATOM | 3558 | H | GLU | C | 83 | 4.345 | 43.600 | −3.724 | 1.00 | 20.00 |
| ATOM | 3559 | N | GLY | C | 84 | 5.078 | 42.229 | −0.019 | 1.00 | 3.83 |
| ATOM | 3560 | CA | GLY | C | 84 | 6.184 | 42.410 | 0.910 | 1.00 | 3.83 |
| ATOM | 3561 | C | GLY | C | 84 | 6.587 | 41.123 | 1.597 | 1.00 | 3.83 |
| ATOM | 3562 | O | GLY | C | 84 | 5.792 | 40.508 | 2.288 | 1.00 | 3.83 |
| ATOM | 3563 | H | GLY | C | 84 | 4.220 | 41.820 | 0.297 | 1.00 | 20.00 |
| ATOM | 3564 | N | LYS | C | 85 | 7.858 | 40.740 | 1.393 | 1.00 | 5.40 |
| ATOM | 3565 | CA | LYS | C | 85 | 8.357 | 39.626 | 2.195 | 1.00 | 5.40 |
| ATOM | 3566 | C | LYS | C | 85 | 9.449 | 40.074 | 3.121 | 1.00 | 5.40 |
| ATOM | 3567 | O | LYS | C | 85 | 10.467 | 40.608 | 2.700 | 1.00 | 5.40 |
| ATOM | 3568 | CB | LYS | C | 85 | 8.934 | 38.514 | 1.341 | 1.00 | 5.40 |
| ATOM | 3569 | CG | LYS | C | 85 | 7.920 | 37.952 | 0.376 | 1.00 | 5.40 |
| ATOM | 3570 | CD | LYS | C | 85 | 8.615 | 36.928 | −0.467 | 1.00 | 5.40 |
| ATOM | 3571 | CE | LYS | C | 85 | 7.652 | 36.380 | −1.469 | 1.00 | 5.40 |
| ATOM | 3572 | NZ | LYS | C | 85 | 8.517 | 35.490 | −2.219 | 1.00 | 5.40 |
| ATOM | 3573 | H | LYS | C | 85 | 8.480 | 41.241 | 0.795 | 1.00 | 20.00 |
| ATOM | 3574 | 1 HZ | LYS | C | 85 | 7.931 | 34.961 | −2.879 | 1.00 | 20.00 |
| ATOM | 3575 | 2 HZ | LYS | C | 85 | 9.259 | 35.921 | −2.806 | 1.00 | 20.00 |
| ATOM | 3576 | 3 HZ | LYS | C | 85 | 8.871 | 34.631 | −1.757 | 1.00 | 20.00 |
| ATOM | 3577 | N | MET | C | 86 | 9.199 | 39.818 | 4.401 | 1.00 | 17.02 |
| ATOM | 3578 | CA | MET | C | 86 | 10.273 | 40.042 | 5.350 | 1.00 | 17.02 |
| ATOM | 3579 | C | MET | C | 86 | 10.556 | 38.784 | 6.131 | 1.00 | 17.02 |
| ATOM | 3580 | O | MET | C | 86 | 9.828 | 38.420 | 7.043 | 1.00 | 17.02 |
| ATOM | 3581 | CB | MET | C | 86 | 9.943 | 41.205 | 6.293 | 1.00 | 17.02 |
| ATOM | 3582 | CG | MET | C | 86 | 9.833 | 42.554 | 5.576 | 1.00 | 17.02 |
| ATOM | 3583 | SD | MET | C | 86 | 11.365 | 43.050 | 4.767 | 1.00 | 17.02 |
| ATOM | 3584 | CE | MET | C | 86 | 12.309 | 43.466 | 6.239 | 1.00 | 17.02 |
| ATOM | 3585 | H | MET | C | 86 | 8.321 | 39.425 | 4.683 | 1.00 | 20.00 |
| ATOM | 3586 | N | MET | C | 87 | 11.689 | 38.147 | 5.793 | 1.00 | 29.14 |
| ATOM | 3587 | CA | MET | C | 87 | 12.120 | 37.112 | 6.742 | 1.00 | 29.14 |
| ATOM | 3588 | C | MET | C | 87 | 13.033 | 37.646 | 7.816 | 1.00 | 29.14 |
| ATOM | 3589 | O | MET | C | 87 | 14.037 | 37.078 | 8.225 | 1.00 | 29.14 |
| ATOM | 3590 | CB | MET | C | 87 | 12.808 | 35.921 | 6.104 | 1.00 | 29.14 |
| ATOM | 3591 | CG | MET | C | 87 | 12.438 | 34.692 | 6.925 | 1.00 | 29.14 |
| ATOM | 3592 | SD | MET | C | 87 | 13.617 | 33.359 | 6.749 | 1.00 | 29.14 |
| ATOM | 3593 | CE | MET | C | 87 | 12.836 | 32.217 | 7.895 | 1.00 | 29.14 |
| ATOM | 3594 | H | MET | C | 87 | 12.251 | 38.496 | 5.044 | 1.00 | 20.00 |
| ATOM | 3595 | N | SER | C | 88 | 12.642 | 38.836 | 8.234 | 1.00 | 17.75 |
| ATOM | 3596 | CA | SER | C | 88 | 13.519 | 39.539 | 9.131 | 1.00 | 17.75 |
| ATOM | 3597 | C | SER | C | 88 | 12.987 | 39.503 | 10.535 | 1.00 | 17.75 |
| ATOM | 3598 | O | SER | C | 88 | 12.814 | 40.509 | 11.205 | 1.00 | 17.75 |
| ATOM | 3599 | CB | SER | C | 88 | 13.644 | 40.935 | 8.587 | 1.00 | 17.75 |
| ATOM | 3600 | OG | SER | C | 88 | 14.562 | 41.686 | 9.373 | 1.00 | 17.75 |
| ATOM | 3601 | H | SER | C | 88 | 11.756 | 39.209 | 7.971 | 1.00 | 20.00 |
| ATOM | 3602 | HG | SER | C | 88 | 14.024 | 42.406 | 9.661 | 1.00 | 20.00 |
| ATOM | 3603 | N | TYR | C | 89 | 12.744 | 38.270 | 10.966 | 1.00 | 19.14 |
| ATOM | 3604 | CA | TYR | C | 89 | 12.590 | 38.127 | 12.407 | 1.00 | 19.14 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM 3605 | C | TYR | C | 89 | 13.964 | 38.248 | 13.072 | 1.00 | 19.14 |
| ATOM 3606 | O | TYR | C | 89 | 14.897 | 38.805 | 12.500 | 1.00 | 19.14 |
| ATOM 3607 | CB | TYR | C | 89 | 11.820 | 36.830 | 12.713 | 1.00 | 19.14 |
| ATOM 3608 | CG | TYR | C | 89 | 12.502 | 35.656 | 12.058 | 1.00 | 19.14 |
| ATOM 3609 | CD1 | TYR | C | 89 | 12.084 | 35.257 | 10.779 | 1.00 | 19.14 |
| ATOM 3610 | CD2 | TYR | C | 89 | 13.554 | 35.014 | 12.738 | 1.00 | 19.14 |
| ATOM 3611 | CE1 | TYR | C | 89 | 12.788 | 34.229 | 10.159 | 1.00 | 19.14 |
| ATOM 3612 | CE2 | TYR | C | 89 | 14.256 | 33.980 | 12.106 | 1.00 | 19.14 |
| ATOM 3613 | CZ | TYR | C | 89 | 13.872 | 33.612 | 10.810 | 1.00 | 19.14 |
| ATOM 3614 | CH | TYR | C | 89 | 14.581 | 32.623 | 10.167 | 1.00 | 19.14 |
| ATOM 3615 | H | TYR | C | 89 | 12.930 | 37.496 | 10.361 | 1.00 | 20.00 |
| ATOM 3616 | HH | TYR | C | 89 | 14.838 | 31.971 | 10.814 | 1.00 | 20.00 |
| ATOM 3617 | N | CYS | C | 90 | 14.075 | 37.727 | 14.294 | 1.00 | 32.37 |
| ATOM 3618 | CA | CYS | C | 90 | 15.400 | 37.814 | 14.906 | 1.00 | 32.37 |
| ATOM 3619 | C | CYS | C | 90 | 15.975 | 36.457 | 15.265 | 1.00 | 32.37 |
| ATOM 3620 | O | CYS | C | 90 | 15.443 | 35.420 | 14.896 | 1.00 | 32.37 |
| ATOM 3621 | CB | CYS | C | 90 | 15.325 | 38.758 | 16.104 | 1.00 | 32.37 |
| ATOM 3622 | SG | CYS | C | 90 | 13.763 | 38.558 | 16.976 | 1.00 | 32.37 |
| ATOM 3623 | H | CYS | C | 90 | 13.312 | 37.291 | 14.773 | 1.00 | 20.00 |
| ATOM 3624 | N | THR | C | 91 | 17.078 | 36.507 | 16.014 | 1.00 | 22.92 |
| ATOM 3625 | CA | THR | C | 91 | 17.631 | 35.291 | 16.602 | 1.00 | 22.92 |
| ATOM 3626 | C | THR | C | 91 | 17.453 | 35.405 | 18.108 | 1.00 | 22.92 |
| ATOM 3627 | O | THR | C | 91 | 16.545 | 36.090 | 18.551 | 1.00 | 22.92 |
| ATOM 3628 | CB | THR | C | 91 | 19.094 | 35.235 | 16.184 | 1.00 | 22.92 |
| ATOM 3629 | OG1 | THR | C | 91 | 19.700 | 36.512 | 16.424 | 1.00 | 22.92 |
| ATOM 3630 | CG2 | THR | C | 91 | 19.238 | 34.862 | 14.705 | 1.00 | 22.92 |
| ATOM 3631 | H | THR | C | 91 | 17.535 | 37.354 | 16.279 | 1.00 | 20.00 |
| ATOM 3632 | HG1 | THR | C | 91 | 20.637 | 36.374 | 16.397 | 1.00 | 20.00 |
| ATOM 3633 | N | THR | C | 92 | 18.348 | 34.794 | 18.904 | 1.00 | 5.61 |
| ATOM 3634 | CA | THR | C | 92 | 18.301 | 35.135 | 20.330 | 1.00 | 5.61 |
| ATOM 3635 | C | THR | C | 92 | 18.369 | 36.632 | 20.618 | 1.00 | 5.61 |
| ATOM 3636 | O | THR | C | 92 | 19.367 | 37.290 | 20.347 | 1.00 | 5.61 |
| ATOM 3637 | CB | THR | C | 92 | 19.432 | 34.407 | 21.051 | 1.00 | 5.61 |
| ATOM 3638 | OG1 | THR | C | 92 | 19.515 | 33.063 | 20.565 | 1.00 | 5.61 |
| ATOM 3639 | CG2 | THR | C | 92 | 19.271 | 34.434 | 22.575 | 1.00 | 5.61 |
| ATOM 3640 | H | THR | C | 92 | 19.014 | 34.112 | 18.603 | 1.00 | 20.00 |
| ATOM 3641 | HG1 | THR | C | 92 | 20.118 | 32.608 | 21.140 | 1.00 | 20.00 |
| ATOM 3642 | N | GLY | C | 93 | 17.252 | 37.135 | 21.164 | 1.00 | 3.78 |
| ATOM 3643 | CA | GLY | C | 93 | 17.202 | 38.570 | 21.396 | 1.00 | 3.78 |
| ATOM 3644 | C | GLY | C | 93 | 15.914 | 38.982 | 22.066 | 1.00 | 3.78 |
| ATOM 3645 | O | GLY | C | 93 | 15.058 | 38.165 | 22.385 | 1.00 | 3.78 |
| ATOM 3646 | H | GLY | C | 93 | 16.427 | 36.586 | 21.303 | 1.00 | 20.00 |
| ATOM 3647 | N | GLN | C | 94 | 15.845 | 40.307 | 22.264 | 1.00 | 15.42 |
| ATOM 3648 | CA | GLN | C | 94 | 14.651 | 40.911 | 22.846 | 1.00 | 15.42 |
| ATOM 3649 | C | GLN | C | 94 | 13.512 | 41.010 | 21.841 | 1.00 | 15.42 |
| ATOM 3650 | O | GLN | C | 94 | 13.470 | 40.305 | 20.841 | 1.00 | 15.42 |
| ATOM 3651 | CB | GLN | C | 94 | 15.036 | 42.284 | 23.412 | 1.00 | 15.42 |
| ATOM 3652 | CG | GLN | C | 94 | 15.919 | 42.225 | 24.662 | 1.00 | 15.42 |
| ATOM 3653 | CD | GLN | C | 94 | 15.129 | 41.654 | 25.826 | 1.00 | 15.42 |
| ATOM 3654 | OE1 | GLN | C | 94 | 15.286 | 40.514 | 26.235 | 1.00 | 15.42 |
| ATOM 3655 | NE2 | GLN | C | 94 | 14.257 | 42.518 | 26.355 | 1.00 | 15.42 |
| ATOM 3656 | H | GLN | C | 94 | 16.578 | 40.882 | 21.907 | 1.00 | 20.00 |
| ATOM 3657 | 1 HE2 | GLN | C | 94 | 14.140 | 43.439 | 25.990 | 1.00 | 20.00 |
| ATOM 3658 | 2 HE2 | GLN | C | 94 | 13.737 | 42.206 | 27.149 | 1.00 | 20.00 |
| ATOM 3659 | N | MET | C | 95 | 12.595 | 41.952 | 22.134 | 1.00 | 18.74 |
| ATOM 3660 | CA | MET | C | 95 | 11.607 | 42.290 | 21.112 | 1.00 | 18.74 |
| ATOM 3661 | C | MET | C | 95 | 12.209 | 42.709 | 19.776 | 1.00 | 18.74 |
| ATOM 3662 | O | MET | C | 95 | 13.317 | 43.223 | 19.684 | 1.00 | 18.74 |
| ATOM 3663 | CB | MET | C | 95 | 10.633 | 43.358 | 21.635 | 1.00 | 18.74 |
| ATOM 3664 | CG | MET | C | 95 | 11.314 | 44.665 | 22.057 | 1.00 | 18.74 |
| ATOM 3665 | SD | MET | C | 95 | 10.183 | 45.997 | 22.487 | 1.00 | 18.74 |
| ATOM 3666 | CE | MET | C | 95 | 11.415 | 47.240 | 22.920 | 1.00 | 18.74 |
| ATOM 3667 | H | MET | C | 95 | 12.616 | 42.449 | 22.996 | 1.00 | 20.00 |
| ATOM 3668 | N | TRP | C | 96 | 11.402 | 42.469 | 18.741 | 1.00 | 3.87 |
| ATOM 3669 | CA | TRP | C | 96 | 11.807 | 42.911 | 17.412 | 1.00 | 3.87 |
| ATOM 3670 | C | TRP | C | 96 | 10.624 | 43.548 | 16.734 | 1.00 | 3.87 |
| ATOM 3671 | O | TRP | C | 96 | 9.518 | 43.043 | 16.852 | 1.00 | 3.87 |
| ATOM 3672 | CB | TRP | C | 96 | 12.327 | 41.730 | 16.579 | 1.00 | 3.87 |
| ATOM 3673 | CG | TRP | C | 96 | 11.268 | 40.652 | 16.436 | 1.00 | 3.87 |
| ATOM 3674 | CD1 | TRP | C | 96 | 11.013 | 39.591 | 17.318 | 1.00 | 3.87 |
| ATOM 3675 | CD2 | TRP | C | 96 | 10.312 | 40.483 | 15.370 | 1.00 | 3.87 |
| ATOM 3676 | NE1 | TRP | C | 96 | 9.998 | 38.804 | 16.881 | 1.00 | 3.87 |
| ATOM 3677 | CE2 | TRP | C | 96 | 9.521 | 39.326 | 15.682 | 1.00 | 3.87 |
| ATOM 3678 | CE3 | TRP | C | 96 | 10.042 | 41.227 | 14.204 | 1.00 | 3.87 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM | 3679 | CZ2 | TRP | C | 96 | 8.495 | 38.923 | 14.503 | 1.00 | 3.87 |
| ATOM | 3680 | CZ3 | TRP | C | 96 | 9.010 | 40.817 | 13.338 | 1.00 | 3.87 |
| ATOM | 3681 | CH2 | TRP | C | 96 | 8.238 | 39.675 | 13.638 | 1.00 | 3.87 |
| ATOM | 3682 | H | TRP | C | 96 | 10.547 | 41.965 | 18.891 | 1.00 | 20.00 |
| ATOM | 3683 | HE1 | TRP | C | 96 | 9.688 | 37.996 | 17.345 | 1.00 | 20.00 |
| ATOM | 3684 | N | ALA | C | 97 | 10.892 | 44.650 | 16.024 | 1.00 | 3.76 |
| ATOM | 3685 | CA | ALA | C | 97 | 9.794 | 45.242 | 15.270 | 1.00 | 3.76 |
| ATOM | 3686 | C | ALA | C | 97 | 10.204 | 45.489 | 13.840 | 1.00 | 3.76 |
| ATOM | 3687 | O | ALA | C | 97 | 11.275 | 46.032 | 13.585 | 1.00 | 3.76 |
| ATOM | 3688 | CB | ALA | C | 97 | 9.340 | 46.560 | 15.900 | 1.00 | 3.76 |
| ATOM | 3689 | H | ALA | C | 97 | 11.817 | 45.020 | 15.972 | 1.00 | 20.00 |
| ATOM | 3690 | N | ARG | C | 98 | 9.326 | 45.029 | 12.930 | 1.00 | 11.69 |
| ATOM | 3691 | CA | ARG | C | 98 | 9.592 | 45.242 | 11.506 | 1.00 | 11.69 |
| ATOM | 3692 | C | ARG | C | 98 | 8.440 | 45.948 | 10.839 | 1.00 | 11.69 |
| ATOM | 3693 | O | ARG | C | 98 | 7.280 | 45.688 | 11.133 | 1.00 | 11.69 |
| ATOM | 3694 | CB | ARG | C | 98 | 9.830 | 43.938 | 10.738 | 1.00 | 11.69 |
| ATOM | 3695 | CG | ARG | C | 98 | 10.886 | 43.027 | 11.347 | 1.00 | 11.69 |
| ATOM | 3696 | CD | ARG | C | 98 | 12.225 | 43.716 | 11.560 | 1.00 | 11.69 |
| ATOM | 3697 | NE | ARG | C | 98 | 13.131 | 42.856 | 12.316 | 1.00 | 11.69 |
| ATOM | 3698 | CZ | ARG | C | 98 | 14.443 | 42.914 | 12.074 | 1.00 | 11.69 |
| ATOM | 3699 | NH1 | ARG | C | 98 | 15.314 | 42.219 | 12.799 | 1.00 | 11.69 |
| ATOM | 3700 | NH2 | ARG | C | 98 | 14.864 | 43.706 | 11.105 | 1.00 | 11.69 |
| ATOM | 3701 | H | ARG | C | 98 | 8.465 | 44.621 | 13.246 | 1.00 | 20.00 |
| ATOM | 3702 | HE | ARG | C | 98 | 12.756 | 42.194 | 12.966 | 1.00 | 20.00 |
| ATOM | 3703 | 1 HH1 | ARG | C | 98 | 16.301 | 42.347 | 12.693 | 1.00 | 20.00 |
| ATOM | 3704 | 2 HH1 | ARG | C | 98 | 14.993 | 41.549 | 13.468 | 1.00 | 20.00 |
| ATOM | 3705 | 1 HH2 | ARG | C | 98 | 15.845 | 43.906 | 11.040 | 1.00 | 20.00 |
| ATOM | 3706 | 2 HH2 | ARG | C | 98 | 14.237 | 44.192 | 10.499 | 1.00 | 20.00 |
| ATOM | 3707 | N | SER | C | 99 | 8.806 | 46.839 | 9.913 | 1.00 | 7.28 |
| ATOM | 3708 | CA | SER | C | 99 | 7.720 | 47.440 | 9.156 | 1.00 | 7.28 |
| ATOM | 3709 | C | SER | C | 99 | 7.749 | 47.126 | 7.678 | 1.00 | 7.28 |
| ATOM | 3710 | O | SER | C | 99 | 8.790 | 47.124 | 7.032 | 1.00 | 7.28 |
| ATOM | 3711 | CB | SER | C | 99 | 7.697 | 48.944 | 9.396 | 1.00 | 7.28 |
| ATOM | 3712 | OG | SER | C | 99 | 8.948 | 49.559 | 9.072 | 1.00 | 7.28 |
| ATOM | 3713 | H | SER | C | 99 | 9.750 | 47.106 | 9.728 | 1.00 | 20.00 |
| ATOM | 3714 | HG | SER | C | 99 | 9.129 | 50.199 | 9.749 | 1.00 | 20.00 |
| ATOM | 3715 | N | SER | C | 100 | 6.533 | 46.894 | 7.168 | 1.00 | 2.73 |
| ATOM | 3716 | CA | SER | C | 100 | 6.417 | 46.751 | 5.722 | 1.00 | 2.73 |
| ATOM | 3717 | C | SER | C | 100 | 5.485 | 47.803 | 5.156 | 1.00 | 2.73 |
| ATOM | 3718 | O | SER | C | 100 | 4.370 | 47.971 | 5.626 | 1.00 | 2.73 |
| ATOM | 3719 | CB | SER | C | 100 | 5.930 | 45.344 | 5.368 | 1.00 | 2.73 |
| ATOM | 3720 | OG | SER | C | 100 | 6.869 | 44.368 | 5.837 | 1.00 | 2.73 |
| ATOM | 3721 | H | SER | C | 100 | 5.720 | 46.875 | 7.758 | 1.00 | 20.00 |
| ATOM | 3722 | HG | SER | C | 100 | 6.414 | 43.534 | 5.838 | 1.00 | 20.00 |
| ATOM | 3723 | N | TYR | C | 101 | 6.001 | 48.510 | 4.133 | 1.00 | 2.72 |
| ATOM | 3724 | CA | TYR | C | 101 | 5.171 | 49.531 | 3.481 | 1.00 | 2.72 |
| ATOM | 3725 | C | TYR | C | 101 | 5.090 | 49.285 | 1.995 | 1.00 | 2.72 |
| ATOM | 3726 | O | TYR | C | 101 | 6.113 | 49.072 | 1.367 | 1.00 | 2.72 |
| ATOM | 3727 | CB | TYR | C | 101 | 5.753 | 50.933 | 3.700 | 1.00 | 2.72 |
| ATOM | 3728 | CG | TYR | C | 101 | 4.918 | 51.981 | 2.993 | 1.00 | 2.72 |
| ATOM | 3729 | CD1 | TYR | C | 101 | 3.771 | 52.511 | 3.618 | 1.00 | 2.72 |
| ATOM | 3730 | CD2 | TYR | C | 101 | 5.309 | 52.384 | 1.703 | 1.00 | 2.72 |
| ATOM | 3731 | CE1 | TYR | C | 101 | 3.003 | 53.473 | 2.941 | 1.00 | 2.72 |
| ATOM | 3732 | CE2 | TYR | C | 101 | 4.534 | 53.331 | 1.021 | 1.00 | 2.72 |
| ATOM | 3733 | CZ | TYR | C | 101 | 3.409 | 53.885 | 1.656 | 1.00 | 2.72 |
| ATOM | 3734 | OH | TYR | C | 101 | 2.706 | 54.874 | 0.997 | 1.00 | 2.72 |
| ATOM | 3735 | H | TYR | C | 101 | 6.935 | 48.332 | 3.829 | 1.00 | 20.00 |
| ATOM | 3736 | HH | TYR | C | 101 | 3.125 | 55.063 | 0.169 | 1.00 | 20.00 |
| ATOM | 3737 | N | LEU | C | 102 | 3.873 | 49.322 | 1.460 | 1.00 | 17.88 |
| ATOM | 3738 | CA | LEU | C | 102 | 3.663 | 49.070 | 0.037 | 1.00 | 17.88 |
| ATOM | 3739 | C | LEU | C | 102 | 2.963 | 50.276 | −0.569 | 1.00 | 17.88 |
| ATOM | 3740 | O | LEU | C | 102 | 2.228 | 50.966 | 0.126 | 1.00 | 17.88 |
| ATOM | 3741 | CB | LEU | C | 102 | 2.818 | 47.798 | −0.127 | 1.00 | 17.88 |
| ATOM | 3742 | CG | LEU | C | 102 | 3.577 | 46.457 | −0.131 | 1.00 | 17.88 |
| ATOM | 3743 | CD1 | LEU | C | 102 | 4.571 | 46.406 | −1.285 | 1.00 | 17.88 |
| ATOM | 3744 | CD2 | LEU | C | 102 | 4.240 | 46.067 | 1.193 | 1.00 | 17.88 |
| ATOM | 3745 | H | LEU | C | 102 | 3.109 | 49.642 | 2.020 | 1.00 | 20.00 |
| ATOM | 3746 | N | GLY | C | 103 | 3.225 | 50.519 | −1.864 | 1.00 | 5.34 |
| ATOM | 3747 | CA | GLY | C | 103 | 2.573 | 51.686 | −2.462 | 1.00 | 5.34 |
| ATOM | 3748 | C | GLY | C | 103 | 2.863 | 51.846 | −3.942 | 1.00 | 5.34 |
| ATOM | 3749 | O | GLY | C | 103 | 4.020 | 51.837 | −4.340 | 1.00 | 5.34 |
| ATOM | 3750 | H | GLY | C | 103 | 3.831 | 49.946 | −2.417 | 1.00 | 20.00 |
| ATOM | 3751 | N | ALA | C | 104 | 1.778 | 51.979 | −4.734 | 1.00 | 6.66 |
| ATOM | 3752 | CA | ALA | C | 104 | 1.962 | 52.109 | −6.184 | 1.00 | 6.66 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3753 | C | ALA C | 104 | 0.713 | 52.555 | −6.929 | 1.00 | 6.66 |
| ATOM 3754 | O | ALA C | 104 | −0.366 | 52.617 | −6.354 | 1.00 | 6.66 |
| ATOM 3755 | CB | ALA C | 104 | 2.428 | 50.784 | −6.771 | 1.00 | 6.66 |
| ATOM 3756 | H | ALA C | 104 | 0.854 | 51.959 | −4.339 | 1.00 | 20.00 |
| ATOM 3757 | N | VAL C | 105 | 0.907 | 52.877 | −8.227 | 1.00 | 2.80 |
| ATOM 3758 | CA | VAL C | 105 | −0.232 | 53.351 | −9.022 | 1.00 | 2.80 |
| ATOM 3759 | C | VAL C | 105 | −0.758 | 52.333 | −10.009 | 1.00 | 2.80 |
| ATOM 3760 | O | VAL C | 105 | −0.016 | 51.701 | −10.751 | 1.00 | 2.80 |
| ATOM 3761 | CB | VAL C | 105 | 0.128 | 54.647 | −9.752 | 1.00 | 2.80 |
| ATOM 3762 | CG1 | VAL C | 105 | −0.998 | 55.205 | −10.620 | 1.00 | 2.80 |
| ATOM 3763 | CG2 | VAL C | 105 | 0.526 | 55.682 | −8.723 | 1.00 | 2.80 |
| ATOM 3764 | H | VAL C | 105 | 1.802 | 52.799 | −8.671 | 1.00 | 20.00 |
| ATOM 3765 | N | PHE C | 106 | −2.094 | 52.216 | −9.978 | 1.00 | 2.81 |
| ATOM 3766 | CA | PHE C | 106 | −2.736 | 51.196 | −10.798 | 1.00 | 2.81 |
| ATOM 3767 | C | PHE C | 106 | −3.996 | 51.740 | −11.470 | 1.00 | 2.81 |
| ATOM 3768 | O | PHE C | 106 | −4.599 | 52.678 | −10.965 | 1.00 | 2.81 |
| ATOM 3769 | CB | PHE C | 106 | −3.028 | 49.984 | −9.900 | 1.00 | 2.81 |
| ATOM 3770 | CG | PHE C | 106 | −1.754 | 49.378 | −9.328 | 1.00 | 2.81 |
| ATOM 3771 | CD1 | PHE C | 106 | −1.411 | 49.587 | −7.974 | 1.00 | 2.81 |
| ATOM 3772 | CD2 | PHE C | 106 | −0.932 | 48.582 | −10.150 | 1.00 | 2.81 |
| ATOM 3773 | CE1 | PHE C | 106 | −0.288 | 48.929 | −7.433 | 1.00 | 2.61 |
| ATOM 3774 | CE2 | PHE C | 106 | 0.193 | 47.923 | −9.623 | 1.00 | 2.81 |
| ATOM 3775 | CZ | PHE C | 106 | 0.487 | 48.084 | −8.256 | 1.00 | 2.81 |
| ATOM 3776 | H | PHE C | 106 | −2.628 | 52.794 | −9.354 | 1.00 | 20.00 |
| ATOM 3777 | N | ASN C | 107 | −4.382 | 51.142 | −12.622 | 1.00 | 6.84 |
| ATOM 3778 | CA | ASN C | 107 | −5.709 | 51.517 | −13.142 | 1.00 | 6.84 |
| ATOM 3779 | C | ASN C | 107 | −6.748 | 50.571 | −12.633 | 1.00 | 6.84 |
| ATOM 3780 | O | ASN C | 107 | −6.746 | 49.387 | −12.948 | 1.00 | 6.84 |
| ATOM 3781 | CB | ASN C | 107 | −5.915 | 51.449 | −14.658 | 1.00 | 6.84 |
| ATOM 3782 | CG | ASN C | 107 | −5.166 | 52.525 | −15.382 | 1.00 | 6.84 |
| ATOM 3783 | OD1 | ASN C | 107 | −5.649 | 53.583 | −15.757 | 1.00 | 6.84 |
| ATOM 3784 | ND2 | ASN C | 107 | −3.922 | 52.156 | −15.595 | 1.00 | 6.84 |
| ATOM 3785 | H | ASN C | 107 | −3.904 | 50.331 | −12.952 | 1.00 | 20.00 |
| ATOM 3786 | 1HD2 | ASN C | 107 | −3.594 | 51.279 | −15.246 | 1.00 | 20.00 |
| ATOM 3787 | 2HD2 | ASN C | 107 | −3.299 | 52.753 | −16.097 | 1.00 | 20.00 |
| ATOM 3788 | N | LEU C | 108 | −7.641 | 51.157 | −11.846 | 1.00 | 5.08 |
| ATOM 3789 | CA | LEU C | 108 | −8.746 | 50.318 | −11.421 | 1.00 | 5.08 |
| ATOM 3790 | C | LEU C | 108 | −9.997 | 50.627 | −12.210 | 1.00 | 5.08 |
| ATOM 3791 | O | LEU C | 108 | −10.079 | 51.625 | −12.924 | 1.00 | 5.08 |
| ATOM 3792 | CB | LEU C | 108 | −8.927 | 50.447 | −9.911 | 1.00 | 5.08 |
| ATOM 3793 | CG | LEU C | 108 | −7.644 | 50.048 | −9.172 | 1.00 | 5.08 |
| ATOM 3794 | CD1 | LEU C | 108 | −7.678 | 50.439 | −7.699 | 1.00 | 5.08 |
| ATOM 3795 | CD2 | LEU C | 108 | −7.303 | 48.569 | −9.359 | 1.00 | 5.08 |
| ATOM 3796 | H | LEU C | 108 | −7.608 | 52.146 | −11.684 | 1.00 | 20.00 |
| ATOM 3797 | N | THR C | 109 | −10.948 | 49.702 | −12.060 | 1.00 | 3.97 |
| ATOM 3798 | CA | THR C | 109 | −12.199 | 49.845 | −12.791 | 1.00 | 3.97 |
| ATOM 3799 | C | THR C | 109 | −13.303 | 49.877 | −11.750 | 1.00 | 3.97 |
| ATOM 3800 | O | THR C | 109 | −13.088 | 49.518 | −10.603 | 1.00 | 3.97 |
| ATOM 3801 | CB | THR C | 109 | −12.356 | 48.647 | −13.749 | 1.00 | 3.97 |
| ATOM 3802 | OG1 | THR C | 109 | −11.129 | 48.393 | −14.446 | 1.00 | 3.97 |
| ATOM 3803 | CG2 | THR C | 109 | −13.487 | 48.810 | −14.772 | 1.00 | 3.97 |
| ATOM 3804 | H | THR C | 109 | −10.874 | 48.979 | −11.366 | 1.00 | 20.00 |
| ATOM 3805 | HG1 | THR C | 109 | −11.301 | 47.635 | −14.983 | 1.00 | 20.00 |
| ATOM 3806 | N | SER C | 110 | −14.510 | 50.283 | −12.158 | 1.00 | 5.78 |
| ATOM 3807 | CA | SER C | 110 | −15.602 | 49.995 | −11.231 | 1.00 | 5.78 |
| ATOM 3808 | C | SER C | 110 | −15.764 | 48.509 | −10.919 | 1.00 | 5.78 |
| ATOM 3809 | O | SER C | 110 | −15.531 | 47.653 | −11.766 | 1.00 | 5.78 |
| ATOM 3810 | CB | SER C | 110 | −16.888 | 50.580 | −11.800 | 1.00 | 5.78 |
| ATOM 3811 | OG | SER C | 110 | −16.641 | 51.935 | −12.192 | 1.00 | 5.78 |
| ATOM 3812 | H | SER C | 110 | −14.690 | 50.720 | −13.039 | 1.00 | 20.00 |
| ATOM 3813 | HG | SER C | 110 | −16.930 | 52.472 | −11.456 | 1.00 | 20.00 |
| ATOM 3814 | N | ALA C | 111 | −16.179 | 48.276 | −9.658 | 1.00 | 23.23 |
| ATOM 3815 | CA | ALA C | 111 | −16.587 | 46.975 | −9.117 | 1.00 | 23.23 |
| ATOM 3816 | C | ALA C | 111 | −15.509 | 46.036 | −8.612 | 1.00 | 23.23 |
| ATOM 3817 | O | ALA C | 111 | −15.815 | 45.076 | −7.911 | 1.00 | 23.23 |
| ATOM 3818 | CB | ALA C | 111 | −17.522 | 46.190 | −10.051 | 1.00 | 23.23 |
| ATOM 3819 | H | ALA C | 111 | −16.131 | 49.058 | −9.033 | 1.00 | 20.00 |
| ATOM 3820 | N | ASP C | 112 | −14.244 | 46.320 | −8.968 | 1.00 | 12.39 |
| ATOM 3821 | CA | ASP C | 112 | −13.272 | 45.377 | −8.430 | 1.00 | 12.39 |
| ATOM 3822 | C | ASP C | 112 | −12.940 | 45.570 | −6.963 | 1.00 | 12.39 |
| ATOM 3823 | O | ASP C | 112 | −13.185 | 46.622 | −6.380 | 1.00 | 12.39 |
| ATOM 3824 | CB | ASP C | 112 | −12.054 | 45.235 | −9.349 | 1.00 | 12.39 |
| ATOM 3825 | CG | ASP C | 112 | −11.065 | 46.384 | −9.373 | 1.00 | 12.39 |
| ATOM 3826 | OD1 | ASP C | 112 | −9.871 | 46.109 | −9.297 | 1.00 | 12.39 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3827 | OD2 | ASP C | 112 | −11.469 | 47.531 | −9.515 | 1.00 | 12.39 |
| ATOM 3828 | H | ASP C | 112 | −13.933 | 47.126 | −9.478 | 1.00 | 20.00 |
| ATOM 3829 | N | HIS C | 113 | −12.439 | 44.465 | −6.385 | 1.00 | 16.60 |
| ATOM 3830 | CA | HIS C | 113 | −12.106 | 44.527 | −4.965 | 1.00 | 16.60 |
| ATOM 3831 | C | HIS C | 113 | −10.614 | 44.536 | −4.754 | 1.00 | 16.60 |
| ATOM 3832 | O | HIS C | 113 | −9.888 | 43.789 | −5.395 | 1.00 | 16.60 |
| ATOM 3833 | CB | HIS C | 113 | −12.651 | 43.333 | −4.183 | 1.00 | 16.60 |
| ATOM 3834 | CG | HIS C | 113 | −14.155 | 43.312 | −4.085 | 1.00 | 16.60 |
| ATOM 3835 | ND1 | HIS C | 113 | −14.951 | 42.861 | −5.068 | 1.00 | 16.60 |
| ATOM 3836 | CD2 | HIS C | 113 | −14.949 | 43.695 | −2.999 | 1.00 | 16.60 |
| ATOM 3837 | CE1 | HIS C | 113 | −16.241 | 42.954 | −4.618 | 1.00 | 16.60 |
| ATOM 3838 | NE2 | HIS C | 113 | −16.242 | 43.465 | −3.346 | 1.00 | 16.60 |
| ATOM 3839 | H | HIS C | 113 | −12.192 | 43.669 | −6.945 | 1.00 | 20.00 |
| ATOM 3840 | HD1 | HIS C | 113 | −14.660 | 42.542 | −5.948 | 1.00 | 20.00 |
| ATOM 3841 | N | LEU C | 114 | −10.190 | 45.370 | −3.799 | 1.00 | 5.46 |
| ATOM 3842 | CA | LEU C | 114 | −8.805 | 45.190 | −3.367 | 1.00 | 5.46 |
| ATOM 3843 | C | LEU C | 114 | −8.771 | 44.644 | −1.968 | 1.00 | 5.46 |
| ATOM 3844 | O | LEU C | 114 | −9.650 | 44.950 | −1.171 | 1.00 | 5.46 |
| ATOM 3845 | CB | LEU C | 114 | −8.000 | 46.485 | −3.364 | 1.00 | 5.46 |
| ATOM 3846 | CG | LEU C | 114 | −7.974 | 47.270 | −4.668 | 1.00 | 5.46 |
| ATOM 3847 | CD1 | LEU C | 114 | −6.918 | 48.360 | −4.584 | 1.00 | 5.46 |
| ATOM 3848 | CD2 | LEU C | 114 | −7.760 | 46.410 | −5.906 | 1.00 | 5.46 |
| ATOM 3849 | H | LEU C | 114 | −10.844 | 45.965 | −3.326 | 1.00 | 20.00 |
| ATOM 3850 | N | TYR C | 115 | −7.735 | 43.842 | −1.701 | 1.00 | 8.89 |
| ATOM 3851 | CA | TYR C | 115 | −7.600 | 43.353 | −0.332 | 1.00 | 8.89 |
| ATOM 3852 | C | TYR C | 115 | −6.159 | 43.351 | 0.095 | 1.00 | 8.89 |
| ATOM 3653 | O | TYR C | 115 | −5.250 | 43.393 | −0.726 | 1.00 | 8.89 |
| ATOM 3854 | CB | TYR C | 115 | −8.093 | 41.932 | −0.146 | 1.00 | 8.89 |
| ATOM 3855 | CG | TYR C | 115 | −9.512 | 41.669 | −0.563 | 1.00 | 8.89 |
| ATOM 3856 | CD1 | TYR C | 115 | −10.527 | 41.731 | 0.410 | 1.00 | 8.89 |
| ATOM 3857 | CD2 | TYR C | 115 | −9.769 | 41.314 | −1.901 | 1.00 | 8.89 |
| ATOM 3858 | CE1 | TYR C | 115 | −11.843 | 41.426 | 0.032 | 1.00 | 8.89 |
| ATOM 3859 | CE2 | TYR C | 115 | −11.085 | 41.006 | −2.275 | 1.00 | 8.89 |
| ATOM 3860 | CZ | TYR C | 115 | −12.111 | 41.094 | −1.310 | 1.00 | 8.89 |
| ATOM 3861 | OH | TYR C | 115 | −13.427 | 40.877 | −1.680 | 1.00 | 8.89 |
| ATOM 3862 | H | TYR C | 115 | −7.089 | 43.583 | −2.428 | 1.00 | 20.00 |
| ATOM 3863 | HH | TYR C | 115 | −13.500 | 40.898 | −2.625 | 1.00 | 20.00 |
| ATOM 3864 | N | VAL C | 116 | −6.003 | 43.353 | 1.429 | 1.00 | 5.15 |
| ATOM 3865 | CA | VAL C | 116 | −4.655 | 43.500 | 1.969 | 1.00 | 5.15 |
| ATOM 3866 | C | VAL C | 116 | −4.427 | 42.616 | 3.167 | 1.00 | 5.15 |
| ATOM 3867 | O | VAL C | 116 | −4.921 | 42.892 | 4.254 | 1.00 | 5.15 |
| ATOM 3868 | CB | VAL C | 116 | −4.391 | 44.958 | 2.347 | 1.00 | 5.15 |
| ATOM 3869 | CG1 | VAL C | 116 | −3.047 | 45.146 | 3.028 | 1.00 | 5.15 |
| ATOM 3870 | CG2 | VAL C | 116 | −4.431 | 45.833 | 1.114 | 1.00 | 5.15 |
| ATOM 3871 | H | VAL C | 116 | −6.795 | 43.259 | 2.033 | 1.00 | 20.00 |
| ATOM 3872 | N | ASN C | 117 | −3.635 | 41.564 | 2.923 | 1.00 | 8.77 |
| ATOM 3873 | CA | ASN C | 117 | −3.425 | 40.689 | 4.070 | 1.00 | 8.77 |
| ATOM 3874 | C | ASN C | 117 | −1.998 | 40.449 | 4.438 | 1.00 | 8.77 |
| ATOM 3875 | O | ASN C | 117 | −1.065 | 40.561 | 3.650 | 1.00 | 8.77 |
| ATOM 3876 | CB | ASN C | 117 | −4.121 | 39.345 | 3.930 | 1.00 | 8.77 |
| ATOM 3877 | CG | ASN C | 117 | −5.592 | 39.615 | 3.829 | 1.00 | 8.77 |
| ATOM 3878 | OD1 | ASN C | 117 | −6.204 | 40.373 | 4.562 | 1.00 | 8.77 |
| ATOM 3879 | ND2 | ASN C | 117 | −6.137 | 38.982 | 2.834 | 1.00 | 8.77 |
| ATOM 3880 | H | ASN C | 117 | −3.275 | 41.370 | 2.006 | 1.00 | 20.00 |
| ATOM 3881 | 1HD2 | ASN C | 117 | −5.613 | 38.450 | 2.164 | 1.00 | 20.00 |
| ATOM 3882 | 2HD2 | ASN C | 117 | −7.069 | 39.135 | 2.531 | 1.00 | 20.00 |
| ATOM 3883 | N | VAL C | 118 | −1.895 | 40.104 | 5.721 | 1.00 | 2.80 |
| ATOM 3884 | CA | VAL C | 118 | −0.593 | 39.711 | 6.231 | 1.00 | 2.80 |
| ATOM 3885 | C | VAL C | 118 | −0.635 | 38.220 | 6.429 | 1.00 | 2.80 |
| ATOM 3886 | O | VAL C | 118 | −1.697 | 37.681 | 6.704 | 1.00 | 2.80 |
| ATOM 3887 | CB | VAL C | 118 | −0.353 | 40.435 | 7.559 | 1.00 | 2.80 |
| ATOM 3888 | CG1 | VAL C | 118 | 0.916 | 40.010 | 8.299 | 1.00 | 2.80 |
| ATOM 3889 | CG2 | VAL C | 118 | −0.376 | 41.939 | 7.324 | 1.00 | 2.80 |
| ATOM 3890 | H | VAL C | 118 | −2.718 | 39.935 | 6.266 | 1.00 | 20.00 |
| ATOM 3891 | N | SER C | 119 | 0.535 | 37.580 | 6.321 | 1.00 | 3.07 |
| ATOM 3892 | CA | SER C | 119 | 0.547 | 36.208 | 6.827 | 1.00 | 3.07 |
| ATOM 3893 | C | SER C | 119 | 0.075 | 36.075 | 8.291 | 1.00 | 3.07 |
| ATOM 3894 | O | SER C | 119 | −1.027 | 35.625 | 8.587 | 1.00 | 3.07 |
| ATOM 3895 | CB | SER C | 119 | 1.928 | 35.591 | 6.539 | 1.00 | 3.07 |
| ATOM 3896 | CG | SER C | 119 | 2.980 | 36.438 | 7.029 | 1.00 | 3.07 |
| ATOM 3897 | H | SER C | 119 | 1.366 | 38.081 | 6.067 | 1.00 | 20.00 |
| ATOM 3898 | HG | SER C | 119 | 3.428 | 35.915 | 7.707 | 1.00 | 20.00 |
| ATOM 3899 | N | GLU C | 120 | 0.930 | 36.509 | 9.223 | 1.00 | 12.56 |
| ATOM 3900 | CA | GLU C | 120 | 0.538 | 36.236 | 10.608 | 1.00 | 12.56 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3901 | C | GLU C | 120 | 0.004 | 37.435 | 11.360 | 1.00 | 12.56 |
| ATOM 3902 | O | GLU C | 120 | 0.721 | 38.386 | 11.647 | 1.00 | 12.56 |
| ATOM 3903 | CB | GLU C | 120 | 1.681 | 35.651 | 11.452 | 1.00 | 12.56 |
| ATOM 3904 | CG | GLU C | 120 | 2.348 | 34.312 | 11.093 | 1.00 | 12.56 |
| ATOM 3905 | CD | GLU C | 120 | 3.027 | 34.367 | 9.742 | 1.00 | 12.56 |
| ATOM 3906 | OE1 | GLU C | 120 | 3.641 | 35.387 | 9.440 | 1.00 | 12.56 |
| ATOM 3907 | OE2 | GLU C | 120 | 2.931 | 33.398 | 8.990 | 1.00 | 12.56 |
| ATOM 3908 | H | GLU C | 120 | 1.813 | 36.922 | 8.983 | 1.00 | 20.00 |
| ATOM 3909 | N | LEU C | 121 | −1.281 | 37.351 | 11.733 | 1.00 | 16.20 |
| ATOM 3910 | CA | LEU C | 121 | −1.776 | 38.546 | 12.420 | 1.00 | 16.20 |
| ATOM 3911 | C | LEU C | 121 | −1.412 | 38.676 | 13.892 | 1.00 | 16.20 |
| ATOM 3912 | O | LEU C | 121 | −1.465 | 39.747 | 14.485 | 1.00 | 16.20 |
| ATOM 3913 | CB | LEU C | 121 | −3.259 | 38.801 | 12.140 | 1.00 | 16.20 |
| ATOM 3914 | CG | LEU C | 121 | −3.542 | 39.252 | 10.702 | 1.00 | 16.20 |
| ATOM 3915 | CD1 | LEU C | 121 | −2.592 | 40.361 | 10.277 | 1.00 | 16.20 |
| ATOM 3916 | CD2 | LEU C | 121 | −3.564 | 38.129 | 9.669 | 1.00 | 16.20 |
| ATOM 3917 | H | LEU C | 121 | −1.868 | 36.575 | 11.492 | 1.00 | 20.00 |
| ATOM 3918 | N | SER C | 122 | −0.917 | 37.546 | 14.431 | 1.00 | 8.33 |
| ATOM 3919 | CA | SER C | 122 | −0.237 | 37.593 | 15.728 | 1.00 | 8.33 |
| ATOM 3920 | C | SER C | 122 | 0.909 | 38.589 | 15.825 | 1.00 | 8.33 |
| ATOM 3921 | O | SER C | 122 | 1.248 | 39.085 | 16.890 | 1.00 | 8.33 |
| ATOM 3922 | CB | SER C | 122 | 0.288 | 36.206 | 16.078 | 1.00 | 8.33 |
| ATOM 3923 | CG | SER C | 122 | −0.667 | 35.221 | 15.673 | 1.00 | 8.33 |
| ATOM 3924 | H | SER C | 122 | −1.050 | 36.661 | 13.986 | 1.00 | 20.00 |
| ATOM 3925 | HG | SER C | 122 | −0.389 | 34.411 | 16.078 | 1.00 | 20.00 |
| ATOM 3926 | N | LEU C | 123 | 1.493 | 38.855 | 14.641 | 1.00 | 10.07 |
| ATOM 3927 | CA | LEU C | 123 | 2.577 | 39.833 | 14.580 | 1.00 | 10.07 |
| ATOM 3928 | C | LEU C | 123 | 2.158 | 41.266 | 14.832 | 1.00 | 10.07 |
| ATOM 3929 | O | LEU C | 123 | 2.977 | 42.114 | 15.160 | 1.00 | 10.07 |
| ATOM 3930 | CB | LEU C | 123 | 3.221 | 39.824 | 13.204 | 1.00 | 10.07 |
| ATOM 3931 | CG | LEU C | 123 | 3.772 | 38.495 | 12.713 | 1.00 | 10.07 |
| ATOM 3932 | CD1 | LEU C | 123 | 3.961 | 38.536 | 11.198 | 1.00 | 10.07 |
| ATOM 3933 | CD2 | LEU C | 123 | 5.031 | 38.075 | 13.468 | 1.00 | 10.07 |
| ATOM 3934 | H | LEU C | 123 | 1.154 | 38.448 | 13.789 | 1.00 | 20.00 |
| ATOM 3935 | N | VAL C | 124 | 0.862 | 41.525 | 14.587 | 1.00 | 5.90 |
| ATOM 3936 | CA | VAL C | 124 | 0.517 | 42.935 | 14.459 | 1.00 | 5.90 |
| ATOM 3937 | C | VAL C | 124 | 0.587 | 43.712 | 15.750 | 1.00 | 5.90 |
| ATOM 3938 | O | VAL C | 124 | 0.065 | 43.349 | 16.797 | 1.00 | 5.90 |
| ATOM 3939 | CB | VAL C | 124 | −0.827 | 43.121 | 13.742 | 1.00 | 5.90 |
| ATOM 3940 | CG1 | VAL C | 124 | −1.211 | 44.586 | 13.507 | 1.00 | 5.90 |
| ATOM 3941 | CG2 | VAL C | 124 | −0.742 | 42.418 | 12.395 | 1.00 | 5.90 |
| ATOM 3942 | H | VAL C | 124 | 0.165 | 40.808 | 14.518 | 1.00 | 20.00 |
| ATOM 3943 | N | ASN C | 125 | 1.286 | 44.839 | 15.593 | 1.00 | 5.82 |
| ATOM 3944 | CA | ASN C | 125 | 1.253 | 45.780 | 16.696 | 1.00 | 5.82 |
| ATOM 3945 | C | ASN C | 125 | 0.001 | 46.605 | 16.639 | 1.00 | 5.82 |
| ATOM 3946 | O | ASN C | 125 | −0.386 | 47.103 | 15.591 | 1.00 | 5.82 |
| ATOM 3947 | CB | ASN C | 125 | 2.455 | 46.712 | 16.655 | 1.00 | 5.82 |
| ATOM 3948 | CG | ASN C | 125 | 3.695 | 45.953 | 17.048 | 1.00 | 5.82 |
| ATOM 3949 | OD1 | ASN C | 125 | 3.674 | 45.044 | 17.871 | 1.00 | 5.82 |
| ATOM 3950 | ND2 | ASN C | 125 | 4.794 | 46.399 | 16.421 | 1.00 | 5.82 |
| ATOM 3951 | H | ASN C | 125 | 1.631 | 45.065 | 14.679 | 1.00 | 20.00 |
| ATOM 3952 | 1HD2 | ASN C | 125 | 4.758 | 47.221 | 15.853 | 1.00 | 20.00 |
| ATOM 3953 | 2HD2 | ASN C | 125 | 5.659 | 45.905 | 16.501 | 1.00 | 20.00 |
| ATOM 3954 | N | PHE C | 126 | −0.588 | 46.754 | 17.829 | 1.00 | 7.35 |
| ATOM 3955 | CA | PHE C | 126 | −1.587 | 47.809 | 17.914 | 1.00 | 7.35 |
| ATOM 3956 | C | PHE C | 126 | −1.199 | 48.815 | 18.956 | 1.00 | 7.35 |
| ATOM 3957 | O | PHE C | 126 | −2.028 | 49.398 | 19.641 | 1.00 | 7.35 |
| ATOM 3958 | CB | PHE C | 126 | −2.980 | 47.275 | 18.224 | 1.00 | 7.35 |
| ATOM 3959 | CG | PHE C | 126 | −3.392 | 46.261 | 17.190 | 1.00 | 7.35 |
| ATOM 3960 | CD1 | PHE C | 126 | −3.254 | 44.893 | 17.499 | 1.00 | 7.35 |
| ATOM 3961 | CD2 | PHE C | 126 | −3.914 | 46.690 | 15.950 | 1.00 | 7.35 |
| ATOM 3962 | CE1 | PHE C | 126 | −3.677 | 43.930 | 16.566 | 1.00 | 7.35 |
| ATOM 3963 | CE2 | PHE C | 126 | −4.343 | 45.727 | 15.017 | 1.00 | 7.35 |
| ATOM 3964 | CZ | PHE C | 126 | −4.235 | 44.358 | 15.343 | 1.00 | 7.35 |
| ATOM 3965 | H | PHE C | 126 | −0.328 | 46.220 | 18.634 | 1.00 | 20.00 |
| ATOM 3966 | N | GLU C | 127 | 0.131 | 48.999 | 19.056 | 1.00 | 24.73 |
| ATOM 3967 | CA | GLU C | 127 | 0.501 | 50.103 | 19.932 | 1.00 | 24.73 |
| ATOM 3968 | C | GLU C | 127 | 0.000 | 51.423 | 19.378 | 1.00 | 24.73 |
| ATOM 3969 | O | GLU C | 127 | −0.527 | 52.267 | 20.088 | 1.00 | 24.73 |
| ATOM 3970 | CB | GLU C | 127 | 2.006 | 50.161 | 20.162 | 1.00 | 24.73 |
| ATOM 3971 | CG | GLU C | 127 | 2.354 | 51.265 | 21.170 | 1.00 | 24.73 |
| ATOM 3972 | CD | GLU C | 127 | 2.781 | 50.661 | 22.483 | 1.00 | 24.73 |
| ATOM 3973 | OE1 | GLU C | 127 | 3.935 | 50.873 | 22.856 | 1.00 | 24.73 |
| ATOM 3974 | OE2 | GLU C | 127 | 1.977 | 49.974 | 23.110 | 1.00 | 24.73 |

TABLE 1-continued

Atomic coordinates of the higher-order structure of Fas ligand

| Atom species | Amino acid residues | | # | X | Y | Z | OCC | B |
|---|---|---|---|---|---|---|---|---|
| ATOM 3975 | H | GLU C | 127 | 0.769 | 48.539 | 18.441 | 1.00 | 20.00 |
| ATOM 3976 | N | GLU C | 128 | 0.196 | 51.549 | 18.052 | 1.00 | 23.04 |
| ATOM 3977 | CA | GLU C | 128 | −0.125 | 52.847 | 17.475 | 1.00 | 23.04 |
| ATOM 3978 | C | GLU C | 128 | −0.744 | 52.724 | 16.096 | 1.00 | 23.04 |
| ATOM 3979 | O | GLU C | 128 | −0.960 | 51.626 | 15.599 | 1.00 | 23.04 |
| ATOM 3980 | CB | GLU C | 128 | 1.159 | 53.647 | 17.451 | 1.00 | 23.04 |
| ATOM 3981 | CG | GLU C | 128 | 1.605 | 54.203 | 18.810 | 1.00 | 23.04 |
| ATOM 3982 | CD | GLU C | 128 | 1.107 | 55.618 | 19.019 | 1.00 | 23.04 |
| ATOM 3983 | OE1 | GLU C | 128 | 0.356 | 56.125 | 18.180 | 1.00 | 23.04 |
| ATOM 3984 | OE2 | GLU C | 128 | 1.493 | 56.211 | 20.027 | 1.00 | 23.04 |
| ATOM 3985 | H | GLU C | 128 | 0.566 | 50.822 | 17.466 | 1.00 | 20.00 |
| ATOM 3986 | N | SER C | 129 | −0.999 | 53.889 | 15.469 | 1.00 | 19.86 |
| ATOM 3987 | CA | SER C | 129 | −1.846 | 53.943 | 14.262 | 1.00 | 19.86 |
| ATOM 3988 | C | SER C | 129 | −1.339 | 53.305 | 12.969 | 1.00 | 19.86 |
| ATOM 3989 | O | SER C | 129 | −1.933 | 53.394 | 11.903 | 1.00 | 19.86 |
| ATOM 3990 | CB | SER C | 129 | −2.223 | 55.400 | 13.991 | 1.00 | 19.86 |
| ATOM 3991 | OG | SER C | 129 | −2.331 | 56.091 | 15.240 | 1.00 | 19.86 |
| ATOM 3992 | H | SER C | 129 | −0.769 | 54.758 | 15.918 | 1.00 | 20.00 |
| ATOM 3993 | HG | SER C | 129 | −2.530 | 57.003 | 15.034 | 1.00 | 20.00 |
| ATOM 3994 | N | GLN C | 130 | −0.171 | 52.674 | 13.114 | 1.00 | 15.57 |
| ATOM 3995 | CA | GLN C | 130 | 0.662 | 52.233 | 12.003 | 1.00 | 15.57 |
| ATOM 3996 | C | GLN C | 130 | 0.054 | 51.392 | 10.884 | 1.00 | 15.57 |
| ATOM 3997 | O | GLN C | 130 | 0.416 | 51.529 | 9.722 | 1.00 | 15.57 |
| ATOM 3998 | CB | GLN C | 130 | 1.870 | 51.549 | 12.624 | 1.00 | 15.57 |
| ATOM 3999 | CG | GLN C | 130 | 1.560 | 50.341 | 13.533 | 1.00 | 15.57 |
| ATOM 4000 | CD | GLN C | 130 | 1.919 | 50.583 | 14.997 | 1.00 | 15.57 |
| ATOM 4001 | OE1 | GLN C | 130 | 1.513 | 49.865 | 15.902 | 1.00 | 15.57 |
| ATOM 4002 | NE2 | GLN C | 130 | 2.705 | 51.641 | 15.229 | 1.00 | 15.57 |
| ATOM 4003 | H | GLN C | 130 | 0.143 | 52.554 | 14.051 | 1.00 | 20.00 |
| ATOM 4004 | 1HE2 | GLN C | 130 | 3.123 | 52.223 | 14.534 | 1.00 | 20.00 |
| ATOM 4005 | 2HE2 | GLN C | 130 | 2.869 | 51.883 | 16.183 | 1.00 | 20.00 |
| ATOM 4006 | N | GLN C | 131 | −0.853 | 50.493 | 11.288 | 1.00 | 3.96 |
| ATOM 4007 | CA | THR C | 131 | −1.370 | 49.568 | 10.285 | 1.00 | 3.96 |
| ATOM 4008 | C | THR C | 131 | −2.605 | 50.079 | 9.567 | 1.00 | 3.96 |
| ATOM 4009 | O | THR C | 131 | −3.688 | 50.213 | 10.133 | 1.00 | 3.96 |
| ATOM 4010 | CB | THR C | 131 | −1.576 | 48.188 | 10.921 | 1.00 | 3.96 |
| ATOM 4011 | OG1 | THR C | 131 | −0.308 | 47.671 | 11.357 | 1.00 | 3.96 |
| ATOM 4012 | CG2 | THR C | 131 | −2.272 | 47.177 | 10.005 | 1.00 | 3.96 |
| ATOM 4013 | H | THR C | 131 | −1.174 | 50.479 | 12.233 | 1.00 | 20.00 |
| ATOM 4014 | HG1 | THR C | 131 | −0.516 | 46.906 | 11.880 | 1.00 | 20.00 |
| ATOM 4015 | N | PHE C | 132 | −2.362 | 50.355 | 8.276 | 1.00 | 6.06 |
| ATOM 4016 | CA | PHE C | 132 | −3.390 | 50.993 | 7.464 | 1.00 | 6.06 |
| ATOM 4017 | C | PHE C | 132 | −3.364 | 50.552 | 6.015 | 1.00 | 6.06 |
| ATOM 4018 | O | PHE C | 132 | −2.350 | 50.071 | 5.530 | 1.00 | 6.06 |
| ATOM 4019 | CB | PHE C | 132 | −3.301 | 52.525 | 7.578 | 1.00 | 6.06 |
| ATOM 4020 | CG | PHE C | 132 | −1.974 | 53.089 | 7.114 | 1.00 | 6.06 |
| ATOM 4021 | CD1 | PHE C | 132 | −1.638 | 53.094 | 5.741 | 1.00 | 6.06 |
| ATOM 4022 | CD2 | PHE C | 132 | −1.094 | 53.624 | 8.078 | 1.00 | 6.06 |
| ATOM 4023 | CE1 | PHE C | 132 | −0.403 | 53.626 | 5.329 | 1.00 | 6.06 |
| ATOM 4024 | CE2 | PHE C | 132 | 0.140 | 54.162 | 7.669 | 1.00 | 6.06 |
| ATOM 4025 | CZ | PHE C | 132 | 0.474 | 54.154 | 6.299 | 1.00 | 6.06 |
| ATOM 4026 | H | PHE C | 132 | −1.463 | 50.132 | 7.889 | 1.00 | 20.00 |
| ATOM 4027 | N | PHE C | 133 | −4.504 | 50.776 | 5.344 | 1.00 | 7.15 |
| ATOM 4028 | CA | PHE C | 133 | −4.576 | 50.554 | 3.898 | 1.00 | 7.15 |
| ATOM 4029 | C | PHE C | 133 | −5.443 | 51.623 | 3.274 | 1.00 | 7.15 |
| ATOM 4030 | O | PHE C | 133 | −6.517 | 51.917 | 3.775 | 1.00 | 7.15 |
| ATOM 4031 | CB | PHE C | 133 | −5.147 | 49.157 | 3.606 | 1.00 | 7.15 |
| ATOM 4032 | CG | PHE C | 133 | −5.481 | 48.927 | 2.144 | 1.00 | 7.15 |
| ATOM 4033 | CD1 | PHE C | 133 | −4.545 | 49.243 | 1.132 | 1.00 | 7.15 |
| ATOM 4034 | CD2 | PHE C | 133 | −6.741 | 48.379 | 1.820 | 1.00 | 7.15 |
| ATOM 4035 | CE1 | PHE C | 133 | −4.873 | 49.013 | −0.217 | 1.00 | 7.15 |
| ATOM 4036 | CE2 | PHE C | 133 | −7.064 | 48.136 | 0.470 | 1.00 | 7.15 |
| ATOM 4037 | CZ | PHE C | 133 | −6.130 | 48.458 | −0.535 | 1.00 | 7.15 |
| ATOM 4038 | H | PHE C | 133 | −5.301 | 51.117 | 5.852 | 1.00 | 20.00 |
| ATOM 4039 | N | GLY C | 134 | −4.955 | 52.195 | 2.170 | 1.00 | 4.00 |
| ATOM 4040 | CA | GLY C | 134 | −5.798 | 53.226 | 1.589 | 1.00 | 4.00 |
| ATOM 4041 | C | GLY C | 134 | −5.561 | 53.468 | 0.120 | 1.00 | 4.00 |
| ATOM 4042 | O | GLY C | 134 | −4.524 | 53.119 | −0.435 | 1.00 | 4.00 |
| ATOM 4043 | H | GLY C | 134 | −4.078 | 51.938 | 1.757 | 1.00 | 20.00 |
| ATOM 4044 | N | LEU C | 135 | −6.594 | 54.081 | −0.479 | 1.00 | 5.48 |
| ATOM 4045 | CA | LEU C | 135 | −6.529 | 54.401 | −1.903 | 1.00 | 5.48 |
| ATOM 4046 | C | LEU C | 135 | −6.875 | 55.847 | −2.125 | 1.00 | 5.48 |
| ATOM 4047 | O | LEU C | 135 | −7.510 | 56.478 | −1.289 | 1.00 | 5.48 |
| ATOM 4048 | CB | LEU C | 135 | −7.547 | 53.645 | −2.759 | 1.00 | 5.48 |

TABLE 1-continued

Atomic coordinates of the higher-order structure of Fas ligand

| Atom species | | Amino acid residues | | # | X | Y | Z | OCC | B |
|---|---|---|---|---|---|---|---|---|---|
| ATOM 4049 | CG | LEU | C | 135 | −7.688 | 52.141 | −2.591 | 1.00 | 5.48 |
| ATOM 4050 | CD1 | LEU | C | 135 | −8.661 | 51.586 | −3.631 | 1.00 | 5.48 |
| ATOM 4051 | CD2 | LEU | C | 135 | −6.357 | 51.409 | −2.618 | 1.00 | 5.48 |
| ATOM 4052 | H | LEU | C | 135 | −7.325 | 54.458 | 0.095 | 1.00 | 20.00 |
| ATOM 4053 | N | TYR | C | 136 | −6.500 | 56.309 | −3.325 | 1.00 | 5.12 |
| ATOM 4054 | CA | TYR | C | 136 | −7.083 | 57.553 | −3.823 | 1.00 | 5.12 |
| ATOM 4055 | C | TYR | C | 136 | −6.940 | 57.684 | −5.318 | 1.00 | 5.12 |
| ATOM 4056 | O | TYR | C | 136 | −5.937 | 57.281 | −5.889 | 1.00 | 5.12 |
| ATOM 4057 | CB | TYR | C | 136 | −6.510 | 58.792 | −3.124 | 1.00 | 5.12 |
| ATOM 4058 | CG | TYR | C | 136 | −5.000 | 58.809 | −3.108 | 1.00 | 5.12 |
| ATOM 4059 | CD1 | TYR | C | 136 | −4.314 | 58.036 | −2.151 | 1.00 | 5.12 |
| ATOM 4060 | CD2 | TYR | C | 136 | −4.321 | 59.629 | −4.030 | 1.00 | 5.12 |
| ATOM 4061 | CE1 | TYR | C | 136 | −2.919 | 58.140 | −2.065 | 1.00 | 5.12 |
| ATOM 4062 | CE2 | TYR | C | 136 | −2.926 | 59.740 | −3.934 | 1.00 | 5.12 |
| ATOM 4063 | CZ | TYR | C | 136 | −2.248 | 59.021 | −2.932 | 1.00 | 5.12 |
| ATOM 4064 | OH | TYR | C | 136 | −0.885 | 59.194 | −2.809 | 1.00 | 5.12 |
| ATOM 4065 | H | TYR | C | 136 | −5.801 | 55.809 | −3.844 | 1.00 | 20.00 |
| ATOM 4066 | HH | TYR | C | 136 | −0.519 | 59.268 | −3.679 | 1.00 | 20.00 |
| ATOM 4067 | N | LYS | C | 137 | −7.985 | 58.263 | −5.926 | 1.00 | 11.54 |
| ATOM 4068 | CA | LYS | C | 137 | −7.861 | 58.523 | −7.359 | 1.00 | 11.54 |
| ATOM 4069 | C | LYS | C | 137 | −6.972 | 59.720 | −7.657 | 1.00 | 11.54 |
| ATOM 4070 | O | LYS | C | 137 | −7.009 | 60.724 | −6.954 | 1.00 | 11.54 |
| ATOM 4071 | CB | LYS | C | 137 | −9.252 | 58.650 | −8.007 | 1.00 | 11.54 |
| ATOM 4072 | CG | LYS | C | 137 | −9.183 | 58.690 | −9.538 | 1.00 | 11.54 |
| ATOM 4073 | CD | LYS | C | 137 | −10.507 | 58.674 | −10.297 | 1.00 | 11.54 |
| ATOM 4074 | CE | LYS | C | 137 | −10.236 | 58.897 | −11.788 | 1.00 | 11.54 |
| ATOM 4075 | NZ | LYS | C | 137 | −11.439 | 58.630 | −12.591 | 1.00 | 11.54 |
| ATOM 4076 | H | LYS | C | 137 | −8.766 | 58.559 | −5.373 | 1.00 | 20.00 |
| ATOM 4077 | 1HZ | LYS | C | 137 | −11.252 | 58.866 | −13.585 | 1.00 | 20.00 |
| ATOM 4078 | 2HZ | LYS | C | 137 | −11.653 | 57.608 | −12.564 | 1.00 | 20.00 |
| ATOM 4079 | 3HZ | LYS | C | 137 | −12.265 | 59.158 | −12.244 | 1.00 | 20.00 |
| ATOM 4080 | N | LEU | C | 138 | −6.177 | 59.542 | −8.723 | 1.00 | 2.56 |
| ATOM 4081 | CA | LEU | C | 138 | −5.383 | 60.647 | −9.256 | 1.00 | 2.56 |
| ATOM 4082 | C | LEU | C | 138 | −6.126 | 61.467 | −10.319 | 1.00 | 2.56 |
| ATOM 4083 | O | LEU | C | 138 | −5.503 | 62.314 | −10.959 | 1.00 | 2.56 |
| ATOM 4084 | CB | LEU | C | 138 | −4.056 | 60.098 | −9.801 | 1.00 | 2.56 |
| ATOM 4085 | CG | LEU | C | 138 | −3.292 | 59.193 | −8.827 | 1.00 | 2.56 |
| ATOM 4086 | CD1 | LEU | C | 138 | −2.105 | 58.525 | −9.511 | 1.00 | 2.56 |
| ATOM 4087 | CD2 | LEU | C | 138 | −2.875 | 59.918 | −7.548 | 1.00 | 2.56 |
| ATOM 4088 | OXT | LEU | C | 138 | −7.329 | 61.259 | −10.516 | 1.00 | 2.56 |
| ATOM 4089 | H | LEU | C | 138 | −6.232 | 58.672 | −9.217 | 1.00 | 20.00 |
| END | | | | | | | | | |

The symbols A, B, and C indicated following the amino acid residues in Table 1 enable differentiation between the segments of the Fas ligand trimer. The symbols X, Y, and Z show the coordinate of each atom to X, Y, and Z axes, respectively, OCC represents Occupancy, and B represents temperature factor.

Figure 22:
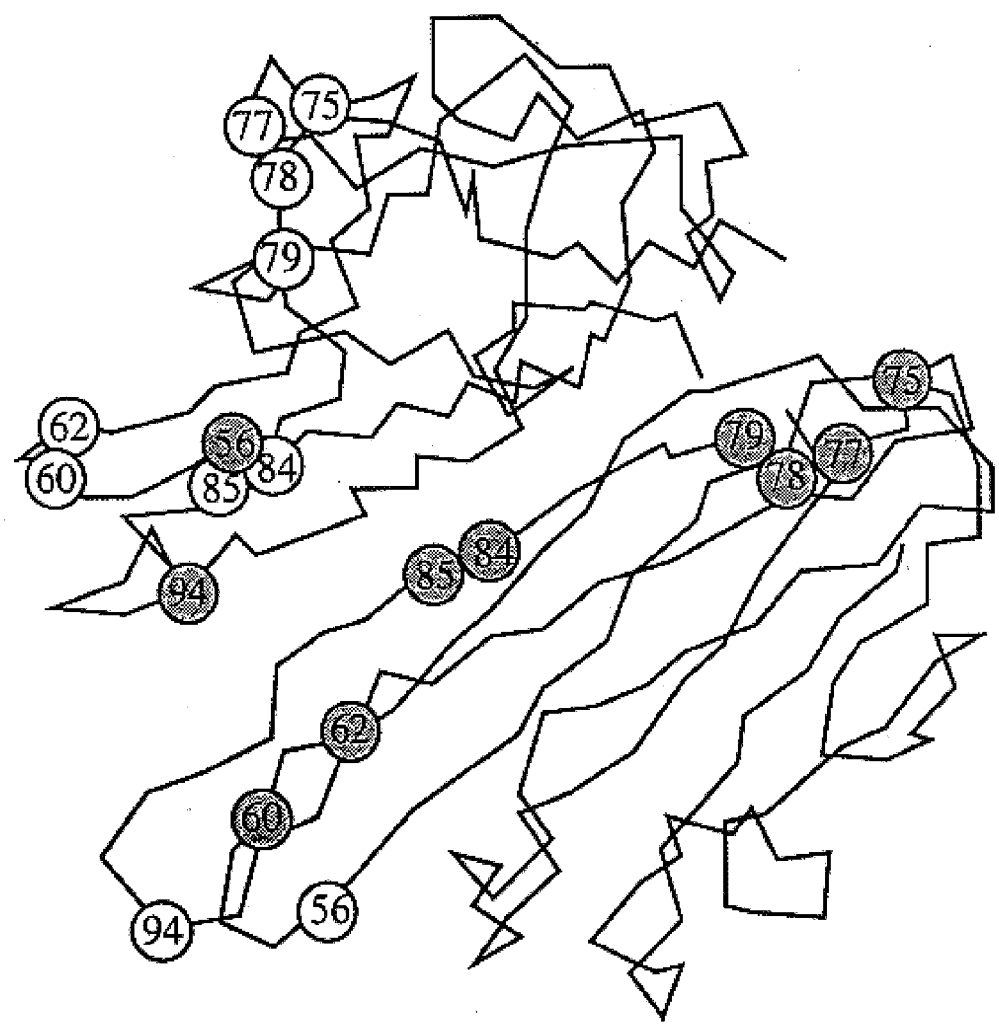
In FIG. 22, the amino acids on the two molecules of Fas ligand trimer, which are recognized by NOK1 antibody are indicated by circles. Shaded circles show the amino acids resided on the same side, whereas open circles show any others.
Figure 23:
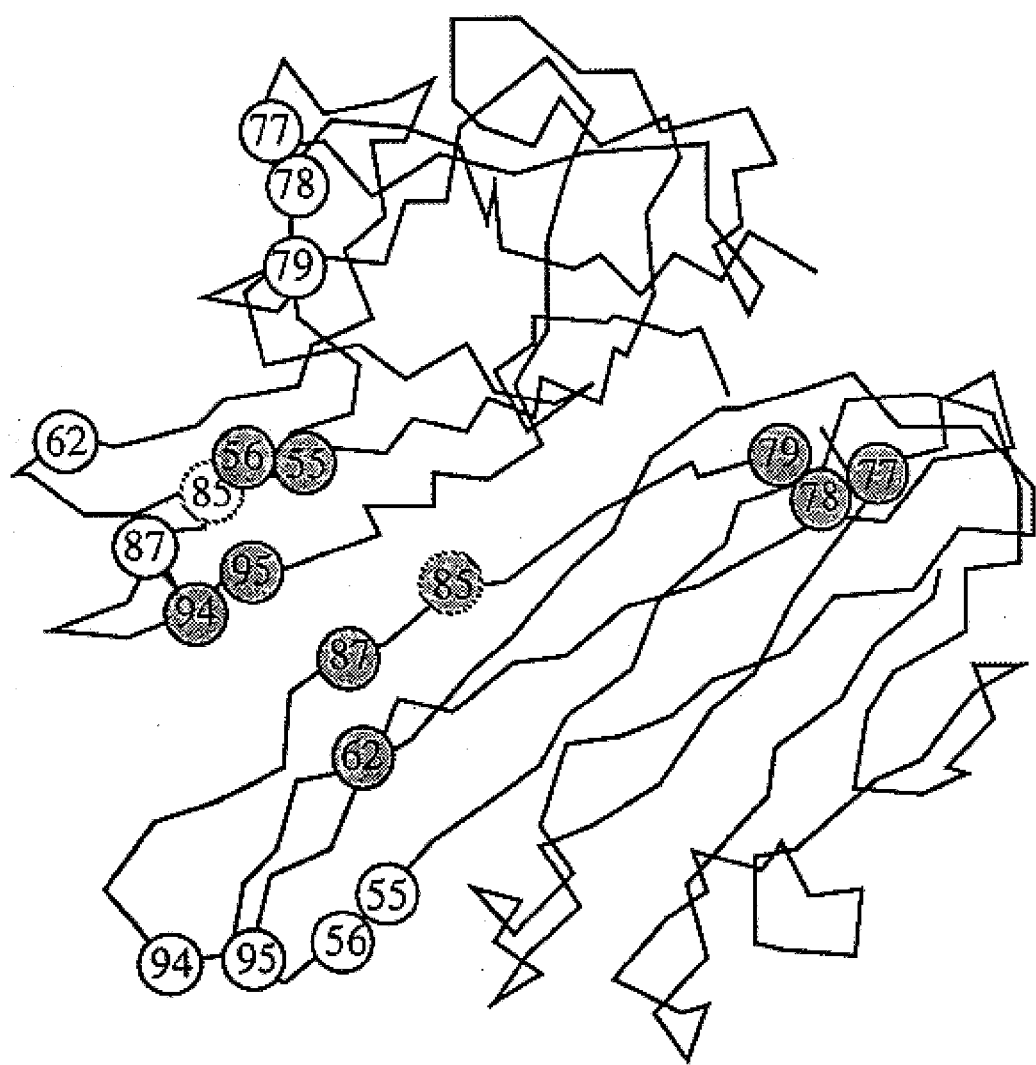
In FIG. 23, the amino acids on the two molecules of Fas ligand trimer, which are recognized by NOK2 and humanized NOK2 antibodies are indicated by circles. Shaded circles show the amino acid resided on the same side, whereas open circles show any others. Circles with dotted line show the amino acids especially recognized by humanized NOK2 antibody.
Figure 24:
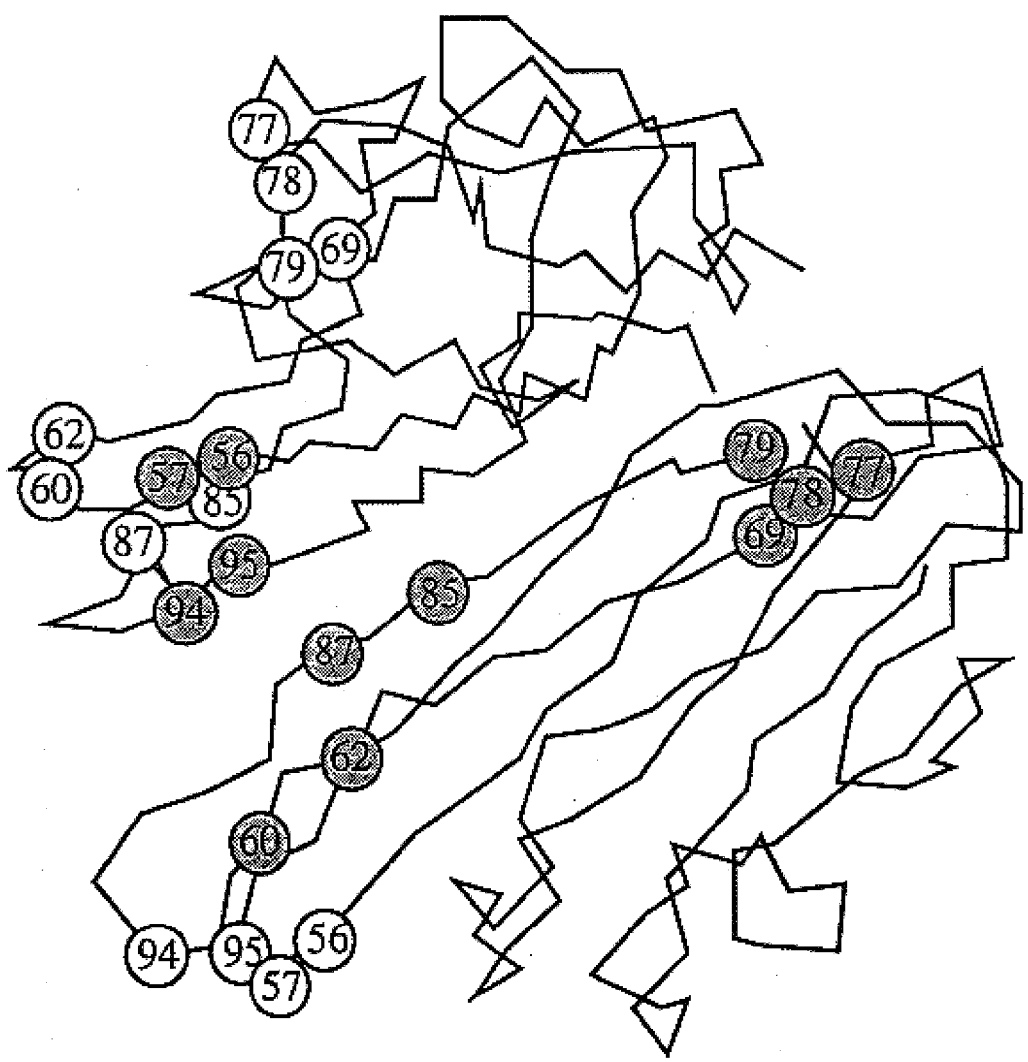
In FIG. 24, the amino acids on the two molecules of Fas ligand trimer, which are recognized by NOK3 antibody are indicated by circles. Shaded circles show the amino acid resided on the same side, whereas open circles show any others.

In FIGS. 22–24, in order to clarify the relationship of the positions between the recognition sites of NOK and humanized NOK2 antibodies on the Fas ligand model constructed as shown above, the Fas ligand trimer is depicted with the lines produced by connecting only the carbon atoms at the α-position of the amino acids on the basis of the data for the atomic coordinates described in Table 1 using QUANTA/CHARMm, as well as, among the amino acid residues in the sites recognized by NOK1, NOK2, humanized NOK2 (RNOK201–203), and NOK3 antibodies as identified in Example 6, the amino acid residues resided on the same side as the Fas ligand trimer are indicated by shaded circles, whereas any other residues are indicated by open circles. In the case of NOK2 and humanized NOK2 antibodies in FIG. 23, the amino acid residues especially recognized by humanized NOK2 antibody are indicated by circles with dotted line. To be clearly understood, only two of the three molecules of Fas ligand, which reside on this side (segments B and C in Table 1) are depicted, and the numerical order of amino acids in the recognition site is in accordance with the order of the Fas ligand model as shown in FIG. 21 as alignment data. Van der Waals contact model of the atoms of Fas ligand was displayed on Ray Trace command of QUANTA/CHARMm, and the amino acids in the recognition site of NOK and humanized NOK2 antibodies as identified in Example 6 were superimposed and displayed. On the van der Waals contact model, the recognition sites of NOK1, NOK2, humanized NOK2, and NOK3 antibodies are those indicated in hatched area in FIGS. 29, 30, and 31, respectively. FIGS. 22–24 and FIGS. 29–31 are substantially the same as each other, and thus both represent the same model from the same view point, which expressions are merely different.

The analysis results noteworthily show that the recognition site which is bound by NOK and humanized NOK2 antibodies should span two molecules of Fas ligand in the light of its stereochemistry. Thus, it has been shown that NOK and humanized NOK2 antibodies recognize the site which appears once the Fas ligand trimer is formed. The finding that the antibody having a strong apoptosis-inhibitory activity such as NOK antibody recognizes the recognition site spanning two molecules of Fas ligand has not been previously reported and thus novel. Accordingly, it is understood that the recognition of and the binding to the site formed by spanning the two molecules of the Fas ligand trimer should be important to provide a strong apoptosis-inhibitory activity.

NOK and humanized NOK2 antibodies recognize the common amino acids as shown in FIGS. 22–24 and 29–31, such as Gly at position 199, Leu at position 205, Gln at position 220, Asp at position 221, Leu at position 222, Gln at position 237 in common between NOK1–3 and humanized NOK2 antibodies; Asn at position 203 in common between NOK1 and 3 antibodies; Lys at position 228 in common between NOK1 and 3, and humanized NOK2 antibodies; Met at position 230, Met at position 238 in common between NOK2 and 3, and humanized NOK2 antibodies, which numerical order of the amino acids is in accordance with Nagata, et al. Int. Immunology, vol. 6, p.1567–1574, 1994, and therefore, it is predicted that these antibodies may share a common recognized region.

On the other hand, the recognition site of antibodies on protein molecule antigens which are as large as the Fas ligand trimer would define a kind of plane considering the size of the antibodies, and when the antibodies recognize the antigens, the plane of the antigens composed of these recognized amino acids and the plane of the recognizing region on the antibodies come into contact each other face-to-face. The recognition site or the common site of NOK1–3 and humanized NOK2 antibodies as shown above should define a plane. In other words, the recognition site on the Fas ligand trimer molecule of the antibodies can be defined as a plane on the protein molecule, and any antibodies which strongly inhibit apoptosis-activity should enter or approach the plane defined by the recognized amino acids on the Fas ligand trimer molecule.

Consequently, the recognized amino acids on the Fas ligand trimer molecule can be examined as a member of plane. In general, plane may be depicted as a flat plane defined by three points A (XA, YA, ZA), B (XB, YB, ZB), and C (XC, YC, ZC) which are not on a straight line. Plane can be estimated by assigning the data for the atomic coordinates of the amino acids recognized by the antibodies to the expression. Thus, plane which is recognized by the antibodies can be depicted by selecting any three amino acids from those recognized by the antibodies and by estimating as such. For example, if Gln at position 57 of the Fas ligand B molecule, Asn at position 60 of the Fas ligand C molecule, and Gln at position 77 of the Fas ligand C molecule as shown in Table 1 from the amino acids recognized by NOK3 antibody, the data for the coordinates of their Cα atoms is estimated to be (20.209, 32.098, 0.872), (11.551, 31.704, 15.937), and (−8.765, 35.501, −9.840), respectively, and thereby, plane defined by these coordinates of the Cα atoms of the amino acids can be estimated. The plane defined by the combination of Gln at position 57 of the Fas ligand B molecule, Asn at position 60 of the Fas ligand C molecule, and Gln at position 77 of the Fas ligand C molecule can cover the plane of the region constituted by the amino acids recognized by NOK3 antibody. The plane which comes into contact with the antibody effectively, that is, the plane through which the antibody atoms approach to the Fas ligand trimer is believed to be a plane which resides opposite to the Fas ligand molecule being apart from the atomic coordinate of each Cα atom by the length of the side chain of the amino acid residues plus about 4.1 Å of the cut off value of the common van der Waals contact.

Example 9

Identification of the Site on Fas Ligand Recognized by NOK2 Antibody

As discussed in Example 8, it is predicted that any antibodies which strongly inhibit apoptosis-activity share a common recognition site since NOK and humanized NOK2 antibodies recognize a certain common amino acids. On the other hand, it is believed that NOK and humanized NOK2 antibodies have the variable region which size is the nearly equal to a usual antibody, in the light of the amino acid length of the variable region of each antibody. Accordingly, in order to identify a common recognition site which is on the Fas ligand trimer of NOK and humanized NOK2 antibodies, modelling was also performed on NOK2 antibody selected as a representative, similarly to Fas ligand, thereby examining if the variable region of the antibody, especially the CDR, can cover the region composed of the recognized amino acids on the Fas ligand trimer, and if the answer is affirmative, what amino acids other than the aforementioned recognized amino acids may be a candidate for the recognized amino acids.

As a model for the stereochemistry of NOK2 antibody, NOK2 antibody model, which had been newly modeled using Modeler was used. First, the variable region of the H chain (VH) of PDB ID:1FOR (SEQ ID No: 131) and the variable region of the L chain (VL) of PDB ID:1TET (SEQ ID No: 132), which show the high homology to the VH and the VL of NOK2 antibody were utilized as templates for the three-dimensional structures. The amino acid sequences of the VH and VL of NOK2 antibody were aligned with those of 1FOR as shown in FIGS. 25 and 26, respectively, and the results were inputted into Modeler. According to the Modeler's instructions, the modelling was performed modifying the conditions to obtain five models, such that Model No. 5 was selected as a model for the variable region of NOK2 antibody, which is lower in the energy following energy-minimizing calculation, the probability density function (i.e. PDF), and the value of Root Mean Square of all atoms (i.e. RMS).

Figure 27:
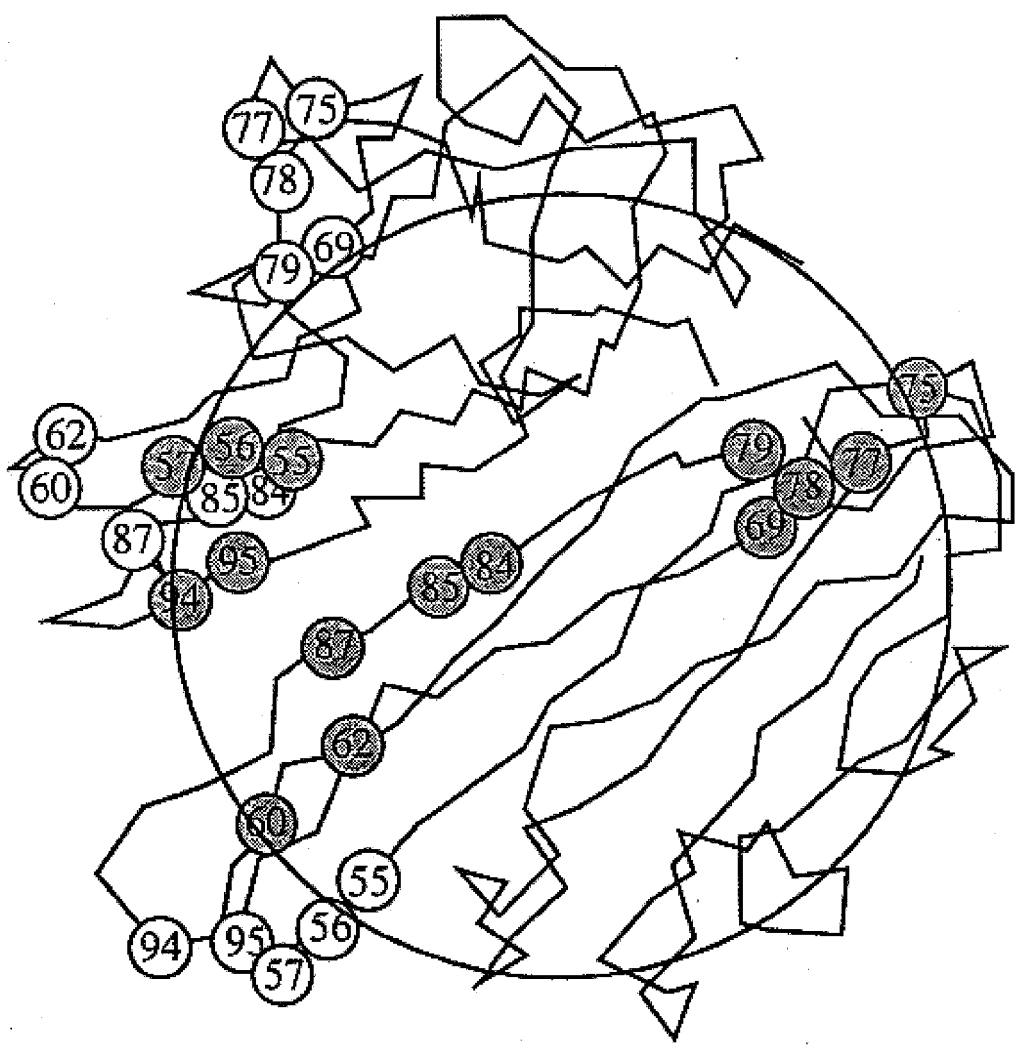
In FIG. 27, the amino acids on the two molecules of Fas ligand trimer, which are recognized by NOK and humanized NOK2 antibodies are indicated by circles. Shaded circles show the amino acids resided on the same side, whereas open circles show any others. The circle encompassing the amino acids indicated by the shaded circles is of about 17 Å (angstrom) radius, which scale is near the CDR of antibody.
Figure 32:
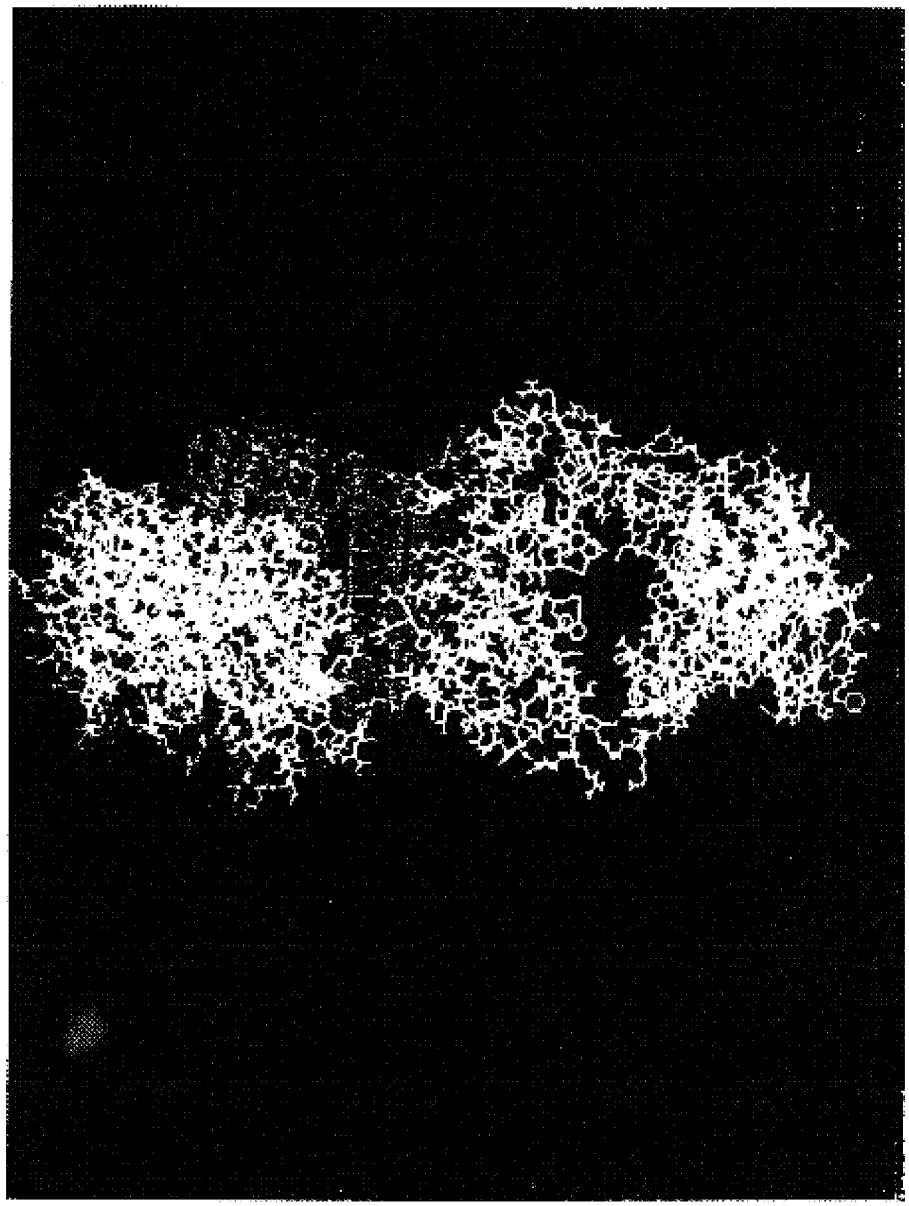
FIGS. 32 and 33 are diagrams representing the site on the Fas ligand trimer recognized by NOK2 antibody, viewing from the side.
Figure 33:
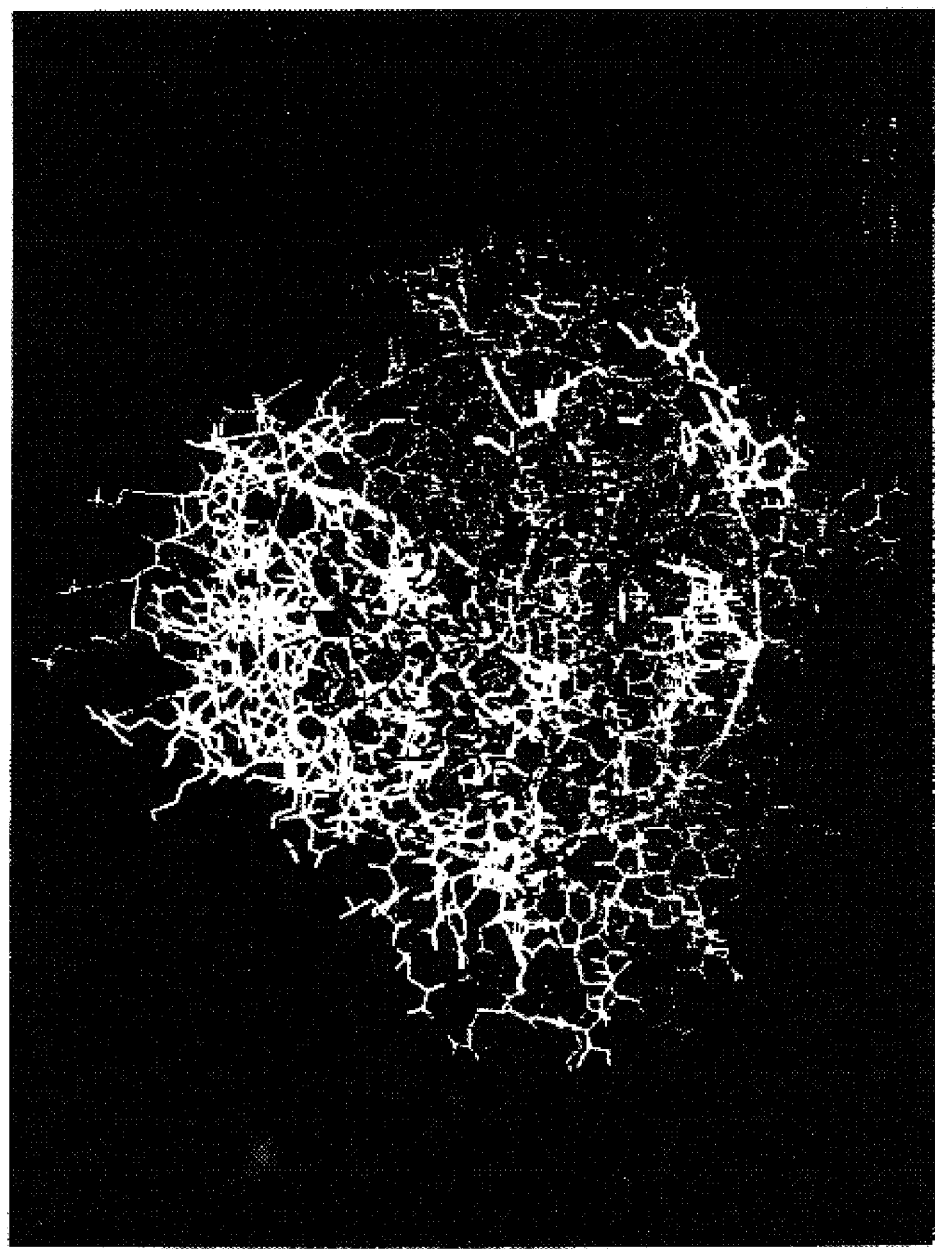

Size of the antigen-recognizing site within the variable region of NOK2 antibody (six CDRs: complementary-determining region) was examined using Graphical Cylinder command of QUANTA/CHARMm. As a result, the antigen-recognizing site of the NOK2 antibody model has the size nearly equal to the circle of about 17 Å (angstrom) radius, as shown in FIGS. 32 and 33. FIG. 33 shows that the amino acids of the CDR of the NOK2 antibody model are just encompassed within the circle of about 17 Å radius. Then, the circle of about 17 Å radius was positioned on QUANTA/CHARMm to cover the plane defined by the amino acids in the recognition site on the Fas ligand trimer and the individual recognized amino acids as shown in FIGS. 22–24, thereby revealing that the region corresponding to the antigen-recognizing site within the variable region of NOK2 antibody really cover all of the amino acids in the site of the Fas ligand trimer recognized by NOK and humanized NOK2 antibodies (FIG. 27). Consequently, it is believed that NOK and humanized NOK2 antibodies should cover the region nearly equal to the site on the Fas ligand trimer although the reactivities are different. This means that any antibodies having a high apoptosis-inhibitory activity in common recognize the site shown herein.

Figure 28:
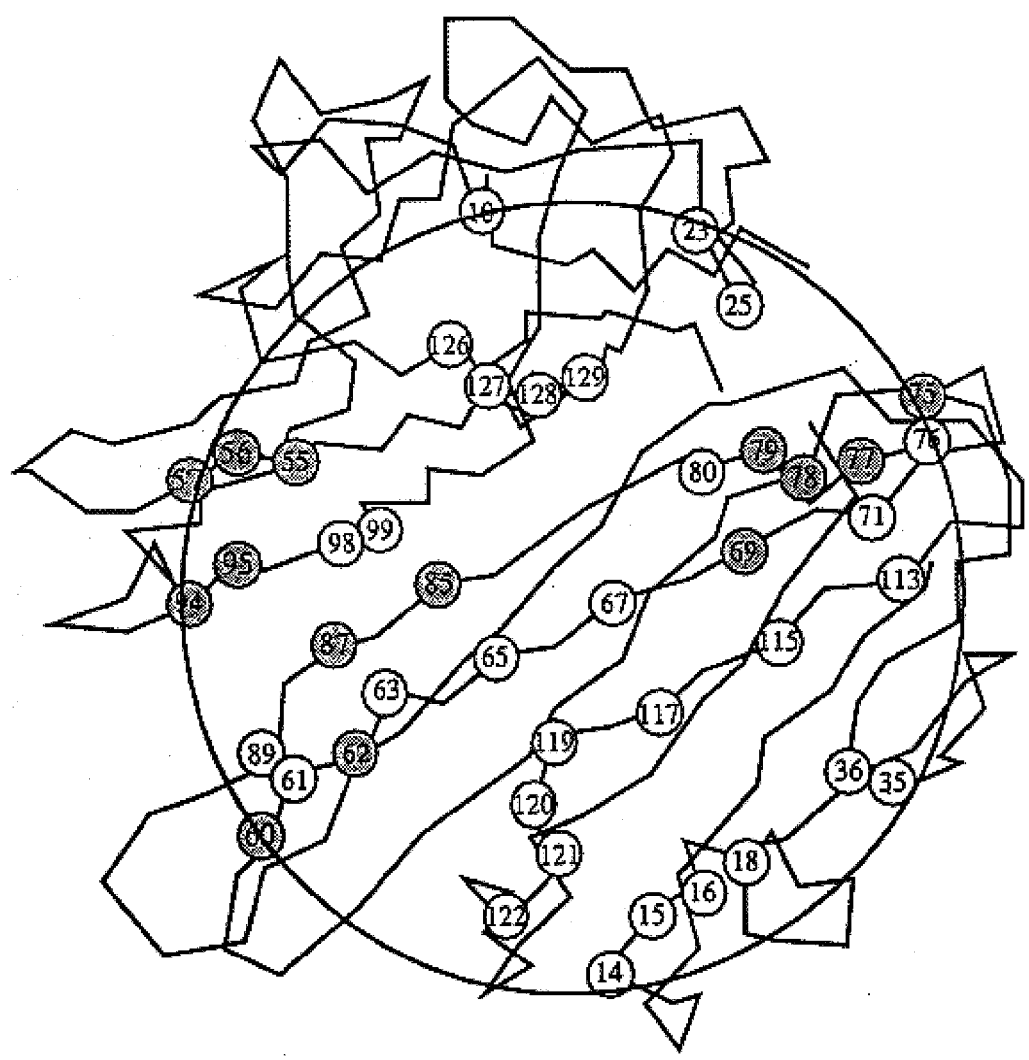
In FIG. 28, the amino acids presented on the surface of Fas ligand (which may be recognized by the antibody, etc.) among all amino acids encompassed by the circle of about 17 Å radius as shown in FIG. 27 are indicated by circles. Shaded circles show the amino acids recognized by NOK and humanized NOK2 antibodies.
Figure 29:
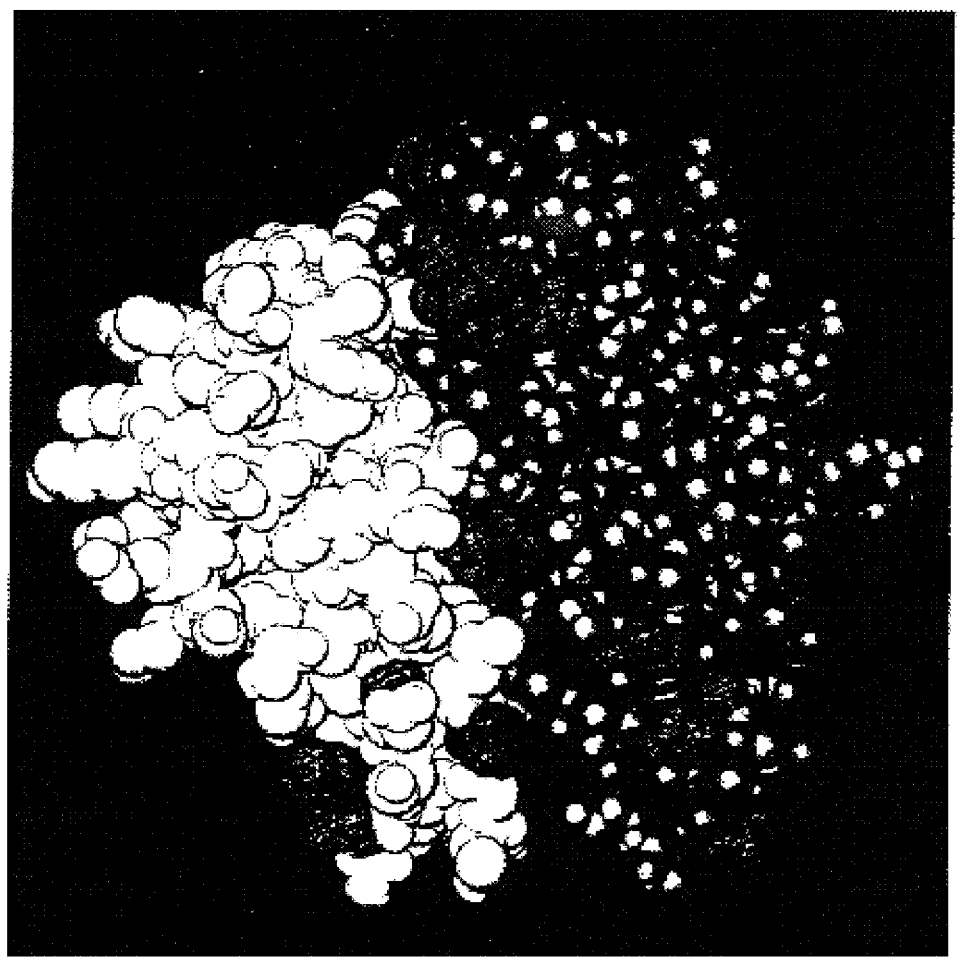
FIGS. 29–31 are diagrams representing a van der Waals contact model for the two molecules of Fas ligand trimer, which are indicated by white and black, respectively. Hatched areas in FIGS. 29, 30, and 31 show the amino acids recognized by NOK1 antibody, those recognized by NOK2 and humanized NOK2 antibodies, and those recognized by NOK3 antibody, respectively.
Figure 30:
Figure 31:
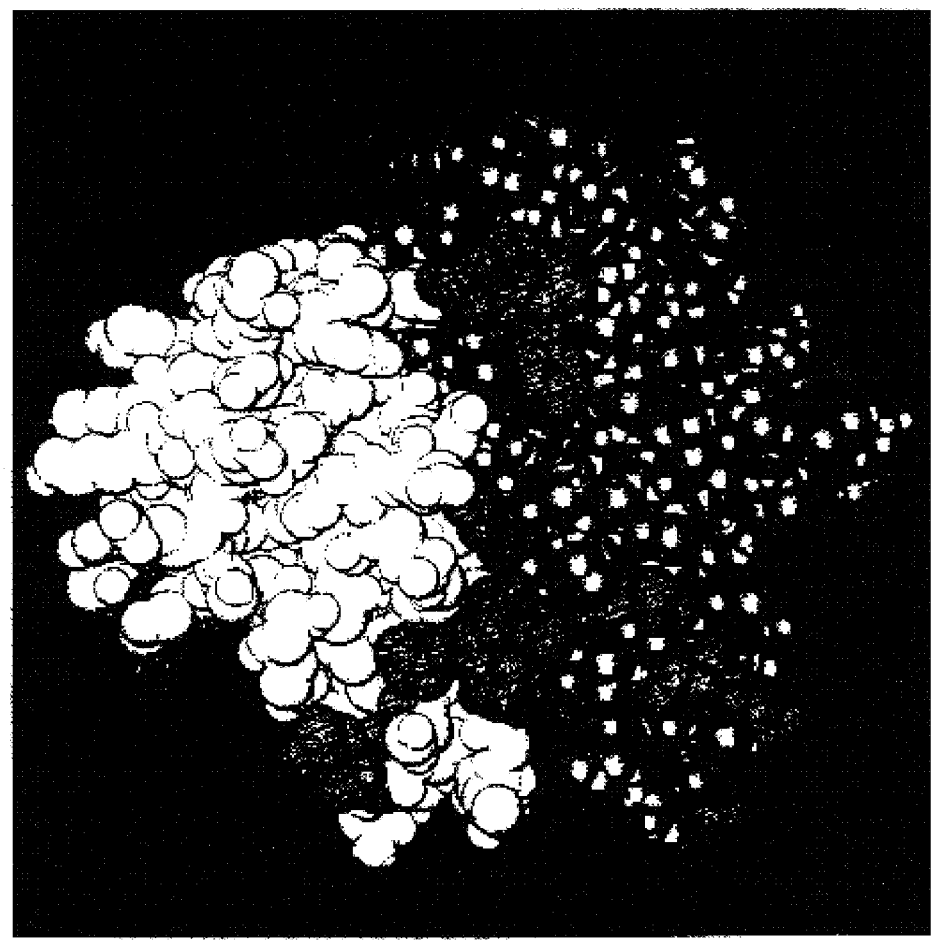
Figure 34:
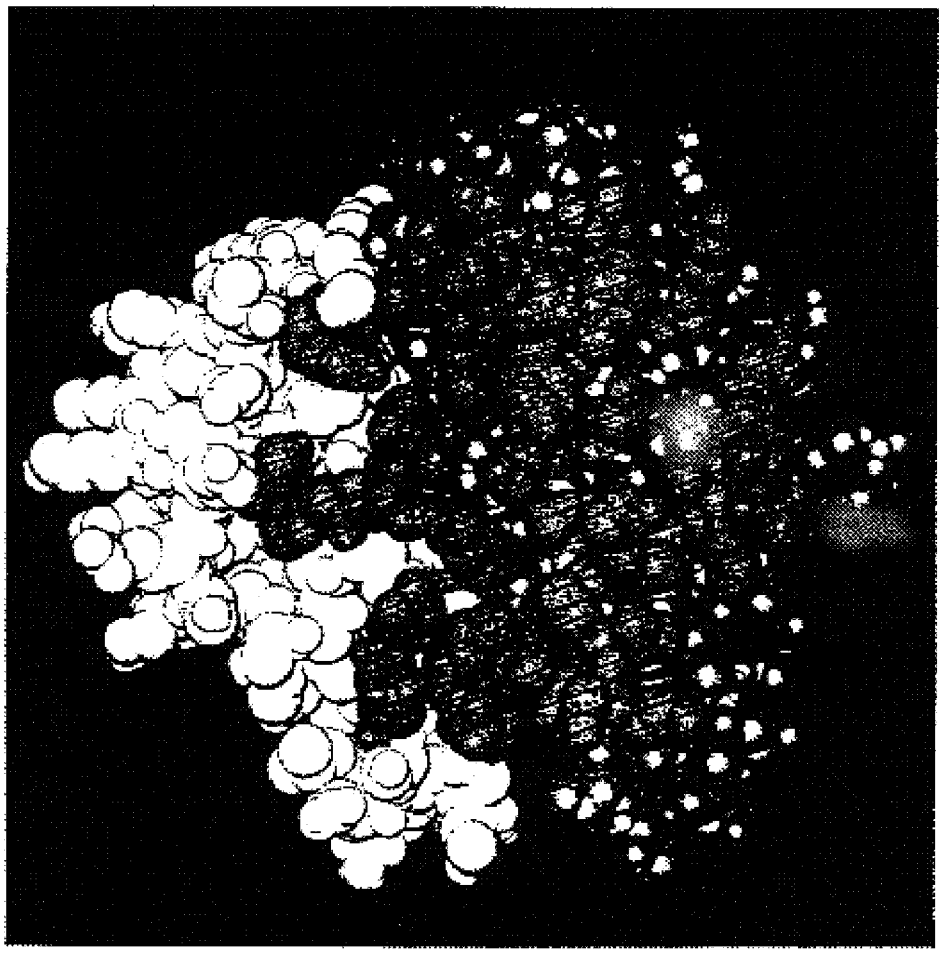
FIG. 34 is the diagram representing a van der Waals contact model similar to in FIGS. 29–31, and the hatched area shows the amino acids having a presenting surface of 15 angstrom square or above within the circle of about 17 Å radius as shown in FIG. 33.

Then, the surface amino acids of the Fas ligand trimer within the circle, having an exposed area with 15 angstrom square or above were selected as a amino acid to be able to interact with the CDR amino acid of the antibody, so as to identify Ser at position 10, Tyr at position 23, Ile at position 25, Arg at position 55, Gly at position 56, Gln at position 57, Gln at position 94, Met at position 95, Arg at position 98, Ser at position 99, Phe at position 126, Glu at position 127, Glu at position 128, and Ser at position 129 of one of adjacent two Fas ligand molecules, as well as Ser at position 14, Met at position 15, Pro at position 16, Glu at position 18, Lys at position 35, Gly at position 36, Asn at position 60, Asn at position 61, Leu at position 62, Pro at position 63, Ser at position 65, Lys at position 67, Tyr at position 69, Arg at position 71, Tyr at position 75, Pro at position 76, Gln at position 77, Asp at position 78, Leu at position 79, Val at position 80, Lys at position 85, Met at position 87, Tyr at position 89, His at position 113, Tyr at position 115, Asn at position 117, Ser at position 119, Glu at position 120, Leu at position 121, and Ser at position 122 of the other Fas ligand molecule, wherein the numerical order of amino acids with respect to any molecules is in accordance with that of the Fas ligand monomer as shown in the alignment data of FIG. 21. These amino acids are shown in FIGS. 28 and 34. In the figures, the large circle encompassing the amino acids is the circle of about 17 Å radius, and among the selected amino acids, those which also correspond to the amino acids in the site recognized by NOK and humanized NOK2 antibodies are indicated by the shaded circles whereas the amino acids newly selected as those in the recognition site of the antibodies indicated by the open circles.

These amino acid numbers are rearranged in accordance with Nagata, et al., Int. Immunology, vol. 6, p1567–1574, 1994, to provide Ser at position 153, Tyr at position 166, Ile at position 168, Arg at position 198, Gly at position 199, Gln at position 200, Gln at position 237, Met at position 238, Arg at position 241, Ser at position 242, Phe at position 269, Glu at position 270, Glu at position 271, and Ser at position 272 of one of adjacent two Fas ligand molecules, as well as Ser at position 157, Met at position 158, Pro at position 159, Glu at position 161, Lys at position 178, Gly at position 179, Asn at position 203, Asn at position 204, Leu at position 205, Pro at position 206, Ser at position 208, Lys at position 210, Tyr at position 212, Arg at position 214, Tyr at position 218, Pro at position 219, Gln at position 220, Asp at position 221, Leu at position 222, Val at position 223, Lys at position 228, Met at position 230, Tyr at position 232, His at position 256, Tyr at position 258, Asn at position 260, Ser at position 262, Glu at position 263, Leu at position 264, and Ser at position 265 of the other Fas ligand molecule.

It is believed that these amino acids include not only the amino acids recognized by NOK3 antibody, but also the common amino acids in the site which is recognized by any antibodies strongly inhibiting apoptosis-activity such as NOK antibody and humanized NOK2 antibody. Thus, it is shown that the interaction with the amino acids encompassed in the site on the Fas ligand trimer is important for proteins, peptides, desirably antibodies or analogues thereof to show a high apoptosis-inhibitory activity.

The present invention is worth not only in firstly finding the site on the Fas ligand trimer recognized by anti-Fas ligand antibodies having a high apoptosis-inhibitory activity, but also in providing important information to design other various molecules for inhibiting apoptosis-activity. Thus, the invention can be utilized to develop new therapeutic or diagnostic agents by creating proteins, peptides, or desirably antibodies or analogues thereof, which are specifically reactive to the aforementioned site and the amino acids within the site (the site and amino acids described in Examples 6–9) so as to inhibit apoptosis.

The present invention provides a humanized immunoglobulins which are specifically reactive to Fas ligand to inhibit the physiological reactions of Fas-Fas ligand, said immunoglobulins being capable of using as a therapeutic agent for diseases such as AIDS, graft-versus-host diseases in bone marrow transplantation, autoimmune diseases (SLE, RA), diabetes mellitus, and possessing the characteristics as follows:

(1) The humanized immunoglobulin is compatible with other aspects of the immune system in human since the effector part thereof is from human, and for example it can lead to more effective dissolution of the targeted cells by complement-dependent cytolysis (CDC) or antibody-dependent cell-mediated cytotoxicity (ADCC);

(2) Human immune system does not recognize the framework or the C region of the humanized immunoglobulin, and therefore, the level of undesirable immune responses to the humanized immunoglobulin is lower than the mouse antibody in which the whole is xenogenic and the chimeric antibody in which the part is xenogenic; and (3) The humanized immunoglobulin can be expected to provide the lower dose and the lower frequency of the administration compared to the mouse antibody since the former has the half life nearer to naturally-occurring human antibodies.

Further, the present invention which has found the site which is on Fas ligand and required to induce apoptosis may be utilized to find a new therapeutic or diagnostic agent by creating a recombinant protein or peptide which is specifically reactive to the amino acids within the site.

What is claimed is:

1. A humanized monoclonal antibody or an antigen-binding fragment thereof, which selectively binds to SEQ ID NO: 140, and which inhibits the binding of Fas ligand and Fas antigen.

2. The antibody or an antigen-binding fragment thereof according to claim 1, wherein the in vitro inhibition of the binding of Fas ligand and Fas antigen results in the inhibition of apoptosis of Fas antigen-expressing cells.

3. The antibody or an antigen-binding fragment thereof according to claim 1, which can inbibit in vitro apoptosis by an apoptosis inhibition rate of 90% or above at an immunoglobulin concentration of 0.06 µg/ml or above, wherein the apoptosis inhibition rate is defined as a viable rate of target cells to which the immunoglobulin was added in the cytotoxic reaction assay comprising the steps of:

reacting both effector molecules which are the soluble Fas ligand at an effective concentration of 4.6 μg/ml prepared from the supernatant of culture of cells transfected with the Fas ligand gene, and target cells which are the cells transfected with the Fas gene, in a 100 μl reaction system on a 96-well plate; and 16 hours thereafter determining the viable rate of the target cells.

4. The antibody or an antigen-binding fragment thereof according to claim 1 which has in vitro apoptosis-inhibitory activity which is equal to or higher than the original donor immunoglobulin of the antibody or the antigen-binding fragment thereof.

5. The antibody or an antigen-binding fragment thereof according to claim 1, which, at an effective concentration of 0.01–8 μg/ml, has higher in vitro apoptosis-inhibitory activity than a Fas-Ig chimeric molecule at the same concentration.

6. The antibody or an antigen-binding fragment thereof according to claim 1, which comprises a dimer of light chain and heavy chain, both of which contain a complementary determining region which are referred to as CDRs, and a human framework region, wherein the CDRs are obtained from a donor immunoglobulin other than the one from which the human framework region is obtained.

7. The antibody or an antigen-binding fragment thereof according to claim 6, wherein the amino acid sequence of the framework region of the acceptor human immunoglobulin shows at least 60% homology to that of the donor immunoglobulin.

8. The antibody or an antigen-binding fragment thereof according to claim 1, wherein the amino acid sequences of CDR1, CDR2, and CDR3 in the heavy chain of the immunoglobulin are the sequences of SEQ ID NO:1, SEQ ID NO:2, and SEQ ID NO:3, respectively, and the amino acid sequence of CDR1, CDR2, and CDR3 in the light chain of the immunoglobulin are the sequences of SEQ ID NO:4, SEQ ID NO:5, and SEQ ID NO:6, respectively.

9. The antibody or an antigen-binding fragment thereof according to claim 1, wherein the donor immunoglobulin is mouse NOK2 antibody which is produced by the hybridoma under Accession No FERM BP-5045.

* * * * *

SEQUENCE LISTING

<160> NUMBER OF SEQ ID NOS: 183

<210> SEQ ID NO 1
<211> LENGTH: 5
<212> TYPE: PRT
<213> ORGANISM: Mouse

<400> SEQUENCE: 1

Asn Tyr Trp Ile Gly
1               5

<210> SEQ ID NO 2
<211> LENGTH: 17
<212> TYPE: PRT
<213> ORGANISM: Mouse

-continued

```
<400> SEQUENCE: 2

Tyr Leu Tyr Pro Gly Gly Leu Tyr Thr Asn Tyr Asn Glu Lys Phe Lys
1               5                   10                  15

Gly

<210> SEQ ID NO 3
<211> LENGTH: 10
<212> TYPE: PRT
<213> ORGANISM: Mouse

<400> SEQUENCE: 3

Tyr Arg Asp Tyr Asp Tyr Ala Met Asp Tyr
1               5                   10

<210> SEQ ID NO 4
<211> LENGTH: 16
<212> TYPE: PRT
<213> ORGANISM: Mouse

<400> SEQUENCE: 4

Lys Ser Thr Lys Ser Leu Leu Asn Ser Asp Gly Phe Thr Tyr Leu Gly
1               5                   10                  15

<210> SEQ ID NO 5
<211> LENGTH: 7
<212> TYPE: PRT
<213> ORGANISM: Mouse

<400> SEQUENCE: 5

Leu Val Ser Asn Arg Phe Ser
1               5

<210> SEQ ID NO 6
<211> LENGTH: 9
<212> TYPE: PRT
<213> ORGANISM: Mouse

<400> SEQUENCE: 6

Phe Gln Ser Asn Tyr Leu Pro Leu Thr
1               5

<210> SEQ ID NO 7
<211> LENGTH: 121
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser His
                20                  25                  30

Trp Met His Trp Val Arg Gln Ala Pro Gly Gln Gly Leu Glu Trp Val
            35                  40                  45

Gly Glu Phe Asn Pro Ser Asn Gly Arg Thr Asn Tyr Asn Glu Lys Phe
        50                  55                  60

Lys Ser Arg Val Thr Met Thr Leu Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
                100                 105                 110
```

```
Gln Gly Thr Leu Val Thr Val Ser Ser
        115                 120

<210> SEQ ID NO 8
<211> LENGTH: 112
<212> TYPE: PRT
<213> ORGANISM: Homo sapiens

<400> SEQUENCE: 8

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys Leu Glu Ile Lys
            100                 105                 110

<210> SEQ ID NO 9
<211> LENGTH: 112
<212> TYPE: PRT
<213> ORGANISM: Homo sapiens

<400> SEQUENCE: 9

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Asn
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 10
aagcttgccg ccaccatgga atggagctgg gtcttt                              36

<210> SEQ ID NO 11
<211> LENGTH: 27
<212> TYPE: DNA
<213> ORGANISM: Artificial Sequence
```

```
<220> FEATURE:
<223> OTHER INFORMATION: Description of Artificial Sequence: DNA Primer

<400> SEQUENCE: 11
ggatccactc acctgaggag acggtga                                              27

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: DNA Primer

<400> SEQUENCE: 12
aagcttcgcc accatgaagt tgcctgttag gctg                                      34

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 13
ggatccactt acgttttatt tccagctt                                             28

<210> SEQ ID NO 14
<211> LENGTH: 357
<212> TYPE: DNA
<213> ORGANISM: Mouse

<400> SEQUENCE: 14
caggtccacc tgcagcagtc tggagctgag ctggtaaggc ctgggacttc agtgaagatg          60
tcctgcaagg ctgctggata caccttcact aactactgga taggttgggt aaagcagagg         120
cctggacatg gccttgagtg gattggatat ctttaccctg aggtctttta tactaactac         180
aatgagaagt tcaagggcaa ggccacactg actgcagaca catcctccag cacagcctac         240
atgcagctca gcagcctgac atctgaggac tctgccatct attactgtgc aagatacagg         300
gattacgact atgctatgga ctactgggt caaggaacct cagtcaccgt ctcctca            357

<210> SEQ ID NO 15
<211> LENGTH: 339
<212> TYPE: DNA
<213> ORGANISM: Mouse

<400> SEQUENCE: 15
gatgttgttc tgacccaaac tccactctct ctgcctgtca atattggaga tcaagcctct          60
atctcttgca gtctactaa gagccttctg aatagtgatg gattcactta tttgggctgg         120
tgcctgcaga agccaggcca gtctccacag ctcctaatat atttggtttc taatcgattt        180
tctggagttc cagacaggtt cagtggtagt gggtcaggga cagatttcac cctcaagatc        240
agcagagtgg aggctgagga tttgggagtt tattattgct tccagagtaa ctatcttcct        300
cttacgttcg gatcggggac caagctggaa ataaaacgt                               339

<210> SEQ ID NO 16
<211> LENGTH: 119
<212> TYPE: PRT
<213> ORGANISM: Mouse

<400> SEQUENCE: 16
```

-continued

```
Gln Val His Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Tyr Leu Tyr Pro Gly Gly Leu Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Tyr Arg Asp Tyr Asp Tyr Ala Met Asp Tyr Trp Gly Gln Gly
            100                 105                 110

Thr Ser Val Thr Val Ser Ser
        115
```

<210> SEQ ID NO 17
<211> LENGTH: 113
<212> TYPE: PRT
<213> ORGANISM: Mouse

<400> SEQUENCE: 17

```
Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Leu Thr Phe Gly Ser Gly Thr Lys Leu Glu Ile Lys
            100                 105                 110

Arg
```

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Gly Trp Val Lys Gln Ala Pro Gly Gln Gly Leu Glu Trp Ile
        35                  40                  45

Gly Tyr Leu Tyr Pro Gly Gly Leu Tyr Thr Asn Tyr Asn Glu Lys Phe
    50                  55                  60

Lys Gly Lys Ala Thr Met Thr Ala Asp Thr Ser Thr Asn Thr Ala Tyr
```

```
                 65                  70                  75                  80
Met Glu Leu Ser Ser Leu Arg Ser Glu Asp Thr Ala Val Tyr Tyr Cys
                         85                  90                  95

Ala Arg Tyr Arg Asp Tyr Asp Tyr Ala Met Asp Tyr Trp Gly Gln Gly
                100                 105                 110

Thr Leu Val Thr Val Ser Ser
            115

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Ile Gly Trp Val Lys Gln Ala Pro Gly Gln Gly Leu Glu Trp Ile
            35                  40                  45

Gly Tyr Leu Tyr Pro Gly Gly Leu Tyr Thr Asn Tyr Asn Glu Lys Phe
        50                  55                  60

Lys Gly Lys Ala Thr Leu Thr Leu Asp Thr Ser Thr Asn Thr Ala Tyr
65                  70                  75                  80

Met Glu Leu Ser Ser Leu Arg Ser Glu Asp Thr Ala Val Tyr Tyr Cys
                    85                  90                  95

Ala Arg Tyr Arg Asp Tyr Asp Tyr Ala Met Asp Tyr Trp Gly Gln Gly
                100                 105                 110

Thr Leu Val Thr Val Ser Ser
            115

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Val Val Met Thr Gln Thr Pro Ser Ser Leu Ser Ala Ser Val Gly
1               5                   10                  15

Asp Arg Ala Ser Ile Ser Cys Lys Ser Thr Lys Ser Leu Leu Asn Ser
                20                  25                  30

Asp Gly Phe Thr Tyr Leu Gly Trp Cys Gln Gln Lys Pro Gly Gln Ser
            35                  40                  45

Pro Gln Leu Leu Ile Tyr Leu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Ser Leu Gln Pro Glu Asp Ile Ala Thr Tyr Tyr Cys Phe Gln Ser
                    85                  90                  95

Asn Tyr Leu Pro Leu Thr Phe Gly Gln Gly Thr Lys Val Glu Ile Lys
                100                 105                 110

Arg
```

```
<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Val Val Met Thr Gln Thr Pro Leu Ser Leu Pro Val Thr Pro Gly
1               5                   10                  15

Glu Pro Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Asn Tyr Leu Pro Leu Thr Phe Gly Gln Gly Thr Lys Leu Glu Ile Lys
            100                 105                 110

Arg

<210> SEQ ID NO 22
<211> LENGTH: 113
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Val Val Met Thr Gln Thr Pro Leu Ser Leu Pro Val Thr Leu Gly
1               5                   10                  15

Gln Pro Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Asn Tyr Leu Pro Leu Thr Phe Gly Gln Gly Thr Lys Leu Glu Ile Lys
            100                 105                 110

Arg

<210> SEQ ID NO 23
<211> LENGTH: 113
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Asp Val Val Met Thr Gln Thr Pro Leu Ser Leu Pro Val Thr Pro Gly
1               5                   10                  15

Gln Pro Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Asn Tyr Leu Pro Leu Thr Phe Gly Gln Gly Thr Lys Leu Glu Ile Lys
            100                 105                 110

Arg
```

<210> SEQ ID NO 24
<211> LENGTH: 113
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Asp Val Val Met Thr Gln Thr Pro Leu Ser Leu Pro Val Thr Leu Gly
1               5                   10                  15

Glu Pro Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Asn Tyr Leu Pro Leu Thr Phe Gly Gln Gly Thr Lys Leu Glu Ile Lys
            100                 105                 110

Arg
```

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: DNA Primer

<400> SEQUENCE: 25
gtgctggttg ttgtgct                                                17

<210> SEQ ID NO 26
<211> LENGTH: 95
<212> TYPE: DNA
<213> ORGANISM: Artificial Sequence
<220> FEATURE:
<223> OTHER INFORMATION: Description of Artificial Sequence:  DNA Primer

<400> SEQUENCE: 26

```
gtataaagac ccccggggta aagatagcca atccactcga gcccttggcc tggggcctgc    60
tttacccaac ctatccagta gttagtgaag gtata                               95

<210> SEQ ID NO 27
<211> LENGTH: 87
<212> TYPE: DNA
<213> ORGANISM: Artificial Sequence
<220> FEATURE:
<223> OTHER INFORMATION: Description of Artificial Sequence: DNA Primer

<400> SEQUENCE: 27
tatctttacc ccgggggtct ttatacaaac tataacgaga agtttaaggg caaggctaca    60
atgaccgcag acacctctac aaacacc                                        87

<210> SEQ ID NO 28
<211> LENGTH: 87
<212> TYPE: DNA
<213> ORGANISM: Artificial Sequence
<220> FEATURE:
<223> OTHER INFORMATION: Description of Artificial Sequence: DNA Primer

<400> SEQUENCE: 28
tatctttacc ccgggggtct ttatacaaac tataacgaga agtttaaggg caaggctaca    60
ctgaccctgg acacctctac aaacacc                                        87

<210> SEQ ID NO 29
<211> LENGTH: 74
<212> TYPE: DNA
<213> ORGANISM: Artificial Sequence
<220> FEATURE:
<223> OTHER INFORMATION: Description of Artificial Sequence: DNA Primer

<400> SEQUENCE: 29
acaagggtac cctgtcccca atagtccata gcgtagtcgt aatccctgta ccttgcgcag    60
tagtagactg cagt                                                      74

<210> SEQ ID NO 30
<211> LENGTH: 86
<212> TYPE: DNA
<213> ORGANISM: Artificial Sequence
<220> FEATURE:
<223> OTHER INFORMATION: Description of Artificial Sequence: DNA Primer

<400> SEQUENCE: 30
gtcgggccca cagcgatgtt gttatgaccc aaactccatc ttctctgtct gccagtgttg    60
gagatcgagc ctctatctct tgcaag                                         86

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: DNA Primer

<400> SEQUENCE: 31
ggcttctgct ggcaccagcc caaataagt                                      29

<210> SEQ ID NO 32
<211> LENGTH: 30
<212> TYPE: DNA
<213> ORGANISM: Artificial Sequence
<220> FEATURE:
```

<223> OTHER INFORMATION: Description of Artificial Sequence: DNA Primer

<400> SEQUENCE: 32
ggctggtgcc agcagaagcc aggccagtct        30

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: DNA Primer

<400> SEQUENCE: 33
atatcctcag gctgcagact gctgatcttg agggtgaa        38

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: DNA Primer

<400> SEQUENCE: 34
agcagtctgc agcctgagga tatagctact tattattgct tccagagtaa c        51

<210> SEQ ID NO 35
<211> LENGTH: 58
<212> TYPE: DNA
<213> ORGANISM: Artificial Sequence
<220> FEATURE:
<223> OTHER INFORMATION: Description of Artificial Sequence: DNA Primer

<400> SEQUENCE: 35
ctcggatcca cttacgtttt atttccacct tggtcccctg tccgaacgta agaggaag        58

<210> SEQ ID NO 36
<211> LENGTH: 86
<212> TYPE: DNA
<213> ORGANISM: Artificial Sequence
<220> FEATURE:
<223> OTHER INFORMATION: Description of Artificial Sequence: DNA Primer

<400> SEQUENCE: 36
gtcgggccca cagcgatgtt gttatgaccc aaactccact ctctctgcct gtcactcytg        60
gasagccagc ctctatctct tgcaag        86

<210> SEQ ID NO 37
<211> LENGTH: 100
<212> TYPE: DNA
<213> ORGANISM: Artificial Sequence
<220> FEATURE:
<223> OTHER INFORMATION: Description of Artificial Sequence: DNA Primer

<400> SEQUENCE: 37
ctcggatcca cttacgtttt atttccagct tggtcccctg tccgaacgta agaggaagat        60
agttactctg gaagcaataa taaactccca catcctcagc        100

<210> SEQ ID NO 38
<211> LENGTH: 81
<212> TYPE: DNA
<213> ORGANISM: Artificial Sequence
<220> FEATURE:
<223> OTHER INFORMATION: Description of Artificial Sequence: DNA Primer

<400> SEQUENCE: 38

```
tctggtacct gtgggcagct cgactacaag gacgacgatg acaagcacct acagaaggag      60
ctagcagaac tccgagagtc t                                                81

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 39
gccaagcttg gatccttaga gcttatataa gccgaa                                36

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: DNA Primer

<400> SEQUENCE: 40
cacctacaga aggagctagc agaactccga gagtcgacca gccag                      45

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 41
ttgaccccgg aaggctactt tggaata                                          27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 42
agattgaccc cgggcgtata ctttgga                                          27

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 43
gttgcaagat tgacccgcga agtatac                                          27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 44
gttgcaagat tgagcccgga agtatac                                          27

<210> SEQ ID NO 45
```

```
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 45
gttgttgcaa gatgcacccc ggaagta                                            27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 46
caggttgttg caagcttgac cccggaa                                            27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 47
gggcaggttg ttggcagatt gaccccg                                            27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 48
caggggcagg ttggcgcaag attgacc                                            27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 49
gctcaggggc agggcgttgc aagattg                                            27

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 50
gtggctcagg ggcgcgttgt tgcaaga                                            27

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 51
```

```
cttgtggctc agggccaggt tgttgca                                            27
```

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 52

```
gaccttgtgg ctcgcgggca ggttgtt                                            27
```

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 53

```
gtagaccttg tgggccaggg gcaggtt                                            27
```

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 54

```
catgtagacc ttggcgctca ggggcag                                            27
```

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 55

```
cctcatgtag accgcgtggc tcagggg                                            27
```

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 56

```
gttcctcatg taggccttgt ggctcag                                            27
```

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 57

```
agagttcctc atggcgacct tgtggct                                            27
```

<210> SEQ ID NO 58
<211> LENGTH: 27
<212> TYPE: DNA

```
<213> ORGANISM: Artificial Sequence
<220> FEATURE:
<223> OTHER INFORMATION: Description of Artificial Sequence: DNA Primer

<400> SEQUENCE: 58
cttagagttc ctcgcgtaga ccttgtg                                          27

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 59
gggatactta gagttcgcca tgtagac                                          27

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 60
gggatactta gaggccctca tgtagac                                          27

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 61
ctggggatac ttagcgttcc tcatgta                                          27

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 62
atcctgggga tacgcagagt tcctcat                                          27

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 63
cagatcctgg ggagccttag agttcct                                          27

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 64
caccagatcc tgggcatact tagagtt                                          27
```

```
<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 65
catcaccaga tccgcgggat acttaga                                              27

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 66
catcatcacc agagcctggg gatactt                                              27

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 67
ctccatcatc accgcatcct ggggata                                              27

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 68
cccctccatc atcgccagat cctgggg                                              27

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 69
cttcccctcc atcgccacca gatcctg                                              27

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 70
catcttcccc tccgccatca ccagatc                                              27

<210> SEQ ID NO 71
<211> LENGTH: 27
<212> TYPE: DNA
<213> ORGANISM: Artificial Sequence
<220> FEATURE:
```

<223> OTHER INFORMATION: Description of Artificial Sequence: DNA Primer

<400> SEQUENCE: 71
catcatcttc cccgccatca tcaccag                                27

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 72
gctcatcatc ttcgcctcca tcatcac                                27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence

<400> SEQUENCE: 73
gtagctcatc atcgccccct ccatcat                                27

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 74
gcagtagctc atcgccttcc cctccat                                27

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 75
agtgcagtag ctcgccatct tcccctc                                27

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 76
agtagtgcag taggccatca tcttccc                                27

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 77
cccagtagtg caggcgctca tcatctt                                27

```
<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 78
ctgcccagta gtggcgtagc tcatcat                                              27

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 79
catctgccca gtagcgcagt agctcat                                              27

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 80
ccacatctgc ccagcagtgc agtagct                                              27

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 81
ggcccacatc tgcgcagtag tgcagta                                              27

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 82
gcgggcccac atcgccccag tagtgca                                              27

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 83
gctgcgggcc cacgcctgcc cagtagt                                              27

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: DNA Primer
```

-continued

```
<400> SEQUENCE: 84
gctgcgggcc gccatctgcc cagtagt                                           27

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 85
caggtagctg ctgcggcccc acatctg                                           27

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 86
tattccaaag tagccttccg gggtcaa                                           27

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 87
tccaaagtat acgcccgggg tcaatct                                           27

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 88
gtatacttcg cgggtcaatc ttgcaac                                           27

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 89
gtatacttcc gggctcaatc ttgcaac                                           27

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 90
tacttccggg gtgcatcttg caacaac                                           27

<210> SEQ ID NO 91
<211> LENGTH: 27
```

```
<212> TYPE: DNA
<213> ORGANISM: Artificial Sequence
<220> FEATURE:
<223> OTHER INFORMATION: Description of Artificial Sequence: DNA Primer

<400> SEQUENCE: 91
ttccggggtc aagcttgcaa caacctg                                    27

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 92
cggggtcaat ctgccaacaa cctgccc                                    27

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 93
ggtcaatctt gcgccaacct gcccctg                                    27

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 94
caatcttgca acgccctgcc cctgagc                                    27

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 95
tcttgcaaca acgcgcccct gagccac                                    27

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 96
tgcaacaacc tggccctgag ccacaag                                    27

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 97
```
aacaacctgc ccgcgagcca caaggtc                                              27

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 98
aacctgcccc tggcccacaa ggtctac                                              27

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 99
ctgcccctga gcgccaaggt ctacatg                                              27

<210> SEQ ID NO 100
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 100
cccctgagcc acgcggtcta catgagg                                              27

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 101
ctgagccaca aggcctacat gaggaac                                              27

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 102
agccacaagg tcgccatgag gaactct                                              27

<210> SEQ ID NO 103
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 103
cacaaggtct acgcgaggaa ctctaag                                              27

<210> SEQ ID NO 104
<211> LENGTH: 27
<212> TYPE: DNA
<213> ORGANISM: Artificial Sequence -continued
<220> FEATURE:
<223> OTHER INFORMATION: Description of Artificial Sequence: DNA Primer

<400> SEQUENCE: 104
gtctacatgg cgaactctaa gtatccc                              27

<210> SEQ ID NO 105
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 105
gtctacatga gggcctctaa gtatccc                              27

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 106
tacatgagga acgctaagta tccccag                              27

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 107
atgaggaact ctgcgtatcc ccaggat                              27

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 108
aggaactcta aggctcccca ggatctg                              27

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 109
aactctaagt atgcccagga tctggtg                              27

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 110
tctaagtatc ccgcggatct ggtgatg                              27

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 111
aagtatcccc aggctctggt gatgatg                              27

<210> SEQ ID NO 112
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 112
tatccccagg atgcggtgat gatggag                              27

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 113
ccccaggatc tggcgatgat ggagggg                              27

<210> SEQ ID NO 114
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 114
caggatctgg tggcgatgga ggggaag                              27

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 115
gatctggtga tggcggaggg gaagatg                              27

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 116
ctggtgatga tggcggggaa gatgatg                              27

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 117
gtgatgatgg aggcgaagat gatgagc            27

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 118
atgatggagg gggcgatgat gagctac            27

<210> SEQ ID NO 119
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 119
atggagggga aggcgatgag ctactgc            27

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 120
gaggggaaga tggcgagcta ctgcact            27

<210> SEQ ID NO 121
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 121
gggaagatga tggcctactg cactact            27

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 122
aagatgatga gcgcctgcac tactggg            27

<210> SEQ ID NO 123
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 123
atgatgagct acgccactac tgggcag            27

<210> SEQ ID NO 124

```
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 124
atgagctact gcgctactgg gcagatg                              27

<210> SEQ ID NO 125
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 125
agctactgca ctgctgggca gatgtgg                              27

<210> SEQ ID NO 126
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 126
tactgcacta ctgcgcagat gtgggcc                              27

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 127
tgcactactg gggcgatgtg ggcccgc                              27

<210> SEQ ID NO 128
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 128
actactgggc aggcgtgggc ccgcagc                              27

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 129
actactgggc agatggcggc ccgcagc                              27

<210> SEQ ID NO 130
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 130
```
cagatgtggg gccgcagcag ctacctg        27

<210> SEQ ID NO 131
<211> LENGTH: 219
<212> TYPE: PRT
<213> ORGANISM: Mouse

<400> SEQUENCE: 131

Gln Gly Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Phe
            20                  25                  30

Trp Val Asn Trp Val Lys Gln Arg Pro Gly Gln Gly Leu Glu Trp Ile
        35                  40                  45

Gly Gln Ile Tyr Pro Gly Asp Gly Asp Asn Lys Tyr Asn Gly Lys Phe
    50                  55                  60

Lys Gly Lys Ala Thr Leu Thr Ala Asp Lys Ser Thr Thr Ala Tyr
65                  70                  75                  80

Met Gln Leu Tyr Ser Leu Thr Ser Glu Asp Ser Ala Val Tyr Phe Cys
                85                  90                  95

Ala Arg Ser Gly Asn Tyr Pro Tyr Ala Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Gly Leu Tyr Thr Leu Ser Ser Ser Val Thr Val Thr Ser Ser
            180                 185                 190

Thr Trp Pro Ser Gln Thr Ile Thr Cys Asn Val Ala His Pro Ala Ser
        195                 200                 205

Ser Thr Lys Val Asp Lys Lys Ile Glu Pro Arg
    210                 215

<210> SEQ ID NO 132
<211> LENGTH: 216
<212> TYPE: PRT
<213> ORGANISM: Mouse

<400> SEQUENCE: 132

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Ser Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

```
Ser His Ile Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Trp His Asn Ser Tyr Thr Cys Glu Ala Thr His Lys Thr Ser Thr Ser
            195                 200                 205

Pro Ile Val Lys Ser Phe Asn Arg
    210                 215
```

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

```
Leu Tyr Phe Val Tyr Ser Lys Val Tyr Phe Arg Gly Gln Ser Cys
1               5                   10                  15
```

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

```
Ser Lys Val Tyr Phe Arg Gly Gln Ser Cys Asn Asn Leu Pro Leu
1               5                   10                  15
```

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

```
Arg Gly Gln Ser Cys Asn Asn Leu Pro Leu Ser His Lys Val Tyr
1               5                   10                  15
```

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

```
Tyr Pro Gln Asp Leu Val Met Met Glu Gly Lys Met Met Ser Tyr
1               5                   10                  15
```

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Val Met Met Glu Gly Lys Met Met Ser Tyr Cys Thr Thr Gly Gln
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Met Met Ser Tyr Cys Thr Thr Gly Gln Met Trp Ala Arg Ser
1               5                   10                  15

<210> SEQ ID NO 139
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Leu Tyr Phe Val Tyr Ser Lys Val Tyr Phe Arg Gly Gln Ser Cys Asn
1               5                   10                  15

Asn Leu Pro Leu Ser His Lys Val Tyr
            20                  25

<210> SEQ ID NO 140
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Tyr Pro Gln Asp Leu Val Met Met Glu Gly Lys Met Met Ser Tyr Cys
1               5                   10                  15

Thr Thr Gly Gln Met Trp Ala Arg Ser
            20                  25

<210> SEQ ID NO 141
<211> LENGTH: 15
<212> TYPE: DNA
<213> ORGANISM: Artificial Sequence
<220> FEATURE:
<223> OTHER INFORMATION: Description of Artificial Sequence: DNA Primer

<400> SEQUENCE: 141
aagcttgccg ccacc                                                   15

<210> SEQ ID NO 142
<211> LENGTH: 421
<212> TYPE: DNA

<213> ORGANISM: Mus musculus

<400> SEQUENCE: 142

```
atggaatgga gctgggtctt tatctttctc ctgtcagtaa ctgcaggtgt ccactcccag      60
gtccacctgc agcagtctgg agctgagctg gtaaggcctg ggacttcagt gaagatgtcc     120
tgcaaggctg ctggatacac cttcactaac tactggatag gttgggtaaa gcagaggcct     180
ggacatggcc ttgagtggat tggatatctt taccctggag gtctttatac taactacaat     240
gagaagttca aggcaaggc cacactgact gcagacacat cctccagcac agcctacatg      300
cagctcagca gcctgacatc tgaggactct gccatctatt actgtgcaag atacagggat     360
tacgactatg ctatggacta ctggggtcaa ggaacctcag tcaccgtctc ctcaggtgag     420
t                                                                    421
```

<210> SEQ ID NO 143
<211> LENGTH: 138
<212> TYPE: PRT
<213> ORGANISM: Mus musculus

<400> SEQUENCE: 143

```
Met Glu Trp Ser Trp Val Phe Ile Phe Leu Leu Ser Val Thr Ala Gly
1               5                   10                  15
Val His Ser Gln Val His Leu Gln Gln Ser Gly Ala Glu Leu Val Arg
            20                  25                  30
Pro Gly Thr Ser Val Lys Met Ser Cys Lys Ala Ala Gly Tyr Thr Phe
        35                  40                  45
Thr Asn Tyr Trp Ile Gly Trp Val Lys Gln Arg Pro Gly His Gly Leu
    50                  55                  60
Glu Trp Ile Gly Tyr Leu Tyr Pro Gly Gly Leu Tyr Thr Asn Tyr Asn
65                  70                  75                  80
Glu Lys Phe Lys Gly Lys Ala Thr Leu Thr Ala Asp Thr Ser Ser Ser
                85                  90                  95
Thr Ala Tyr Met Gln Leu Ser Ser Leu Thr Ser Glu Asp Ser Ala Ile
            100                 105                 110
Tyr Tyr Cys Ala Arg Tyr Arg Asp Tyr Asp Tyr Ala Met Asp Tyr Trp
        115                 120                 125
Gly Gln Gly Thr Ser Val Thr Val Ser Ser
    130                 135
```

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 144

```
tcaccgtctc ctcaggtgag tggatcc                                         27
```

<210> SEQ ID NO 145
<211> LENGTH: 13
<212> TYPE: DNA
<213> ORGANISM: Artificial Sequence
<220> FEATURE:
<223> OTHER INFORMATION: Description of Artificial Sequence: DNA Primer

<400> SEQUENCE: 145

```
aagcttcgcc acc                                                        13
```

<210> SEQ ID NO 146
<211> LENGTH: 409
<212> TYPE: DNA
<213> ORGANISM: Mus musculus

<400> SEQUENCE: 146

| | | | | | |
|---|---|---|---|---|---|
| atgaagttgc | ctgttaggct | gttggtgctg | ctattgttca | tgagtccagc | ttcaagcagt | 60 |
| gatgttgttc | tgacccaaac | tccactctct | ctgcctgtca | atattggaga | tcaagcctct | 120 |
| atctcttgca | agtctactaa | gagccttctg | aatagtgatg | gattcactta | tttgggctgg | 180 |
| tgcctgcaga | agccaggcca | gtctccacag | ctcctaatat | atttggtttc | taatcgattt | 240 |
| tctggagttc | cagacaggtt | cagtggtagt | gggtcaggga | cagatttcac | cctcaagatc | 300 |
| agcagagtgg | aggctgagga | tttgggagtt | tattattgct | tccagagtaa | ctatcttcct | 360 |
| cttacgttcg | gatcggggac | caagctggaa | ataaaacgta | agtggatcc | | 409 |

<210> SEQ ID NO 147
<211> LENGTH: 132
<212> TYPE: PRT
<213> ORGANISM: Mus musculus

<400> SEQUENCE: 147

Met Lys Leu Pro Val Arg Leu Leu Val Leu Leu Leu Phe Met Ser Pro
1               5                   10                  15

Ala Ser Ser Ser Asp Val Val Leu Thr Gln Thr Pro Leu Ser Leu Pro
            20                  25                  30

Val Asn Ile Gly Asp Gln Ala Ser Ile Ser Cys Lys Ser Thr Lys Ser
        35                  40                  45

Leu Leu Asn Ser Asp Gly Phe Thr Tyr Leu Gly Trp Cys Leu Gln Lys
    50                  55                  60

Pro Gly Gln Ser Pro Gln Leu Leu Ile Tyr Leu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Phe Gln Ser Asn Tyr Leu Pro Leu Thr Phe Gly Ser Gly Thr Lys
        115                 120                 125

Leu Glu Ile Lys
    130

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 148
aagctggaaa taaaacgtaa gtggatcc                                           28

<210> SEQ ID NO 149
<211> LENGTH: 119
<212> TYPE: PRT
<213> ORGANISM: Mus musculus

<400> SEQUENCE: 149

Gln Val His Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Tyr Leu Tyr Pro Gly Gly Leu Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Tyr Arg Asp Tyr Asp Tyr Ala Met Asp Tyr Trp Gly Gln Gly
            100                 105                 110

Thr Ser Val Thr Val Ser Ser
        115

<210> SEQ ID NO 151
<211> LENGTH: 87
<212> TYPE: PRT
<213> ORGANISM: Homo sapiens

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Lys Gln Ala Pro Gly Gln Gly Leu Glu Trp Ile Gly Lys Ala Thr Leu
        35                  40                  45

Thr Leu Asp Thr Ser Thr Asn Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
            85

<210> SEQ ID NO 151
<211> LENGTH: 88
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Trp Val
            20                  25                  30

Arg Gln Ala Pro Gly Gln Gly Leu Glu Trp Val Gly Arg Val Thr Met
        35                  40                  45

Thr Leu Asp Thr Ser Thr Asn Thr Ala Tyr Met Glu Leu Ser Ser Leu
    50                  55                  60

Arg Ser Glu Asp Thr Ala Val Tyr Tyr Cys Ala Ser Arg Trp Gly Gln
65                  70                  75                  80

Gly Thr Leu Val Thr Val Ser Ser
            85

<210> SEQ ID NO 152

```
<211> LENGTH: 87
<212> TYPE: PRT
<213> ORGANISM: Mus musculus

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Val Gly Lys Ala Thr Met
        35                  40                  45

Thr Ala Asp Thr Ser Thr Asn Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 153
<211> LENGTH: 113
<212> TYPE: PRT
<213> ORGANISM: Mus musculus

<400> SEQUENCE: 153

Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Leu Thr Phe Gly Ser Gly Thr Lys Leu Glu Ile Lys
            100                 105                 110

Arg

<210> SEQ ID NO 154
<211> LENGTH: 81
<212> TYPE: PRT
<213> ORGANISM: Homo sapiens

<400> SEQUENCE: 154

Asp Ile Val Met Thr Gln Ser Pro Leu Ser Leu Pro Val Thr Pro Gly
1               5                   10                  15

Glu Pro Ala Ser Ile Ser Cys Trp Tyr Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Leu Glu Ile Lys
65                  70                  75                  80

Arg
```

<210> SEQ ID NO 155
<211> LENGTH: 81
<212> TYPE: PRT
<213> ORGANISM: Homo sapiens

<400> SEQUENCE: 155

```
Asp Val Val Met Thr Gln Ser Pro Leu Ser Leu Pro Val Thr Leu Gly
1               5                   10                  15

Gln Pro Ala Ser Ile Ser Cys Trp Phe Gly Gln Arg Pro Gly Gln Ser
            20                  25                  30

Pro Arg Arg Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Leu Glu Ile Lys
65                  70                  75                  80

Arg
```

<210> SEQ ID NO 156
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

```
Asp Val Val Met Thr Gln Thr Pro Leu Ser Leu Pro Val Thr Pro Gly
1               5                   10                  15

Glu Pro Ala Ser Ile Ser Cys Trp Cys Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Leu Glu Ile Lys
65                  70                  75                  80

Arg
```

<210> SEQ ID NO 157
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

```
Asp Val Val Met Thr Gln Thr Pro Leu Ser Leu Pro Val Thr Leu Gly
1               5                   10                  15

Gln Pro Ala Ser Ile Ser Cys Trp Cys Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Leu Glu Ile Lys
65                  70                  75                  80
```

Arg

<210> SEQ ID NO 158
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Val Val Met Thr Gln Thr Pro Leu Ser Leu Pro Val Thr Pro Gly
1               5                   10                  15

Gln Pro Ala Ser Ile Ser Cys Trp Cys Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Leu Glu Ile Lys
65                  70                  75                  80

Arg

<210> SEQ ID NO 159
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Val Val Met Thr Gln Thr Pro Leu Ser Leu Pro Val Thr Leu Gly
1               5                   10                  15

Glu Pro Ala Ser Ile Ser Cys Trp Cys Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Leu Glu Ile Lys
65                  70                  75                  80

Arg

<210> SEQ ID NO 160
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

```
Ser Gly Thr Asp Phe Thr Phe Thr Ile Ser Ser Leu Gln Pro Glu Asp
    50                  55                  60

Ile Ala Thr Tyr Tyr Cys Phe Gly Gln Gly Thr Lys Val Glu Ile Lys
65                  70                  75                  80

Arg

<210> SEQ ID NO 161
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Val Val Met Thr Gln Thr Pro Ser Ser Leu Ser Ala Ser Val Gly
1               5                   10                  15

Asp Arg Ala Ser Ile Ser Cys Trp Cys Gln Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Ser Leu Gln Pro Glu Asp
    50                  55                  60

Ile Ala Thr Tyr Tyr Cys Phe Gly Gln Gly Thr Lys Val Glu Ile Lys
65                  70                  75                  80

Arg

<210> SEQ ID NO 162
<211> LENGTH: 95
<212> TYPE: DNA
<213> ORGANISM: Artificial Sequence
<220> FEATURE:
<223> OTHER INFORMATION: Description of Artificial Sequence: DNA Primer

<400> SEQUENCE: 162
tataccttca ctaactactg gataggttgg gtaaagcagg ccccaggcca agggctcgag    60
tggattggct atctttaccc cgggggtctt tatac                              95

<210> SEQ ID NO 163
<211> LENGTH: 87
<212> TYPE: DNA
<213> ORGANISM: Artificial Sequence
<220> FEATURE:
<223> OTHER INFORMATION: Description of Artificial Sequence:
      Double-stranded DNA Primer

<400> SEQUENCE: 163
tatctttacc ccgggggtct ttatacaaac tataacgaga agtttaaggg caaggctaca    60
atgaccgcag acacctctac aaacacc                                       87

<210> SEQ ID NO 164
<211> LENGTH: 87
<212> TYPE: DNA
<213> ORGANISM: Artificial Sequence
<220> FEATURE:
<223> OTHER INFORMATION: Description of Artificial Sequence: DNA Primer

<400> SEQUENCE: 164
tatctttacc ccgggggtct ttatacaaac tataacgaga agtttaaggg caaggctaca    60
ctgaccctgg acacctctac aaacacc                                       87
```

<210> SEQ ID NO 165
<211> LENGTH: 74
<212> TYPE: DNA
<213> ORGANISM: Artificial Sequence
<220> FEATURE:
<223> OTHER INFORMATION: Description of Artificial Sequence:
       Double-stranded DNA Primer

<400> SEQUENCE: 165
actgcagtct actactgcgc aaggtacagg gattacgact acgctatgga ctattgggga     60
cagggtaccc ttgt                                                       74

<210> SEQ ID NO 166
<211> LENGTH: 86
<212> TYPE: DNA
<213> ORGANISM: Artificial Sequence
<220> FEATURE:
<223> OTHER INFORMATION: Description of Artificial Sequence: DNA Primer

<400> SEQUENCE: 166
gtcgggccca cagcgatgtt gttatgaccc aaactccatc ttctctgtct gccagtgttg     60
gagatcgagc ctctatctct tgcaag                                          86

<210> SEQ ID NO 167
<211> LENGTH: 29
<212> TYPE: DNA
<213> ORGANISM: Artificial Sequence
<220> FEATURE:
<223> OTHER INFORMATION: Description of Artificial Sequence:
       Double-stranded DNA Primer

<400> SEQUENCE: 167
acttatttgg gctggtgcca gcagaagcc                                       29

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: DNA Primer

<400> SEQUENCE: 168
ggctggtgcc agcagaagcc aggccagtct                                      30

<210> SEQ ID NO 169
<211> LENGTH: 38
<212> TYPE: DNA
<213> ORGANISM: Artificial Sequence
<220> FEATURE:
<223> OTHER INFORMATION: Description of Artificial Sequence:
       Double-stranded DNA Primer

<400> SEQUENCE: 169
ttcaccctca agatcagcag tctgcagcct gaggatat                             38

<210> SEQ ID NO 170
<211> LENGTH: 51
<212> TYPE: DNA
<213> ORGANISM: Artificial Sequence
<220> FEATURE:
<223> OTHER INFORMATION: Description of Artificial Sequence: DNA Primer

<400> SEQUENCE: 170
agcagtctgc agcctgagga tatagctact tattattgct tccagagtaa c              51

```
<210> SEQ ID NO 171
<211> LENGTH: 58
<212> TYPE: DNA
<213> ORGANISM: Artificial Sequence
<220> FEATURE:
<223> OTHER INFORMATION: Description of Artificial Sequence:
      Double-stranded DNA Primer

<400> SEQUENCE: 171
cttcctctta cgttcggaca ggggaccaag gtggaaataa aacgtaagtg gatccgag        58

<210> SEQ ID NO 172
<211> LENGTH: 88
<212> TYPE: DNA
<213> ORGANISM: Artificial Sequence
<220> FEATURE:
<223> OTHER INFORMATION: Description of Artificial Sequence: DNA Primer

<400> SEQUENCE: 172
gtcgggccca cagcgatgtt gttatgaccc aaactccact ctctctgcct gtcactcctt      60
ggagcagcca gcctctatct cttgcaag                                         88

<210> SEQ ID NO 173
<211> LENGTH: 100
<212> TYPE: DNA
<213> ORGANISM: Artificial Sequence
<220> FEATURE:
<223> OTHER INFORMATION: Description of Artificial Sequence:
      Double-stranded DNA Primer

<400> SEQUENCE: 173
gctgaggatg tgggagttta ttattgcttc cagagtaact atcttcctct tacgttcgga      60
caggggacca agctggaaat aaaacgtaag tggatccgag                           100

<210> SEQ ID NO 174
<211> LENGTH: 578
<212> TYPE: DNA
<213> ORGANISM: Homo sapiens

<400> SEQUENCE: 174
ggattgggcc tgggatgtt tcagctcttc cacctacaga aggagctggc agaactccga       60
gagtctacca gccagatgca cacagcatca tctttggaga agcaaatagg ccaccccagt     120 ccacccctg aaaaaaagga gctgaggaaa gtggcccatt taacaggcaa gtccaactca      180
aggtccatgc ctctggaatg ggaagacacc tatggaattg tcctgctttc tggagtgaag     240
tataagaagg gtggccttgt gatcaatgaa actgggctgt actttgtata ttccaaagta     300
tacttccggg gtcaatcttg caacaacctg cccctgagcc acaaggtcta catgaggaac     360
tctaagtatc cccaggatct ggtgatgatg aggggaaga tgatgagcta ctgcactact       420
gggcagatgt gggcccgcag cagctacctg ggggcagtgt tcaatcttac cagtgctgat     480
catttatatg tcaacgtatc tgagctctct ctggtcaatt ttgaggaatc tcagacgttt     540
ttcggcttat ataagctcta agagaagcac tttgggat                             578

<210> SEQ ID NO 175
<211> LENGTH: 186
<212> TYPE: PRT
<213> ORGANISM: Homo sapiens

<400> SEQUENCE: 175

Gly Leu Gly Leu Gly Met Phe Gln Leu Phe His Leu Gln Lys Glu Leu
```

```
  1               5                  10                 15
Ala Glu Leu Arg Glu Ser Thr Ser Gln Met His Thr Ala Ser Ser Leu
                20                  25                 30

Glu Lys Gln Ile Gly His Pro Ser Pro Pro Glu Lys Lys Glu Leu
                35                  40                 45

Arg Lys Val Ala His Leu Thr Gly Lys Ser Asn Ser Arg Ser Met Pro
                50                  55                 60

Leu Glu Trp Glu Asp Thr Tyr Gly Ile Val Leu Leu Ser Gly Val Lys
 65                  70                 75                     80

Tyr Lys Lys Gly Gly Leu Val Ile Asn Glu Thr Gly Leu Tyr Phe Val
                    85                 90                  95

Tyr Ser Lys Val Tyr Phe Arg Gly Gln Ser Cys Asn Asn Leu Pro Leu
                100                105                 110

Ser His Lys Val Tyr Met Arg Asn Ser Lys Tyr Pro Gln Asp Leu Val
                115                120                 125

Met Met Glu Gly Lys Met Met Ser Tyr Cys Thr Thr Gly Gln Met Trp
                130                135                 140

Ala Arg Ser Ser Tyr Leu Gly Ala Val Phe Asn Leu Thr Ser Ala Asp
145                 150                155                     160

His Leu Tyr Val Asn Val Ser Glu Leu Ser Leu Val Asn Phe Glu Glu
                    165                170                 175

Ser Gln Thr Phe Phe Gly Leu Tyr Lys Leu
                180                185
```

<210> SEQ ID NO 176
<211> LENGTH: 179
<212> TYPE: PRT
<213> ORGANISM: Homo sapiens

<400> SEQUENCE: 176

```
Gln Leu Phe His Leu Gln Lys Glu Leu Ala Glu Leu Arg Glu Ser Thr
 1               5                  10                 15

Ser Gln Met His Thr Ala Ser Ser Leu Glu Lys Gln Ile Gly His Pro
                20                  25                 30

Ser Pro Pro Glu Lys Lys Glu Leu Arg Lys Val Ala His Leu Thr
                35                  40                 45

Gly Lys Ser Asn Ser Arg Ser Met Pro Leu Glu Trp Glu Asp Thr Tyr
 50                  55                 60

Gly Ile Val Leu Leu Ser Gly Val Lys Tyr Lys Lys Gly Gly Leu Val
 65                  70                 75                     80

Ile Asn Glu Thr Gly Leu Tyr Phe Val Tyr Ser Lys Val Tyr Phe Arg
                    85                 90                  95

Gly Gln Ser Cys Asn Asn Leu Pro Leu Ser His Lys Val Tyr Met Arg
                100                105                 110

Asn Ser Lys Tyr Pro Gln Asp Leu Val Met Met Glu Gly Lys Met Met
                115                120                 125

Ser Tyr Cys Thr Thr Gly Gln Met Trp Ala Arg Ser Ser Tyr Leu Gly
                130                135                 140

Ala Val Phe Asn Leu Thr Ser Ala Asp His Leu Tyr Val Asn Val Ser
145                 150                155                     160

Glu Leu Ser Leu Val Asn Phe Glu Glu Ser Gln Thr Phe Phe Gly Leu
                    165                170                 175

Tyr Lys Leu
```

-continued

<210> SEQ ID NO 177
<211> LENGTH: 138
<212> TYPE: PRT
<213> ORGANISM: Homo sapiens

<400> SEQUENCE: 177

Arg Lys Val Ala His Leu Thr Gly Lys Ser Asn Ser Arg Ser Met Pro
1               5                   10                  15

Leu Glu Trp Glu Asp Thr Tyr Gly Ile Val Leu Leu Ser Gly Val Lys
            20                  25                  30

Tyr Lys Lys Gly Gly Leu Val Ile Asn Glu Thr Gly Leu Tyr Phe Val
        35                  40                  45

Tyr Ser Lys Val Tyr Phe Arg Gly Gln Ser Cys Asn Asn Leu Pro Leu
    50                  55                  60

Ser His Lys Val Tyr Met Arg Asn Ser Lys Tyr Pro Gln Asp Leu Val
65                  70                  75                  80

Met Met Glu Gly Lys Met Met Ser Tyr Cys Thr Thr Gly Gln Met Trp
                85                  90                  95

Ala Arg Ser Ser Tyr Leu Gly Ala Val Phe Asn Leu Thr Ser Ala Asp
            100                 105                 110

His Leu Tyr Val Asn Val Ser Glu Leu Ser Leu Val Asn Phe Glu Glu
        115                 120                 125

Ser Gln Thr Phe Phe Gly Leu Tyr Lys Leu
    130                 135

<210> SEQ ID NO 178
<211> LENGTH: 152
<212> TYPE: PRT
<213> ORGANISM: Homo sapiens

<400> SEQUENCE: 178

Arg Thr Pro Ser Asp Lys Pro Val Ala His Val Ala Asn Pro Gln
1               5                   10                  15

Ala Glu Gly Gln Leu Gln Trp Leu Asn Arg Arg Ala Asn Ala Leu Leu
            20                  25                  30

Ala Asn Gly Val Glu Leu Arg Asp Asn Gln Leu Val Val Pro Ser Glu
        35                  40                  45

Gly Leu Tyr Leu Ile Tyr Ser Gln Val Leu Phe Lys Gly Gln Gly Cys
    50                  55                  60

Pro Ser Thr His Val Leu Leu Thr His Thr Ile Ser Arg Ile Ala Val
65                  70                  75                  80

Ser Tyr Gln Thr Lys Val Asn Leu Leu Ser Ala Ile Lys Ser Pro Cys
                85                  90                  95

Gln Arg Glu Thr Pro Glu Gly Ala Glu Ala Lys Pro Trp Tyr Glu Pro
            100                 105                 110

Ile Tyr Leu Gly Gly Val Phe Gln Leu Glu Lys Gly Asp Arg Leu Ser
        115                 120                 125

Ala Glu Ile Asn Arg Pro Asp Tyr Leu Asp Phe Ala Glu Ser Gly Gln
    130                 135                 140

Val Tyr Phe Gly Ile Ile Ala Leu
145                 150

<210> SEQ ID NO 179
<211> LENGTH: 144
<212> TYPE: PRT
<213> ORGANISM: Homo sapiens

<400> SEQUENCE: 179

```
Lys Pro Ala Ala His Leu Ile Gly Asp Pro Ser Lys Gln Asn Ser Leu
  1               5                  10                  15

Leu Trp Arg Ala Asn Thr Asp Arg Ala Phe Leu Gln Asp Gly Phe Ser
             20                  25                  30

Leu Ser Asn Asn Ser Leu Leu Val Pro Thr Ser Gly Ile Tyr Phe Val
         35                  40                  45

Tyr Ser Gln Val Val Phe Ser Gly Lys Ala Tyr Ser Pro Lys Ala Thr
 50                  55                  60

Ser Ser Pro Leu Tyr Leu Ala His Glu Val Gln Leu Phe Ser Ser Gln
 65                  70                  75                  80

Tyr Pro Phe His Val Pro Leu Leu Ser Ser Gln Lys Met Val Tyr Pro
             85                  90                  95

Gly Leu Gln Glu Pro Trp Leu His Ser Met Tyr His Gly Ala Ala Phe
            100                 105                 110

Gln Leu Thr Gln Gly Asp Gln Leu Ser Thr His Thr Asp Gly Ile Pro
            115                 120                 125

His Leu Val Leu Ser Pro Ser Thr Val Phe Phe Gly Ala Phe Ala Leu
            130                 135                 140
```

<210> SEQ ID NO 180
<211> LENGTH: 219
<212> TYPE: PRT
<213> ORGANISM: Mus musculus

<400> SEQUENCE: 180

```
Gln Val His Leu Gln Gln Ser Gly Ala Glu Leu Val Arg Pro Gly Thr
  1               5                  10                  15

Ser Val Lys Met Ser Cys Lys Ala Ala Gly Tyr Thr Phe Thr Asn Tyr
             20                  25                  30

Trp Ile Gly Trp Val Lys Gln Arg Pro Gly His Gly Leu Glu Trp Ile
         35                  40                  45

Gly Tyr Leu Tyr Pro Gly Gly Leu Tyr Thr Asn Tyr Asn Glu Lys Phe
 50                  55                  60

Lys Gly Lys Ala Thr Leu Thr Ala Asp Thr Ser Ser Thr Ala Tyr
 65                  70                  75                  80

Met Gln Leu Ser Ser Leu Thr Ser Glu Asp Ser Ala Ile Tyr Tyr Cys
             85                  90                  95

Ala Arg Tyr Arg Asp Tyr Asp Tyr Ala Met Asp Tyr Trp Gly Gln Gly
            100                 105                 110

Thr Ser Val Thr Val Ser Ser Ala Lys Thr Thr Ala Pro Ser Val Tyr
            115                 120                 125

Pro Leu Ala Pro Val Cys Gly Gly Thr Thr Gly Ser Ser Val Thr Leu
            130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
            165                 170                 175

Gln Ser Gly Leu Tyr Thr Leu Ser Ser Val Thr Val Thr Ser Ser
            180                 185                 190

Thr Trp Pro Ser Gln Thr Ile Thr Cys Asn Val Ala His Pro Ala Ser
            195                 200                 205

Ser Thr Lys Val Asp Lys Lys Ile Glu Pro Arg
            210                 215
```

```
<210> SEQ ID NO 181
<211> LENGTH: 219
<212> TYPE: PRT
<213> ORGANISM: Homo sapiens

<400> SEQUENCE: 181

Gln Gly Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Phe
            20                  25                  30

Trp Val Asn Trp Val Lys Gln Arg Pro Gly Gln Gly Leu Glu Trp Ile
        35                  40                  45

Gly Gln Ile Tyr Pro Gly Asp Gly Asp Asn Lys Tyr Asn Gly Lys Phe
    50                  55                  60

Lys Gly Lys Ala Thr Leu Thr Ala Asp Lys Ser Thr Thr Ala Tyr
65                  70                  75                  80

Met Gln Leu Tyr Ser Leu Thr Ser Glu Asp Ser Ala Val Tyr Phe Cys
                85                  90                  95

Ala Arg Ser Gly Asn Tyr Pro Tyr Ala Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Gly Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Gly Leu Tyr Thr Leu Ser Ser Ser Val Thr Val Thr Ser Ser
            180                 185                 190

Thr Trp Pro Ser Gln Thr Ile Thr Cys Asn Val Ala His Pro Ala Ser
        195                 200                 205

Ser Thr Lys Val Asp Lys Lys Ile Glu Pro Arg
    210                 215

<210> SEQ ID NO 182
<211> LENGTH: 216
<212> TYPE: PRT
<213> ORGANISM: Mus musculus

<400> SEQUENCE: 182

Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Leu Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
```

-continued

```
            115                 120                 125
Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Trp His Asn Ser Tyr Thr Cys Glu Ala Thr His Lys Thr Ser Thr Ser
            195                 200                 205

Pro Ile Val Lys Ser Phe Asn Arg
        210                 215

<210> SEQ ID NO 183
<211> LENGTH: 216
<212> TYPE: PRT
<213> ORGANISM: Homo sapiens

<400> SEQUENCE: 183

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Ser Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Trp His Asn Ser Tyr Thr Cys Glu Ala Thr His Lys Thr Ser Thr Ser
            195                 200                 205

Pro Ile Val Lys Ser Phe Asn Arg
        210                 215
```